(12) United States Patent
Brady et al.

(10) Patent No.: US 12,240,816 B2
(45) Date of Patent: *Mar. 4, 2025

(54) DEUTERATED COMPOUNDS AND USES THEREOF

(71) Applicant: Aldeyra Therapeutics, Inc., Lexington, MA (US)

(72) Inventors: Todd Brady, Carlisle, MA (US); Scott Young, E. Falmouth, MA (US); William A. Kinney, Newtown, PA (US); Susan MacDonald, Danvers, MA (US)

(73) Assignee: Aldeyra Therapeutics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/504,672

(22) Filed: Nov. 8, 2023

(65) Prior Publication Data

US 2024/0132451 A1 Apr. 25, 2024

Related U.S. Application Data

(63) Continuation of application No. 17/929,505, filed on Sep. 2, 2022, now Pat. No. 11,845,722, which is a continuation of application No. 17/324,318, filed on May 19, 2021, now Pat. No. 11,459,300, which is a continuation of application No. 16/720,645, filed on Dec. 19, 2019, now Pat. No. 11,046,650, which is a continuation of application No. 15/754,065, filed as application No. PCT/US2016/048054 on Aug. 22, 2016, now Pat. No. 10,550,085.

(60) Provisional application No. 62/208,223, filed on Aug. 21, 2015.

(51) Int. Cl.
| | | |
|---|---|---|
| C07D 215/38 | (2006.01) | |
| A61K 31/47 | (2006.01) | |
| A61K 45/06 | (2006.01) | |
| A61P 17/00 | (2006.01) | |
| A61P 27/02 | (2006.01) | |
| A61P 39/00 | (2006.01) | |

(52) U.S. Cl.
CPC ............ *C07D 215/38* (2013.01); *A61K 31/47* (2013.01); *A61K 45/06* (2013.01); *A61P 17/00* (2018.01); *A61P 27/02* (2018.01); *A61P 39/00* (2018.01); *C07B 2200/05* (2013.01)

(58) Field of Classification Search
None
See application file for complete search history.

(56) References Cited

U.S. PATENT DOCUMENTS

| | | | |
|---|---|---|---|
| 2,086,186 A | 7/1937 | Messer | |
| 3,912,748 A | 10/1975 | Evans et al. | |
| 4,668,626 A | 5/1987 | Kobayashi et al. | |
| 4,956,351 A | 9/1990 | Mesens et al. | |
| 5,024,998 A | 6/1991 | Bodor | |
| 5,032,392 A | 7/1991 | Varma | |
| 5,364,637 A | 11/1994 | De et al. | |
| 5,376,645 A | 12/1994 | Stella et al. | |
| 5,419,898 A | 5/1995 | Ikejiri et al. | |
| 5,472,954 A | 12/1995 | Loftsson | |
| 5,493,027 A | 2/1996 | Nichols et al. | |
| 5,576,311 A | 11/1996 | Guy | |
| 5,668,117 A | 9/1997 | Shapiro | |
| 5,767,109 A | 6/1998 | Sanchez et al. | |
| 5,998,488 A | 12/1999 | Shinohara et al. | |
| 6,107,300 A | 8/2000 | Bakthavatchalam et al. | |
| 6,191,127 B1 | 2/2001 | Holscher et al. | |
| 6,358,948 B1 | 3/2002 | Zhang et al. | |
| 6,444,221 B1 | 9/2002 | Shapiro | |
| 6,492,520 B1 | 12/2002 | Chen | |
| 6,498,154 B1 | 12/2002 | Grubb et al. | |
| 6,515,010 B1 | 2/2003 | Franchini et al. | |
| 6,525,056 B2 | 2/2003 | Arvanitis et al. | |
| 6,569,879 B2 | 5/2003 | Liu et al. | |
| 7,083,803 B2 | 8/2006 | Peyman | |
| 7,297,709 B2 | 11/2007 | Dai et al. | |
| 7,531,564 B2 | 5/2009 | Malamas et al. | |
| 7,563,906 B2 | 7/2009 | Hagihara et al. | |
| 7,842,312 B2 | 11/2010 | Burgermeister et al. | |
| 7,956,189 B2 | 6/2011 | Chen et al. | |
| 7,973,025 B2 | 7/2011 | Jordan et al. | |
| 7,982,071 B2 | 7/2011 | Scott et al. | |
| 8,158,609 B1 | 4/2012 | Marsh et al. | |
| 8,435,965 B2 | 5/2013 | Tabuchi et al. | |

(Continued)

FOREIGN PATENT DOCUMENTS

| | | |
|---|---|---|
| CA | 3032609 A1 | 3/2018 |
| CN | 1830964 A | 9/2006 |

(Continued)

OTHER PUBLICATIONS

U.S. Appl. No. 18/568,566 of Brockman et al., filed Dec. 8, 2023.
"Shin iyakuhin no kikaku oyobi shaken houhou no settei nituite nituite ( Regarding the setting of the standard and test method of a new medical product" PMSB/ELD Notification No. 568, May 2001.
Abelson and Loeffler, "Conjunctival allergen challenge: models in the investigation of ocular allergy," Curr Allergy Asthma Rep., 2003, 3(4):363-368.

(Continued)

*Primary Examiner* — Samantha L Shterengarts
(74) *Attorney, Agent, or Firm* — Dechert LLP; Andrea L. C. Reid; Joseph W. Arico

(57) ABSTRACT

The present invention provides for the treatment, prevention, and/or reduction of a risk of a disease, disorder, or condition in which aldehyde toxicity is implicated in the pathogenesis, including ocular disorders, skin disorders, conditions associated with injurious effects from blister agents, and autoimmune, inflammatory, neurological and cardiovascular diseases by the use of a primary amine to scavenge toxic aldehydes, such as MDA and HNE.

20 Claims, 47 Drawing Sheets

(56) References Cited

U.S. PATENT DOCUMENTS

| | | |
|---|---|---|
| 8,490,764 B2 | 7/2013 | Simester |
| 8,575,221 B2 | 11/2013 | Masse et al. |
| 8,722,669 B2 | 5/2014 | Palczewski et al. |
| 8,791,154 B2 | 7/2014 | Gamache et al. |
| 8,940,721 B2 | 1/2015 | Jordan et al. |
| 8,940,764 B2 | 1/2015 | Jordan et al. |
| 9,067,963 B2 | 6/2015 | Thompson et al. |
| 9,084,730 B2 | 7/2015 | Bedos et al. |
| 9,259,427 B2 | 2/2016 | Tierney et al. |
| 9,265,759 B2 | 2/2016 | Jordan et al. |
| 9,364,430 B2 | 6/2016 | Babul |
| 9,364,471 B2 | 6/2016 | Jordan et al. |
| 9,375,408 B2 | 6/2016 | Singh |
| 9,562,039 B2 | 2/2017 | Julia Jane et al. |
| 9,604,997 B2 | 3/2017 | Jordan et al. |
| 9,650,342 B2 | 5/2017 | Jordan et al. |
| 9,663,526 B2 | 5/2017 | Fensome et al. |
| 9,687,481 B2 | 6/2017 | Brady et al. |
| 9,814,701 B2 | 11/2017 | Jordan et al. |
| 9,817,701 B2 | 11/2017 | Baptist et al. |
| 9,896,419 B2 | 2/2018 | Jordan et al. |
| 10,058,095 B2 | 8/2018 | Czarnik |
| 10,098,894 B2 | 10/2018 | Amadio et al. |
| 10,111,862 B2 | 10/2018 | Chabala et al. |
| 10,202,348 B2 | 2/2019 | Jordan et al. |
| 10,213,395 B2 | 2/2019 | Brady et al. |
| 10,414,732 B2 | 9/2019 | Buist et al. |
| 10,426,790 B2 | 10/2019 | Young et al. |
| 10,463,687 B2 | 11/2019 | Rodriguez-Boulan et al. |
| 10,543,181 B2 | 1/2020 | Brady et al. |
| 10,550,085 B2 | 2/2020 | Brady et al. |
| 10,588,874 B2 | 3/2020 | Brady et al. |
| 10,736,842 B2 | 8/2020 | Misra |
| 10,744,144 B2 | 8/2020 | Shah |
| 10,781,158 B2 | 9/2020 | Singh |
| 10,864,166 B2 | 12/2020 | Venkatesh et al. |
| 10,913,722 B2 | 2/2021 | Jordan et al. |
| 11,007,157 B2 | 5/2021 | Brady et al. |
| 11,040,039 B2 | 6/2021 | Macdonald et al. |
| 11,046,650 B2 | 6/2021 | Brady et al. |
| 11,129,823 B2 | 9/2021 | Brady et al. |
| 11,197,821 B2 | 12/2021 | Clark et al. |
| 11,312,692 B1 | 4/2022 | Machatha et al. |
| 11,459,300 B2 | 10/2022 | Brady et al. |
| 11,583,529 B2 | 2/2023 | Macdonald et al. |
| 11,701,331 B2 | 7/2023 | Brady et al. |
| 11,724,987 B2 | 8/2023 | Jordan et al. |
| 11,771,664 B2 | 10/2023 | Brady et al. |
| 11,786,518 B2 | 10/2023 | Clark et al. |
| 11,845,722 B2 | 12/2023 | Brady et al. |
| 12,006,298 B2 | 6/2024 | Machatha et al. |
| 12,029,735 B2 | 7/2024 | Machatha et al. |
| 12,064,516 B2 | 8/2024 | Brady et al. |
| 12,097,188 B2 | 9/2024 | Jordan et al. |
| 12,098,132 B2 | 9/2024 | Machatha et al. |
| 2004/0132636 A1 | 7/2004 | Dooley et al. |
| 2004/0198828 A1 | 10/2004 | Abelson et al. |
| 2004/0235892 A1 | 11/2004 | Dai et al. |
| 2005/0020603 A1 | 1/2005 | Dai et al. |
| 2005/0090553 A1 | 4/2005 | Shapiro |
| 2005/0130906 A1 | 6/2005 | Matier et al. |
| 2005/0197292 A1 | 9/2005 | Smithson et al. |
| 2005/0234018 A1 | 10/2005 | Lyons et al. |
| 2006/0014786 A1 | 1/2006 | Raut |
| 2006/0111318 A1 | 5/2006 | Okamoto |
| 2006/0183909 A1 | 8/2006 | Schmitt et al. |
| 2006/0189608 A1 | 8/2006 | Bingaman |
| 2006/0257488 A1 | 11/2006 | Hubbard |
| 2007/0129404 A1 | 6/2007 | Hagihara et al. |
| 2007/0135481 A1 | 6/2007 | Jordan et al. |
| 2007/0243257 A1 | 10/2007 | Bedos et al. |
| 2007/0297981 A1 | 12/2007 | Ousler et al. |
| 2008/0108818 A1 | 5/2008 | Chen et al. |
| 2008/0241256 A1 | 10/2008 | Kuhn |
| 2009/0118503 A1 | 5/2009 | Sprott et al. |
| 2009/0182009 A1 | 7/2009 | Jordan et al. |
| 2010/0160304 A1 | 6/2010 | Katayama |
| 2010/0240624 A1 | 9/2010 | Chapin et al. |
| 2010/0331315 A1 | 12/2010 | Haddach et al. |
| 2011/0071091 A1 | 3/2011 | Chowhan et al. |
| 2011/0105450 A1 | 5/2011 | Chapin et al. |
| 2011/0257271 A1 | 10/2011 | Masse et al. |
| 2011/0263645 A1 | 10/2011 | Jordan et al. |
| 2012/0108585 A1 | 5/2012 | Vu |
| 2012/0295967 A1 | 11/2012 | Gamache et al. |
| 2012/0302601 A1 | 11/2012 | Jordan et al. |
| 2013/0165419 A1 | 6/2013 | Lindstrom et al. |
| 2013/0190500 A1 | 7/2013 | Greiner et al. |
| 2014/0038918 A1 | 2/2014 | Rodriguez-Boulan et al. |
| 2014/0050797 A1 | 2/2014 | Venkatesh et al. |
| 2014/0235604 A1 | 8/2014 | Palczewski et al. |
| 2014/0235722 A1 | 8/2014 | Jordine et al. |
| 2015/0209333 A1 | 7/2015 | Jordan et al. |
| 2015/0209345 A1 | 7/2015 | Jordan et al. |
| 2015/0258120 A1 | 9/2015 | Zarnitsyn et al. |
| 2015/0335632 A1 | 11/2015 | Brady et al. |
| 2015/0344432 A1 | 12/2015 | Jordan et al. |
| 2015/0344447 A1 | 12/2015 | Chabala et al. |
| 2016/0009698 A1 | 1/2016 | Julia Jane et al. |
| 2016/0030449 A1 | 2/2016 | Persicaner et al. |
| 2016/0052930 A1 | 2/2016 | Fensome et al. |
| 2016/0136231 A1 | 5/2016 | Gadek |
| 2016/0151381 A1 | 6/2016 | Blackburn et al. |
| 2016/0168098 A1 | 6/2016 | Jordan et al. |
| 2017/0029354 A1 | 2/2017 | Singh |
| 2017/0095449 A1 | 4/2017 | Winters et al. |
| 2017/0143627 A1 | 5/2017 | Misra |
| 2017/0239196 A1 | 8/2017 | Brady et al. |
| 2017/0266220 A1 | 9/2017 | Young et al. |
| 2017/0320829 A1 | 11/2017 | Jordan et al. |
| 2017/0354655 A1 | 12/2017 | Beaupre et al. |
| 2018/0050989 A1 | 2/2018 | Machatha et al. |
| 2018/0092882 A1 | 4/2018 | Jordan et al. |
| 2018/0194733 A1 | 7/2018 | Jordan et al. |
| 2018/0235980 A1 | 8/2018 | Shah |
| 2018/0250306 A1 | 9/2018 | Brady et al. |
| 2018/0265474 A1 | 9/2018 | Buist et al. |
| 2018/0354905 A1 | 12/2018 | Brady et al. |
| 2019/0054023 A1 | 2/2019 | Seaman et al. |
| 2019/0087646 A1 | 3/2019 | Goulden et al. |
| 2019/0105322 A1 | 4/2019 | Macdonald et al. |
| 2019/0125729 A1 | 5/2019 | Chabala et al. |
| 2019/0183878 A1 | 6/2019 | Brady et al. |
| 2019/0210971 A1 | 7/2019 | Jordan et al. |
| 2019/0231715 A1 | 8/2019 | Brady et al. |
| 2019/0247334 A1 | 8/2019 | Brady et al. |
| 2020/0038392 A1 | 2/2020 | Brady et al. |
| 2020/0062712 A1 | 2/2020 | Machatha et al. |
| 2020/0121591 A1 | 4/2020 | Clark et al. |
| 2020/0199075 A1 | 6/2020 | Brady et al. |
| 2020/0246345 A1 | 8/2020 | Brady et al. |
| 2020/0323841 A1 | 10/2020 | Clark et al. |
| 2020/0368182 A1 | 11/2020 | Brady et al. |
| 2021/0269402 A1 | 9/2021 | Jordan et al. |
| 2021/0275469 A1 | 9/2021 | Brady et al. |
| 2021/0317385 A1 | 10/2021 | Macdonald et al. |
| 2021/0347735 A1 | 11/2021 | Brady et al. |
| 2021/0353628 A1 | 11/2021 | Macdonald et al. |
| 2021/0393527 A1 | 12/2021 | Brady et al. |
| 2021/0393612 A1 | 12/2021 | Machatha et al. |
| 2022/0017475 A1 | 1/2022 | Machatha et al. |
| 2022/0089542 A1 | 3/2022 | Machatha et al. |
| 2022/0133629 A1 | 5/2022 | Clark et al. |
| 2022/0133697 A1 | 5/2022 | Machatha et al. |
| 2022/0184057 A1 | 6/2022 | Brady et al. |
| 2022/0202745 A1 | 6/2022 | Brady et al. |
| 2022/0211691 A1 | 7/2022 | Brady et al. |
| 2022/0354857 A1 | 11/2022 | Brady et al. |
| 2023/0041335 A1 | 2/2023 | Jordan et al. |
| 2023/0131929 A1 | 4/2023 | Brady et al. |
| 2023/0149383 A1 | 5/2023 | Brady et al. |
| 2023/0174491 A1 | 6/2023 | Brady et al. |
| 2023/0228744 A1 | 7/2023 | Brady et al. |
| 2023/0248727 A1 | 8/2023 | Macdonald et al. |

(56) References Cited

U.S. PATENT DOCUMENTS

| | | |
|---|---|---|
| 2023/0293527 A1 | 9/2023 | Macdonald et al. |
| 2024/0139173 A1 | 5/2024 | Clark et al. |
| 2024/0148700 A1 | 5/2024 | Jordan et al. |
| 2024/0174614 A1 | 5/2024 | Jordan et al. |
| 2024/0189260 A1 | 6/2024 | Brady et al. |

FOREIGN PATENT DOCUMENTS

| | | |
|---|---|---|
| CN | 1882339 A | 12/2006 |
| CN | 101048384 A | 10/2007 |
| CN | 101321742 A | 12/2008 |
| CN | 101534826 A | 9/2009 |
| CN | 101611009 A | 12/2009 |
| CN | 104884049 A | 9/2015 |
| CN | 105120866 A | 12/2015 |
| CN | 105704440 A | 6/2016 |
| CN | 108135867 A | 6/2018 |
| CN | 109640983 A | 4/2019 |
| CN | 111527530 A | 8/2020 |
| CN | 112541870 A | 3/2021 |
| CN | 112800947 A | 5/2021 |
| CN | 113168511 A | 7/2021 |
| EP | 0186367 A2 | 7/1986 |
| EP | 0245054 A1 | 11/1987 |
| EP | 0483881 A1 | 5/1992 |
| EP | 1621199 A1 | 2/2006 |
| EP | 1679308 A1 | 7/2006 |
| EP | 1888548 A1 | 2/2008 |
| EP | 2301549 A1 | 3/2011 |
| GB | 2327672 A | 2/1999 |
| JP | H04264422 A | 9/1992 |
| JP | H06239748 A | 8/1994 |
| JP | H07025758 A | 1/1995 |
| JP | H08175985 A | 7/1996 |
| JP | H09169647 A | 6/1997 |
| JP | H09285529 A | 11/1997 |
| JP | H10306022 A | 11/1998 |
| JP | 2001041757 A | 2/2001 |
| JP | 2001318350 A | 11/2001 |
| JP | 2002003364 A | 1/2002 |
| JP | 2003519698 A | 6/2003 |
| JP | 2005132834 A | 5/2005 |
| JP | 2005187407 A | 7/2005 |
| JP | 3736916 B2 | 1/2006 |
| JP | 2006008568 A | 1/2006 |
| JP | 2007532648 A | 11/2007 |
| JP | 2008542291 A | 11/2008 |
| JP | 4466875 B2 | 5/2010 |
| JP | 4748289 B2 | 8/2011 |
| JP | 2011203665 A | 10/2011 |
| JP | 2012506449 A | 3/2012 |
| JP | 5194218 B2 | 5/2013 |
| JP | 2014515355 A | 6/2014 |
| JP | 2015057437 A | 3/2015 |
| JP | 2015535293 A | 12/2015 |
| JP | 2016508994 A | 3/2016 |
| JP | 2018530524 A | 10/2018 |
| JP | 2019507756 A | 3/2019 |
| KR | 20180073554 A | 7/2018 |
| RU | 2010137842 A | 3/2012 |
| RU | 2565448 C2 | 10/2015 |
| SU | 50906 A1 | 11/1936 |
| SU | 509046 A1 | 6/1984 |
| WO | WO9507274 A1 | 3/1995 |
| WO | WO9622992 A1 | 8/1996 |
| WO | WO9805645 A1 | 2/1998 |
| WO | WO9946237 A1 | 9/1999 |
| WO | WO0141757 A1 | 6/2001 |
| WO | WO0151919 A2 | 7/2001 |
| WO | WO2004082622 A2 | 9/2004 |
| WO | WO2004091630 A1 | 10/2004 |
| WO | WO2005035506 A1 | 4/2005 |
| WO | WO2005040151 A1 | 5/2005 |
| WO | WO2005051328 A2 | 6/2005 |
| WO | WO2005079774 A2 | 9/2005 |
| WO | WO2005105067 A2 | 11/2005 |
| WO | WO2006000421 A2 | 1/2006 |
| WO | WO2006002473 A1 | 1/2006 |
| WO | WO2006049968 A1 | 5/2006 |
| WO | WO2006077821 A1 | 7/2006 |
| WO | WO2006127945 A1 | 11/2006 |
| WO | WO2007118276 A1 | 10/2007 |
| WO | WO2008014602 A1 | 2/2008 |
| WO | WO2008052086 A1 | 5/2008 |
| WO | WO2009045479 A1 | 4/2009 |
| WO | WO2009102418 A1 | 8/2009 |
| WO | WO2010048332 A2 | 4/2010 |
| WO | WO2010133672 A1 | 11/2010 |
| WO | WO2011008202 A1 | 1/2011 |
| WO | WO2011071995 A2 | 6/2011 |
| WO | WO2011072141 A1 | 6/2011 |
| WO | WO2011078204 A1 | 6/2011 |
| WO | WO2012097173 A2 | 7/2012 |
| WO | WO2012105887 A1 | 8/2012 |
| WO | WO2014100425 A1 | 6/2014 |
| WO | WO2014116593 A1 | 7/2014 |
| WO | WO2014116836 A2 | 7/2014 |
| WO | WO2015002893 A1 | 1/2015 |
| WO | WO2015187942 A1 | 12/2015 |
| WO | WO2016085939 A2 | 6/2016 |
| WO | WO2016165626 A1 | 10/2016 |
| WO | WO2017035077 A1 | 3/2017 |
| WO | WO2017035082 A1 | 3/2017 |
| WO | WO2017147617 A1 | 8/2017 |
| WO | WO2017196881 A1 | 11/2017 |
| WO | WO2017214201 A1 | 12/2017 |
| WO | WO2018039192 A1 | 3/2018 |
| WO | WO2018039197 A1 | 3/2018 |
| WO | WO2018064354 A1 | 4/2018 |
| WO | WO2018067860 A1 | 4/2018 |
| WO | WO2018071619 A1 | 4/2018 |
| WO | WO2018091859 A1 | 5/2018 |
| WO | WO2018170476 A1 | 9/2018 |
| WO | WO2019075136 A1 | 4/2019 |
| WO | WO2020018498 A1 | 1/2020 |
| WO | WO2020028820 A1 | 2/2020 |
| WO | WO2020033344 A1 | 2/2020 |
| WO | WO2020068986 A1 | 4/2020 |
| WO | WO2020072621 A1 | 4/2020 |
| WO | WO2020118045 A1 | 6/2020 |
| WO | WO2020198064 A1 | 10/2020 |
| WO | WO2020223685 A1 | 11/2020 |
| WO | WO2020223717 A1 | 11/2020 |
| WO | WO2021051003 A1 | 3/2021 |
| WO | WO2021195211 A1 | 9/2021 |
| WO | WO2021211625 A1 | 10/2021 |
| WO | WO2021231792 A1 | 11/2021 |
| WO | WO2021248031 A1 | 12/2021 |
| WO | WO2022150580 A1 | 7/2022 |
| WO | WO2023278816 A1 | 1/2023 |
| WO | 2023192372 A1 | 10/2023 |

OTHER PUBLICATIONS

Abelson and Spitalny, "Combined analysis of two studies using the conjunctival allergen challenge model to evaluate olopatadine hydrochloride, a new ophthalmic antiallergic agent with dual activity," Am J Ophthalmol. 1998, 125(6):797-804.

Abelson et al., "Conjunctival allergen challenge. A clinical approach to studying allergic conjunctivitis," Arch Ophthalmol., 1990, 108(1):84-88.

Abelson et al., "The conjunctival provocation test model of ocular allergy: utility for assessment of an ocular corticosteroid, loteprednol etabonate," J Ocul Pharmacol Ther., 1998, 14(6):533-542.

Abramovitz et al., "The utilization of recombinant prostanoid receptors to determine the affinities and selectivities of prostaglandins and related analogs," Biochim Biophys Acta. 2000, 1483(2):285-293.

Ackerman et al., "Ocular itch associated with allergic conjunctivitis: latest evidence and clinical management," Ther Adv Chronic Dis., 2016, 7(1):52-67.

Acland et al., "Gene therapy restores vision in a canine model of childhood blindness," Nat Genet. 2001, 28(1):92-95.

(56) References Cited

OTHER PUBLICATIONS

Aharony et al., "Pharmacological characterization of cloned human NK-2 (neurokinin A) receptor expressed in a baculovirus/Sf-21 insect cell system," Mol Pharmacol. 1993, 44(2):356-363.
Aktürk et al., "Nitric oxide and malondialdehyde levels in plasma and tissue of psoriasis patients," J Eur Acad Dermatol Venereol. 2012, 26(7):833-837.
Albano et al., "Immune response towards lipid peroxidation products as a predictor of progression of non-alcoholic fatty liver disease to advanced fibrosis," Gut. 2005, 54(7):987-993.
Al-Bari, "Chloroquine analogues in drug discovery: new directions of uses, mechanisms of actions and toxic manifestations from malaria to multifarious diseases," J Antimicrob Chemother, 2015, 70(6):1608-1621.
Aldeyra Therapeutics, "Aldeyra Therapeutics Abstract Accepted at 2015 American Academy of Allergy Asthma & Immunology Annual Meeting: Novel Anti-Inflammatory Data Selected for Late-Breaking Poster Presentation," Press Release, Dec. 16, 2014, 2 pages.
Aldeyra Therapeutics, "Aldeyra Therapeutics Abstract Accepted for Presentation at the 2015 Multinational Association of Supportive Care in Cancer-International Society of Oral Oncology (MASCCISOO) Annual Meeting", Press Release, Apr. 23, 2015, 2 pages.
Aldeyra Therapeutics, "Aldeyra Therapeutics Abstracts Accepted for Presentation at the 2015 Annual Meeting of the Association for Research in Vision and Ophthalmology," Press Release, Feb. 2, 2015, 2 pages.
Aldeyra Therapeutics, "Aldeyra Therapeutics Announces Agreement with Johnson & Johnson Innovation to Advance Novel Immune-Modulating Drugs for Systemic Inflammatory Diseases", Press Release, Feb. 27, 2018, 2 pages.
Aldeyra Therapeutics, "Aldeyra Therapeutics Announces Clinical Development Update for Phase 3 Programs", Press Release, Jan. 25, 2017, 2 pages.
Aldeyra Therapeutics, "Aldeyra Therapeutics Announces Collaboration With the National Organization for Rare Disorders to Enhance Awareness for Sjogren-Larsson Syndrome Patients", Press Release, Dec. 4, 2014, 2 pages.
Aldeyra Therapeutics, "Aldeyra Therapeutics Announces Development Programs at 2018 Research Day", Press Release, Jun. 26, 2018, 2 pages.
Aldeyra Therapeutics, "Aldeyra Therapeutics Announces First Patient Enrolled in Allergic Conjunctivitis Phase 2b Clinical Trial", Press Release, Feb. 7, 2017, 2 pages.
Aldeyra Therapeutics, "Aldeyra Therapeutics Announces First Patient Enrolled in Allergic Conjunctivitis Phase 3 Clinical Trial", Press Release, Apr. 24, 2018, 2 pages.
Aldeyra Therapeutics, "Aldeyra Therapeutics Announces First Patient Enrolled in Allergic Conjunctivitis Phase IIa Clinical Trial", Press Release, Sep. 29, 2015, 2 pages.
Aldeyra Therapeutics, "Aldeyra Therapeutics Announces First Patient Enrolled in Dry Eye Disease Phase 2a Clinical Trial", Press Release, Jun. 6, 2017, 2 pages.
Aldeyra Therapeutics, "Aldeyra Therapeutics Announces First Patient Enrolled in Dry Eye Disease Phase 2b Clinical Trial", Press Release, Jan. 30, 2018, 2 pages.
Aldeyra Therapeutics, "Aldeyra Therapeutics Announces First Patient Enrolled in Noninfectious Anterior Uveitis Phase 3 Clinical Trial", Press Release, Apr. 27, 2017, 2 pages.
Aldeyra Therapeutics, "Aldeyra Therapeutics Announces First Patient Enrolled in Noninfectious Anterior Uveitis Phase II Clinical Trial", Press Release, Apr. 16, 2015, 2 pages.
Aldeyra Therapeutics, "Aldeyra Therapeutics Announces First Patient Enrolled in Sjogren-Larsson Syndrome Phase II Clinical Trial", Press Release, Mar. 24, 2015, 2 pages.
Aldeyra Therapeutics, "Aldeyra Therapeutics Announces First Patient Enrolled in Sjögren-Larsson Syndrome Pivotal Phase 3 Clinical Trial", Press Release, Jul. 24, 2018, 2 pages.
Aldeyra Therapeutics, "Aldeyra Therapeutics Announces Last Patient Dosed in Dry Eye Disease Phase 2a Clinical Trial", Press Release, Jul. 18, 2017, 2 pages.
Aldeyra Therapeutics, "Aldeyra Therapeutics Announces Last Patient Dosed in Dry Eye Disease Phase 2b Clinical Trial", Press Release, Jul. 12, 2018, 2 pages.
Aldeyra Therapeutics, "Aldeyra Therapeutics Announces Last Patient Dosed in Phase II Trial of NS2 in Patients with Allergic Conjunctivitis", Press Release, Dec. 16, 2015, 2 pages.
Aldeyra Therapeutics, "Aldeyra Therapeutics Announces Last Patient Dosed in the Alleviate Phase 3 Clinical Trial", Press Release, Dec. 20, 2018, 2 pages.
Aldeyra Therapeutics, "Aldeyra Therapeutics Announces Positive Mesothelioma Investigator-Sponsored Clinical Trial Results Presented at the International Association for the Study of Lung Cancer 19th World Conference on Lung Cancer", Press Release, Sep. 25, 2018, 2 pages.
Aldeyra Therapeutics, "Aldeyra Therapeutics Announces Positive Results from Dry Eye Disease Phase 2a Clinical Trial", Press Release, Sep. 12, 2017, 3 pages.
Aldeyra Therapeutics, "Aldeyra Therapeutics Announces Positive Results from Phase 2b Dry Eye Disease Clinical Trial", Press Release, Sep. 26, 2018, 2 pages.
Aldeyra Therapeutics, "Aldeyra Therapeutics Announces Positive Top-Line Results from the Phase 3 Alleviate Trial in Patients with Allergic Conjunctivitis", Press Release, Mar. 26, 2019, 2 pages.
Aldeyra Therapeutics, "Aldeyra Therapeutics Announces Positive Top-Line Symptom and Sign Results from Run-In Cohort of Phase 3 Tranquility Trial in Dry Eye Disease," Jan. 7, 2021, 3 pages.
Aldeyra Therapeutics, "Aldeyra Therapeutics Announces Presentation of Novel Data on the Efficacy of ADX-102 in a Model of Succinic Semialdehyde Dehydrogenase Activity at the 2017 American Society of Human Genetics Annual Meeting", Press Release, Oct. 5, 2017, 2 pages.
Aldeyra Therapeutics, "Aldeyra Therapeutics Announces Presentation of Phase 2 Allergic Conjunctivitis Results at the 2016 American College of Allergy, Asthma and Immunology Annual Scientific Meeting", Press Release, Nov. 7, 2016, 2 pages.
Aldeyra Therapeutics, "Aldeyra Therapeutics Announces Presentation of Results on the Efficacy of ADX-102 in Noninfectious Anterior Uveitis at the American Uveitis Society Held at the American Academy of Ophthalmology 2017 Annual Meeting", Press Release, Oct. 25, 2017, 2 pages.
Aldeyra Therapeutics, "Aldeyra Therapeutics Announces Results from Allergic Conjunctivitis Phase 2b Clinical Trial and Plans for Phase 3 Clinical Testing", Press Release, Jun. 14, 2017, 3 pages.
Aldeyra Therapeutics, "Aldeyra Therapeutics Announces Third Quarter 2017 Financial Results", Press Release, Nov. 9, 2017, 4 pages.
Aldeyra Therapeutics, "Aldeyra Therapeutics' Data on Lead Candidate NS2 to be Presented at Society for Investigative Dermatology 2014 Annual Meeting", Press Release, May 8, 2014, 2 pages.
Aldeyra Therapeutics, "Aldeyra Therapeutics Launches the Aldeyra Registry for Patients with Sjogren-Larsson Syndrome", Press Release, Feb. 22, 2017, 2 pages.
Aldeyra Therapeutics, "Aldeyra Therapeutics Opens Enrollment in Noninfectious Anterior Uveitis Phase II Clinical Trial", Press Release, Mar. 26, 2015, 2 pages.
Aldeyra Therapeutics, "Aldeyra Therapeutics Opens Enrollment in Sjogren-Larsson Syndrome Clinical Trial and Finalizes Noninfectious Anterior Uveitis Clinical Trial Protocol", Press Release, Mar. 17, 2015, 2 pages.
Aldeyra Therapeutics, "Aldeyra Therapeutics Presents Dry Eye Disease Phase 2a Clinical Trial Results at the Association for Research in Vision and Ophthalmology 2018 Annual Meeting", Press Release, May 1, 2018, 2 pages.
Aldeyra Therapeutics, "Aldeyra Therapeutics Presents Evidence for Aldehyde Sequestration as a Potential Therapeutic Approach in Succinic Semialdehyde Dehydrogenase Deficiency at the American Society of Human Genetics 2017 Annual Meeting", Press Release, Oct. 24, 2017, 2 pages.
Aldeyra Therapeutics, "Aldeyra Therapeutics Presents Noninfectious Anterior Uveitis Phase 2 Clinical Trial Data at the Association for Research in Vision and Ophthalmology 2017 Annual Meeting", Press Release, May 17, 2017, 3 pages.

(56) References Cited

OTHER PUBLICATIONS

Aldeyra Therapeutics, "Aldeyra Therapeutics Presents Noninfectious Anterior Uveitis Phase 2 Clinical Trial Data to the American Uveitis Society Held at the American Academy of Ophthalmology 2017 Annual Meeting", Press Release, Nov. 29, 2017, 2 pages.
Aldeyra Therapeutics, "Aldeyra Therapeutics Provides Update on Late-Stage Clinical Trials at 2016 Research and Development Day", Press Release, Sep. 26, 2016, 2 pages.
Aldeyra Therapeutics, "Aldeyra Therapeutics Provides Update on NS2 Clinical Program", Press Release, Mar. 2, 2015, 2 pages.
Aldeyra Therapeutics, "Aldeyra Therapeutics Provides Update on Ophthalmic Programs at 2019 Research & Development Day", Press Release, Feb. 28, 2019, 2 pages.
Aldeyra Therapeutics, "Aldeyra Therapeutics Reaches Agreement with the US Food and Drug Administration for the Use of RASP as an Objective Sign for the Treatment of Dry Eye Disease," Press Release, Jun. 4, 2020, 1 page.
Aldeyra Therapeutics, "Aldeyra Therapeutics Schedules Conference Call and Webcast to Announce Results from Allergic Conjunctivitis Phase 2b Clinical Trial", Press Release, Jun. 13, 2017, 1 pages.
Aldeyra Therapeutics, "Aldeyra Therapeutics Schedules Conference Call to Present Results of a Randomized, Double-Blind, Vehicle-Controlled Clinical Trial in Sjogren-Larsson Syndrome", Press Release, Aug. 8, 2016, 2 pages.
Aldeyra Therapeutics, "Aldeyra Therapeutics Schedules Webcast and Conference Call to Announce Results from Dry Eye Disease Phase 2a Clinical Trial", Press Release, Sep. 11, 2017, 1 page.
Aldeyra Therapeutics, "Aldeyra Therapeutics Selected for Podium Presentation of Phase 2a Dry Eye Disease Results at the 2018 Association for Research in Vision and Ophthalmology (ARVO) Annual Meeting", Press Release, Feb. 21, 2018, 3 pages.
Aldeyra Therapeutics, "Aldeyra Therapeutics Submits FDA IND Filing for Noninfectious Anterior Uveitis", Press Release, Dec. 18, 2014, 2 pages.
Aldeyra Therapeutics, "Aldeyra Therapeutics Submits IND Filing to FDA for Clinical Testing of NS2 in Patients With Sjogren-Larsson Syndrome", Press Release, Jan. 5, 2015, 2 pages.
Aldeyra Therapeutics, "Aldeyra Therapeutics to Host 2019 Research & Development Day", Press Release, Feb. 12, 2019, 1 pages.
Aldeyra Therapeutics, "Aldeyra Therapeutics to Present at the 2016 SSADH Symposium", Press Release, Mar. 24, 2016, 1 page.
Aldeyra Therapeutics, "Aldeyra Therapeutics to Present Novel Data on a Potential Treatment for Sjogren-Larsson Syndrome at the 2015 Society for Inherited Metabolic Disorders Annual Meeting", Press Release, Jan. 29, 2015, 2 pages.
Aldeyra Therapeutics, "Aldeyra Therapeutics to Present Novel Data on a Potential Treatment for Succinic Semi-Aldehyde Dehydrogenase Deficiency at the 2015 American Society of Human Genetics (ASHG) Annual Meeting", Press Release, Sep. 9, 2015, 2 pages.
Aldeyra Therapeutics, "Aldeyra Therapeutics, Inc. Announces Last Patient Dosed in Allergic Conjunctivitis Phase 2b Clinical Trial", Press Release, Apr. 18, 2017, 2 pages.
Aldeyra Therapeutics, "Aldeyra Therapeutics, Inc. Announces Last Patient Dosed in Phase II Clinical Trial of Topical Dermatologic NS2 in Patients With Sjögren-Larsson Syndrome", Press Release, Jun. 7, 2016, 2 pages.
Aldeyra Therapeutics, "Aldeyra Therapeutics, Inc. Receives Orphan Drug Designation from the U.S. Food and Drug Administration for ADX-102 in Sjögren-Larsson Syndrome", Press Release, Apr. 20, 2017, 2 pages.
Aldeyra Therapeutics, "Phase II Allergic Conjunctivitis", Press Release, Feb. 29, 2016, 3 pages.
Aldeyra Therapeutics, "Positive Results From Phase II Clinical Trial in Subjects With Noninfectious Anterior Uveitis", Press Release, May 9, 2016, 4 pages.
Aldeyra Therapeutics, "Positive Results from Phase IIa Clinical Trials in Subjects with Allergic Conjunctivitis", Press Release, Feb. 29, 2016, 3 pages.
Aldeyra Therapeutics, Inc., "A Randomized, Double Masked, Clinical Study of Subjects with Dry Eye Syndrome," ClinicalTrials.gov identifier NCT03162783, https://clinicaltrials.gov/ct2/show/NCT03162783, First Posted May 22, 2017, 6 pages.
Aldeyra Therapeutics, Inc., "A Safety and Activity Study of NS2 in Subjects with Allergic Conjunctivitis," ClinicalTrials.gov identifier NCT02578914, https://clinicaltrials.gov/ct2/show/NCT02578914, Oct. 19, 2015, 6 pages.
Aldeyra Therapeutics, Inc., "A Safety and Efficacy Study of NS2 in Patients with Anterior Uveitis," ClinicalTrials.gov identifier NCT02406209, https://clinicaltrials.gov/ct2/show/NCT02406209, Apr. 2, 2015, 4 pages.
Aldeyra Therapeutics, Inc., "A Study of Topical NS2 Cream to Treat Ichthyosis in Sjogren-Larsson Syndrome (SLS)," ClinicalTrials.gov Identifier NCT02402309, https://clinicaltrials.gov/ct2/show/NCT02402309, Mar. 30, 2015, 3 pages.
Aldini et al., "Lipoxidation-derived reactive carbonyl species as potential drug targets in preventing protein carbonylation and related cellular dysfunction," ChemMedChem. 2006, 1(10):1045-1058.
Aldini et al., "The carbonyl scavenger carnosine ameliorates dyslipidaemia and renal function in Zucker obese rats," J Cell Mol Med. 2011, 15(6):1339-1354.
Al-Essa et al., "Clinical, fluorine-18 labeled 2-fluoro-2-deoxyglucose positron emission tomography (FDG PET), MRI of the brain and biochemical observations in a patient with 4-hydroxybutyric aciduria; a progressive neurometabolic disease," Brain Dev. 2000, 22(2):127-131.
Al-Hasani et al., "Phosphoryl exchange is involved in the mechanism of the insulin receptor kinase," FEBS Lett. 1994, 349(1):17-22.
Allergan, "Restasis® Prescribing Information," copyright 2016, revised 2017, 15 pages.
Amara et al., "Autoantibodies to malondialdehyde-modified epitope in connective tissue diseases and vasculitides," Clin Exp Immunol. 1995, 101(2):233-238.
Ao et al., "Methyl-(beta)-Cyclodextrin Impairs the Monocyte-Adhering Ability of Endothelial Cells by Down-Regulating Adhesion Molecules and Caveolae and Reorganizing the Actin Cytoskeleton," Biol Pharm Bull. 2016, 39(6):1029-1034.
Apparsundaram et al., "Molecular cloning of a human, hemicholinium-3-sensitive choline transporter," Biochem Biophys Res Commun. 2000, 276(3):862-867.
Ardati et al., "Interaction of [3H]orphanin FQ and 125I-Tyr14-orphanin FQ with the orphanin FQ receptor: kinetics and modulation by cations and guanine nucleotides," Mol Pharmacol. 1997, 51(5):816-824.
Ashton et al., "Location of penetration and metabolic barriers to levobunolol in the corneal epithelium of the pigmented rabbit," J Pharmacol Exp Ther. 1991, 259(2):719-724.
Atkinson et al., "Triazaphenanthrenes. Part VI.* Further Observations on the Widman-Stoermer and Brosche Reactions," J Chem Soc C. 1966, 2053-2060.
Augustin et al., "Oxidative reactions in the tear fluid of patients suffering from dry eyes," Graefes Arch Clin Exp Ophthalmol. 1995, 233(11):694-698.
Axelsson et al., "Experimental colitis induced by dextran sulphate sodium in mice: beneficial effects of sulphasalazine and olsalazine," Aliment Pharmacol Ther. 1998, 12(9):925-934.
Bachman and Welton, "Quinoline derivatives from 3-nitro-4-hydroxyquinoline," J Am Chem Soc. 1947, 69(2):365-371.
Bacsi et al., "Effect of pollen-mediated oxidative stress on immediate hypersensitivity reactions and late-phase inflammation in allergic conjunctivitis," J Allergy Clin Immunol., 2005, 116(4):836-843.
Badii, "Allergic Conjunctivitis," Healthline, Retrieved 2019: https://www.healthline.com/health/allergic-conjunctivitis, 2016, 12 pages.
Balci et al., "Effects of computer monitor-emitted radiation on oxidant/antioxidant balance in cornea and lens from rats," Mol Vis. 2009, 15:2521-2525.
Balci et al., "Investigation of oxidative stress in pterygium tissue," Mol Vis. 2011, 17:443-447.

(56) References Cited

OTHER PUBLICATIONS

Ballard et al., "Effects of sildenafil on the relaxation of human corpus cavernosum tissue in vitro and on the activities of cyclic nucleotide phosphodiesterase isozymes," J Urol. 1998, 159(6):2164-2171.
Baltatzis et al., "Mycophenolate mofetil as an immunomodulatory agent in the treatment of chronic ocular inflammatory disorders," Ophthalmology. 2003, 110(5):1061-1065.
Bardwell et al., "Docking sites on mitogen-activated protein kinase (MAPK) kinases, MAPK phosphatases and the Elk-1 transcription factor compete for MAPK binding and are crucial for enzymic activity," Biochem J. 2003, 370(Pt 3):1077-1085.
Baron et al., "[3H]MDL 105,519, a high-affinity radioligand for the N-methyl-D-aspartate receptor-associated glycine recognition site," J Pharmacol Exp Ther. 1996, 279(1):62-68.
Bartoli et al., "Malondialdehyde in exhaled breath condensate as a marker of oxidative stress in different pulmonary diseases," Mediators Inflamm. 2011, 2011:891752, 7 pages.
Bastin et al., "Salt Selection and Optimisation Procedures for Pharmaceutical New Chemical Entities," Org Proc Res Dev. 2000, 4(5):427-435.
Batista et al., "Age-dependent changes in rat lacrimal gland antioxidant and vesicular related protein expression profiles," Mol Vis. 2012, 18:194-202.
Batista et al., "Short-term treatment with bisphenol-A leads to metabolic abnormalities in adult male mice," PLoS One, 2012, 7(3):e33814 (10 pages).
Baum et al., "Omega 3 fatty acid inhibition of inflammatory cytokine-mediated Connexin43 regulation in the heart," Front Physiol. 2012, 3:272(10 pages).
Baz et al., "Plasma reactive oxygen species activity and antioxidant potential levels in rosacea patients: correlation with seropositivity to Helicobacter pylori," Int J Dermatol., 2004, 43(7):494-497.
Berge et al., "Pharmaceutical salts," J Pharm Sci. 1977, 66(1):1-19.
Berkhout et al., "Cloning, in vitro expression, and functional characterization of a novel human CC chemokine of the monocyte chemotactic protein (MCP) family (MCP-4) that binds and signals through the CC chemokine receptor 2B," J Biol Chem., 1997, 272(26):16404-16413.
Bermudez et al., "Thermosensitive poloxamer-based injectables as controlled drug release platforms for veterinary use: Development and in-vitro evaluation," Int Res J Pharm Pharmacol., 2011, 1(6):109-118.
Bernstein et al., "Mechanism of action of aromatic amines that short-circuit the visual cycle," Biochemistry, 1986, 25(11):3370-3377.
Bernstein et al., "Retinal toxicity associated with occupational exposure to the fish anesthetic MS-222," Am J Ophthalmol., 1997, 124(6):843-844.
Bernstein et al., "Short-circuiting the visual cycle with retinotoxic aromatic amines," Proc Natl Acad Sci U. S. A., 1986, 83(6):1632-1635.
Bernstein et al., "The specific inhibition of 11-cis-retinyl palmitate formation in the frog eye by diaminophenoxypentane, an inhibitor of rhodopsin regeneration," Vision Res., 1985, 25(6):741-748.
Bickett et al., "A high throughput fluorogenic substrate for interstitial collagenase (MMP-1) and gelatinase (MMP-9)," Anal Biochem., 1993, 212(1):58-64.
Bignon et al., "SR146131: a new potent, orally active, and selective nonpeptide cholecystokinin subtype 1 receptor agonist. I. In vitro studies," J Pharmacol Exp Ther., 1999, 289(2):742-751.
Blindauer et al., "A randomized controlled trial of etilevodopa in patients with Parkinson disease who have motor fluctuations," Arch Neurol, Feb. 2006, 63(2):210-216.
Boldogh et al., "ROS generated by pollen NADPH oxidase provide a signal that augments antigen-induced allergic airway inflammation," J Clin Invest. 2005, 115(8):2169-2179.
Boner et al., "Bronchodilating activity of oral clenbuterol in asthmatic children after single administration of different dosages," Pediatr Pulmonol., Jan.-Feb. 1987, 3(1):34-37.

Bousquet et al., "How to design and evaluate randomized controlled trials in immunotherapy for allergic rhinitis: an ARIA-GA(2) Len statement," Allergy. 2011, 66(6):765-774.
Boyer et al., "Lipofuscin and N-retinylidene-N-retinylethanolamine (A2E) accumulate in retinal pigment epithelium in absence of light exposure: their origin is 11-cis-retinal," J Biol Chem. 2012, 287(26):22276-22286.
Bozkir et al., "Effect of hydroxypropyl-beta-cyclodextrin on the solubility, stability and in-vitro release of ciprofloxacin for ocular drug delivery," Acta Pol Pharm., 2012, 69(4):719-724.
Bragagni et al., "Cyclodextrin complexation highly enhances efficacy of arylsulfonylureido benzenesulfonamide carbonic anhydrase inhibitors as a topical antiglaucoma agents," Bioorg Med Chem., 2015, 23(18):6223-6227.
Brandt et al., "The Prevalence of Non-Alcoholic Fatty Liver Disease in Patients With Inflammatory Bowel Disease," American Journal of Gastroenterology 2017, 112:S542, S544.
Brenneman et al., "Cannabidiol Provides Protection from Ethanol and Ammonium toxicity in a Hippocampal Model of Hepatic Encephalopathy," 24th Annual Symposium of the International Cannabinoid Research Society, Baveno, Italy, Jun. 28-Jun. 3, 2014, p. 73.
Brenneman et al., "Small molecule anticonvulsant agents with potent in vitro neuroprotection," Journal of Molecular Neuroscience, 2012, 47(2):368-379.
Brewitt et al., "Dry eye disease: the scale of the problem," Survey of Ophthalmol, 2001, 45(Suppl 2):S199-S202.
Brockhaus et al., "Identification of two types of tumor necrosis factor receptors on human cell lines by monoclonal antibodies," Proc Natl Acad Sci U S A., 1990, 87(8):3127-3131.
Brown, "3H-batrachotoxinin-A benzoate binding to voltage-sensitive sodium channels: inhibition by the channel blockers tetrodotoxin and saxitoxin," J Neurosci., 1986, 6(7):2064-2070.
Brozek et al., "Grading quality of evidence and strength of recommendations in clinical practice guidelines: Part 2 of 3. The GRADE approach to grading quality of evidence about diagnostic tests and strategies," Allergy., 2009, 64(8):1109-1116.
Bryant et al., "A novel class of 5-HT2A receptor antagonists: aryl aminoguanidines," Life Sci., 1996, 59(15):1259-1268.
Bucciantini et al., "Inherent toxicity of aggregates implies a common mechanism for protein misfolding diseases," Nature, 2002, 416(6880):507-511.
Buchan et al., "Characterization of three non-peptide endothelin receptor ligands using human cloned ETA and ETB receptors," Br J Pharmacol., 1994, 112(4):1251-1257.
Buddi et al., "Evidence of oxidative stress in human corneal diseases," J Histochem Cytochem., 2002, 50(3):341-351.
Bundgaard, "(C) Means to Enhance Penetration: (1) Prodrugs as a means to improve the delivery of peptide drugs," Adv Drug Deliv Rev., 1992, 8:1-38.
Burcham et al., "Aldehyde-sequestering drugs: tools for studying protein damage by lipid peroxidation products," Toxicology., 2002, 181-182:229-236.
Burstein, "Preservative cytotoxic threshold for benzalkonium chloride and chlorhexidine digluconate in cat and rabbit corneas," Invest Ophthalmol Vis Sci., 1980, 19(3):308-313.
Burstein, "The effects of topical drugs and preservatives on the tears and corneal epithelium in dry eye," Trans Ophthalmol Soc U K (1962), 1985, 104(Pt 4):402-409.
Caira, "Crystalline Polymorphism of Organic Compounds", Topics in Current Chemistry, Jan. 1999, 198:163-208.
Canonica et al., "Recommendations for standardization of clinical trials with Allergen Specific Immunotherapy for respiratory allergy. A statement of a World Allergy Organization (WAO) taskforce," Allergy., 2007, 62(3):317-324.
Canonica et al., "Sub-lingual immunotherapy: World Allergy Organization Position Paper 2009," Allergy, 2009, 64(Suppl 91):1-59.
Casanaro et al., "A convenient solvent system for cellulose dissolution and derivatization: Mechanistic aspects of the acylation of the biopolymer in tetraallylammonium fluoride/dimethyl sulfoxide," Carbohydr Polym., 2011, 8(3):1395-1402.

(56) References Cited

OTHER PUBLICATIONS

Casanaro et al., "Efficacy of vigabatrin intervention in a mild phenotypic expression of succinic semialdehyde dehydrogenase deficiency," JIMD Rep., 2012, 2:119-123.
Cejková et al., "The role of conjunctival epithelial cell xanthine oxidoreductase/xanthine oxidase in oxidative reactions on the ocular surface of dry eye patients with Sjögren's syndrome," Histol Histopathol., 2007, 22(9):997-1003.
Cesura et al., "Characterization of the binding of [3H]Ro 41-1049 to the active site of human monoamine oxidase-A," Mol Pharmacol., 1990, 37(3):358-366.
Chao et al., "Co-existence of non-alcoholic fatty liver disease and inflammatory bowel disease: A review article," World J Gastroenterol. 2016, 22(34):7727-7734.
Chapple et al., "Unfolding retinal dystrophies: a role for molecular chaperones?" Trends Mol Med., 2001, 7(9):414-421.
Chen et al., "Methazolamide Calcium Phosphate Nanoparticles in an Ocular Delivery System," Pharm Soc Japan, 2010, 130(3):419-424.
Cheng et al., "A synthetic peptide derived from p34cdc2 is a specific and efficient substrate of src-family tyrosine kinases," J Biol Chem., May 5, 1992, 267(13):9248-9256.
Chiarpotto et al., "Role of 4-hydroxy-2,3-nonenal in the pathogenesis of fibrosis," Biofactors., 2005, 24(1-4):229-236.
Chicchi et al., "Alterations in receptor activation and divalent cation activation of agonist binding by deletion of intracellular domains of the glucagon receptor," J Biol Chem., 1997, 272(12):7765-7769.
Choi et al., "Expression of Lipid Peroxidation Markers in the Tear Film and Ocular Surface of Patients with Non-Sjogren Syndrome: Potential Biomarkers for Dry Eye Disease," Curr Eye Res., 2016, 41(9):1143-1149.
Choi et al., "The human serotonin 5-HT2B receptor: pharmacological link between 5-HT2 and 5-HT1D receptors," FEBS Letter, 1994, 352(3):393-399.
Ciolino et al., "Effect of alcaftadine 0.25% on ocular itch associated with seasonal or perennial allergic conjunctivitis: a pooled analysis of two multicenter randomized clinical trials," Clin Ophthalmol., 2015, 9:765-772.
Clark et al., "Inhibition of dexamethasone-induced cytoskeletal changes in cultured human trabecular meshwork cells by tetrahydrocortisol," Invest Ophthalmol Vis Sci., 1996, 37(5):805-813.
Clinical Trials Results for Outcome Measures of Ocular Itching and Ocular Tearing, 2016, 1 page.
Clinical Trials Results of Treatment with Aldehyde Trapping Compound NS2, 2015, 1 page.
Clinical Trials Results of Treatment with NS2 Topical Formulation, 2015, 1 page.
Conover et al., "Thiazole Analogs of Pyridoxine," Journal of the American Chemical Society, 1950, 72(11):5221-5225.
Cooper et al., "Clinicopathologic study of dextran sulfate sodium experimental murine colitis," Lab Invest, Aug. 1993, 69(2):238-249.
Couvineau et al., "Molecular identification and structural requirement of vasoactive intestinal peptide (VIP) receptors in the human colon adenocarcinoma cell line, HT-29," Biochem. J., 1985, 231:139-143.
Cullen et al., "Administration of the small molecule aldehyde trap NS2 in a hamster model of radiation-induced oral mucositis," ISOO 2015 Annual Meeting Abstract, Support Care Cancer, Jun. 2015, 23(Suppl. 1):S107.
Cullen et al., "The small molecule aldehyde trap NS2 exhibits potent anti-inflammatory activity in three murine models of inflammation," AAAAI Annual Meeting Abstract, Feb. 2015, 1 page.
Davies, "Biopharmaceutical considerations in topical ocular drug delivery," Clin Exp Pharmacol Physiol, 2000, 27(7):558-562.
De Jong, "Age-Related Macular Degeneration," N Engl J Med, 2006, 355(14):1474-1485.
Del Valle, "Cyclodextrins and their uses: a review," Process Biochemistry, 2004, 39(9):1033-1046.
Demir et al., "Oxidative stress of intracameral lidocaine and levobupivacaine on ocular tissues," Br J Ophthalmol, 2010, 94(8):1083-1087.
Demir et al., "The protective effect of alpha-lipoic acid against oxidative damage in rabbit conjunctiva and cornea exposed to ultraviolet radiation," Ophthalmologica, 2005, 219(1):49-53.
Dente et al., "Modified phage peptide libraries as a tool to study specificity of phosphorylation and recognition of tyrosine containing peptides," J. Mol. Biol., 1997, 269:694-703.
Devedjian et al., "Further characterization of human alpha 2-adrenoceptor subtypes: [31-1]RX821002 binding and definition of additional selective drugs," Eur. J. Pharmacol., 1994, 252:43-49.
Devillier et al., "The allergen challenge chamber: A valuable tool for optimizing the clinical development of pollen immunotherapy," Allergy, 2011, 66(2):163-169.
Division of AIDS, National Institute of Allergy and Infectious Diseases, National Institutes of Health, US Department of Health and Human Services, Division of AIDS (DAIDS) Table for Grading the Severity of Adult and Pediatric Adverse Events, V2.0, Nov. 2014, 33 pages.
Dolmotova et al., "Cardiomyocyte ATP release through pannexin 1 aids in early fibroblast activation," Am. J. Physiol Heart Circ Physiol., 2012, 303(10):H1208-H1218.
Dorje et al., "Antagonist binding profiles of five cloned human muscarinic receptor subtypes," J. Pharmacol. Exp. Ther., 1991, 256:727-733.
Dowling, "Neural and Photochemical Mechanisms of Visual Adaptation in the Rat," Journal of General Physiology, 1963, 46(6):1287-1291.
Drysdale et al., "Complex Promoter and Coding Region Beta 2-adrenergic Receptor Haplotypes Alter Receptor Expression and Predict in vivo Responsiveness," Proc Natl Acad Sci USA, 2000, 97(19):10483-10488.
Egger, et al., "Keratinocyte growth factor ameliorates dextran sodium sulfate colitis in mice," Dig Dis Sci, Apr. 1999, 44(4):836-844.
Ellis et al., "Multiple Doses of Trodusquemine Improve Glucose Tolerance in Type 2 Diabetic Subjects," 69th Scientific Sessions of the American Diabetes Association, Abstract No. 2071-PO, 2009, 2 pages.
Ellman et al., "A new and rapid colorimetric determination of acetylcholinesterase activity," Biochem. Pharmacol., 1961, 7:88-95.
Erdos et al, "Neutral endopeptidase 24.11 (enkephalinase) and related regulators of peptide hormones," FASEB J. 1989, 3:145(10 pages).
Ermolieff et al., "Proteolytic activation of recombinant pro-memapsin 2 (pro-beta-secretase) studied with new fluorogenic substrates," Biochemistry, 2000, 39:12450-12456.
Escalera et al., "Succinic semialdehyde dehydrogenase deficiency: decrease in 4-OH-butyric acid levels with low doses of vigabatrin," An Pediatr (Barc)., 2010, 72(2):128-132.
Esterbauer et al., "Chemistry and Biochemistry of 4-Hydroxynonenal, Malonaldehyde and Related Aldehydes," Free Radic Biol Med, 1991, 11:81-128.
Everest-Todd M., "Topical Application of Cyclodextrin Ethers in the Control of Pain," Proceedings of the Eighth International Symposium on Cyclodextrins, 1998, pp. 495-498.
Farid et al., "Detection of corneal fibrosis by imaging second harmonic-generated signals in rabbit corneas treated with mitomycin C after excimer laser surface ablation," Invest Ophthalmol Vis Sci., 2008, 49(10):4377-4383.
FDA, "Bam R59: Phosphate-Buffered Saline (PBS), pH 7.4," Jan. 2001, retrieved online at <http://www.fda.gov/Food/FoodScienceR. esearch/LaboratoxyMethods/ucm062268.htm> on Apr. 18, 2015, 1 page.
Feighner et al., "Receptor for motilin identified in the human gastrointestinal system," Science, 1999, 284:2184-2188.
Fernandes et al., "Characterization of angiotensin-converting enzymes 1 and 2 in the soleus and plantaris muscles of rats," Braz J Med Biol Res., 2010, 43:837-842.
Ferry et al., "Binding of prostaglandins to human PPAR?: Tool assessment and new natural ligands," Eur. J. Pharmacol., 2001, 417:77-89.

(56) References Cited

OTHER PUBLICATIONS

Feve et al., "Transcriptional down-regulation by insulin of the beta 3-adrenergic receptor expression in 3T3-F442A adipocytes: a mechanism for repressing the cAMP signaling pathway," Proc Natl Acad Sci USA. 1994, 91:5677.

Fiske et al., "The Colormetric Determination of Phosphorus," J. Biol. Chem., 1925, 66:375-400.

Fitzmaurice et al., "Aldehyde dehydrogenase inhibition as a pathogenic mechanism in Parkinson disease," Proc. Natl Acad Sci U.S.A, 2013, 110(2):636-641.

Ford et al., "Pharmacological pleiotropism of the human recombinant alpha1A-adrenoceptor: implications for alpha1-adrenoceptor classification," Brit. J. Pharmacol., 1997, 121:1127-1135.

Fowler et al., "Coloured Complexes of all-trans-retinal with Benzocaine and Other Local Anesthetics," J Photochem Photobiol B, 1991, 8(2):183-188.

Frantz et al., "The Activation State of p38 Mitogen-Activated Protein Kinase Determines the Efficiency of ATP Competition for Pyridinylimidazole Inhibitor Binding," Biochemistry, 1998, 37:13846-13853.

Friesen et al., "Optimization of a Tertiary Alcohol Series of Phosphodiesterase-4 (PDE4) Inhibitors: Structure-Activity Relationship Related to PDE4 Inhibition and Human Ether-a-go-go Related Gene Potassium Channel Binding Affinity," J. Med. Chem., 2003, 46(12):2413-2426.

Fuchs et al., "Functional characterization of three mutations of the endothelin B receptor gene in patients with Hirschsprung's disease: evidence for selective loss of Gi coupling," Mol. Med., 2001, 7:115-124.

Fukunaga et al., "Single nucleotide polymorphism of human platelet-activating factor receptor impairs G-protein activation," J. Biol. Chem., 2001, 276:43025-43030.

Full 1H NMR assignment for RAL-NS2 in CDClJ, submitted to Japanese Patent Office, Mar. 1, 2012.

Ganapathy et al., "Molecular and ligand-binding characterization of the sigma-receptor in the Jurkat human T lymphocyte cell line," JPET, 1999, 289:251-260.

Gasper et al., "2-Hydroxypropyl-beta-cyclodextrin (HPßCD) reduces age-related lipofuscin accumulation through a cholesterol-associated pathway," Scientific Reports, 2017, 7(2197):1-7.

Gibson et al., "Stable isotope dilution analysis of 4-hydroxybutyric acid: an accurate method for quantification in physiological fluids and the prenatal diagnosis of 4-hydroxybutyric aciduria," Biomed Environ Mass Spectrom., 1990, 19(2):89-93.

Gibson et al., "Stable-isotope dilution analysis of D- and L-2-hydroxyglutaric acid: application to the detection and prenatal diagnosis of D- and L-2-hydroxyglutaric acidemias," Pediatr Res., 1993, 34(3):277-280.

Gibson et al., "The Aldehyde Trap NS2 Mitigates Dense Haze in a Rabbit Model of Photorefractive Keratectomy" ARVO Annual Meeting Abstract, Jun. 2015, 1 page.

Godard et al., "Surles orthoamino formyl quinoleines, nouveaux synthons heterocycliques," J Heterocyclic Chem, 1980, 17(3):465-473.

Goldstein et al., "A Phase 2 Exploratory Study of a Novel Interleukin-1 Receptor Inhibitor (EBI-005) in the Treatment of Moderate-to-Severe Allergic Conjunctivitis," Eye Contact Lens, May 2015, 41(3):145-155.

Gole et al., "Plasma Proteins Modified by Tyrosine Nitration in Acute Respiratory Distress Syndrome," Am J Physiol Lung Cell Mol Physiol, 2000, 278:L961-L967.

Gomez et al., "Dimethyltin(IV) 2,6-disubstituted pyridine complexes," J. Organometallic Chemistry, Apr. 2003, 672(2):115-122.

Good, "Measuring field loss in children administered vigabatrin: a problem in search of a solution," J AAPOS. 2011, 15(5):411-412.

Gopalakrishnan et al., "Stable expression, pharmacologic properties and regulation of the human neuronal nicotinic acetylcholine alpha 4 beta 2 receptor," J. Pharmacol. Exp. Ther., Jan. 1996, 276(1):289-297.

Gould et al., "[3H]nitrendipine-labeled calcium channels discriminate inorganic calcium agonists and antagonists," Proc. Natl. Acad. Sci. U.S.A., Jun. 1982, 79(11):3656-3660.

Grandy et al., "Cloning of the cDNA and gene for a human D2 dopamine receptor," Proc. Natl. Acad. Sci. U.S.A., Dec. 1989, 86(24):9762-9766.

Green et al., "Characterization of [(3)H]-CGP54626A binding to heterodimeric GABA(B) receptors stably expressed in mammalian cells," Brit. J. Pharmacol., Dec. 2000, 131(8):1766-1774.

Green et al., "Influence of Various Agents on Corneal Permeability," American Journal of Ophthalmology, 1971, 72(5):897-905.

Grob et al., "Die Synthese von 5-Oxy-benz(cd)indolin and dessen Umpagerung in 5-Keto-1,3,4,5-tetrahydro-benz(cd)indol," Helvetica Chimica Acta, Verlag Helvetica Chimica Acta, CH, 1950, 33(6):1796-1808.

Gromachevskaya et al., "4H-3,1-benzoxazines. 2. Synthesis of 2,4-substituted 1 2-dihydro-4H-3,1-benzoxazines," Chemistry of Heterocyclic Compounds, Jun. 1988, 24(6):692-697.

Grotto et al., "Importance of the lipid peroxidation biomarkers and methodological aspects for malondialdehyde quantification," Quim Nova, 2009, 32(1):169-174.

Halilovic et al., "ADX-103, a Novel Small Molecule Aldehyde Sequestering Agent, Decreases Retinal Edema and Inflammation in a Rat Model of Diabetic Macular Edema," ARVO Annual Meeting Abstract, Jul. 2018, 2 pages.

Hampson et al., "Cannabidiol and (−)Delta9-tetrahydrocannabinol are neuroprotective antioxidants," Proc. Nat. Acad. Sci, Jul. 1998, 95(14):8268-8273.

Hassan et al., "Oxidative stress in systemic lupus erythematosus and rheumatoid arthritis patients: relationship to disease manifestations and activity," International Journal of Rheumatic Diseases, Oct. 2011, 14(4):325-331.

Herbort et al., "Endotoxin-induced uveitis in the rat," Graefe's Arch Clin Exp Ophthalmol, Nov. 1988, 226:553-558.

Hessen et al., "Dry Eye: an Inflammatory Ocular Disease," J Ophthalmic Vis Res, 2014, 9(2):240-250.

Heuillet et al., "Characterization of a Human NK1 Tachykinin Receptor in the Astrocytoma Cell Line U 373 MG," J. Neurochem., Mar. 1993, 60(3):868-876.

Highlights of Prescribing Information, Bridion® (sugammadex) Injection, for intravenous use, Initial U.S. Approval: 2015, Last Revised Dec. 2015, 19 pages.

Hogema et al., "Pharmacologic rescue of lethal seizures in mice deficient in succinate semialdehyde dehydrogenase," Nat Genet. Oct. 2001, 29:212-216.

Hom et al., "Allergic conjunctivitis and dry eye syndrome," Ann Allergy Asthma Immunol, 2012, 108(3):163-166.

Hong et al., "Laboratory scale production of injectable liposomes by using cell disruptor to avoid the probe sonication process," Journal of Pharmaceutical Investigation, 2015, 45(1):73-78.

Hope et al., "Characterization of a human 5-hydroxytryptamine3 receptor type A (h5-HT3R-AS) subunit stably expressed in HEK 293 cells," Brit. J. Pharmacol., Jul. 1996, 118(5):1237-1245.

Horner et al., "Analogs of 3-Amino-7-chloro-1,2,4-benzotriazine 1-Oxide as Antimalarial Agents," J. Med. Chem., Sep. 1968, 11(5):946-949.

Hoyer et al., "Characterization of the 5-HT1B recognition site in rat brain: binding studies with (−)[125I]iodocyanopindolol," Eur. J. Pharmacol., Nov. 1985, 118(1-2):1-12.

Huang et al., "Characterization of Calcium Phosphate Nanoparticles Based on a PEGylated Chelator for Gene Delivery," ACS Appl Mater Interfaces, Mar. 2017, 9(12):10435-10445.

Huang et al., "Identification of human Ether-a-go-go related gene modulators by three screening platforms in an academic drug-discovery setting," Assay Drug Dev Technol., Dec. 2010, 8(6):727-742.

Huang et al., "Novel peptide inhibitors of angiotensin-converting enzyme 2," J. Biol. Chem., May 2003, 278(18):15532-15540.

Hubbard, "Geometrical Isomerization of Vitamin A, Retinene and Retinene Oxime," Journal of the American Chemical Society, 1956, 78(18):4662-4667.

(56) References Cited

OTHER PUBLICATIONS

Hugues et al., "Preparation of a pure monoiodo derivative of the bee venom neurotoxin apamin and its binding properties to rat brain synaptosomes," J. Biol. Chem., Mar. 1982, 257(6):2762-2769.

Hurd et al., "Reaction of Propiolactone with Aniline Derivatives," Journal of the American Chemical Society, 1952, 74(23):5889-5893.

Inoue et al., "Filter-binding assay procedure for thyroid hormone receptors," Anal Biochem. 1983, 134(1):176-183.

Iriyama et al., "A2E, a pigment of the lipofuscin of retinal pigment epithelial cells, is an endogenous ligand for retinoic acid receptor," J Biol Chem., 2008, 283(18):11947-11953.

Irons, "Fluvoxamine in the treatment of anxiety disorders," Neuropsychiatr Dis Treat. 2005, 1(4):289-299.

Ishida et al., "Stabilization of calmodulin-dependent protein kinase II through the autoinhibitory domain," J. Biol. Chem., Feb. 1995, 270(5):2163-2170.

Ito et al., "A Medium-Term Rat Liver Bioassay for Rapid in vivo Detection of Carcinogenic Potential of Chemicals," Cancer Science, Jan. 2003, 94(1):3-8.

Itokawa et al., "Antiangiogenic effect by SU5416 is partly attributable to inhibition of Flt-1 receptor signaling," Mol. Cancer Ther., Mar. 2002, 1(5):295-302.

Jacobs et al., "Responses to ragweed pollen in a pollen challenge chamber versus seasonal exposure identify allergic rhinoconjunctivitis endotypes," J. Allergy Clin. Immunol., 2012, 130(1):122-127.

Jafari et al., "Evaluation of plasma, erythrocytes, and bronchoalveolar lavage fluid antioxidant defense system in sulfur mustard-injured patients," Clin Toxicol (Phila)., Mar. 2010, 48(3):184-192.

Janowski et al., "Structural requirements of ligands for the oxysterol liver X receptors LXRalpha and LXRbeta," Proc. Natl. Acad. Sci. USA, Jan. 1999, 96(1):266-271.

Jarrett et al., "Mitochondrial DNA damage and impaired base excision repair during epileptogenesis," Neurobiology of Disease, Apr. 2008, 30(1):130-138.

Jellinger et al., "American Association of Clinical Endocrinologists and American College of Endocrinology Guidelines for Management of Dyslipidemia and Prevention of Cardiovascular Disease," Endocr Pract. 2017, 23(Suppl 2):1-87.

Ji et al., "Exploration of diverse hinge-binding scaffolds for selective Aurora kinase inhibitors," Bioorg. & Med. Chem. Let. 2012, 22:4528.

Johannsdottir et al., "Development of a Cyclodextrin-Based Aqueous Cyclosporin A Eye Drop Formulations," International Journal of Pharmaceutics, 2015, 493(1-2):86-95.

Johnson et al., "2-Hydroxypropyl-ß-Cyclodextrin Removes All-Trans Retinol from Frog Rod Photoreceptors in a Concentration-Dependent Manner," Journal of Ocular Pharmacology and Therapeutics, 2010, 26(3):245-248.

Joseph et al., "Binding of (−)-[3H]-CGP12177 at two sites in recombinant human beta 1-adrenoceptors and interaction with beta-blockers," Naun.-Sch. Arch. Pharm., 2004, 369:525-532.

Kam et al., "Topical Cyclodextrin Reduces Amyloid Beta and Inflammation Improving Retinal Function in Ageing Mice," Experimental Eye Research, 2015, 135:59-66.

Kamino et al., "Deficiency in mitochondrial aldehyde dehydrogenase increases the risk for late-onset Alzheimer's disease in the Japanese population," Biochemical and Biophysical Research Communications, 2000, 273(1):192-196.

Karahashi et al., "Changes of caspase activities involved in apoptosis of a macrophage-like cell line J774.1/JA-4 treated with lipopolysaccharide (LPS) and cycloheximide," Biol. Pharm. Bull., 2000, 23:140-144.

Karan et al., Lipofuscin Accumulation, Abnormal Electrophysiology, and Photoreceptor Degeneration in Mutant ELOVL4 Transgenic Mice: A Model for Macular Degeneration, Proc Natl Acad Sci USA, 2005, 102(11):4164-4169.

Katugampola et al., "[(125)I]-(Pyr(1))Apelin-13 is a novel radioligand for localizing the APJ orphan receptor in human and rat tissues with evidence for a vasoconstrictor role in man," Brit. J. Pharmacol., 2001, 132:1255-1260.

Kawaguchi et al., "Drug and crystal polymorphism," Journal of human environmental engineering, 2002, 4(2):310-317.

Keister et al., "Inflammatory Bowel Disease and Irritable Bowel Syndrome Similarities and Differences," Crohn's & Colitis Foundation of America, 2014, 12 pages.

Kenney et al., "The Cascade Hypothesis of Keratoconus," Contact Lens & Ant Eye, 2003, 26:139-146.

Keri, "Rosacea," Merck Manual, Professional Version, https://www.merckmanuals.com/professional/dermatologic-disorders/acne-and-related-disorders/rosacea, 2017, 7 pages.

Knapp et al., "Intraocular Availability of Topically Applied Mycophenolate Mofetil in Rabbits," J. Ocul. Pharmacol. Ther., 2003, 19(2):181-192.

La Rosa et al., "Allergic conjunctivitis: a comprehensive review of the literature," Ital J Pediatr, 2013, 39:18 (8 pages).

Landor et al., "Allenes. Part 49, 4-Amino-2-(1-hydroxyalkyl)quinolones from Phenylhydroxylamine and Allenic Nitrites," J Chem Soc Perkin Trans 1, 1989, pp. 251-254.

Langin et al., "[3H]RX821002: a new tool for the identification of alpha 2A-adrenoceptors," Eur. J. Pharmacol., 1989, 167:95-104.

Lankin et al., "Role of Oxidative Stress in the Genesis of Atherosclerosis and Diabetes Mellitus: A Personal Look Back on 50 Years of Research," Curr. Aging Sci., 2017, 10(1):18-25.

Le et al., "Ligand binding and functional properties of human angiotensin AT1 receptors in transiently and stably expressed CHO-K1 cells," Eur. J. Pharmacol., 2005, 513:35-45.

Lee et al., "Human recombinant soluble guanylyl cyclase: expression, purification, and regulation," Proc. Natl. Acad. Sci. USA, 2000, 97(20):10763-10768.

Lee et al., "The human brain cholecystokinin-B/gastrin receptor. Cloning and characterization," J. Biol. Chem., 1993, 268:8164-8169.

Leibundgut et al., "Oxidation-specific epitopes and immunological responses: Translational biotheranostic implications for atherosclerosis," Current Opinion in Pharmacology, 2013, 13(2):168-179.

Leonardi et al., "Correlation Between Conjunctival Provocation Test (CPT) and Systemic Allergometric Tests in Allergic Conjunctivitis," Eye, 1990, 4:760-764.

Leonardi, "Allergy and allergic mediators in tears," Exp. Eye Res., 2013, 117:106-117.

Leurs et al., "Pharmacological characterization of the human histamine H2 receptor stably expressed in Chinese hamster ovary cells," Brit. J. Pharmacol., 1994, 112:847-854.

Levey et al., "A new equation to estimate glomerular filtration rate," Ann Intern Med. 2009, 150(9):604-612.

Levin et al., "The myocardium-protective Gly-49 variant of the beta 1-adrenergic receptor exhibits constitutive activity and increased desensitization and down-regulation," J. Biol.Chem., 2002, 277:30429-30435.

Lewin et al., "meta- and para-isothiocyanato-t-butylbicycloorthobenzoate: irreversible ligands of the gamma-aminobutyric acid-regulated chloride ionophore," Mol. Pharmacol., 1989, 35:189-194.

Li et al., "Effect of Vitamin A Supplementation on Rhodopsin Mutants Threonine-17-> Methionine and Proline-347-> Serine in Transgenic Mice and in Cell Cultures," Proc Natl Acad Sci USA, 1998, 95(20):11933-11938.

Liang et al., "Ocular safety of cationic emulsion of cyclosporine in an in vitro corneal wound-healing model and an acute in vivo rabbit model," Mol Vis, 2012, 18:2195-204.

Liu et al., "Comparison of human, mouse, rat, and guinea pig histamine H4 receptors reveals substantial pharmacological species variation," J. Pharmacol. Exp. Ther., 2001, 299:121-130.

Loftsson et al., "Cyclodextrin Microparticles for Drug Delivery to the Posterior Segment of the Eye: Aqueous Dexamethasone Eye Drops," Journal of Pharmacy and Pharmacology, 2007, 59(5):629-635.

Loftsson et al., "Cyclodextrins in Eye Drop Formulations: Enhanced Topical Delivery of Corticosteroids to the Eye," Acta Ophthalmologica Scandinavica, 2002, 80(2):144-150.

(56) References Cited

OTHER PUBLICATIONS

Lopachin et al., "Molecular mechanisms of aldehyde toxicity: a chemical perspective," Chem Res Toxicol, 2014, 27(7):1081-1091.
Lovenberg et al., "Cloning and functional expression of the human histamine H3 receptor," Mol. Pharmacol., 1999, 55:1101-1107.
Lukas, R.J., "Characterization of curaremimetic neurotoxin binding sites on membrane fractions derived from the human medulloblastoma clonal line, T15671," J. Neurochem., 1986, 46:1936-1941.
Luthin et al., "Characterization of two affinity states of adenosine A2a receptors with a new radioligand, 2-[2-(4-amino-3-[125I]iodophenyl)ethylamino]adenosine," Mol. Pharmacol., 1995, 47:307-313.
MacDonald et al., "ADX-102, a novel aldehyde trap, reduces nociceptive behavior in mouse models of carrageenan and CFA induced pain," Int'l Conference on Pain Research & Management Abstract, J Pain Relief, Oct. 2016, 5(5 Suppl):50.
MacDonald et al., "Inhibition of fibroblast activation to the myofibroblast phenotype in neonatal rat cardiac fibroblasts using a small molecule aldehyde trap," ASCB Annual Meeting Abstract, Dec. 2016, p. 2.
MacDonald et al., "Molecular characterization of the melanin-concentrating hormone/receptor complex: identification of critical residues involved in binding and activation," Mol. Pharmacol., 2000, 58:217-225.
MacDonald et al., "Novel Small Molecule Aldehyde Sequestering Agents Demonstrate Broad Therapeutic Potential for Ocular Inflammation," ARVO Annual Meeting Abstract, Jul. 2018, 2 pages.
MacDonald et al., "The novel aldehyde trap, ADX-102, reduces inflammation-mediated lung infiltrate in a mouse model of LPS-induced acute lung injury," 13th World Congress on Inflammation Abstract, Jul. 2017, p. 192.
MacKenzie et al., "Characterization of the human dopamine D3 receptor expressed in transfected cell lines," Eur. J. Pharmacol., 1994, 266:79-85.
Maeda et al., "Involvement of All-trans-retinal in Acute Light-induced Retinopathy of Mice," J Biol Chem, May 2009, 284(22):15173-15183.
Maeda et al., "Primary amines protect against retinal degeneration in mouse models of retinopathies," Nat Chem Biol, 2011, 8(2):170-178.
Maghsoodi et al., "Physicomechanical Properties of Naproxen-Loaded Microparticles Prepared from Eudragit L100", AAPS PharmSciTech., Mar. 2009, 10(1):120-128.
Maguire et al., "Orphan-receptor ligand human urotensin II: receptor localization in human tissues and comparison of vasoconstrictor responses with endothelin-1," Brit. J. Pharmacol., 2000, 131:441-446.
Malondialdehyde, Wikipedia, retrieved from the internet on Aug. 4, 2021 at https://en.wikipedia.org/wiki/Malondialdehyde, 2008, 4 pages.
Mandell et al., "The Aldehyde Trap NS2 Reduces Ocular Inflammation in an Endotoxin-Induced Model in Rats," Investigative ophthalmology & visual science. 2015, 56(7):3095.
Mantey et al., "Discovery of a high affinity radioligand for the human orphan receptor, bombesin receptor subtype 3, which demonstrates that it has a unique pharmacology compared with other mammalian bombesin receptors," J. Biol. Chem., 1997, 272:26062-26071.
Marnett, "Oxy radicals, lipid peroxidation and DNA damage," Toxicology, 2002, 181-182:219-222.
Martin et al., "Molecular cloning and functional characterization of murine cysteinyl-leukotriene 1 (CysLT(1)) receptors.," Biochem. Pharmacol., 2001, 62:1193-1200.
Matern et al., "Seizures in a boy with succinic semialdehyde dehydrogenase deficiency treated with vigabatrin (gamma-vinyl-GABA)," J Inherit Metab Dis., 1996, 19(3):313-318.
Mathew et al., "Updates in the management of diabetic macular edema," J Diabetes Res., 2015, 2015:794036(8 pages).
Maurice et al., "Advances in targeting cyclic nucleotide phosphodiesterases," Nat Rev Drug Discov., 2014, 13:290-314.

McCord et al., "Superoxide dismutase. An enzymic function for erythrocuprein (hemocuprein).," J. Biol. Chem., 1969, 244:6049-6055.
McGinnity et al., "Evaluation of fresh and cryopreserved hepatocytes as in vitro drug metabolism tools for the prediction of metabolic clearance." Drug Metab. Dispos., 2004, 32(11):1247-1253.
McLaurin et al., "Phase 3 Randomized Double-Masked Study of Efficacy and Safety of Once-Daily 0.77% Olopatadine Hydrochloride Ophthalmic Solution in Subjects with Allergic Conjunctivitis Using the Conjunctival Allergen Challenge Model," Clinical Science, 2015, 34(10):1245-1251.
Medline Plus. Macular Degeneration—age-related, 2013, 6 pages.
Meijer et al., "Biochemical and cellular effects of roscovitine, a potent and selective inhibitor of the cyclin-dependent kinases cdc2, cdk2 and cdk5," Eur. J. Biochem., 1997, 243:527-536.
Meng et al., "Cloning and pharmacological characterization of a rat kappa opioid receptor," Proc. Natl. Acad. Sci. U.S.A., 1993, 90:9954-9958.
Mialet et al., "Isolation of the serotoninergic 5-HT4(e) receptor from human heart and comparative analysis of its pharmacological profile in C6-glial and CHO cell lines," Brit. J. Pharmacol., 2000, 129:771-781.
Miceli et al., "Efficacy of keratinocyte growth factor-2 in dextran sulfate sodium-induced murine colitis," J Pharmacol Exp Ther, Jul. 1999, 290(1):464-471.
Mishra et al., "Recent Patents and Emerging Therapeutics in the Treatment of Allergic Conjunctivitis," Recent Pat. Inflamm. Allergy Drug Discov.; 2011, 5(1):26-36.
Mittl et al., "Structure of recombinant human CPP32 in complex with the tetrapeptide acetyl-Asp-Val-Ala-Asp fluoromethyl ketone," J. Biol. Chem., Jul. 1999, 272:6539-6547.
Monaghan et el., "The distribution of [3H]kainic acid binding sites in rat CNS as determined by autoradiography," Brain Res., 1982, 252:91-100.
Monsma et al., "Cloning and expression of a novel serotonin receptor with high affinity for tricyclic psychotropic drugs," Mol. Pharmacol., 1993, 43:320-327.
Mulheron et al., "Human 5-HT1A receptor expressed in insect cells activates endogenous G(o)-like G protein(s)," J. Biol. Chem., 1994, 269:12954-12962.
Muller-Enoch et al., "[6.7-Dihydroxycoumarin (Aesculetin) as a substrate for catechol-o-methyltransferase (author's transl)]," Z. Naturforsch., 1976, 31:280-284.
Munro et al., "Molecular characterization of a peripheral receptor for cannabinoids," Nature, 1993, 365:61-65.
Murphy et al., "Characterization of quisqualate recognition sites in rat brain tissue using DL-[3H]alpha-amino-3-hydroxy-5-methylisoxazole-4-propionic acid (AMPA) and a filtration assay," Neurochem. Res., 1987, 12:775-781.
Na et al., "Molecular profiling of a 6-hydroxydopamine model of Parkinson's disease," Neurochem Res. 2010, 35(5):761-772.
Nagai et al., "Improved corneal toxicity and permeability of tranilast by the preparation of ophthalmic formulations containing its nanoparticles," J Oleo Sci, 2014, 63(2):177-186.
Nagase et al., "Design and characterization of a fluorogenic substrate selectively hydrolyzed by stromelysin 1 (matrix metalloproteinase-3)," J. Biol. Chem., 1994, 269:20952-20957.
Nakamura et al., "Involvement of Oxidative Stress on Corneal Epithelial Alterations in a Blink-Suppressed Dry Eye," Investigative Ophthalmology and Visual Science, 2007, 48(4):1552-1558.
Negre-Salvayre et al., "Advanced Lipid Peroxidation End Products in Oxidative Damage to Proteins. Potential Role in Diseases and Therapeutic Prospects for the Inhibitors," Br J Pharmacol, 2008, 153(1):6-20.
Nema et al., "Excipients and Their Use in injectable Products," PDA J Pharm Sci Technol, 1997, 51(4):166-171.
*Neptune Generics, LLC v. Auspex Pharmaceuticals, Inc.*, IPR2015-01313, Paper No. 25, Dec. 9, 2015, 23 pages.
Nerurkar et al., "Beta-Arylglutaconic Acids. II. Imides of Certain Beta-Arylglutaconic and Glutaric Acids," J Org Chem, 1959, 24(12):2055-2056.

(56) References Cited

OTHER PUBLICATIONS

Nielsen et al., "Glycolamide esters as biolabile prodrugs of carboxylic acid agents: synthesis, stability, bioconversion, and physicochemical properties," J Pharm Sci. 1988, 77(4):285-298.
Niwa et al., "Protein oxidative damage in the stratum corneum: Evidence for a link between environmental oxidants and the changing prevalence and nature of atopic dermatitis in Japan," Br J Dermatol., 2003, 149(2):248-254.
Nociari et al., "Beta cyclodextrins bind, stabilize, and remove lipofuscin bisretinoids from retinal pigment epithelium," Proc Natl Acad Sci U.S.A., 2014, E1402-E1408.
Noorwez et al., "Pharmacological Chaperone-mediated in Vivo Folding and Stablization of the P23H-Opsin Mutant Associated with Autosomal Dominant Retinitis Pigmentosa," J Biol Chem, 2003, 278:14442-14450.
Noriyuki Takada "Souyaku dankai ni okeru genyaku Form sukuri ningu to sentaku (Bulk drug screening and selection in a drug development phase," Pharm Stage, Jan. 2007, 6(10):20-25.
Obourn et al., "Hormone- and DNA-binding mechanisms of the recombinant human estrogen receptor," Biochemistry, 1993, 32(24):6229-6236.
O'Brien et al., "Aldehyde Sources, Metabolism, Molecular Toxicity Mechanisms, and Possible Effects on Human Health," Crit Rev Toxicol, 2005, 35:609-662.
Okayasu et al., "A novel method in the induction of reliable experimental acute and chronic ulcerative colitis in mice," Gastroenterology, 1990, 98(3):694-702.
Ono, "Analysis of Salt Selection of Current Active Pharmaceutical Ingredients (API)," Journal of Pharmaceutical Science and Technology, 2013, 73(3):176-182.
O'Regan et al., "Filaggrin in atopic dermatitis," J Allergy Clin Immunol. 2009, 124(3 Suppl 2):R2-6.
Organisciak et al., "Susceptibility to Retinal Light Damage in Transgenic Rats with Rhodopsin Mutations," Invest Ophthalmol Vis Sci, 2003, 44(2):486-492.
Ousler et al., "Use of the Controlled Adverse Environment (CAE) in Clinical Research: A Review," Opthalmology and Therapy, 2017; 6:263-276.
Pacholczyk et al., "Expression cloning of a cocaine- and antidepressant-sensitive human noradrenaline transporter," Nature, 1991, 350:350-354.
Pal et al., "Sulfur mustard analog induces oxidative stress and activates signaling cascades in the skin of SKH-1 hairless mice," Free Radic Biol Med., 2009, 47(11):1640-1651.
Palchaudhuri et al., "Corticotropin-releasing factor receptor type 1 from Tupaia belangeri-cloning, functional expression and tissue distribution," Eur. J. Biochem., 1998, 258:78-84.
Parish et al., "Isolation and One-Step Preparation of A2E and iso-A2E, Fluorophores from Human Retinal Pigment Epithelium," Proc Natl Acad Sci USA, 1998, 95(25):14609-14613.
Park et al., "Modulation of Acute Inflammation and Keratocyte Death by Suturing, Blood, and Amniotic Membrane in PRK," Invest. Opthalmol Vis Sci. 2000, 41(10):2906-2914.
Park et al., "Homogeneous proximity tyrosine kinase assays: scintillation proximity assay versus homogeneous time-resolved fluorescence," Anal. Biochem., 1999, 269:94-104.
Parracho et al., "Differences between the gut microflora of children with autistic spectrum disorders and that of healthy children," Journal of Medical Microbiology, 2005, 54:987-991.
Patel C.Y., "Subtype selectivity of peptide analogs for all five cloned human somatostatin receptors (hsstr 1-5)," Endocrinology, 1994, 135:2814-2817.
Pearl et al., "Inherited disorders of gamma-aminobutyric acid metabolism and advances in ALDH5A1 mutation identification," Dev Med Child Neurol., 2015, 57(7):611-617.
Pellock, "Balancing clinical benefits of vigabatrin with its associated risk of vision loss," Acta Neurologica. Scandinavica. Supplementum., 2011, 124(s192):83-91.

Peralta et al., "Distinct primary structures, ligand-binding properties and tissue-specific expression of four human muscarinic acetylcholine receptors," EMBO. J., 1987, 6(13):3923-3929.
Petroski et al., "Selective labeling of embryonic neurons cultured on astrocyte monolayers with 5(6)-carboxyfluorescein diacetate (CFDA)," Journal of Neuroscience Methods, 1994, 52(1):23-32.
Pfaar et al., "Perspectives in allergen immunotherapy: 2017 and beyond," Allergy, 2018, 73(Suppl 104):5-23.
Pickering, D.S., "Pharmacological characterization of melatonin binding sites in Syrian hamster hypothalamus," Eur. J. Pharmacol., 1990, 175(1):71-77.
Pontikis et al., "Cyclodextrin alleviates neuronal storage of cholesterol in Niemann-Pick C disease without evidence of detectable blood-brain barrier permeability," Journal of Inherited Metabolic Disease, 2013, 36(3):491-498.
Pozzi et al., "Modification of Collagen IV by Glucose or Methylglyoxal Alters Distinct Mesangial Cell Function," Journal of the American Society of Nephrology, 2009, 20(10):2119-2125.
Pred Forte Prescribing Information, Allergan, 2017, 5 pages.
Pristupa et al., "Pharmacological heterogeneity of the cloned and native human dopamine transporter: disassociation of [3H]WIN 35,428 and [3H]GBR 12,935 binding.," Mol. Pharmacol., 1994, 45(1):125-135.
Pruneau et al., "LF 16.0335, a novel potent and selective nonpeptide antagonist of the human bradykinin B2 receptor," Brit. J. Pharmacol., 1998, 125(2):365-372.
Pubchem CID 149143404, Aug. 12, 2020, 2 pages.
Pubchem CID 4391047, Sep. 14, 2005, 2 pages.
Pubchem, 1824609-67-7, SID 333824451, Apr. 24, 2017, 6 pages.
Pubchem, 2-(3-Aminoquinolin-2-yl)propan-2-ol, CID 117758222, modified Jun. 13, 2020, Feb. 23, 2016, 11 pages.
Pubchem, SCHEMBL16316728, CID 117758222, modified Sep. 30, 2017, Feb. 23, 2016, 13 pages.
Pufhal et al., "Development of a Fluorescence-based enzyme assay of human 5-lipoxygenase," Anal. Biochem., 2007, 364(2):204-212.
Quinlan et al., "4-Hydroxy-2-Nonenal Levels Increase in the Plasma of Patients with Adult Respiratory Distress Syndrome as Linoleic Acid Appears to Fall," Free Radic Res. 1994, 21(2):95-106.
Radu et al., "Isotretinoin treatment inhibits lipofuscin accumulation in a mouse model of recessive Stargardt's macular degeneration," Novartis Foundation Symposium, 2004, 25:51-63. (Abstract Only).
Radu et al., "Treatment with isoretinin inhibits lipofusion accumulation in a mouse model of recessive Stargardt's macular degeneration," Proc Natl Acad Sci. USA, 2003, 100(8):4742-4747.
Rajewski et al., "Pharmaceutical applications of cyclodextrins. 2. In vivo drug delivery," J Pharm Sci, 1996; 85(11):1142-1169.
Rapp et al., "The effects of local anesthetics on retinal function," Vision Research, 1982, 22(9):1097-1103.
Rauli et al., "Validation ofMalondialdehyde and 4-Hydroxy-2-trans-Nonenal Measurement in Plasma by NICI-GC-MSI," J Biochem, 1998, 123(5):918-923.
Reed, "Lipid preoxidation and neurodegenerative disease", Free Radical Biology and Medicine, 2011, 51(7):1302-1319.
Rees et al., "Cloning and characterisation of the human 5-HT5A serotonin receptor," FEBS Lett., 1994, 355:242-246.
Reproxalap (Medchem Express), 2013, 3 pages.
Reynolds et al., "(-)-[3H] desmethoxyverapamil labels multiple calcium channel modulator receptors in brain and skeletal muscle membranes: differentiation by temperature and dihydropyridines," J. Pharmacol. Exp. Ther., 1986, 237(3):731-738.
Ricca et al., "Amphetamine derivatives and obesity," Appetite, Apr. 2009, 52(2):405-409.
Rinaldi-Carmona et al., "Characterization of two cloned human CB1 cannabinoid receptor isoforms," J. Pharmacol. Exp. Ther., 1996, 278(2):871-878.
Rivkees et al., "Identification of domains of the human A1 adenosine receptor that are important for binding receptor subtype-selective ligands using chimeric A1/A2a adenosine receptors," J. Biol. Chern., 1995, 270(35):20485-20490.
Rizzo et al., "Aldehyde Trapping Agent NS2 Blocks Formation of Fatty Aldehyde Adducts with Phosphatidylethanolamine and Sug-

(56) References Cited

OTHER PUBLICATIONS gests Potential Therapeutic Approach for Sjogren-Larsson Syndrome," Mol Genet and Metab, 114(3):362A (Mar. 2015) [Abstract Only].
Rizzo et al., "Ichthyosis in Sjogren-Larsson syndrome reflects defective barrier function due to abnormal lamellar body structure and secretion," Arch Dermatol Res, 2010, 302(6):443-451.
Rizzo et al., "Endogenous antioxidants and radical scavengers," Advances in Experimental Medicine and Biology, 2010, 698:52-56.
Rizzo et al., "Sjogren-Larsson syndrome: molecular genetics and biochemical pathogenesis of fatty aldehyde dehydrogenase deficiency," Mol Genet Metab., 2007, 90(1):1-9.
Rizzo, "Fatty aldehyde and fatty alcohol metabolism: review and importance for epidermal structure and function", Biochim Biophys Acta, 2014, 1841(3):377-389.
Rizzo, "Genetics and prospective therapeutic targets for Sjogren-Larsson Syndrome," Expert Ooin Orphan Druos. 2016, 4(4):395-406.
Rizzo, "The role of fatty aldehyde dehydrogenase in epidermal structure and function" Dermato-Endocrinol, 2011, 3(2):91-99.
Roat, "Allergic Conjunctivitis," Merck Manual Professional Version, Available at: https://www.merckmanuals.com/professional/eye-disorders/conjunctival-and-scleral-disorders/allergic-conjunctivitis, 2016, 3 pages.
Roat, "Keratoconjunctivitis Sicca," Merck Manual Professional Version, Available at: https://www.merckmanuals.com/professional/eye-disorders/corneal-disorders/keratoconjunctivitis-sicca., 2016, 5 pages.
Roat, "Ocular Mucous Membrane Pemphigoid," Merck Manual Professional Version, Available at: https://www.merckmanuals.com/professional/eye-disorders/conjunctival-and-scleral-disorders/ocular-mucous-membrane-pemphigoid, 2016, 3 pages.
Roat, "Scleritis," Merck Manual Professional Version, Available at: https://www.merckmanuals.com/professional/eye-disorders/conjunctival-and-scleral-disorders/scleritis., 2016, 3 pages.
Roberts et al., "Basic Principles of Organic Chemistry," 2nd edition, copyright 1977 W. A. Benjamin, Inc., pp. 580-582.
Roberts et al., "Experimental Organic Chemistry—A Miniscale Approach," copyright 1994 by Saunders College Publishing, pp. 580-581 and 584-586.
Roche, "Tween 20," Sigma-Aldrich Datasheet. Retrieved Nov. 19, 2020: https://www.sigmaaldrich.com/catalog/product/roche/11332465001?lang=en&region=US#:~:text=Tween%2020%>, Nov. 2020, 3 pages.
Rohrer et al., "Cloning and characterization of a fourth human somatostatin receptor," Proc. Natl. Acad. Sci. U.S.A., 1993, 90:4196-4200.
Rønborg et al., "Exposure chamber for allergen challenge. The development and validation of a new concept," Allergy, 1996, 51(2):82-88.
Roumen et al., "Serum Lipofuscin as a Prognostic Indicator of Adult Respiratory Distress Syndrome and Multiple Organ Failure," British Journal of Surgery, 1994, 81(9):1300-1305.
Saal, et al. "Pharmaceutical salts: A summary on doses of salt formers from the Orange Book", European Journal of Pharmaceutical Sciences, Jul. 16, 2013, 49(4):614-623.
Sahi et al., "Hepatocytes as a tool in drug metabolism, transport and safety evaluations in drug discovery." Current Drug Discov. Technol., 2010, 7(3):188-198.
Salvatore et al., "Molecular cloning and characterization of the human A3 adenosine receptor," Proc. Natl. Acad. Sci. U.S.A., 1993, 90:10365-10369.
Samsonov et al., "Impact of Atherosclerosis- and Diabetes-Related Dicarbonyls on Vascular Endothelial Permeability: A Comparative Assessment," Oxid. Med. Cell Longev, 2017, Article 1625130, 10 pages.
Sanchez et al., "Allergic Conjunctivitis," J Investig Allergol Clin Immunol., 2011, 21(2):1-19.

Sandikci et al., "Lipid Peroxidation and Antioxidant Defence System in Patients with Active or Inactive Behcet's Disease," Acta Derm Venereol, 2003, 83:342-346.
Sarafian et al., "Synergistic cytotoxicity of Delta(9)-tetrahydrocannabinol and butylated hydroxyanisole," Toxicology Letters, 2002, 133(2-3):171-179.
Sarfare et al., "Biocompatibility of a Synthetic Biopolymer for the Treatment of Rhegmatogenous Retinal Detachment," J Clin Exp Ophthalmol. 2015, 6(5):475.
Sarup et al., "Resolution of high and low affinity progesterone receptors from human breast carcinoma T47D cells," J. Biol. Chem., 1988, 263:5624-5633.
Sasaki et al., "Retinal drug delivery using eyedrop preparations of poly-L-lysine-modified liposomes," Eur J Pharm Biopharm, 2013, 83(3):364-369.
Satici et al., "Malondialdehyde and antioxidant enzyme levels in the aqueous humor of rabbits in endotoxin-induced uveitis," Eur J Ophthalmol, 2003, 13(9-10):779-783.
Sayed et al., "Metabolic Activation of R,S-1-(Tetrahydro-2-turanyI)-5-fluorouracil (Ftorafur) to 5-fluorouracil by Soluble Enzymes," Cancer Research, 1983, 43:4039-4044.
Schaumberg et al., "Prevalence of dry eye syndrome among US women," Am J Ophthalmol. 2003, 136(2):318-326.
Schaumberg et al., "Epidemiology of dry eye syndrome," Lacrimal Gland, Tear Film, and Dry Eye Syndromes 3, Kluwer Academic/Plenum Publishers, 2002, pp. 989-998.
Schaumberg et al., "Prevalence of Dry Eye Disease among US Men: Estimates from the Physicians' Health Studies," Arch Ophthalmol, 2009, 127(6):763-768.
Schioth et al., "Characterization of the binding of MSH-B, HB-228, GHRP-6 and 153N-6 to the human melanocortin receptor subtypes," Neuropeptides, 1997, 31:565-571.
Schramm et al., "The Cross-linked Biopolymer Hyaluronic Acid as an Artificial Vitreous Substitute," Invest Ophthalmol Vis Sci, Feb. 2012, 53(2):613-621.
Schwartz and Work, "Measurement and estimation of GFR in children and adolescents," Clin J Am Soc Nephrol. 2009, 4(11):1832-1843.
Schwartz et al., "Tamponade in surgery for retinal detachment associated with proliferative vitreoretinopathy," Cochrane Database Syst Rev. 2020, 5(5):CD006126, 41 pages.
Schwinn et al., "Molecular cloning and expression of the cDNA for a novel alpha 1-adrenergic receptor subtype," J. Biol. Chem., 1990, 265:8183-8189.
Sciuto et al., "Therapeutic Treatments of Phosgene-Induced Lung Injury," Inhal Toxicol, 2004, 16(8):565-580.
Serajuddin, "Salt formation to improve drug solubility," Adv Drug Deliv Rev. 2007, 59(7):603-616.
Serbecic et al., "Anti-oxidative vitamins prevent lipid-peroxidation and apoptosis in corneal endothelial cells," Cell Tissue Res, Jun. 2005, 320(3):465-475.
Shank et al., "Ion and temperature effects on the binding of gamma-aminobutyrate to its receptors and the high-affinity transport system," J. Neurochem., 1990, 54:2007-2015.
Shen et al., "Molecular cloning and expression of a 5-hydroxytryptamine7 serotonin receptor subtype," J. Biol. Chem., 1993, 268:18200-18204.
Sheppard et al., "Targeting Anterior Uveitis: A Focus on Iontophoresis and Other Advanced Technologies", Retrieved from Internet URL: https://www.nyee.edu/files/NYEE/Health%20Professionals/Continuing%20Medical%20Education/Enduring%20CME%20Activities/158_supplement.small_v1_FINAL%20082818.pdf, Sep. 1, 2018, 8 pages.
Sheppard et al., "A Randomized, Comparator-Controlled Phase 2 Clinical Trial of ADX-102 Ophthalmic Solution in Noninfectious Anterior Uveitis," ARVO Annual Meeting Abstract, Invest Ophth Vis Sci. 2017, 58(8):1231.
Sherman et al., "Cellular Defenses Against Unfolded Proteins: A Cell Biologist Thinks about Neurodegenerative Diseases," Neuron, 2001, 29(1):15-32.

(56) References Cited

OTHER PUBLICATIONS

Shipp et al., "Common acute lymphoblastic leukemia antigen (CALLA) is active neutral endopeptidase 24.11 ("enkephalinase"): direct evidence by cDNA transfection analysis," Proc Natl Acad Sci USA. 1989, 86:297-301.
Shoemaker et al., "[3H]diltiazem binding to calcium channel antagonists recognition sites in rat cerebral cortex," Eur. J. Pharmacol., 1985, 111:273-277.
Siegrist et al., "Radioreceptor assay for alpha-MSH using mouse B16 melanoma cells+.," J. Recep. Res., 1988, 8:323-343.
Sieving et al., "Inhibition of the Visual Cycle in vivo by 13-cis Retinoic Acid Protects from Light Damage and Provides a Mechanism for Night Blindness in Isotretinoin Therapy," Proc Natl Acad Sci USA, 2001, 98(4):1835-1840.
Sills et al., "[3H]CGP 39653: a new N-methyl-D-aspartate antagonist radioligand with low nanomolar affinity in rat brain," Eur. J. Pharmacol., 1991, 192:19-24.
Simeone et al., "Modification of the Pyridine Moiety of Nonpeptidyl Indole GnRH Receptor Antagonists," Bioorganic & Medicinal Chemistry Letters, 2002, 12(22):3329-3332.
Simonin et al., "The human delta-opioid receptor: genomic organization, cDNA cloning, functional expression, and distribution in human brain," Mol. Pharmacol., 1994, 46:1015-1021.
Singh et al., "The epidemiology of ocular and nasal allergy in the United States, 1988-1994," J. Allergy Clin. Immunol., 2010, 126(4):778-783.
Smalley, Science of Synthesis, 2002, 11:289.
Smit et al., "Regulation of the human histamine H1 receptor stably expressed in Chinese hamster ovary cells," Brit. J. Pharmacol., 1996, 117:1071-1080.
Smith and Cass, "Oxidative stress and dopamine depletion in an intrastriatal 6-hydroxydopamine model of Parkinson's disease," Neuroscience, 2007, 144(3):1057-1066.
Smith et al., "Basic pathogenic mechanisms operating in experimental models of acute anterior uveitis," Immunol Cell Biol, 1998, 76:497-512.
Snead et al., "Gamma-hydroxybutyric acid," New England Journal of Medicine, 2005, 352(26):2721-2732.
Snell et al., "Novel structure having antagonist actions at both the glycine site of the N-Methyl-D-Aspartate receptor and neuronal voltage-sensitive sodium channels. Biochemical, electrophysiological, and behavioral characterization," J Pharmacol Exp Ther, 2000, 292(1):215-227.
Spadea et al., "Corneal wound healing after laser vision correction," Br J Ophthalmol., 2016, 100(1):28-33.
Spagnol et al., "Efficient synthesis of tricyclic benzobisoxazines by silica gel catalysis," J Org Chem, 2, Mar. 2007, 72(5):1867-1869.
Sparrow et al. "Phospholipid meets all-trans-retinal: the making of RPE bisretmoids," Journal of Lipid Research, 2010, 51:247-261.
Speth et al., "Benzodiazepine receptors: temperature dependence of [3H]flunitrazepam binding," Life Sci., 1979, 24:351-358.
Stefánsson and Loftsson, "Cyclodextrins in Eye Drop Formulations," J Incl Phenom Macrocycl Chem. 2002, 44:23-27(abstract), 2 pages.
Stehle et al., "Molecular cloning and expression of the cDNA for a novel A2-adenosine receptor subtype," Mol. Endocrinol., 1992, 6:384-393.
Stevenson et al., "Dry eye disease: an immune-mediated ocular surface disorder," Arch Ophthalmol. 2012, 130(1): 90-100.
Struys et al., "Determination of the GABA analogue succinic semialdehyde in urine and cerebrospinal fluid by dinitrophenylhydrazine derivatization and liquid chromatography-tandem mass spectrometry: application to SSADH deficiency," J Inherit Metab Dis., 2005, 28(6):913-920.
Struys et al., "Metabolism of gamma-hydroxybutyrate to d-2-hydroxyglutarate in mammals: further evidence for d-2-hydroxyglutarate transhydrogenase," Metabolism, 2006, 55(3):353-358.

Study showing effect of ADX-102 on Fibrotic Changes in Cardiac Fibroblasts Following Cell Stress, American Society for Cell Biology Annual Meeting, Dec. 3-7, 2016, 2 pages.
Sus et al., "Uber die Lichtreaktion der o-Chinondiazide Mitteilungl) Ubergange heterocyclischer 6-Ringe in heterocyclische 5-Ringe," Liebigs Ann. Chem., 1953, 583:150.
Tahara et al., "Pharmacological characterization of the human vasopressin receptor subtypes stably expressed in Chinese hamster ovary cells," Brit. J. Pharmacol., 1998, 125:1463-1470.
Tang-Liu et al., "Effects of four penetration enhancers on corneal permeability of drugs in vitro," Journal of Pharmaceutical Sciences, 1994, 83(1):85-90.
Tanna et al., "Stargardt disease: clinical features, molecular genetics, animal models and therapeutic options," Br J Ophthalmol. 2017; 101 (1):25-30.
Tatsumi et al., "Pharmacological profile of neuroleptics at human monoamine transporters," Eur. J. Pharmacol., 1999, 368:277-283.
Tayeh et al., "Macrophage oxidation of L-arginine to nitric oxide, nitrite, and nitrate. Tetrahydrobiopterin is required as a cofactor," J. Biol. Chem., 1989, 264:19654-19658.
Tempest-Roe et al., "Local therapies for inflammatory eye disease in translation: past, present and future," BMC Ophthalmol., 2013, 13(1):39, 8 pages.
Tewari-Singh et al., "Silibinin attenuates sulfur mustard analog-induced skin injury by targeting multiple pathways connecting oxidative stress and inflammation," PLoS One 2012, 7(9):e46149.
Tian et al., "First total synthesis and determination of the absolute configuration of 1-N-methy 1-3-methylamino-[N-butanoicacid-3-(9-methyl-8-propen-7-one)-amide]-benzo [f][1,7]naphthyridine-2-one, a novel benzonaphthyridine alkaloid," Tetrahedron Letters, 2012, 53:4892-4895.
Tikly et al., "Lipid peroxidation and trace elements in systemic sclerosis," Clinical Rheumatology, 2006, 25(3):320-324.
Torkildsen et al., "Efficacy and safety of olopatadine hydrochloride 0.77% in patients with allergic conjunctivitis using a conjunctival allergen-challenge model," Clinical Ophthalmology, 2015, 9:1703-1713.
Toth et al., "A simple, continuous fluorometric assay for HIV protease," Int. J. Pept. Protein Res., 1990, 36:544-550.
Tripathi et al., "Monoamine oxidase-B inhibitors as potential neurotherapeutic agents: An overview and update", Med Res Rev. Sep. 2019, 39(5):1603-1706.
Tsugeno et al., "Regions of the molecule responsible for substrate specificity of monoamine oxidase A and B: a chimeric enzyme analysis," J. Biochem., 1995, 118(5):974-980.
Tsuzuki et al., "Molecular cloning and expression of the gene encoding human angiotensin II type 2 receptor.," Biochem. Biophys. Res. Commun., 1994, 200:1449-1454.
Tukozkan et al., "Measurement of Total Malondialdehyde in Plasma and tissues by High-Performance Liquid Chromatography and Thiobarbituric Acid Assay," Firat Tip Dergisi, 2006, 11(2):88-92.
Turk et al., "Serum anti-carbonic anhydrase antibodies and oxidant-antioxidant balance in patients with acute anterior uveitis," Ocul Immunol Inflamm, Apr. 2014, 22(2):127-132.
Ueda et al., "Evaluation of a Sulfobutyl Ether 13-Cyclodextrin as a Solubilizing/Stabilizing Agent for Several Drugs," Drug Dev Ind Pharm, 1998, 24(9):863-867.
Upadhyaya et al., "The sphingolipid degradation product trans-2-hexadecenal forms adducts with DNA," Biochem Biophy Res Comm., 2012, 424(1):18-21.
Vanachayangkul et al., "Inhibition of heme peroxidases by melamine," Enzyme Research, 2012, 2012:416062(7 pages).
Vignon et al., "[3H]thienyl-phencyclidine ([3H]TCP) binds to two different sites in rat brain. Localization by autoradiographic and biochemical techniques," Brain Res., 1986, 378:133-141.
Vlaskina et al., "Novel Synthesis of Substituted Benzimidazoles by Reduction of Esters of 4-Alkylamino-3,5-dinitrobenzoic Acids by Tin Chloride," Chemistry of Heterocyclic Compounds, 2004, 40(4):523-524.
Vogel et al., "Thirty years beyond discovery—clinical trials in succinic semialdehyde dehydrogenase deficiency, a disorder of GABA metabolism," J Inherit Metab Dis., 2013, 36(3):401-410.

(56) References Cited

OTHER PUBLICATIONS

Voziyan et al., "A Post-Amadori Inhibitor Pyridoxamine also Inhibits Chemical Modification of Proteins by Scavenging Carbonyl Intermediates for Carbohydrate and Lipid Degradation," J Biol Chem, 2002, 277(5):3397-3403.
Wagner et al., "Omega-conotoxin GVIA binding to a high-affinity receptor in brain: characterization, calcium sensitivity, and solubilization," J. Neurosci., 1988, 8:3354-3359.
Wakamatsu et al., "Evaluation of lipid oxidative stress status and inflammation in atopic ocular surface disease," Mol Vis, Nov. 2010, 16:2465-2475.
Wall et al., "Plant Antitumor Agents. 30. Synthesis and Structure Activity of Novel Camptothecin Analogs," J. Med. Chem., 1993, 36(18):2689-2700.
Walter et al., "Novel Complex N-Heterocycles via Intramolecular 1,5-Electrocyclizations: 1,2,3,4,4a,5,5a,10-Octahydropyrido-[4",3":2',3']cyclobuta[1',2':4,5]pyrrolo[2,3-b]pyridines," Heterocycles, 1998, 48(8):1581-1591.
Wang et al., "A facile one-pot synthesis of 2-substituted-3-aminoquinolines: Preparation of benzo[b]naphthyridine-3-carbonitriles," Tetrahedron, 2004, 60(13):2937-2942.
Wang et al., "Human mu opiate receptor. cDNA and genomic clones, pharmacologic characterization and chromosomal assignment," FEBS Lett., 1994, 338:217-222.
Wang et al., "Markers of oxidative and nitrosative stress in systemic lupus erythematosus: correlation with disease activity," Arthritis and Rheumatism, 2010, 62(7):2064-2072.
Wang, X.K., "Pharmacological study on recombinant human GABA-A receptor complex containing alphas (leucine 155 to valine) combined with beta3gamma2s subunits," Acta. Pharmacol. Sin., 2001, 22:521-523.
Waslidge et al., "A colorimetric method for the determination of lipoxygenase activity suitable for use in a high throughput assay format," Anal. Biochem., 1995, 231:354-358.
Weaver et al., "The Th17 pathway and inflammatory diseases of the intestines, lungs, and skin," Annu. Rev. Pathol., 2013, 8:477-512.
Webb et al., "Intralesional cytokines in chronic oxazolone-induced contact sensitivity suggest roles for tumor necrosis factor alpha and interleukin-4," J Invest Dermatol, Jul. 1998, 111(1):86-92.
Weishaar et al., "Multiple molecular forms of cyclic nucleotide phosphodiesterase in cardiac and smooth muscle and in platelets. Isolation, characterization, and effects of various reference phosphodiesterase inhibitors and cardiotonic agents," Biochem. Pharmacol., 1986, 35:787-800.
Weng et al., "Insights into the Function of Rim Protein in Photoreceptors and Etiology of Stargardt's Disease from the Phenotype in abcr Knockout Mice," Cell, 1999, 98(1):13-23.
Wermuth, "The Practice of Medicinal Chemistry," Elsevier, Second vol. 1999, pp. 347-365.
Westphal et al., "Reactions with Pryridinium Pyruvic Acid Esters," Pharmazie, 1976, 31(11):770-773.[English Translation].
Wieland et al., "Subtype selectivity and antagonistic profile of the nonpeptide Y1 receptor antagonist BIBP 3226," J. Pharmacol. Exp. Ther., 1995, 275:143-149.
Winfield and Richards, "Ophthalmic products," Pharmaceutical Practice, Churchill Livingstone, 2004, pp. 265-268.
Witt-Enderby et al., "Characterization and regulation of the human ML1A melatonin receptor stably expressed in Chinese hamster ovary cells," Mol. Pharmacol., 1996, 50:166-174.
Wolkenberg et al., "Design, synthesis, and evaluation of novel 3,6-diary 1-4-aminoalkoxyquinolines as selective agonists of somatostatin receptor subtype 2," J Med Chem, 2011, 54(7):2351-2358.
Wood et al., "Aldehyde Load in Ischemia-Reperfusion Brain Injury: Neuroprotection by Neutralization of reactive Aldehydes with Phenelzine," Brain Res, 2006, 1122(1):184-190.
Wood et al., "The concept of "aldehyde load" in neurodegenerative mechanisms: cytotoxicity of the polyamine degradation products hydrogen peroxide, acrolein, 3-aminopropanal, 3-acetamidiorioanal and 4-aminobutanal in a retinal ganglion cell line," Brain Research, 2007, 1145:150-156.
Wurch et al., "Sequence and functional analysis of cloned guinea pig and rat serotonin 5-HT1D receptors: common pharmacological features within the 5-HT1D receptor subfamily," J. Neurochem., 1997, 68:410-418.
Wynn, "Cellular and molecular mechanisms of fibrosis," J Pathol. 2008, 214(2):199-210.
Yadav et al., "Regulation of NF-kB-Induced Inflammatory Signaling by Lipid Peroxidation-Derived Aldehydes," Oxidative Med & Cell Longev, 2013, Art ID 690545, 2013, 11 pages.
Yamano, "Approach to Crystal Polymorph in Process Research of New Drug," Journal of Synthetic Organic Chemistry, 2007, 65:907-913.
Yarnell, "Light Flips the Lipid Switch: Palmitoylation—the reversible attachment of palmitate to proteins—gets a new role in vision," C&EN, 2004, 82(29):22-23.
Yoko et al., "Drug and Crystal Polymorphism", Journal of Human Environmental Engineering, 2002, 4(2):310-317.
Yokomizo et al., "Hydroxyeicosanoids bind to and activate the low affinity leukotriene B4 receptor, BLT2," J. Biol. Chem., 2001, 276:12454-12459.
Young et al., "NS2, a novel aldehyde trap, decreases aldehyde levels in dry skin and eye models," Aldeyra therapeutics, 2014, 1 page.
Yu et al., "Injectable Chemically Crosslinked Hydrogel for the Controlled Release of Bevacizumab in Vitreous: A 6-Month In Vivo Study," Transl Vis Sci Technol, 2015, 4(2,5):1-11.
Zagol-Ikapitte et al., "Characterization of scavengers of y-ketoaldehydes that do not inhibit prostaglandin biosynthesis," Chem Res Toxicol, 2010, 23(1):240-250.
Zarkovic "4-hydroxynonenal and neurodegenerative diseases," Molecular Aspects of Medicine, 2003, 24(4-5):293-303.
Zava et al., "Androgen receptor assay with [3H]methyltrienolone (R1881) in the presence of progesterone receptors," Endocrinology, 1979, 104:1007-1012.
Zhang et al., "Potent nonsteroidal progesterone receptor agonists: synthesis and SAR study of 6-aryl benzoxazines," Bioorg Med Chem Lett, Mar. 2002, 12(5):787-790.
Zhang et al., "Practical ophthalmic pharmacology," People's Military Medical Press, 2015, p. 590.
Zhou et al., "Chemical and biological evidence for base propenals as the major source of the endogenous MldG adduct in cellular DNA," J Biol Chem., 2005, 280(27):25377-25382.
Zhou et al., "Cloning and expression of human and rat D1 dopamine receptors," Nature, 1990, 347:76-80.
Zhou et al., "Mechanisms for the induction of HNE-MDA- and AGE-adducts, RAGE and VEGF in retinal pigment epithelial cells," Exp Eye Res., Apr. 2005, 80(4):567-580.
PCT International Preliminary Report on Patentability received for PCT/US2006/020320, dated Nov. 30, 2007, 8 pages.
PCT International Preliminary Report on Patentability received for PCT/US2010/059719, dated Jun. 21, 2012, 7 pages.
PCT International Preliminary Report on Patentability received for PCT/US2013/076592, dated Jul. 2, 2015, 7 pages.
PCT International Preliminary Report on Patentability received for PCT/US2014/012356, dated Jul. 28, 2015, 7 pages.
PCT International Preliminary Report on Patentability received for PCT/US2014/012762, dated Aug. 6, 2015, 9 pages.
PCT International Preliminary Report on Patentability received for PCT/US2016/048054, dated Feb. 27, 2018, 5 pages.
PCT International Preliminary Report on Patentability received for PCT/US2016/048064, dated Feb. 27, 2018, 6 pages.
PCT International Preliminary Report on Patentability received for PCT/US2017/020020, dated Sep. 7, 2018, 10 pages.
PCT International Preliminary Report on Patentability received for PCT/US2017/047945, dated Mar. 7, 2019, 7 pages.
PCT International Preliminary Report on Patentability received for PCT/US2017/047958, dated Mar. 7, 2019, 08 pages.
PCT International Preliminary Report on Patentability received for PCT/US2018/023000, dated Sep. 26, 2019, 7 pages.
PCT International Preliminary Report on Patentability received for PCT/US2018/055310, dated Apr. 23, 2020, 6 pages.
PCT International Preliminary Report on Patentability received for PCT/US2019/064669, dated Jun. 17, 2021, 10 pages.

(56) References Cited

OTHER PUBLICATIONS

PCT International Preliminary Report on Patentability received for PCT/US2020/024022, dated Oct. 7, 2021, 9 pages.
PCT International Preliminary Report on Patentability received for PCT/US2020/031138, dated Nov. 11, 2021, 6 pages.
PCT International Preliminary Report on Patentability received for PCT/US2020/031219, dated Nov. 11, 2021, 11 pages.
PCT International Preliminary Report on Patentability received for PCT/US2021/023884, dated Oct. 6, 2022, 8 pages.
PCT International Preliminary Report on Patentability received for PCT/US2021/027148, dated Oct. 27, 2022, 7 pages.
PCT International Preliminary Report on Patentability received for PCT/US2021/032335, dated Nov. 24, 2022, 9 pages.
PCT International Preliminary Report on Patentability received for PCT/US2021/035948, dated Dec. 15, 2022, 8 pages.
PCT International Search Report and Written Opinion received for PCT/CN2022/113284, dated Nov. 2, 2022, 6 pages.
PCT International Search Report and Written Opinion received for PCT/US2006/020320, dated Sep. 26, 2006, 10 pages.
PCT International Search Report and Written Opinion received for PCT/US2010/059719, dated Feb. 8, 2011, 8 pages.
PCT International Search Report and Written Opinion received for PCT/US2013/076592, dated Apr. 30, 2014, 10 pages.
PCT International Search Report and Written Opinion received for PCT/US2014/012356, dated May 30, 2014, 11 pages.
PCT International Search Report and Written Opinion received for PCT/US2014/012762, dated Jul. 18, 2014, 12 pages.
PCT International Search Report and Written Opinion received for PCT/US2016/040064, dated Sep. 2, 2016.
PCT International Search Report and Written Opinion received for PCT/US2016/048054, dated Nov. 4, 2016, 8 pages.
PCT International Search Report and Written Opinion received for PCT/US2016/048064, dated Nov. 15, 2016, 8 pages.
PCT International Search Report and Written Opinion received for PCT/US2017/020020, dated May 24, 2017, 12 pages.
PCT International Search Report and Written Opinion received for PCT/US2017/031808, dated Aug. 11, 2017, 10 pages.
PCT International Search Report and Written Opinion received for PCT/US2017/047945, dated Oct. 20, 2017, 9 pages.
PCT International Search Report and Written Opinion received for PCT/US2017/047958, mailed on Oct. 31, 2017, 10 pages.
PCT International Search Report and Written Opinion received for PCT/US2018/023000, dated Jun. 1, 2018, 8 pages.
PCT International Search Report and Written Opinion received for PCT/US2018/055310, dated Jan. 29, 2019, 9 pages.
PCT International Search Report and Written Opinion received for PCT/US2019/041942, dated Sep. 30, 2019, 18 pages.
PCT International Search Report and Written Opinion received for PCT/US2019/044929, dated Nov. 20, 2019, 15 pages.
PCT International Search Report and Written Opinion received for PCT/US2019/045206, dated Oct. 17, 2019, 13 pages.
PCT International Search Report and Written Opinion received for PCT/US2019/052961, dated Dec. 10, 2019, 11 pages.
PCT International Search Report and Written Opinion received for PCT/US2019/054263, dated Jan. 6, 2020, 13 pages.
PCT International Search Report and Written Opinion received for PCT/US2019/064669, dated Feb. 27, 2020, 12 pages.
PCT International Search Report and Written Opinion received for PCT/US2019/069097 dated Apr. 30, 2020, 9 pages.
PCT International Search Report and Written Opinion received for PCT/US2020/024022, dated Jun. 17, 2020, 11 pages.
PCT International Search Report and Written Opinion received for PCT/US2020/031138, dated Jul. 13, 2020, 7 pages.
PCT International Search Report and Written Opinion received for PCT/US2020/031219, dated Aug. 31, 2020, 14 pages.
PCT International Search Report and Written Opinion received for PCT/US2020/050565, dated Dec. 22, 2020, 9 pages.
PCT International Search Report and Written Opinion received for PCT/US2021/023884, dated Jul. 28, 2021, 11 pages.
PCT International Search Report and Written Opinion received for PCT/US2021/027148, dated Jun. 28, 2021, 9 pages.
PCT International Search Report and Written Opinion received for PCT/US2021/032335, dated Jul. 27, 2021, 11 pages.
PCT International Search Report and Written Opinion received for PCT/US2021/035948, dated Oct. 26, 2021, 12 pages.
PCT International Search Report and Written Opinion received for PCT/US2022/011604, dated Mar. 25, 2022, 12 pages.
PCT International Search Report and Written Opinion received for PCT/US2022/035898, dated Nov. 16, 2022, 13 pages.
Extended European Search Report received for European Patent Application No. 13865015.5 dated Mar. 31, 2016, 9 pages.
Extended European Search Report received for European Patent Application No. 19891719.7 dated Jul. 27, 2022, 9 pages.
Partial Supplementary European Search Report received for European Patent Application No. 14743711.5 dated Jul. 20, 2016, 14 pages.
Search Report and Written Opinion received for Singapore Patent Application No. 11201504859Y, dated Aug. 1, 2016, 12 pages.
Search Report and Written Opinion received for Singapore Patent Application No. 11201505587Y, dated Jul. 12, 2016, 12 pages.
Search Report and Written Opinion received for Singapore Patent Application No. 11201505599Y, dated 11201505599Y dated Sep. 14, 2016, 5 pages.
U.S. Appl. No. 15/437,699 of Jordan et al., filed Feb. 21, 2017.
U.S. Appl. No. 16/547,930 of Buist et al., filed Aug. 22, 2019.
U.S. Appl. No. 17/305,915 of Machatha et al., filed Jul. 16, 2021.
Ebenezer et al., "S1P and Plasmalogen Derived Fatty Aldehydes in Cellular Signaling and Functions", Biochim Biophys Acta Mol Cell Biol Lipids., Jul. 2020, 1865(7):158681, pp. 1-35.
PCT International Search Report and Written Opinion received for PCT/US2023/016713, dated Jun. 26, 2023, 9 pages.
U.S. Appl. No. 18/904,373 of Brady et al., filed Oct. 2, 2024.
U.S. Appl. No. 18/786,975 of Jordan, filed Jul. 29, 2024.
U.S. Appl. No. 18/850,826 of Brady et al., filed Sep. 25, 2024.

\* Significantly different from HP treatment alone

Logistic Curve Fitting and EC50

Logistic Curve Fitting and EC50

Logistic Curve Fitting and EC50

Logistic Curve Fitting and EC50

Effect of ALD-6 on Neuronal Viability in Hippocampal Cultures Treated with 10 μM Hydrogen Peroxide Effect of ALD-5 on Neuronal Viability in Hippocampal Cultures Treated with 10 μM Hydrogen Peroxide Effect of ALD-5 on Cell Death in Hippocampal Cultures Treated with 10 μM Hydrogen Peroxide Effect of ALD-2 on Neuronal Viability in Hippocampal Cultures Treated with 10 μM Hydrogen Peroxide

DEUTERATED COMPOUNDS AND USES THEREOF

CROSS-REFERENCE TO RELATED APPLICATIONS

This application is a continuation of U.S. patent application Ser. No. 17/929,505, filed Sep. 2, 2022; which is a continuation of U.S. patent application Ser. No. 17/324,318, filed May 19, 2021, now U.S. Pat. No. 11,459,300; which is a continuation of U.S. patent application Ser. No. 16/720,645, filed Dec. 19, 2019, now U.S. Pat. No. 11,046,650; which is a continuation of U.S. patent application Ser. No. 15/754,065, filed Feb. 21, 2018, now U.S. Pat. No. 10,550,085; which is a § 371 National Stage of PCT International Application No. PCT/US2016/048054, filed Aug. 22, 2016; which claims the benefit of U.S. Provisional Patent Application No. 62/208,223, filed Aug. 21, 2015. The entirety of each application is incorporated herein by reference thereto.

BACKGROUND OF THE INVENTION

Metabolic and inflammatory processes in cells generate toxic aldehydes, such as malondialdehyde (MDA) and 4-hydroxyl-2-nonenal (HNE or 4HNE). These aldehydes are highly reactive to proteins, carbohydrates, lipids and DNA, leading to chemically modified biological molecules, activation of inflammatory mediators such as NF-kappaB, and damage in diverse organs. For example, retinaldehyde can react with phosphatidylethanolamine (PE) to form a highly toxic compound called A2E, which is a component of lipofuscin believed to be involved in the development and progression of Age Related Macular Degeneration (AMD). Many bodily defense mechanisms function to remove or lower the levels of toxic aldehydes. Novel small molecule therapeutics can be used to scavenge "escaped" retinaldehyde in the retina, thus reducing A2E formation and lessening the risk of AMD (Jordan et al. (2006)).

Aldehydes are implicated in diverse pathological conditions such as dry eye, cataracts, keratoconus, Fuch's endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjogren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., lupus), cardiovascular disorders (e.g., atherosclerosis), and conditions associated with the injurious effects of blister agents (Negre-Salvagre et al. (2008), Nakamura et al. (2007), Batista et al. (2012), Kenney et al. (2003), Int J Dermatol 43: 494 (2004), Invest Ophthalmol Vis Sci 48: 1552 (2007), Graefe's Clin Exp Ophthalmol 233: 694 (1994), Molecular Vision 18: 194 (2012)). Reducing or eliminating aldehydes should thus ameliorate the symptoms and slow the progression of these pathological conditions.

MDA, HNE and other toxic aldehydes are generated by a myriad of metabolic mechanisms involving: fatty alcohols, sphingolipids, glycolipids, phytol, fatty acids, arachadonic acid metabolism (Rizzo (2007)), polyamine metabolism (Wood et al. (2006)), lipid peroxidation, oxidative metabolism (Buddi et al. (2002), Zhou et al. (2005)), and glucose metabolism (Pozzi et al. (2009)). Aldehydes can cross link with primary amino groups and other chemical moieties on proteins, phospholipids, carbohydrates, and DNA, leading in many cases to toxic consequences, such as mutagenesis and carcinogenesis (Marnett (2002)). MDA is associated with diseased corneas, keratoconus, bullous and other keratopathy, and Fuch's endothelial dystrophy corneas (Buddi et al. (2002)). Also, skin disorders, e.g., Sjogren-Larsson Syndrome, are likely connected with the accumulation of fatty aldehydes such as octadecanal and hexadecanal (Rizzo et al. (2010)). Further, increased lipid peroxidation and resultant aldehyde generation are associated with the toxic effects of blister agents (Sciuto et al. (2004) and Pal et al. (2009)).

There has been no suggestion in the art for treating the various conditions associated with toxic aldehydes by the administration of small molecule therapeutics acting as a scavenger for aldehydes, such as MDA and/or HNE. Thus, there is a need for treating, preventing, and/or reducing a risk of a disease or disorder in which aldehyde toxicity is implicated in the pathogenesis. The present invention addresses such a need.

Accordingly, there remains a need for treating, preventing, and/or reducing a risk of a disease, disorder, or condition in which aldehyde toxicity is implicated in the pathogenesis.

SUMMARY OF THE INVENTION

It has now been found that compounds of the present invention, and compositions thereof, are useful for treating, preventing, and/or reducing a risk of a disease, disorder, or condition in which aldehyde toxicity is implicated in the pathogenesis. Such compounds have general formula I:

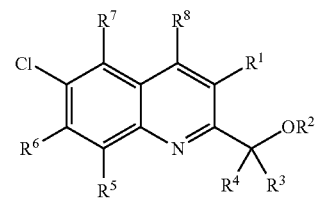

or a pharmaceutically acceptable salt thereof, wherein each of $R^1$, $R^2$, $R^3$, $R^4$, $R^5$, $R^6$, $R^7$, and $R^8$ is as defined herein.

Compounds of the present invention, and pharmaceutically acceptable compositions thereof, are useful for treating a variety of diseases, disorders or conditions, associated with toxic aldehydes. Such diseases, disorders, or conditions include those described herein.

Compounds provided by this invention are also useful for the study of certain aldehydes in biology and pathological phenomena.

DETAILED DESCRIPTION OF THE INVENTION

Figure 1:
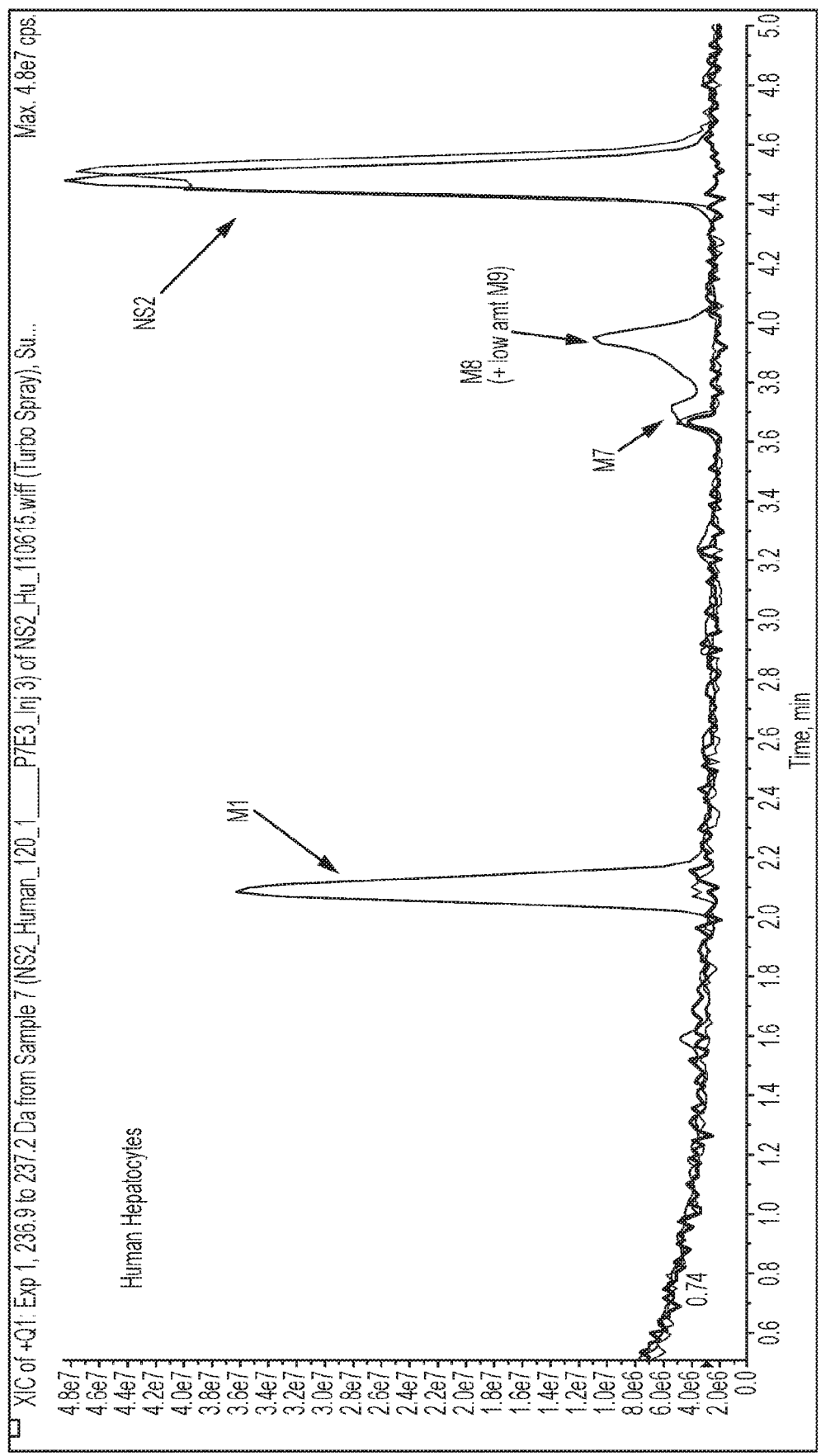
FIG. 1 shows overlays of EICs (extracted ion chromatograms) of the metabolite profiles of NS2 at 0 min and 120 min in human hepatocytes compared with a reference (blank hepatocytes). As the overlays show, after 120 min NS2 is metabolized to M1, M7, M8, and a low amount of M9, with some unchanged NS2 remaining.

1. General Description of Certain Aspects of the Invention

In certain embodiments, the present invention provides compounds, compositions, and methods for treatment, prevention, and/or reduction of a risk of diseases, disorders, or conditions in which aldehyde toxicity is implicated in the pathogenesis. In some embodiments, such compounds include those of the formulae described herein, or a pharmaceutically acceptable salt thereof, wherein each variable is as defined herein and described in embodiments. In one aspect, the present invention provides a compound of formula I:

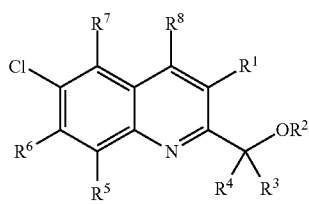

I or a pharmaceutically acceptable salt thereof, wherein:
$R^1$ is selected from —$NH_2$, —NHD, or —$ND_2$;
$R^2$ is selected from hydrogen or deuterium;
$R^3$ and $R^4$ are independently selected from —$CH_3$, —$CH_2D$, —$CHD_2$, or —$CD_3$; and
$R^5$, $R^6$, $R^7$, and $R^8$ are each independently selected from hydrogen or deuterium;
provided that at least one of $R^1$, $R^2$, $R^3$, $R^4$, $R^5$, $R^6$, $R^7$, or $R^8$ is or contains deuterium.

2. Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

The "retina" is a region of the central nervous system with approximately 150 million neurons. It is located at the back of the eye where it rests upon a specialized epithelial tissue called retinal pigment epithelium (RPE). The retina initiates the first stage of visual processing by transducing visual stimuli in specialized neurons called "photoreceptors". Their synaptic outputs are processed by elaborate neural networks in the retina and are then transmitted to the brain. The retina has evolved two specialized classes of photoreceptors to operate under a wide range of light conditions. "Rod" photoreceptors transduce visual images under low light conditions and mediate achromatic vision. "Cone" photoreceptors transduce visual images in dim to bright light conditions and mediate both color vision and high acuity vision.

Every photoreceptor is compartmentalized into two regions called the "outer" and "inner" segment. The inner segment is the neuronal cell body containing the cell nucleus. The inner segment survives for a lifetime in the absence of retinal disease. The outer segment is the region where the light sensitive visual pigment molecules are concentrated in a dense array of stacked membrane structures. Part of the outer segment is routinely shed and regrown in a diurnal process called outer segment renewal. Shed outer segments are ingested and metabolized by RPE cells.

The "macula" is the central region of the retina which contains the fovea where visual images are processed by long slender cones in high spatial detail ("visual acuity"). "Macular degeneration" is a form of retinal neurodegeneration which attacks the macula and destroys high acuity vision in the center of the visual field. Age-Related Macular Degeneration (AMD) begins in a "dry form" characterized by residual lysosomal granules called lipofuscin in RPE cells, and by extracellular deposits called "drusen". Drusen contain cellular waste products excreted by RPE cells. "Lipofuscin" and drusen can be detected clinically by ophthalmologists and quantified using fluorescence techniques. They can be the first clinical signs of macular degeneration.

Lipfuscin contains aggregations of A2E. Lipofuscin accumulates in RPE cells and poisons them by multiple known mechanisms. As RPE cells become poisoned, their biochemical activities decline and photoreceptors begin to degenerate. Extracellular drusen may further compromise RPE cells by interfering with their supply of vascular nutrients. Drusen also trigger inflammatory processes, which lead to choroidal neovascular invasions of the macula in one patient in ten who progresses to wet form AMD. Both the dry form and wet form progress to blindness.

"ERG" is an acronym for electroretinogram, which is the measurement of the electric field potential emitted by retinal neurons during their response to an experimentally defined light stimulus. ERG is a non-invasive measurement which can be performed on either living subjects (human or animal) or a hemisected eye in solution that has been removed surgically from a living animal.

As used herein, the term "RAL" means retinaldehyde. The term "RAL-trap" means a therapeutic compound that binds free RAL and thereby prevents the RAL from Schiff base condensation with membrane phosphatidylethanolamine (PE). "Free RAL" is defined as RAL that is not bound to a visual cycle protein. The terms "trans-RAL" and "all-trans-RAL" are used interchangeably and mean all trans-retinaldehyde.

A2E is a reaction by-product of a complex biochemical pathway called the "visual cycle" which operates collaboratively in both RPE cells and photoreceptor outer segments. The visual cycle recycles a photoreactive aldehyde chromophore called "retinaldehyde" which is derived from vitamin A and is essential for vision. In simplified terms, the visual cycle has four principal steps: 1) it converts vitamin A in the RPE into an aldehyde chromophore with one photoreactive strained double bond (11-cis-RAL); 2) it transports 11-cis-RAL to the retina where it binds to a specialized photoreceptor protein called opsin; 3) light photoisomerizes bound 11-cis-RAL to trans-RAL, which initiates the release of bound RAL from the opsin binding site; and 4) it converts trans-RAL (an aldehyde) to vitamin A (an alcohol) and transports vitamin A back to the RPE where the cycle begins again.

The aldehyde group of RAL helps bind the molecule to opsin by forming a reversible chemical bond to an amino acid sidechain in the opsin binding site. While the aldehyde group on RAL is essential for anchoring the molecule to the opsin binding site, it is otherwise hazardous because of its propensity to form Schiff bases with other biological amines. The first three reactions take place in photoreceptor outer segments and produce an intermediary product called A2PE. Once formed, A2PE partitions into the lipid phase and accumulates in photoreceptor outer segment membranes. When RPE cells ingest discarded outer segments, their accumulated A2PE is routed to their lysosomes.

As described above, macular degeneration and other forms of retinal disease whose etiology involves the accumulation of A2E and/or lipofuscin may be treated or prevented by lowering the amount of A2E formed. Compounds useful for doing so include RAL-traps. RAL-traps lower the amount of A2E formed, for example by forming a covalent bond with RAL that has escaped sequestering. RAL that has reacted with a RAL-trap compound is thereby unavailable to react with phosphatidyl ethanolamine.

The present invention is also directed to the use of a compound described herein in the manufacture of a medicament for the treatment, prevention, and/or reduction of a risk of a disease, disorder, or condition in which aldehyde toxicity is implicated in the pathogenesis. More specifically this aspect of the invention is directed to the use of a compound described herein in the manufacture of a medicament for the treatment, prevention, and/or reduction of a risk of (1) an ocular disease, disorder, or condition, including, but not limited to, a corneal disease (e.g., dry eye syndrome, cataracts, keratoconus, bullous and other keratopathy, and Fuch's endothelial dystrophy), other ocular disorders or conditions (e.g., allergic conjunctivitis, ocular cicatricial pemphigoid, conditions associated with PRK healing and other corneal healing, and conditions associated with tear lipid degradation or lacrimal gland dysfunction), and other ocular conditions associated with high aldehyde levels as a result of inflammation (e.g., uveitis, scleritis, ocular Stevens Johnson Syndrome, and ocular rosacea (with or without meibomian gland dysfunction)), (2) a skin disorder or condition or a cosmetic indication. For example, the disease, disorder, or condition includes, but is not limited to, psoriasis, topical (discoid) lupus, contact dermatitis, atopic dermatitis, allergic dermatitis, radiation dermatitis, acne vulgaris, Sjogren-Larsson Syndrome and other ichthyosis, solar elastosis/wrinkles, skin tone firmness, puffiness, eczema, smoke or irritant induced skin changes, dermal incision, and a skin condition associated burn and wound, (3) a condition associated with the toxic effects of blister agents or burns from alkali agents, or (4) an autoimmune, immune-mediated, inflammatory, cardiovascular, or neurological disease (e.g., lupus, scleroderma, asthma, chronic obstructive pulmonary disease (COPD), rheumatoid arthritis, inflammatory bowel disease, sepsis, atherosclerosis, ischemic-reperfusion injury, Parkinson's disease, Alzheimer's disease, multiple sclerosis, amyotrophic lateral sclerosis, diabetes, metabolic syndrome, and fibrotic diseases).

The present invention is also directed to the use of a compound described herein in treating, preventing, and/or reducing a risk of a disease, disorder, or condition in which aldehyde toxicity is implicated in the pathogenesis. More specifically this aspect of the invention is directed to the use of a compound described herein in treating, preventing, and/or reducing a risk of (1) an ocular disease, disorder, or condition, including, but not limited to, a corneal disease (e.g., dry eye syndrome, cataracts, keratoconus, bullous and other keratopathy, and Fuch's endothelial dystrophy), other ocular disorders or conditions (e.g., allergic conjunctivitis, ocular cicatricial pemphigoid, conditions associated with PRK healing and other corneal healing, and conditions associated with tear lipid degradation or lacrimal gland dysfunction), and other ocular conditions associated with high aldehyde levels as a result of inflammation (e.g., uveitis, scleritis, ocular Stevens Johnson Syndrome, and ocular rosacea (with or without meibomian gland dysfunction)), (2) a skin disorder or condition or a cosmetic indication. For example, the disease, disorder, or condition includes, but is not limited to, psoriasis, topical (discoid) lupus, contact dermatitis, atopic dermatitis, allergic dermatitis, radiation dermatitis, acne vulgaris, Sjogren-Larsson Syndrome and other ichthyosis, solar elastosis/wrinkles, skin tone firmness, puffiness, eczema, smoke or irritant induced skin changes, dermal incision, and a skin condition associated burn and wound, (3) a condition associated with the toxic effects of blister agents or burns from alkali agents, or (4) an autoimmune, immune-mediated, inflammatory, cardiovascular, or neurological disease (e.g., lupus, scleroderma, asthma, chronic obstructive pulmonary disease (COPD), rheumatoid arthritis, inflammatory bowel disease, sepsis, atherosclerosis, ischemic-reperfusion injury, Parkinson's disease, Alzheimer's disease, multiple sclerosis, amyotrophic lateral sclerosis, diabetes, metabolic syndrome, and fibrotic diseases).

The compounds described herein can also be administered topically, such as directly to the eye, e.g., as an eye-drop or ophthalmic ointment. Eye drops typically comprise an effective amount of at least one compound described herein and a carrier capable of being safely applied to an eye. For example, the eye drops are in the form of an isotonic solution, and the pH of the solution is adjusted so that there is no irritation of the eye. In many instances, the epithelial barrier interferes with penetration of molecules into the eye. Thus, most currently used ophthalmic drugs are supplemented with some form of penetration enhancer. These penetration enhancers work by loosening the tight junctions of the most superior epithelial cells (Burstein, Trans Ophthalmol Soc UK 104: 402 (1985); Ashton et al., J Pharmacol Exp Ther 259: 719 (1991); Green et al., Am J Ophthalmol 72: 897 (1971)). The most commonly used penetration enhancer is benzalkonium chloride (Tang et al., J Pharm Sci 83: 85 (1994); Burstein et al, Invest Ophthalmol Vis Sci 19: 308 (1980)), which also works as preservative against microbial contamination.

Topical administration may be in the form of a cream, suspension, emulsion, ointment, drops, oil, lotion, patch, tape, inhalant, spray, or controlled release topical formulations including gels, films, patches, and adhesives. Intraocular administration may take the form of subconjunctival, subtenon's capsule, retrobulbar or intravitreal injections, depots or implants. Compounds administered by these routes may be in solution or suspension form. Administration of compounds by depot injection may contain pharmaceutically acceptable carriers or excipients; these may be natural or synthetic and may be biodegradable or non-biodegradable and facilitate drug release in a controlled manner. Implants used for controlled release of compound may be composed of natural or synthetic, biodegradable or non-biodegradable materials. The carrier is acceptable in that it is compatible with the other components of the composition and is not injurious to the patient. Some examples of carriers include (1) sugars such as lactose glucose and sucrose, (2) starches such as corn starch and potato starch, (3) cellulose and (4) cyclodextrins. A useful topical formulation is described in PCT publication WO 2011/072141, the contents of which are herein incorporated by reference.

Formulations for topical administration to the skin can include, for example, ointments, creams, gels and pastes comprising the primary amine compound in a pharmaceutical acceptable carrier. The formulation of the primary amine compound for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

The formulations for topical administration may contain the compound used in the present application at a concentration in the range of 0.001-10%, 0.05-10%, 0.1-10%, 0.2-10%, 0.5-10%, 1-10%, 2-10%, 3-10%, 4-10%, 5-10%, or 7-10% (weight/volume), or in the range of 0.001-2.0%, 0.001-1.5%, or 0.001-1.0%, (weight/volume), or in the range of 0.05-2.0%, 0.05-1.5%, or 0.05-1.0%, (weight/volume), or in the range of 0.1-5.0%, 0.1-2.0%, 0.1-1.5%, or 0.1-1.0% (weight/volume), or in the range of 0.5-5.0%, 0.5-2.0%, 0.5-1.5%, or 0.5-1.0% (weight/volume), or in the range of 1-5.0%, 1-2.0%, or 1-1.5% (weight/volume). The formulations for topical administration may also contain the compound used in the present application at a concentration in the range of 0.001-2.5%, 0.01-2.5%, 0.05-2.0%, 0.1-2.0%, 0.2-2.0%, 0.5-2.0%, or 1-2.0% (weight/weight), or in the range of 0.001-2.0%, 0.001-1.5%, 0.001-1.0%, or 0.001-5% (weight/weight).

In an eye drop formulation the composition may contain the active compound at a concentration of 0.01-20%, 0.02-15%, 0.04-10%, 0.06-5%, 0.08-1%, or 0.09-0.5% (weight/volume) with or without pH and/or osmotic adjustment to the solution. More particularly, the eye drop formulation may contain a compound described herein at a concentration of 0.09-0.5% (weight/volume), such as 0.1%.

In one exemplification, the pharmaceutical compositions encompass a composition made by admixing a therapeutically effective amount of a compound described herein with an oligomeric or a polymeric carrier such as a cyclodextrin, or chemically modified cyclodextrin, including trimethyl-β-cyclodextrin, 2-hydroxyethyl-β-cyclodextrin, 2-hydroxypropyl-β-cyclodextrin, 3-hydroxypropyl-β-cyclodextrin, and β-cyclodextrin sulfobutylether sodium salt (or potassium salt). Exemplifying an oligomeric or a polymeric carrier is β-cyclodextrin sulfobutylether sodium salt. The amount of β-cyclodextrin sulfobutylether sodium salt in the composition may range from about 0.01% to 30% weight/volume. In one illustration, the concentration of β-cyclodextrin sulfobutylether sodium salt is 5-25% weight/volume. Further illustrating the concentration of β-cyclodextrin sulfobutylether sodium salt is 6-20% weight/volume. In one exemplification the concentration of β-cyclodextrin sulfobutylether is 6-12% weight/volume. Further exemplifying the concentration of β-cyclodextrin sulfobutylether is 9-10% weight/volume, including 9.5% weight/volume. The amount of the compound described herein in the composition may range 0.01-20%, 0.02-15%, 0.04-10%, 0.06-5%, 0.08-1%, or 0.09-0.5% (weight/volume). More particularly, the composition may contain a compound described herein at a concentration of 0.09-0.5% (weight/volume), such as 0.1%.

The compounds described herein may be administered orally and as such the pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

For oral administration in the form of a tablet or capsule (e.g., a gelatin capsule), the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrators include, without limitation, starch, methyl cellulose, agar, bentonite, xanthan gum starches, agar, alginic acid or its sodium salt, or effervescent mixtures, croscarmellose or its sodium salt, and the like. Diluents, include, e.g., lactose, dextrose, sucrose, mannitol, sorbitol, cellulose and/or glycine.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A therapeutically effective dose, of a compound described herein in an oral formulation, may vary from 0.01 mg/kg to 50 mg/kg patient body weight per day, more particularly 0.01 to 10 mg/kg, which can be administered in single or multiple doses per day. For oral administration the drug can be delivered in the form of tablets or capsules containing 1 mg to 500 mg of the active ingredient specifically, 1 mg, 5 mg, 10 mg, 20 mg, 50 mg, 100 mg, 250 mg, and 500 mg, or in the forms of tables or capsules containing at least 1%, 2%, 5%, 10%, 15%, 20%, 25%, 30%, 40%, 50% (w/w) of the active ingredient. For example, the capsules may contain 50 mg of the active ingredient, or 5-10% (w/w) of the active ingredient. For example, the tablets may contain 100 mg of the active ingredient, or 20-50% (w/w) of the active ingredient. For example, the tablet may contain, in addition to the active ingredient, a disintegrant (e.g., croscarmellose or its sodium salt and methyl cellulose), a diluent (e.g., microcrystalline cellulose), and a lubricant (e.g., sodium stearate and magnesium stearate). The drug can be administered on a daily basis either once, twice or more per day.

For administration by inhalation, the compounds are delivered in the form of an aerosol spray from pressured container or dispenser, which contains a suitable propellant, e.g., a gas such as carbon dioxide, or a nebulizer.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Parenteral formulations comprising a compound described herein can be prepared in aqueous isotonic solutions or suspensions, and suppositories are advantageously prepared from fatty emulsions or suspensions. The formulations may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional methods, and may contain about 0.1 to 75%, preferably about 1 to 50%, of a compound described herein.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

3. Description of Exemplary Compounds

Deuterium (D or $^2$H) is a stable, non-radioactive isotope of hydrogen and has an atomic weight of 2.0144. Hydrogen naturally occurs as a mixture of the isotopes $^1$H (hydrogen or protium), D ($^2$H or deuterium), and T ($^3$H or tritium). One skilled in the art appreciates that the designation "hydrogen" in hydrogen-containing chemical compounds actually represents a mixture of hydrogen and about 0.015% deuterium.

Complete deuteration, or 100% deuteration, at any one site can be difficult to achieve in the laboratory. When a deuterium atom is indicated at a given site on any compound described herein, it is understood that a small percentage of hydrogen may still be present. Such compounds are said to be enriched with deuterium. Deuterium-enriched compounds are prepared via synthesis utilizing appropriately enriched starting materials. As used herein, the terms "deuterium-enriched" or "deuterium enrichment" refer to a compound, or a particular site of said compound, which comprises deuterium in an amount that is greater than its natural isotopic abundance (0.015%). Accordingly, in some embodiments, the present invention provides compounds comprising deuterium at a given site, wherein the percentage or level of deuterium incorporation is greater than its natural isotopic abundance.

According to one aspect, the present invention provides a compound of formula I:

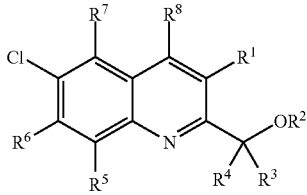

I or a pharmaceutically acceptable salt thereof, wherein:
R$^1$ is selected from —NH$_2$, —NHD, or —ND$_2$;
R$^2$ is selected from hydrogen or deuterium;
R$^3$ and R$^4$ are independently selected from —CH$_3$, —CH$_2$D, —CHD$_2$, or —CD$_3$; and
R$^5$, R$^6$, R$^7$, and R$^8$ are each independently selected from hydrogen or deuterium;
provided that at least one of R$^1$, R$^2$, R$^3$, R$^4$, R$^5$, R$^6$, R$^7$, or R$^8$ is or contains deuterium.

According to another aspect, the present invention provides a compound of formula I-A:

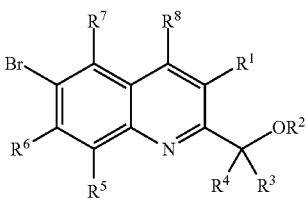

I-A or a pharmaceutically acceptable salt thereof, wherein:
R$^1$ is selected from —NH$_2$, —NHD, or —ND$_2$;
R$^2$ is selected from hydrogen or deuterium;
R$^3$ and R$^4$ are independently selected from —CH$_3$, —CH$_2$D, —CHD$_2$, or —CD$_3$; and
R$^5$, R$^6$, R$^7$, and R$^8$ are each independently selected from hydrogen or deuterium;
provided that at least one of R$^1$, R$^2$, R$^3$, R$^4$, R$^5$, R$^6$, R$^7$, or R$^8$ is or contains deuterium.

According to another aspect, the present invention provides a compound of formulae II-A or II-B:

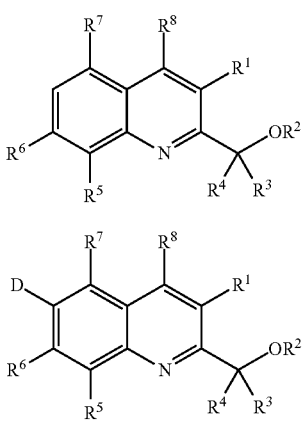

II-A

II-B or a pharmaceutically acceptable salt thereof, wherein:
R$^1$ is selected from —NH$_2$, —NHD, or —ND$_2$;
R$^2$ is selected from hydrogen or deuterium;
R$^3$ and R$^4$ are independently selected from —CH$_3$, —CH$_2$D, —CHD$_2$, or —CD$_3$; and
R$^5$, R$^6$, R$^7$, and R$^8$ are each independently selected from hydrogen or deuterium;
provided that at least one of R$^1$, R$^2$, R$^3$, R$^4$, R$^5$, R$^6$, R$^7$, or R$^8$ in formula TI-A is or contains deuterium.

According to another aspect, the present invention provides a compound of formulae III-A, III-B, or III-C:

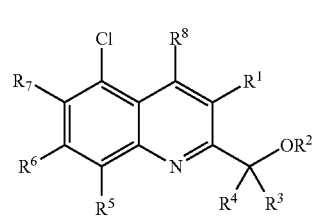

III-A

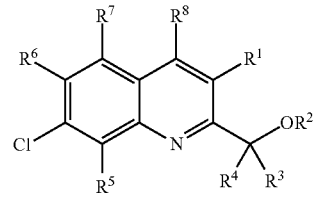

III-B

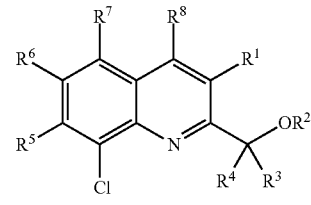

III-C or a pharmaceutically acceptable salt thereof, wherein:
R$^1$ is selected from —NH$_2$, —NHD, or —ND$_2$;
R$^2$ is selected from hydrogen or deuterium;
R$^3$ and R$^4$ are independently selected from —CH$_3$, —CH$_2$D, —CHD$_2$, or —CD$_3$; and
R$^5$, R$^6$, R$^7$, and R$^8$ are each independently selected from hydrogen or deuterium;
provided that at least one of R$^1$, R$^2$, R$^3$, R$^4$, R$^5$, R$^6$, R$^7$, or R$^8$ is or contains deuterium.

According to another aspect, the present invention provides a compound of formula IV:

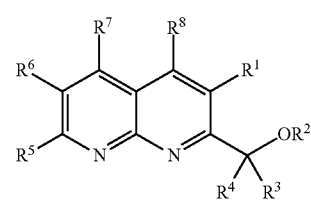

IV or a pharmaceutically acceptable salt thereof, wherein:
R$^1$ is selected from —NH$_2$, —NHD, or —ND$_2$;
R$^2$ is selected from hydrogen or deuterium;
R$^3$ and R$^4$ are independently selected from —CH$_3$, —CH$_2$D, —CHD$_2$, or —CD$_3$; and $R^5$, $R^6$, $R^7$, and $R^8$ are each independently selected from hydrogen or deuterium;

provided that at least one of $R^1$, $R^2$, $R^3$, $R^4$, $R^5$, $R^6$, $R^7$, or $R^8$ is or contains deuterium.

According to another aspect, the present invention provides a compound of formula V:

[Structure V]

or a pharmaceutically acceptable salt thereof, wherein:
$R^1$ is selected from —$NH_2$, —NHD, or —$ND_2$;
$R^2$ is selected from hydrogen or deuterium;
$R^3$ and $R^4$ are independently selected from —$CH_3$, —$CH_2D$, —$CHD_2$, or —$CD_3$; and
$R^5$, $R^6$, $R^7$, and $R^8$ are each independently selected from hydrogen or deuterium;
provided that at least one of $R^1$, $R^2$, $R^3$, $R^4$, $R^5$, $R^6$, $R^7$, or $R^8$ is or contains deuterium.

According to another aspect, the present invention provides a compound of formulae VI-A or VI-B:

[Structure VI-A]

[Structure VI-B]

or a pharmaceutically acceptable salt thereof, wherein:
each A is independently hydrogen or deuterium;
$R^1$ is selected from —$NH_2$, —NHD, or —$ND_2$;
$R^2$ is selected from hydrogen or deuterium; and
$R^5$, $R^6$, $R^7$, and $R^8$ are each independently selected from hydrogen or deuterium;
provided that at least one of A, $R^1$, $R^2$, $R^5$, $R^6$, $R^7$, or $R^8$ is or contains deuterium.

According to another aspect, the present invention provides a compound of formulae VII-A or VII-B:

[Structure VII-A]

[Structure VII-B]

or a pharmaceutically acceptable salt thereof, wherein:
each A is independently hydrogen or deuterium;
$R^1$ is selected from —$NH_2$, —NHD, or —$ND_2$;
$R^2$ is selected from hydrogen or deuterium;
$R^3$ and $R^4$ are independently selected from —$CH_3$, —$CH_2D$, —$CHD_2$, or —$CD_3$; and
$R^8$ is selected from hydrogen or deuterium;
provided that at least one of $R^1$, $R^2$, $R^3$, $R^4$, A, or $R^8$ is or contains deuterium.

According to another aspect, the present invention provides a compound of formulae VIII-A or VIII-B:

[Structure VIII-A]

[Structure VIII-B]

or a pharmaceutically acceptable salt thereof, wherein:
each A is independently hydrogen or deuterium;
$R^1$ is selected from —$NH_2$, —NHD, or —$ND_2$;
$R^2$ is selected from hydrogen or deuterium;
$R^3$ and $R^4$ are independently selected from —$CH_3$, —$CH_2D$, —$CHD_2$, or —$CD_3$; and
$R^5$ and $R^8$ are each independently selected from hydrogen or deuterium;
provided that at least one of A, $R^1$, $R^2$, $R^3$, $R^4$, $R^5$, or $R^8$ is or contains deuterium.

According to another aspect, the present invention provides a compound of formula IX-A or IX—B:

IX-A

[Structure IX-A: chloroquinoline with substituents R¹–R⁸, OR², R³, R⁴, R⁷]

IX-B

[Structure IX-B: fluoro, chloroquinoline with substituents R¹, R³, R⁴, R⁵, R⁶, R⁸, OR²]

or a pharmaceutically acceptable salt thereof, wherein:
  $R^1$ is selected from —NH$_2$, —NHD, or —ND$_2$;
  $R^2$ is selected from hydrogen or deuterium;
  $R^3$ and $R^4$ are independently selected from —CH$_3$, —CH$_2$D, —CHD$_2$, or —CD$_3$; and
  $R^5$, $R^6$, $R^7$, and $R^8$ are each independently selected from hydrogen or deuterium;
  provided that at least one of $R^1$, $R^2$, $R^3$, $R^4$, $R^5$, $R^6$, $R^7$, or $R^8$ is or contains deuterium.

According to another aspect, the present invention provides a compound of formula X:

X

[Structure X: pyridine core with two —C(R³)(R⁴)OR² groups and R¹, R⁵, R⁶ substituents]

or a pharmaceutically acceptable salt thereof, wherein:
  $R^1$ is selected from —NH$_2$, —NHD, or —ND$_2$;
  $R^2$ is selected from hydrogen or deuterium;
  $R^3$ and $R^4$ are independently selected from —CH$_3$, —CH$_2$D, —CHD$_2$, or —CD$_3$; and
  $R^5$ and $R^6$ are each independently selected from hydrogen or deuterium;
  provided that at least one of $R^1$, $R^2$, $R^3$, $R^4$, $R^5$, or $R^6$ is or contains deuterium.

The following embodiments are applicable to each of the preceding formulae.

As defined above and described herein, $R^1$ is selected from —NH$_2$, —NHD, or —ND$_2$.

In some embodiments, $R^1$ is —NH$_2$. In some embodiments, $R^1$ is —NH$_2$ and at least one of $R^2$, $R^3$, $R^4$, $R^5$, $R^6$, $R^7$, or $R^8$ is or contains deuterium.

In some embodiments, $R^1$ is —NHD. In some embodiments, $R^1$ is —NHD and at least one of $R^2$, $R^3$, $R^4$, $R^5$, $R^6$, $R^7$, or $R^8$ is or contains deuterium.

In some embodiments, $R^1$ is —ND$_2$. In some embodiments, $R^1$ is —ND$_2$ and at least one of $R^2$, $R^3$, $R^4$, $R^5$, $R^6$, $R^7$, or $R^8$ is or contains deuterium.

As defined above and described herein, A is selected from hydrogen or deuterium.

In some embodiments, A is hydrogen. In some embodiments, A is hydrogen and at least one of $R^1$, $R^3$, $R^4$, $R^5$, $R^6$, $R^7$, or $R^8$ is or contains deuterium. In some embodiments, A is deuterium. In some embodiments, A is deuterium and at least one of $R^1$, $R^3$, $R^4$, $R^5$, $R^6$, $R^7$, or $R^8$ is or contains deuterium.

As defined above and described herein, $R^2$ is selected from hydrogen or deuterium.

In some embodiments, $R^2$ is hydrogen. In some embodiments, $R^2$ is hydrogen and at least one of $R^1$, $R^3$, $R^4$, $R^5$, $R^6$, $R^7$, or $R^8$ is or contains deuterium. In some embodiments, $R^2$ is deuterium. In some embodiments, $R^2$ is deuterium and at least one of $R^1$, $R^3$, $R^4$, $R^5$, $R^6$, $R^7$, or $R^8$ is or contains deuterium.

As defined above and described herein, $R^3$ is selected from —CH$_3$, —CH$_2$D, —CHD$_2$, or —CD$_3$.

In some embodiments, $R^3$ is —CH$_3$. In some embodiments, $R^3$ is —CH$_3$ and at least one of $R^1$, $R^2$, $R^4$, $R^5$, $R^6$, $R^7$, or $R^8$ is or contains deuterium.

In some embodiments, $R^3$ is —CH$_2$D. In some embodiments, $R^3$ is —CH$_2$D and at least one of $R^1$, $R^2$, $R^4$, $R^5$, $R^6$, $R^7$, or $R^8$ is or contains deuterium.

In some embodiments, $R^3$ is —CHD$_2$. In some embodiments, $R^3$ is —CHD$_2$ and at least one of $R^1$, $R^2$, $R^4$, $R^5$, $R^6$, $R^7$, or $R^8$ is or contains deuterium.

In some embodiments, $R^3$ is —CD$_3$. In some embodiments, $R^3$ is —CD$_3$ and at least one of $R^1$, $R^2$, $R^4$, $R^5$, $R^6$, $R^7$, or $R^8$ is or contains deuterium.

As defined above and described herein, $R^4$ is selected from —CH$_3$, —CH$_2$D, —CHD$_2$, or —CD$_3$.

In some embodiments, $R^4$ is —CH$_3$. In some embodiments, $R^4$ is —CH$_3$ and at least one of $R^1$, $R^2$, $R^3$, $R^5$, $R^6$, $R^7$, or $R^8$ is or contains deuterium.

In some embodiments, $R^4$ is —CH$_2$D. In some embodiments, $R^4$ is —CH$_2$D and at least one of $R^1$, $R^2$, $R^3$, $R^5$, $R^6$, $R^7$, or $R^8$ is or contains deuterium.

In some embodiments, $R^4$ is —CHD$_2$. In some embodiments, $R^4$ is —CHD$_2$ and at least one of $R^1$, $R^2$, $R^3$, $R^5$, $R^6$, $R^7$, or $R^8$ is or contains deuterium.

In some embodiments, $R^4$ is —CD$_3$. In some embodiments, $R^4$ is —CD$_3$ and at least one of $R^1$, $R^2$, $R^3$, $R^5$, $R^6$, $R^7$, or $R^8$ is or contains deuterium.

As defined above and described herein, $R^5$ is selected from hydrogen or deuterium.

In some embodiments, $R^5$ is hydrogen. In some embodiments, $R^5$ is hydrogen and at least one of $R^1$, $R^2$, $R^3$, $R^4$, $R^6$, $R^7$, or $R^8$ is or contains deuterium. In some embodiments, $R^5$ is deuterium. In some embodiments, $R^5$ is deuterium and at least one of $R^1$, $R^2$, $R^3$, $R^4$, $R^6$, $R^7$, or $R^8$ is or contains deuterium.

As defined above and described herein, $R^6$ is selected from hydrogen or deuterium.

In some embodiments, $R^6$ is hydrogen. In some embodiments, $R^6$ is hydrogen and at least one of $R^1$, $R^2$, $R^3$, $R^4$, $R^5$, $R^7$, or $R^8$ is or contains deuterium. In some embodiments, $R^6$ is deuterium. In some embodiments, $R^6$ is deuterium and at least one of $R^1$, $R^2$, $R^3$, $R^4$, $R^5$, $R^7$, or $R^8$ is or contains deuterium.

As defined above and described herein, $R^7$ is selected from hydrogen or deuterium.

In some embodiments, $R^7$ is hydrogen. In some embodiments, $R^7$ is hydrogen and at least one of $R^1$, $R^2$, $R^3$, $R^4$, $R^5$, $R^6$, or $R^7$ is or contains deuterium. In some embodiments, $R^7$ is deuterium. In some embodiments, $R^7$ is deuterium and at least one of $R^1$, $R^2$, $R^3$, $R^4$, $R^5$, $R^6$, or $R^7$ is or contains deuterium.

As defined above and described herein, $R^8$ is selected from hydrogen or deuterium.

In some embodiments, $R^8$ is hydrogen. In some embodiments, $R^8$ is hydrogen and at least one of $R^1$, $R^2$, $R^3$, $R^4$, $R^5$, $R^6$, or $R^7$ is or contains deuterium. In some embodiments, $R^8$ is deuterium. In some embodiments, $R^8$ is deuterium and at least one of $R^1$, $R^2$, $R^3$, $R^4$, $R^5$, $R^6$, or $R^7$ is or contains deuterium.

In some embodiments, the present invention provides a compound of formulae I, I-A, II-A, II-B, III-A, III-B, III-C, IV, or V, wherein each of $R^3$, $R^4$, $R^5$, $R^6$, $R^7$, and $R^8$ is as defined above and described herein, and wherein each of $R^1$ and $R^2$ is as defined in an entry set forth in Table 1a, below.

TABLE 1a

| Entry | $R^1$ | $R^2$ |
|---|---|---|
| i | —NH$_2$ | H |
| ii | —NH$_2$ | D |
| iii | —NHD | H |
| iv | —NHD | D |
| v | —ND$_2$ | H |
| vi | —ND$_2$ | D |

In some embodiments, the present invention provides a compound of formulae I, I-A, II-A, II-B, III-A, III-B, III-C, IV, or V, wherein each of $R^1$, $R^2$, $R^5$, $R^6$, $R^7$, and $R^8$ is as defined above and described herein, and wherein each of $R^3$ and $R^4$ is as defined in an entry set forth in Table 1b, below.

TABLE 1b

| Entry | $R^3$ | $R^4$ |
|---|---|---|
| i | —CH$_3$ | —CH$_3$ |
| ii | —CH$_3$ | —CH$_2$D |
| iii | —CH$_3$ | —CHD$_2$ |
| iv | —CH$_3$ | —CD$_3$ |
| v | —CH$_2$D | —CH$_3$ |
| vi | —CH$_2$D | —CH$_2$D |
| vii | —CH$_2$D | —CHD$_2$ |
| viii | —CH$_2$D | —CD$_3$ |
| ix | —CHD$_2$ | —CH$_3$ |
| x | —CHD$_2$ | —CH$_2$D |
| xi | —CHD$_2$ | —CHD$_2$ |
| xii | —CHD$_2$ | —CD$_3$ |
| xiii | —CD$_3$ | —CH$_3$ |
| xiv | —CD$_3$ | —CH$_2$D |
| xv | —CD$_3$ | —CHD$_2$ |
| xvi | —CD$_3$ | —CD$_3$ |

In some embodiments, the present invention provides a compound of formulae I, I-A, II-A, II-B, III-A, III-B, III-C, IV, or V, wherein each of $R^1$, $R^2$, $R^3$, and $R^4$ is as defined above and described herein, and wherein each of $R^5$, $R^6$, $R^7$, and $R^8$ is as defined in an entry set forth in Table 1c, below.

TABLE 1c

| Entry | $R^5$ | $R^6$ | $R^7$ | $R^8$ |
|---|---|---|---|---|
| i | H | H | H | H |
| ii | H | H | H | D |
| iii | H | H | D | H |
| iv | H | D | H | H |
| v | D | H | H | H |
| vi | H | H | D | D |
| vii | H | D | H | D |
| viii | D | H | H | D |
| ix | H | D | D | H |
| x | D | H | D | H |
| xi | D | D | H | H |
| xii | H | D | D | D |
| xiii | D | H | D | D |
| xiv | D | D | H | D |
| xv | D | D | D | H |
| xvi | D | D | D | D |

In some embodiments, the present invention provides a compound of formulae I, I-A, II-A, II-B, III-A, III-B, III-C, IV, or V, wherein each of $R^1$ and $R^2$ is as defined in an entry set forth in Table 1a, above, each of $R^3$ and $R^4$ is as defined in an entry set forth in Table 1b, above, and each of $R^5$, $R^6$, $R^7$, and $R^8$, is as defined in an entry set forth in Table 1c, above.

In some embodiments, the present invention provides a compound selected from those recited in any of Table 1a, Table 1b, or Table 1c, or a pharmaceutically acceptable salt thereof.

In some embodiments, present invention provides a compound of formula I selected from these depicted in Table 2, below.

TABLE 2

Representative Compounds of Formula I

I-1

I-2

I-3

I-4

TABLE 2-continued

Representative Compounds of Formula I

| Compound | Structure |
|---|---|
| I-5 | 6-chloro-3-amino-8-D-quinolin-2-yl-2-propanol (H at 4,5,7; D at 8) |
| I-6 | 6-chloro-3-amino-quinolin-2-yl-2-propanol (D at 5,7; H at 4,8) |
| I-7 | 6-chloro-3-amino-quinolin-2-yl-2-propanol (H at 4,5; D at 7,8) |
| I-8 | 6-chloro-3-amino-quinolin-2-yl-2-propanol (D at 5,8; H at 4,7) |
| I-9 | 6-chloro-3-amino-quinolin-2-yl-2-propanol (D at 5,7,8; H at 4) |
| I-10 | 6-chloro-3-amino-quinolin-2-yl-2-propanol (D at 4,5; H at 7,8) |
| I-11 | 6-chloro-3-amino-quinolin-2-yl-2-propanol (H at 5; D at 4,7; H at 8) |
| I-12 | 6-chloro-3-amino-quinolin-2-yl-2-propanol (H at 5,7; D at 4,8) |
| I-13 | 6-chloro-3-amino-quinolin-2-yl-2-propanol (D at 4,5,7; H at 8) |
| I-14 | 6-chloro-3-amino-quinolin-2-yl-2-propanol (H at 5; D at 4,7,8) |
| I-15 | 6-chloro-3-amino-quinolin-2-yl-2-propanol (D at 4,5,7,8) |
| I-16 | 6-chloro-3-amino-quinolin-2-yl-2-propanol (D at 4,5,7,8) |
| I-17 | 6-chloro-3-amino-quinolin-2-yl-2-propanol with CD3 groups (D at 4; H at 5,7,8; D3C, CD3) |
| I-18 | 6-chloro-3-amino-quinolin-2-yl-2-propanol with CD3 groups (D at 5; H at 4,7,8; D3C, CD3) |

TABLE 2-continued

Representative Compounds of Formula I

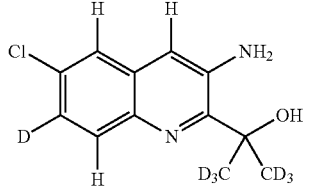 I-19

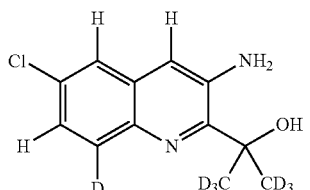 I-20

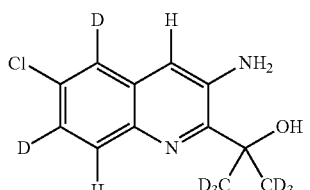 I-21

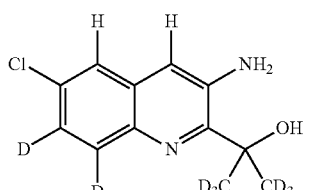 I-22

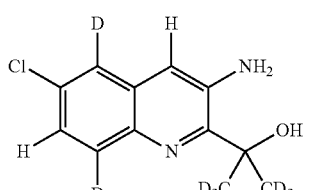 I-23

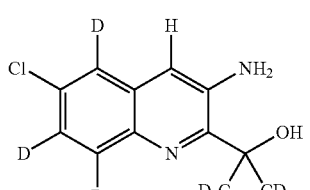 I-24

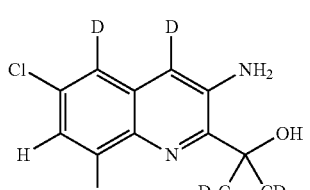 I-25

TABLE 2-continued

Representative Compounds of Formula I

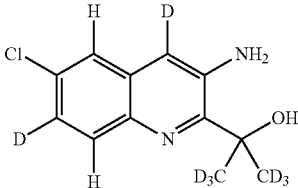 I-26

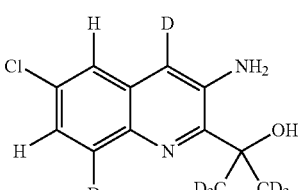 I-27

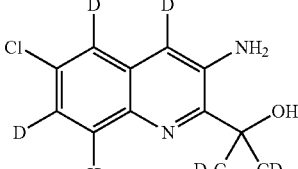 I-28

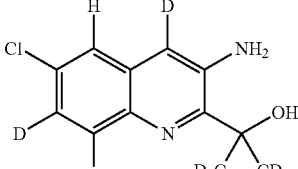 I-29

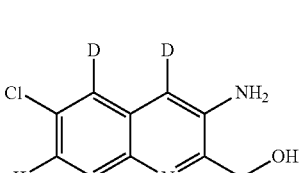 I-30

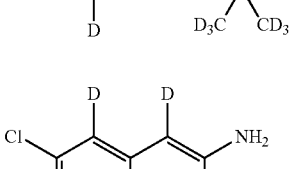 I-31

In some embodiments, the present invention provides a compound depicted in Table 2, above, or a pharmaceutically acceptable salt thereof.

In some embodiments, the present invention provides a deuterium-enriched analogue of a compound depicted in Table 2A, below, or a pharmaceutically acceptable salt thereof, in which deuterium is enriched at any available hydrogen.

TABLE 2A

| Structure | ID |
|---|---|
| (quinoline with 3-NH2 and 2-C(CH3)2OH) | I-32 |
| (5-Cl quinoline with 3-NH2 and 2-C(CH3)2OH) | I-33 |
| (6-Cl quinoline with 3-NH2 and 2-C(CH3)2OH) | I-34 |
| (8-Cl quinoline with 3-NH2 and 2-C(CH3)2OH) | I-35 |
| (6-Br quinoline with 3-NH2 and 2-C(CH3)2OH) | I-36 |
| (quinoxaline with 3-NH2 and 2-C(CH3)2OH) | I-37 |
| (1,8-naphthyridine with 3-NH2 and 2-C(CH3)2OH) | I-38 |
| (6-Cl quinoline with 3-NH2 and 2-C(Et)2OH) | I-39 |
| (6-Cl quinoline with 3-NH2 and 2-(1-hydroxycyclobutyl)) | I-40 |
| (2-cyclobutyl-7-Cl-benzoxazole with NH2 and C(CH3)2OH) | I-41 |
| (3-cyclopropyl-4-Cl-benzisoxazole with NH2 and C(CH3)2OH) | I-42 |
| (pyridine with 4-C(CH3)2OH, 3-NH2, 2-C(CH3)2OH) | I-43 |
| (2-phenylbenzoxazole with NH2 and C(CH3)2OH) | I-44 |
| (2-phenyl-7-Cl-benzoxazole with NH2 and C(CH3)2OH) | I-45 |
| (5-F, 6-Cl quinoline with 3-NH2 and 4-C(CH3)2OH) | I-46 |
| (6-Cl quinoline with 3-NH2 and 4-C(CH3)2OH) | I-47 |

In some embodiments, the present invention provides any compound described herein comprising one, two, three, four, five, six, seven, eight, nine, ten, eleven, twelve, or thirteen deuterium atoms.

In some embodiments, provided compounds comprise deuterium in an amount of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. As used herein in the context of deuterium enrichment, the term "about" means±2%.

In certain embodiments, the present invention provides any compound described above and herein, or a pharmaceutically acceptable salt thereof.

In some embodiments, the present invention provides any compound described above and herein in isolated form.

4. Uses of Compounds and Pharmaceutically Acceptable Compositions Thereof

Certain compounds described herein are found to be useful in scavenging toxic aldehydes, such as MDA and HNE. The compounds described herein undergo a Schiff base condensation with MDA, HNE, or other toxic aldehydes, and form a complex with the aldehydes in an energetically favorable reaction, thus reducing or eliminating aldehydes available for reaction with a protein, lipid, carbohydrate, or DNA. Importantly, compounds described herein can react with aldehydes to form a compound having a closed-ring structure that contains the aldehydes, thus trapping the aldehydes and preventing the aldehydes from being released back into the cellular milieu.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent, delay or lessen the severity of their recurrence.

The invention relates to compounds described herein for the treatment, prevention, and/or reduction of a risk of diseases, disorders, or conditions in which aldehyde toxicity is implicated in the pathogenesis.

Examples of the diseases, disorders, or conditions in which aldehyde toxicity is implicated include an ocular disease, disorder, or condition, including, but not limited to, a corneal disease (e.g., dry eye syndrome, cataracts, keratoconus, bullous and other keratopathy, and Fuch's endothelial dystrophy), other ocular disorders or conditions (e.g., allergic conjunctivitis, ocular cicatricial pemphigoid, conditions associated with PRK healing and other corneal healing, and conditions associated with tear lipid degradation or lacrimal gland dysfunction), and other ocular conditions associated with high aldehyde levels as a result of inflammation (e.g., uveitis, scleritis, ocular Stevens Johnson Syndrome, ocular rosacea (with or without meibomian gland dysfunction)). In one example, the ocular disease, disorder, or condition is not macular degeneration, such as age-related macular degeneration ("AMD"), or Stargardt's disease. In a further example, the ocular disease, disorder, or condition is dry eye syndrome, ocular rosacea, or uveitis.

Examples of the diseases, disorders, conditions, or indications in which aldehyde toxicity is implicated also include non-ocular disorders, including psoriasis, topical (discoid) lupus, contact dermatitis, atopic dermatitis, allergic dermatitis, radiation dermatitis, acne vulgaris, Sjogren-Larsson Syndrome and other ichthyosis, solar elastosis/wrinkles, skin tone firmness, puffiness, eczema, smoke or irritant induced skin changes, dermal incision, a skin condition associated burn and/or wound, lupus, scleroderma, asthma, chronic obstructive pulmonary disease (COPD), rheumatoid arthritis, inflammatory bowel disease, sepsis, atherosclerosis, ischemic-reperfusion injury, Parkinson's disease, Alzheimer's disease, succinic semialdehyde dehydrogenase deficiency, multiple sclerosis, amyotrophic lateral sclerosis, diabetes, metabolic syndrome, age-related disorders, and fibrotic diseases. In a further example, the non-ocular disorder is a skin disease, disorder, or condition selected from contact dermatitis, atopic dermatitis, allergic dermatitis, and radiation dermatitis. In another example, the non-ocular disorder is a skin disease, disorder, or condition selected from Sjogren-Larsson Syndrome and a cosmetic indication associated burn and/or wound.

In a further example, the diseases, disorders, or conditions in which aldehyde toxicity is implicated are an age-related disorder. Examples of age-related diseases, disorders, or conditions include wrinkles, dryness, and pigmentation of the skin.

Examples of the diseases, disorders, or conditions in which aldehyde toxicity is implicated further include conditions associated with the toxic effects of blister agents or burns from alkali agents. The compounds described herein reduce or eliminate toxic aldehydes and thus treat, prevent, and/or reduce a risk of these diseases or disorders.

In one embodiment, the invention relates to the treatment, prevention, and/or reduction of a risk of an ocular disease, disorder, or condition in which aldehyde toxicity is implicated in the pathogenesis, comprising administering to a subject in need thereof a compound described herein. The ocular disease, disorder, or condition includes, but is not limited to, a corneal disease (e.g., dry eye syndrome, cataracts, keratoconus, bullous and other keratopathy, and Fuch's endothelial dystrophy in the cornea), other ocular disorders or conditions (e.g., allergic conjunctivitis, ocular cicatricial pemphigoid, conditions associated with PRK healing and other corneal healing, and conditions associated with tear lipid degradation or lacrimal gland dysfunction), and other ocular conditions where inflammation leads to high aldehyde levels (e.g., uveitis, scleritis, ocular Stevens Johnson Syndrome, ocular rosacea (with or without meibomian gland dysfunction)). The ocular disease, disorder, or condition does not include macular degeneration, such as AMD, or Stargardt's disease. In one illustration, in the ocular disease, disorder, or condition, the amount or concentration of MDA or HNE is increased in the ocular tissues or cells. For example, the amount or concentration of aldehydes (e.g., MDA or HNE) is increased for at least 1.1 fold, 1.2 fold, 1.3 fold, 1.4 fold, 1.5 fold, 2 fold, 2.5 fold, 5 fold, 10 fold as compared to that in normal ocular tissues or cells. Compounds described herein, such as Compound 9, decrease aldehyde (e.g., MDA and HNE) concentration in a time-dependent manner. The amount or concentration of aldehydes (e.g., MDA or HNE) can be measured by methods or techniques known in the art, such as those described in Tukozkan et al., Furat Tip Dergisi 11: 88-92 (2006).

In one class, the ocular disease, disorder, or condition is dry eye syndrome. In a second class, the ocular disease, disorder, or condition is a condition associated with PRK healing and other corneal healing. For example, the invention is directed to advancing PRK healing or other corneal healing, comprising administering to a subject in need thereof a compound described herein. In a third class, the ocular disease, disorder, or condition is an ocular condition associated with high aldehyde levels as a result of inflammation (e.g., uveitis, scleritis, ocular Stevens Johnson Syndrome, and ocular rosacea (with or without meibomian gland dysfunction). In a fourth class, the ocular disease, disorder, or condition is keratoconus, cataracts, bullous and other keratopathy, Fuchs' endothelial dystrophy, ocular cicatricial pemphigoid, or allergic conjunctivitis. The compound described herein may be administered topically or systemically, as described herein below.

In a second embodiment, the invention relates to the treatment, prevention, and/or reduction of a risk of a skin disorder or condition or a cosmetic indication, in which aldehyde toxicity is implicated in the pathogenesis, comprising administering to a subject in need thereof a compound described herein. The skin disorder or condition includes, but is not limited to, psoriasis, scleroderma, topical (discoid) lupus, contact dermatitis, atopic dermatitis, allergic dermatitis, radiation dermatitis, acne vulgaris, and Sjogren-Larsson Syndrome and other ichthyosis, and the cosmetic indication is solar elastosis/wrinkles, skin tone firmness, puffiness, eczema, smoke or irritant induced skin changes, dermal incision, or a skin condition associated burn and/or wound. In some embodiments, the invention related to age-related diseases, disorders, or conditions of the skin, as described herein.

Various skin disorders or conditions, such as atopic dermatitis, topical (discoid) lupus, psoriasis and scleroderma, are characterized by high MDA and HNE levels (Br J Dermatol 149: 248 (2003); JEADV 26: 833 (2012); Clin Rheumatol 25: 320 (2006)). In addition, ichthyosis characteristic of the Sjogren-Larsson Syndrome (SLS) originates from accumulation of fatty aldehydes, which disrupts the normal function and secretion of lamellar bodies (LB) and leads to intercellular lipid deposits in the Strateum Corneum (SC) and a defective water barrier in the skin layer (W. B. Rizzo et al. (2010)). The enzyme, fatty aldehyde dehydrogenase, that metabolizes aldehydes is dysfunctional in SLS patients. Thus, compounds that reduce or eliminate aldehydes, such as the compounds described herein, can be used to treat, prevent, and/or reduction of a risk of skin disorders or conditions in which aldehyde toxicity is implicated in the pathogenesis, such as those described herein. Furthermore, with an improvement to the water barrier and prevention of aldehyde-mediated inflammation (including fibrosis and elastosis (Chairpotto et al. (2005)), many cosmetic indications, such as solar elastosis/wrinkles, skin tone, firmness (puffiness), eczema, smoke or irritant induced skin changes and dermal incision cosmesis, and skin conditions associated with burn and/or wound can be treated using the method of the invention.

In one class, the skin disease, disorder, or condition is psoriasis, scleroderma, topical (discoid) lupus, contact dermatitis, atopic dermatitis, allergic dermatitis, radiation dermatitis, acne vulgaris, or Sjogren-Larsson Syndrome and other ichthyosis. In one exemplification, the skin disease, disorder, or condition is contact dermatitis, atopic dermatitis, allergic dermatitis, radiation dermatitis, or Sjogren-Larsson Syndrome and other ichthyosis. In a second class, the cosmetic indication is solar elastosis/wrinkles, skin tone firmness, puffiness, eczema, smoke or irritant induced skin changes, dermal incision, or a skin condition associated burn and/or wound.

In a third embodiment, the invention relates to the treatment, prevention, and/or reduction of a risk of a condition associated with the toxic effects of blister agents or burns from alkali agents in which aldehyde toxicity is implicated in the pathogenesis, comprising administering to a subject in need thereof a compound described herein.

Blister agents include, but are not limited to, sulfur mustard, nitrogen mustard, and phosgene oxime. Toxic or injurious effects of blister agents include pain, irritation, and/or tearing in the skin, eye, and/or mucous, and conjunctivitis and/or corneal damage to the eye. Sulfur mustard is the compound bis(2-chlorethyl) sulfide. Nitrogen mustard includes the compounds bis(2-chlorethyl)ethylamine, bis(2-chlorethyl)methylamine, and tris(2-chlorethyl)amine. Sulfur mustard or its analogs can cause an increase in oxidative stress and in particular in HNE levels, and by depleting the antioxidant defense system and thereby increasing lipid peroxidation, may induce an oxidative stress response and thus increase aldehyde levels (Jafari et al. (2010); Pal et al. (2009)). Antioxidants, such as Silibinin, when applied topically, attenuate skin injury induced from exposure to sulfur mustard or its analogs, and increased activities of antioxidant enzymes may be a compensatory response to reactive oxygen species generated by the sulfur mustard (Jafari et al. (2010); Tewari-Singh et al. (2012)). Further, intervention to reduce free radical species was an effective treatment post exposure for phosgene induced lung injury (Sciuto et al. (2004)). Thus, compounds that reduce or eliminate aldehydes, such as compounds described herein, can be used to treat, prevent, and/or reduce a risk of a condition associated with the toxic effects of blister agents, such as sulfur mustard, nitrogen mustard, and phosgene oxime.

Alkali agents include, but are not limited to, lime, lye, ammonia, and drain cleaners. Compounds that reduce or eliminate aldehydes, such as compounds described herein, can be used to treat, prevent, and/or reduce a risk of a condition associated with burns from an alkali agent.

In a fourth embodiment, the invention relates to the treatment, prevention, and/or reduction of a risk of an autoimmune, immune-mediated, inflammatory, cardiovascular, or neurological disease, disorder, or condition, or metabolic syndrome, or diabetes, in which aldehyde toxicity is implicated in the pathogenesis, comprising administering to a subject in need thereof a compound described herein. The autoimmune or immune-mediated disease, disorder, or condition includes, but is not limited to, lupus, scleroderma, asthma, chronic obstructive pulmonary disease (COPD), and rheumatoid arthritis. The inflammatory disease, disorder, or condition includes, but is not limited to, rheumatoid arthritis, inflammatory bowel disease (e.g., Crohn's disease and ulcerative colitis), sepsis, and fibrosis (e.g., renal, hepatic, pulmonary, and cardiac fibrosis). The cardiovascular disease, disorder, or condition includes, but is not limited to, atherosclerosis and ischemic-reperfusion injury. The neurological disease, disorder, or condition includes, but is not limited to, Parkinson's disease, Alzheimer's disease, succinic semialdehyde dehydrogenase deficiency, multiple sclerosis, amyotrophic lateral sclerosis, and the neurological aspects of Sjogren-Larsson Syndrome (cognitive delay and spasticity).

A skilled person would understand that the disease, disorder, or condition listed herein may involve more than one pathological mechanism. For example, a disease, disorder, or condition listed herein may involve dysregulation in the immunological response and inflammatory response. Thus, the above categorization of a disease, disorder, or condition is not absolute, and the disease, disorder, or condition may be considered an immunological, an inflammatory, a cardiovascular, a neurological, and/or metabolic disease, disorder, or condition.

Individuals with deficiencies in aldehyde dehydrogenase are found to have high aldehyde levels and increased risk of Parkinson's disease (PNAS 110:636 (2013)) and Alzheimer's disease (BioChem Biophys Res Commun. 273:192 (2000)). In Parkinson's disease, aldehydes specifically interfere with dopamine physiology (Free Radic Biol Med, 51: 1302 (2011); Mol Aspects Med, 24: 293 (2003); Brain Res, 1145: 150 (2007)). In addition, aldehydes levels are elevated in multiple sclerosis, amyotrophic lateral sclerosis, autoimmune diseases such as lupus, rheumatoid arthritis, lupus, psoriasis, scleroderma, and fibrotic diseases, and increased levels of HNE and MDA are implicated in the progression of atherosclerosis and diabetes (J. Cell. Mol. Med., 15: 1339 (2011); Arthritis Rheum 62: 2064 (2010); Clin Exp Immunol, 101: 233 (1995); Int J Rheum Dis, 14: 325 (2011); JEADV 26: 833 (2012); Clin Rheumatol 25: 320 (2006); Gut 54: 987 (2005); J Am Soc Nephrol 20: 2119 (2009)). MDA is further implicated in the increased formation of foam cells leading to atherosclerosis (Leibundgut et al., Current Opinion in Pharmacology 13: 168 (2013)). Also, aldehyde-related toxicity plays an important role in the pathogenesis of many inflammatory lung diseases, such as asthma and chronic obstructive pulmonary disease (COPD) (Bartoli et al., Mediators of Inflammation 2011, Article 891752). Thus, compounds that reduce or eliminate aldehydes, such as compounds described herein, can be used to treat, prevent, and/or reduce a risk of an autoimmune, immune-mediated, inflammatory, cardiovascular, or neurological disease, disorder, or condition, or metabolic syndrome, or diabetes. For example, compounds described herein prevent aldehyde-mediated cell death in neurons. Further, compounds described herein downregulate a broad spectrum of pro-inflammatory cytokines and/or upregulate anti-inflammatory cytokines, which indicates that compounds described herein are useful in treating inflammatory diseases, such as multiple sclerosis and amyotrophic lateral sclerosis.

As discussed above, a disclosed composition may be administered to a subject in order to treat or prevent macular degeneration and other forms of retinal disease whose etiology involves the accumulation of A2E and/or lipofuscin. Other diseases, disorders, or conditions characterized by the accumulation A2E may be similarly treated.

In one embodiment, a compound is administered to a subject that reduces the formation of A2E. For example, the compound may compete with PE for reaction with trans-RAL, thereby reducing the amount of A2E formed. In another embodiment, a compound is administered to a subject that prevents the accumulation of A2E. For example, the compound competes so successfully with PE for reaction with trans-RAL, no A2E is formed.

Individuals to be treated fall into three groups: (1) those who are clinically diagnosed with macular degeneration or other forms of retinal disease whose etiology involves the accumulation of A2E and/or lipofuscin on the basis of visual deficits (including but not limited to dark adaptation, contrast sensitivity and acuity) as determined by visual examination and/or electroretinography, and/or retinal health as indicated by fundoscopic examination of retinal and RPE tissue for drusen accumulations, tissue atrophy and/or lipofuscin fluorescence; (2) those who are pre-symptomatic for macular degenerative disease but thought to be at risk based on abnormal results in any or all of the same measures; and (3) those who are pre-symptomatic but thought to be at risk genetically based on family history of macular degenerative disease and/or genotyping results showing one or more alleles or polymorphisms associated with the disease. The compositions are administered topically or systemically at one or more times per month, week or day. Dosages may be selected to avoid side effects, if any, on visual performance in dark adaptation. Treatment is continued for a period of at least one, three, six, or twelve or more months. Patients may be tested at one, three, six, or twelve months or longer intervals to assess safety and efficacy. Efficacy is measured by examination of visual performance and retinal health as described above.

In one embodiment, a subject is diagnosed as having symptoms of macular degeneration, and then a disclosed compound is administered. In another embodiment, a subject may be identified as being at risk for developing macular degeneration (risk factors include a history of smoking, age, female gender, and family history), and then a disclosed compound is administered. In another embodiment, a subject may have dry AMD in both eye, and then a disclosed compound is administered. In another embodiment, a subject may have wet AMD in one eye but dry AMD in the other eye, and then a disclosed compound is administered. In yet another embodiment, a subject may be diagnosed as having Stargardt disease and then a disclosed compound is administered. In another embodiment, a subject is diagnosed as having symptoms of other forms of retinal disease whose etiology involves the accumulation of A2E and/or lipofuscin, and then the compound is administered. In another embodiment a subject may be identified as being at risk for developing other forms of retinal disease whose etiology involves the accumulation of A2E and/or lipofuscin, and then the disclosed compound is administered. In some embodiments, a compound is administered prophylactically. In some embodiments, a subject has been diagnosed as having the disease before retinal damage is apparent. For example, a subject is found to carry a gene mutation for ABCA4 and is diagnosed as being at risk for Stargardt disease before any ophthalmologic signs are manifest, or a subject is found to have early macular changes indicative of macular degeneration before the subject is aware of any effect on vision. In some embodiments, a human subject may know that he or she is in need of the macular generation treatment or prevention.

In some embodiments, a subject may be monitored for the extent of macular degeneration. A subject may be monitored in a variety of ways, such as by eye examination, dilated eye examination, fundoscopic examination, visual acuity test, and/or biopsy. Monitoring can be performed at a variety of times. For example, a subject may be monitored after a compound is administered. The monitoring can occur, for example, one day, one week, two weeks, one month, two months, six months, one year, two years, five years, or any other time period after the first administration of a compound. A subject can be repeatedly monitored. In some embodiments, the dose of a compound may be altered in response to monitoring.

In some embodiments, the disclosed methods may be combined with other methods for treating or preventing macular degeneration or other forms of retinal disease whose etiology involves the accumulation of A2E and/or lipofuscin, such as photodynamic therapy. For example, a patient may be treated with more than one therapy for one or more diseases or disorders. For example, a patient may have one eye afflicted with dry form AMD, which is treated with a compound of the invention, and the other eye afflicted with wet form AMD which is treated with, e.g., photodynamic therapy.

In some embodiments, a compound for treating or preventing macular degeneration or other forms of retinal disease whose etiology involves the accumulation of A2E and/or lipofuscin may be administered chronically. The compound may be administered daily, more than once daily, twice a week, three times a week, weekly, biweekly, monthly, bimonthly, semiannually, annually, and/or biannually.

Sphingosine 1-phosphate, a bioactive signaling molecule with diverse cellular functions, is irreversibly degraded by the endoplasmic reticulum enzyme sphingosine 1-phosphate lyase, generating trans-2-hexadecenal and phosphoethanolamine. It has been demonstrated that trans-2-hexadecenal causes cytoskeletal reorganization, detachment, and apoptosis in multiple cell types via a JNK-dependent pathway. See Biochem Biophys Res Commun. 2012 Jul. 20; 424(1): 18-21. These findings and the known chemistry of related α,β-unsaturated aldehydes raise the possibility that trans-2-hexadecenal interact with additional cellular components. It was shown that it reacts readily with deoxyguanosine and DNA to produce the diastereomeric cyclic 1,N(2)-deoxyguanosine adducts 3-(2-deoxy-β-d-erythro-pentofuranosyl)-5,6,7,8-tetrahydro-8R-hydroxy-6R-tridecylpyrimido[1,2-a]purine-10(3H) one and 3-(2-deoxy-β-d-erythro-pentofuranosyl)-5,6,7,8-tetrahydro-8S-hydroxy-6S-tridecylpyrimido[1,2-a]purine-10(3H) one. These findings demonstrate that trans-2-hexadecenal produced endogenously by sphingosine 1-phosphate lyase react directly with DNA forming aldehyde-derived DNA adducts with potentially mutagenic consequences.

Succinic semialdehyde dehydrogenase deficiency (SSADHD), also known as 4-hydroxybutyric aciduria or gamma-hydroxybutyric aciduria, is the most prevalent autosomal-recessively inherited disorder of GABA metabolism (Vogel et al. 2013), manifests a phenotype of developmental delay and hypotonia in early childhood, and severe expressive language impairment and obsessive-compulsive disorder in adolescence and adulthood. Epilepsy occurs in half of patients, usually as generalized tonic-clonic seizures although sometimes absence and myoclonic seizures occur (Pearl et al. 2014). Greater than two-thirds of patients manifest neuropsychiatric problems (i.e., ADHD, OCD and aggression) in adolescence and adulthood, which can be disabling. Metabolically, there is accumulation of the major inhibitory neurotransmitter GABA and gamma-hydroxybutyrate (GHB), a neuromodulatory monocarboxylic acid (Snead and Gibson 2005). In addition, several other intermediates specific to this disorder have been detected both in patients and the corresponding murine model. Vigabatrin (VGB; γ-vinylGABA), an irreversible inhibitor of GABA-transaminase, is a logical choice for treatment of SSADH deficiency because it will prevent the conversion of GABA to GHB. Outcomes have been mixed, and in selected patients treatment has led to deterioration (Good 2011; Pellock 2011; Escalera et al. 2010; Casarano et al. 2011; Matern et al. 1996; Al-Essa et al. 2000). Targeted therapy for SSADH deficiency remains elusive and interventions palliative.

5. Pharmaceutically Acceptable Compositions

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, the compounds of the invention are administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention can also be administered topically, such as directly to the eye, e.g., as an eye-drop or ophthalmic ointment. Eye drops typically comprise an effective amount of at least one compound of the invention and a carrier capable of being safely applied to an eye. For example, the eye drops are in the form of an isotonic solution, and the pH of the solution is adjusted so that there is no irritation of the eye. In many instances, the epithelial barrier interferes with penetration of molecules into the eye. Thus, most currently used ophthalmic drugs are supplemented with some form of penetration enhancer. These penetration enhancers work by loosening the tight junctions of the most superior epithelial cells (Burstein, 1985, Trans Ophthalmol Soc U K 104(Pt 4): 402-9; Ashton et al., 1991, J Pharmacol Exp Ther 259(2): 719-24; Green et al., 1971, Am J Ophthalmol 72(5): 897-905). The most commonly used penetration enhancer is benzalkonium chloride (Tang et al., 1994, J Pharm Sci 83(1): 85-90; Burstein et al, 1980, Invest Ophthalmol Vis Sci 19(3): 308-13), which also works as preservative against microbial contamination. It is typically added to a final concentration of 0.01-0.05%.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1. General Reaction Sequence for Compounds

Deuterium-labeled aldehyde trapping agents were made as described in U.S. patent application publication US 2013/0190500, published Jul. 23, 2013, optionally using deuterium-labeled intermediates at the sites indicated in Scheme 1. Exemplary methods are described further below.

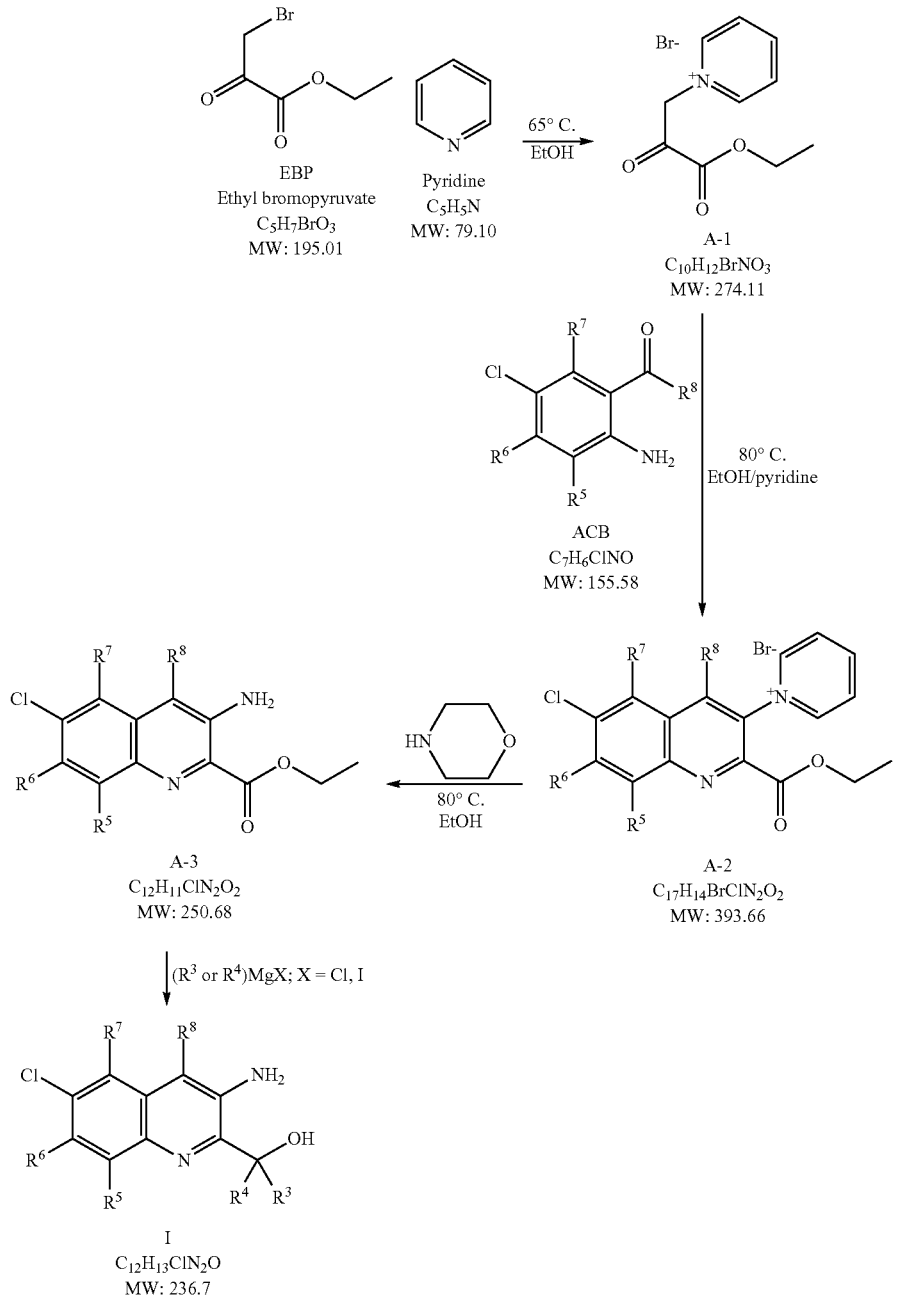

Example 2: Synthesis of A-1

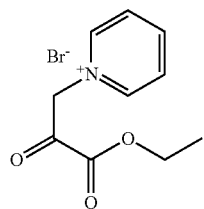

A-1

1-(3-ethoxy-2,3-dioxopropyl)pyridin-1-ium bromide. To a 2 L round bottom flask was charged ethanol (220 mL) and pyridine (31 g, 392 mmol), and the resulting solution was stirred at a moderate rate of agitation under nitrogen. To this solution was added ethyl bromopyruvate (76.6 g, 354 mmol) in a slow, steady stream. The reaction mixture was allowed to stir at 65 5° C. for 2 hours.

Example 3: Synthesis of A-2a

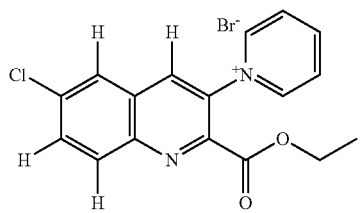

A-2a 1-(6-chloro-2-(ethoxycarbonyl)quinolin-3-yl)pyridin-1-ium bromide. Upon completion of the 2 hour stir time in Example 2, the reaction mixture was slowly cooled to 18-22° C. The flask was vacuum-purged three times at which time 2-amino-5-chloro-benzaldehyde (ACB) (50.0 g, 321 mmol) was added directly to the reaction flask as a solid using a long plastic funnel. Pyridine (64.0 g, 809 mmol) was added followed by an EtOH rinse (10 mL) and the reaction mixture was heated at 80±3° C. under nitrogen for about 16 hours (overnight) at which time HPLC analysis indicated that the reaction was effectively complete.

Example 4: Synthesis of A-2b

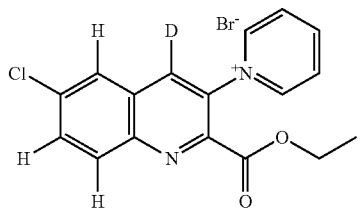

A-2b 1-(6-chloro-2-(ethoxycarbonyl)quinolin-3-yl-4-d)pyridin-1-ium. Compound A-2b is prepared in a manner similar to A-2a (See Example 3), substituting 2-amino-5-chloro-benzaldehyde (ACB) for 2-amino-5-chloro-benzaldehyde-d.

Example 5: Synthesis of A-3a

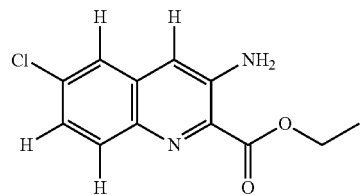

A-3a

Ethyl 3-amino-6-chloroquinoline-2-carboxylate. The reaction mixture from Example 3 was cooled to about 70° C. and morpholine (76.0 g, 873 mmol)) was added to the 2 L reaction flask using an addition funnel. The reaction mixture was heated at 80±2° C. for about 2.5 hours at which time the reaction was considered complete by HPLC analysis (area % of A-3a stops increasing). The reaction mixture was cooled to 10-15° C. for the quench, work up, and isolation.

To the 2 L reaction flask was charged water (600 g) using the addition funnel over 30-60 minutes, keeping the temperature below 15° C. by adjusting the rate of addition and using a cooling bath. The reaction mixture was stirred for an additional 45 minutes at 10-15° C. then the crude A-3a was isolated by filtration using a Buchner funnel. The cake was washed with water (100 mL×4) each time allowing the water to percolate through the cake before applying a vacuum. The cake was air dried to provide crude A-3a as a nearly dry brown solid. The cake was returned to the 2 L reaction flask and heptane (350 mL) and EtOH (170 mL) were added, and the mixture heated to 70±3° C. for 30-60 minutes. The slurry was cooled to 0-5° C. and isolated by filtration under vacuum. The A-3a was dried in a vacuum drying oven under vacuum and 35±3° C. overnight (16-18 hours) to provide A-3a as a dark green solid.

Example 6: Synthesis of A-3b

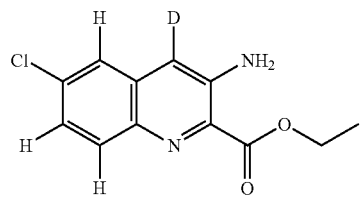

A-3b

Ethyl 3-amino-6-chloroquinoline-2-carboxylate-4-d. Compound A3-b is prepared in a similar manner as compound A3-a (See Example 5), substituting the reaction mixture of A2-a for that of A2-b.

Example 7: Synthesis of NS2

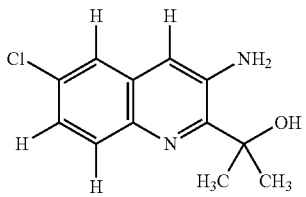

2-(3-amino-6-chloroquinolin-2-yl)propan-2-ol. To a 2 L round bottom flask was charged methylmagnesium chloride (200 mL of 3.0 M solution in THF, 600 mmol). The solution was cooled to 0-5° C. using an ice bath.

A 500 mL flask (magnetic stirring) was charged with 22.8 grams A-3a from Example 5 and THF (365 mL), stirred to dissolve, and then transferred to an addition funnel on the 2 L Reaction Flask. The A-3a solution was added drop-wise to the reaction flask over 5.75 hours, keeping the temperature of the reaction flask between 0-5° C. throughout the addition. At the end of the addition the contents of the flask were stirred for an additional 15 minutes at 0-5° C. then the cooling bath was removed and the reaction was allowed to stir overnight at ambient temperature.

The flask was cooled in an ice bath and the reaction mixture was carefully quenched by adding EtOH (39.5 g, 857 mmol) drop-wise to the reaction mixture, keeping the temperature of the reaction mixture below 15° C. during the course of the addition. An aqueous solution of $NH_4Cl$ (84.7 g $NH_4Cl$ in 415 mL water) was then carefully added and the mixture stirred under moderate agitation for about 30 minutes then transferred to a separatory funnel to allow the layers to separate. Solids were present in the aqueous phase so HOAc (12.5 g) was added and the contents swirled gently to obtain a nearly homogeneous lower aqueous phase. The lower aqueous layer was transferred back to the 2 L reaction flask and stirred under moderate agitation with 2-methyl-THF (50 mL) for about 15 minutes. The original upper organic layer was reduced in volume to approximately 40 mL using a rotary evaporator at ≤40° C. and vacuum as needed. The phases in the separatory funnel were separated and the upper 2-MeTHF phase combined with the product residue, transferred to a 500 mL flask, and vacuum distilled to an approximate volume of 25 mL. To this residue was added 2-MeTHF (50 mL) and distilled to an approximate volume of 50 mL. The crude compound NS2 solution was diluted with 2-MeTHF (125 mL), cooled to 5-10° C., and 2M $H_2SO_4$ (aq) (250 mL) was slowly added and the mixture stirred for 30 minutes as the temperature was allowed to return to ambient. Heptane (40 mL) was charged and the reaction mixture stirred for an additional 15 minutes then transferred to a separatory funnel, and the layers were allowed to separate. The lower aqueous product layer was extracted with additional heptane (35 mL), then the lower aqueous phase was transferred to a 1 L reaction flask equipped with a mechanical stirrer, and the mixture was cooled to 5-10° C. The combined organic layers were discarded. A solution of 25% NaOH (aq) was prepared (NaOH, 47 g, water, 200 mL) and slowly added to the 1 L reaction flask to bring the pH to a range of 6.5-8.5.

EtOAc (250 mL) was added and the mixture was stirred overnight. The mixture was transferred to a separatory funnel and the lower phase discarded. The upper organic layer was washed with brine (25 mL), then the upper organic product layer was reduced in volume on a rotary evaporator to obtain a obtain the crude compound NS2 as a dark oil that solidified within a few minutes. The crude compound NS2 was dissolved in EtOAc (20 mL) and filtered through a plug of silica gel (23 g) eluting with 3/1 heptane/EtOAc until all compound NS2 was eluted (approximately 420 mL required) to remove most of the dark color of compound NS2. The solvent was removed in vacuo to provide 14.7 g of compound NS2 as a tan solid. Compound NS2 was taken up in EtOAc (25 mL) and eluted through a column of silica gel (72 g) using a mobile phase gradient of 7/1 heptane/EtOAc to 3/1heptane/EtOAc (1400 mL total). The solvent fractions containing compound NS2 were stripped. Compound NS2 was diluted with EtOAc (120 mL) and stirred in a flask with Darco G-60 decolorizing carbon (4.0 g) for about 1 hour. The mixture was filtered through celite using a firtted funnel, rinsing the cake with EtOAc (3×15 mL). The combined filtrates were stripped on a rotary evaporator and compound NS2 dissolved in heptane (160 mL)/EtOAc(16 mL) at 76° C. The homogeneous solution was slowly cooled to 0-5° C., held for 2 hours, then compound NS2 was isolated by filtration. After drying in a vacuum oven for 5 hours at 35° C. under best vacuum, compound NS2 was obtained as a white solid. HPLC purity: 100% (AUC); HPLC (using standard conditions): A-2: 7.2 minutes; A-3: 11.6 minutes.

Example 8: Synthesis of I-1

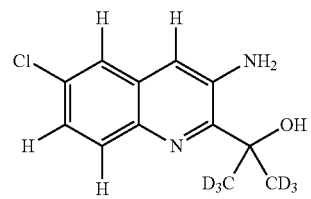 [SMILES: [2H]c1c(Cl)cc2cc(N)c(C(O)(C([2H])([2H])[2H])C([2H])([2H])[2H])nc2c1[2H]]

2-(6-chloroquinolin-2-yl)propan-1,1,1,3,3,3-$d_6$-2-ol. Compound I-1 was prepared in a similar manner to compound NS2 (See Example 7), substituting methylmagnesium chloride with methyl-$d_3$-magnesium iodide (99atom % D). The reaction of A3-a with 5.3 mol equiv 1.0 M methyl-$d_3$-magnesium iodide (99atom % D) in ether/THF gave a 20% yield of I-1. MS (ESI): m/z 242.9 (M+1); $^1$H NMR (CDCl$_3$, 300 MHz) δ: 7.80 (d, J=6 Hz, 1H), 7.51 (d, J=2 Hz, 1H), 7.33 (dd, J=2 and 2 Hz, 1H), 7.07 (s, 1H), 4.68 (br s, 2H), 3.83 (br s, 1H); $^{13}$C NMR (CDCl$_3$, 75 MHz) δ: 154.3, 139.5, 139.1, 132.4, 130.6, 130.0, 126.3, 123.7, 116.4, 76.8, 74.9.

Example 9: Synthesis of I-2

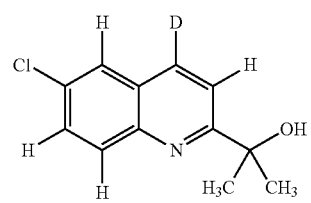

2-(6-chloroquinolin-2-yl-4-d)propan-2-ol. Compound 1-2 is prepared in a similar manner to compound NS2 (See Example 7), substituting A3-a for A3-b.

Preparation of ACB

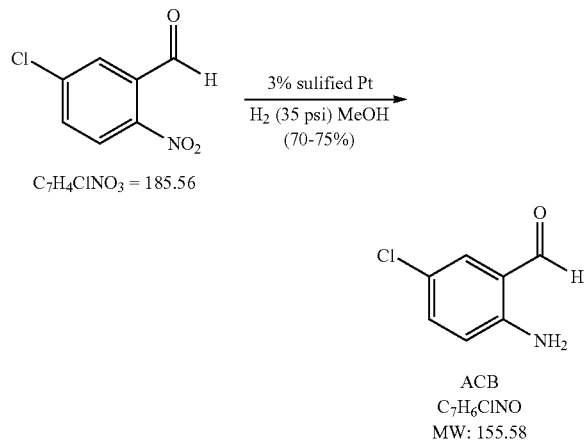

After a $N_2$ atmosphere had been established and a slight stream of $N_2$ was flowing through the vessel, platinum, sulfided, 5 wt % on carbon, reduced, dry (9.04 g, 3.0 wt % vs the nitro substrate) was added to a 5 L heavy walled pressure vessel equipped with a large magnetic stir-bar and a thermocouple. MeOH (1.50 L), 5-chloro-2-nitrobenzaldehyde (302.1 g, 1.63 mol), further MeOH (1.50 L) and $Na_2CO_3$ (2.42 g, 22.8 mmol, 0.014 equiv) were added. The flask was sealed and stirring was initiated at 450 rpm. The solution was evacuated and repressurized with $N_2$ (35 psi), 2×. The flask was evacuated and repressurized with $H_2$ to 35 psi. The temperature of the solution reached 30° C. w/in 20 min. The solution was then cooled with a water bath. Ice was added to the water bath to maintain a temperature below 35° C. Every 2 h, the reaction was monitored by evacuating and repressurizing with $N_2$ (5 psi), 2× prior to opening. The progress of the reaction could be followed by TLC: 5-Chloro-2-nitrobenzaldehyde ($R_f$=0.60, $CH_2Cl_2$, UV) and the intermediates ($R_f$=0.51, $CH_2Cl_2$, UV and $R_f$=0.14, $CH_2Cl_2$, UV) were consumed to give ACB ($R_f$=0.43, $CH_2Cl_2$, UV). At 5 h, the reaction had gone to 98% completion (GC), and was considered complete. To a 3 L medium fritted funnel was added celite (ca. 80 g). This was settled with MeOH (ca. 200 mL) and pulled dry with vacuum. The reduced solution was transferred via cannula into the funnel while gentle vacuum was used to pull the solution through the celite plug. This was chased with MeOH (150 mL 4×). The solution was transferred to a 5 L three-necked round-bottom flask. At 30° C. on a rotavap, solvent (ca. 2 L) was removed under reduced pressure. An $N_2$ blanket was applied. The solution was transferred to a 5 L four-necked round-bottomed flask equipped with mechanical stirring and an addition funnel. Water (2.5 L) was added dropwise into the vigorously stirring solution over 4 h. The slurry was filtered with a minimal amount of vacuum. The collected solid was washed with water (1.5 L 2×), 2-propanol (160 mL) then hexanes (450 mL 2×). The collected solid (a canary yellow, granular solid) was transferred to a 150×75 recrystallizing dish. The solid was then dried under reduced pressure (26-28 in Hg) at 40° C. overnight in a vacuum-oven. ACB (>99A % by HPLC) was stored under a $N_2$ atmosphere at 5° C.

Example 10: In Vitro Assays

LDH Cytotoxicity Assay

Primary rat cortical cultures are placed in an incubator for 24 or 48 hours and treated with various concentrations of disclosed compounds. Then 20 μL of the culture media is removed for an LDH assay as described in Bergmeyer et al., Methods of Enzymatic Analysis, $3^{rd}$ ed. (1983).

ELISA Assay to Determine Amount of Circulating Cytokines

Male C57Bl/6 mice are dosed with disclosed compounds 30 minutes before they were exposed to LPS (20 mg/kg). Two hours after the LPS exposure, blood is collected from the mice and an ELISA is conducted to determine the amount of circulating cytokines. Treatment with disclosed compounds leads to reduction in proinflammatory cytokines, such as IL-5 and IL-13, IL-17, and TNF. Also, treatment with disclosed compounds results in elevated anti-inflammatory cytokines, such as IL-10. In addition, various other chemokines, such as eotaxin, IL-12, IP-10, LIF, MCP-1, MIG, MIP, and RANTES, are also decreased by treatment with disclosed compounds.

Assay to Evaluate Efficacy in Treating Contact Dermatitis

To determine the efficacy of the disclosed compounds in treating contact dermatitis, phorbol myristate acetate ("PMA") is applied topically (2.5 μg in 20 μL) to both the anterior and posterior portions of the right pinna of mice (N=10 per group). As a control, the left pinna receives 20 μL of ethanol (PMA excipient) to both the anterior and posterior portions. Six hours after the PMA application, both the right and left pinna thickness is determined. Measurements are determined at least twice from the same region of both ears, with care taken not to include hair or folded pinna.

Assay to Evaluate the Efficacy in Treating Allergic Dermatitis

To measure the efficacy of the disclosed compounds in treating allergic dermatitis, oxazolone ("OXL") is applied (1.5%, 100 μL in acetone) to the shaved abdomens of mice. Seven days later, the thickness of the pinna of the OXL treated mice is determined. Then the disclosed compounds (100 mg/kg) or the vehicle (i.e., Captisol) is administered intraperitoneally to mice followed by topical application of OXL (1%, 20 μL) 30 min later to both the anterior and posterior portions of the right pinna. As a control, the left pinna receives 20 μL of acetone (OXL excipient) to both the anterior and posterior portions. The thickness of the pinna of both ears is measured again 24 hours later. N=10 per group.

Assay to Measure Aldehyde Trapping

To separate reaction vials is added each disclosed compound, (0.064 mmol), MDA salt (22.7% MDA, 0.064 mmol), and glyceryl trioleate (600 mg). To the mixture is added 20 wt % Capitsol in aqueous PBS (~2.5 ml), followed by linoleic acid (600 mg). The reaction mixture is stirred vigorously at ambient temperature and monitored by LC/MS. The disclosed compounds quickly react with MDA to form MDA adducts.

Schiff Base Confirmation

UV/VIS spectroscopy is used to monitor Schiff base condensation of RAL with the primary amine of a compound of the invention. The in vitro analysis of the Schiff base condensation product with RAL is performed for the disclosed compounds.

In the solution phase analysis, the $\lambda_{max}$ value of both the free compound and the RAL Schiff base condensation product (RAL-SBC) are measured along with the value for tau of the RAL-SBC. As used herein, "RAL-SBC" means the Schiff base condensation product of RAL and a RAL-compound. Solution phase analysis is performed using a 100:1 mixture of compound and RAL using protocols known in the art. Several solvent systems were tested including aqueous, ethanol, octanol, and chloroform:methanol (various e.g., 2:1). The solution kinetics are measured and found to be highly dependent on solvent conditions.

Solid phase analysis of the Schiff base condensation is also performed using a 1:1 mixture of compound to RAL. The solid phase analysis is performed using protocols known in the art. The mixture is dried under nitrogen and condensation reaction occurs to completion.

Lipid phase analysis is performed using protocols known in the art and $\lambda_{max}$, tau (RAL-SBC vs. APE/A2PE), and competitive inhibition are measured. Liposome conditions are closer to in situ conditions.

ERG Analysis of Dark Adaptation

Dark adaptation is the recovery of visual sensitivity following exposure to light. Dark adaptation has multiple components including both fast (neuronal) processes and a slow (photochemical) process. Regeneration of visual pigment is related to the slow photochemical process. Dark adaptation rates are measured for several reasons. Night blindness results from a failure to dark adapt (loss of visual light sensitivity). It is possible to find a safe dose for night vision by measuring drug effects on dark adapted visual light sensitivity.

An electroretinogram (ERG) is used to measure dark adaptation under normal vs. drug conditions. ERG is the measurement of the electric field potential emitted by retinal neurons during their response to an experimentally defined light stimulus. More specifically, ERG measures retinal field potentials at the cornea after a flash of light (e.g., 50 ms). Field strengths are 102 to 103 microvolts, originating in retinal cells.

ERG is a non-invasive measurement which can be performed on either living subjects (human or animal) or a hemisected eye in solution that has been removed surgically from a living animal. ERG requires general anesthesia which slows dark adaptation and must be factored into experimental design.

In a typical ERG analysis of dark adaptation experiment, every rat is dark adapted for hours to reach a consistent state of light sensitivity. The rat is then "photo-bleached," i.e., exposed briefly to light strong enough to transiently deplete the retina of free 11-cis-RAL (e.g., 2 min at 300 lux). The rat is then returned to dark immediately to initiate dark adaptation, i.e., recovery of light sensitivity due to regeneration of visual pigment. ERG is used to measure how quickly the rat adapts to dark and recovers light sensitivity. Specifically, a criterion response variable is defined for light sensitivity.

The ERG measurement is taken after a specific duration of post-bleach dark recovery (e.g., 30 min) determined previously by kinetic analysis. A curve fit is used to calculate value for the sensitivity variable and shows recovery with anesthesia in the same rat including dark adaptation kinetics for $Y_{50}$ and σ. Slower adaptation is observed with less light sensitivity where $Y_{50}$ reaches −4.0 and tau=22.6 min. Faster adaptation is observed with more light sensitivity where $Y_{50}$ reaches −5.5 and tau=9.2 min.

The same paradigm as described above is followed for dose ranging. In the ERG dose ranging protocol, compounds i.p. lowers light sensitivity of dark adapted rats in a dose dependent manner. The effect on vision decreases after 3 hours.

NMR Analysis of RAL Reaction

NMR spectroscopy is used to monitor Schiff base condensation and ring formation of RAL with the primary amine of a compound of the invention.

Inhibition of A2E Formation

This experiment is designed to establish proof of concept that chronic i.p. injection of a RAL-trap compound lowers the accumulation rate of A2E in wild type Sprague Dawley rats. These experiments compare the treatment efficacy of RAL-trap compounds to that of control compounds and lack of treatment.

Materials and Methods:

The study is performed with wild type Sprague Dawley rats. Rat treatment groups include, for example, 8 rats of mixed gender per treatment condition. Each animal is treated with one of the following conditions:

Controls: (1) 13-cis retinoic acid to inhibit retinoid binding sites of visual cycle proteins as a protocol control, in that such treatment reduces the amount of free trans-RAL that is released and thereby available to form A2E, but with undesirable side effects of night blindness, and (2) a commercially available compound known clinically to modulate retinal function in humans and known experimentally to form a Schiff base adduct with free RAL, both in vitro and in vivo in animal models.

Vehicle

Compound

Untreated

The disclosed compounds are tested across a dose range including 1, 5, 15, and 50 mg/kg. Treatment is administered daily for 8 weeks by i.p. injection.

Chemistry:

The experiments use a variety of chemistry services. For example, these experiments use commercially available compounds with analytical specification sheets to characterize the impurities. Compounds are also synthesized. Compounds are prepared in quantities sufficient for the required dosing. Formulations of the compound are suitable for use in initial animal safety studies involving intraperitoneal (i.p.) injection. The following three attributes of the Schiff base reaction product of trans-RAL with compounds of the invention are determined:

stability with respect to reaction rates absorption properties, specifically uv-vis absorption maxima and extinction coefficients (see e.g., FIG. 5 in Rapp and Basinger, Vision Res. 22:1097, 1982) or NMR spectral analysis of reaction kinetics log P and log D solubility values e.g. calculated Biology and Biochemistry:

The experiments described herein use a variety of biology and biochemistry services. A "no effect level" (NOEL) dose of compounds of the invention for daily treatment with an eye drop formation is established, e.g., in the rabbit with an ocular irritation protocol and in the rodent with ERG measurement of dark adaptation in visual responses to light stimulation. After treatment and before eye enucleation, the following non-invasive assays are performed in animals, e.g., rabbits:

RPE and photoreceptor cell degeneration, as evident by fundus photography (Karan, et al. 2005, PNAS 102: 4164)

Extracellular drusen and intracellular lipofuscin as measured by fundus fluorescent photography (Karan et al. 2005)

Light responses are characterized by ERG (Weng, et al., Cell 98:13, 1999). Intracellular A2E concentration of retinal RPE cell extracts is measured in all treated animals upon the conclusion of the treatment protocol using an analytical method such as those described by Karan et al., 2005; Radu et al., 2003; and Parish et al., PNAS 95:14609, 1998. For example, in a sample of treated animals, one eye is assayed, and the other eye is saved for histology analysis (as described below). In the remaining animals, both eyes are assayed separately for A2E formation.

In the post-treatment eyes set aside for histology (as described above), the morphology of retinal and RPE tissue is assessed with light microscopy histology techniques (Karan et al. 2005, with the exception that electron microscopy is not used in the experiments described herein).

The safety of the treatment regimen is assessed for example using a combination of:
Daily documented observation of animal behavior and feeding habits throughout the treatment period
Visual performance as measured by ERG at the end of the treatment period
Ocular histology at the end of the treatment

Example 11: Cross-Species Metabolite Profiling Test of Deuterated NS2 (NS2-D6; Compound I-1)

Purpose:

Once administered to an animal, small molecules may undergo a variety of reactions to produce an array of metabolites. The exact metabolites produced depend on many factors such as the animal, the molecular structure, and the tissue distribution of the molecule. Metabolism of small molecules may serve the purpose of increasing water solubility to aid in excretion of the molecule in the urine or feces, or may simply be the result of adventitious enzyme-catalyzed reactions. Exemplary metabolites include oxidation and glucuronidation products. It is often impossible to predict the distribution and amount of metabolites produced. One purpose of this study was to conduct a cross species metabolite profiling of test article NS2 in cryopreserved primary hepatocytes. As described below, a variety of NS2 metabolites were produced and the distribution of metabolites varied significantly across different species. It is often desirable to decrease the number and amount of metabolites of small molecule drugs, for example to increase drug half-life in the body and/or prevent conversion to toxic or inactive metabolites. With this knowledge in hand, deuteration of NS2 was explored as a possible route to decrease the number and amount of metabolites. Deuteration of a molecule (i.e., replacement of one or more hydrogen atoms with deuterium) often has significant effects on the rates of production of metabolites; however, the effects of deuteration on a given molecule are almost impossible to predict in most cases. Therefore, metabolite profiling was performed for deuterated-NS2 in human hepatocytes.

Study Conditions:

This study was performed under non-GLP conditions. All work was performed with appropriate local health regulations and ethical approval.

Experimental Design:

Sample Analysis

Samples were analyzed by LC-MS/MS using a SCIEX QTrap 5500 mass spectrometer coupled with an Agilent 1290 HPLC Infinity series, a CTC PAL chilled autosampler, all controlled by Analyst software. After separation on a C18 reverse phase HPLC column (Acquity UPLC HSS T3, 1.8, 2.1×50 mm) using an acetonitrile-water gradient system, peaks were analyzed by mass spectrometry (MS) using ESI ionization in Q1 scan mode. LC conditions are shown in Table 3 below.

TABLE 3

| | LC Gradient | | |
|---|---|---|---|
| Time (min) | Flow rate (mL/min) | % A Mobile Phase | % B Mobile Phase |
| 0.05 | 0.6 | 100 | 2 |
| 5.0 | 0.6 | 60 | 40 |
| 6.0 | 0.6 | 5 | 95 |
| 6.4 | 0.6 | 5 | 95 |
| 6.41 | 0.6 | 100 | 0 |
| 6.8 | 0.6 | 100 | 0 |

Solution A: $H_2O$ with 0.1% formic acid;
Solution B: Acetonitrile with 0.1% formic acid Table 4 shows experimental parameters for metabolite profiling.

TABLE 4

| Metabolite Profiling in Hepatocytes: Experimental Conditions | | | | | |
|---|---|---|---|---|---|
| Test Article | Test conc. | Hepatocyte source | Cell count | Time Points Profiled | Analytical method |
| NS2 (all 4 species) D-NS2 (human only) | 3 μM | Rat, dog, monkey (cyno) and human | $1 \times 10^6$ viable cells/mL | 0 and 120 min | LC-MS/MS |

Experimental Procedure

The test article was incubated in duplicate with primary, cryopreserved hepatocytes at 37° C. The cells were thawed, viable cells counted, and equilibrated according to the supplier's directions. After 30 min equilibration at 37° C. with gentle agitation, the test compound was added into the cells to give the desired final concentration of 3 μM. The cell suspension was incubated at 37° C. as described above. At the indicated times, samples were removed and mixed with an equal volume of ice-cold stop solution (methanol).

In parallel, a blank hepatocyte sample in the absence of test agent was incubated for 120 min and was used as a control to show the presence of peaks derived from the hepatocytes. Stopped reactions were incubated at least ten minutes on ice, and an additional volume of water was added. The samples are centrifuged to remove precipitated protein, and the supernatants were analyzed by LC-MS/MS.

A full scan mass spectrum (100-800 m/z) in both positive and negative ionization modes were run across the gradient to look for the presence of potential metabolites (novel masses and known Phase I and II metabolites such as: oxidation, sulfation, di-oxidation, dehydrogenation, sulfation+oxidation, glucuronidation, oxidation+glucuronidation, and glutathione conjugation). The mass spectrometry method is shown below in Table 5.

TABLE 5

Mass Spectrometry Method Development

| Test Article | MW | ESI Polarization | Full Scan Mass Range |
|---|---|---|---|
| NS2 CoteRX micronized Lot 093 (Origin Lot BR-NS2-11-01) | 236.7 | Positive | 100-800 |
| D-NS2 (Lot 1509342002) D-NS2: deuterated N32 (C12H7ClN2Od6) | 242.7 | Positive | 100-800 |

Results

Figure 2:
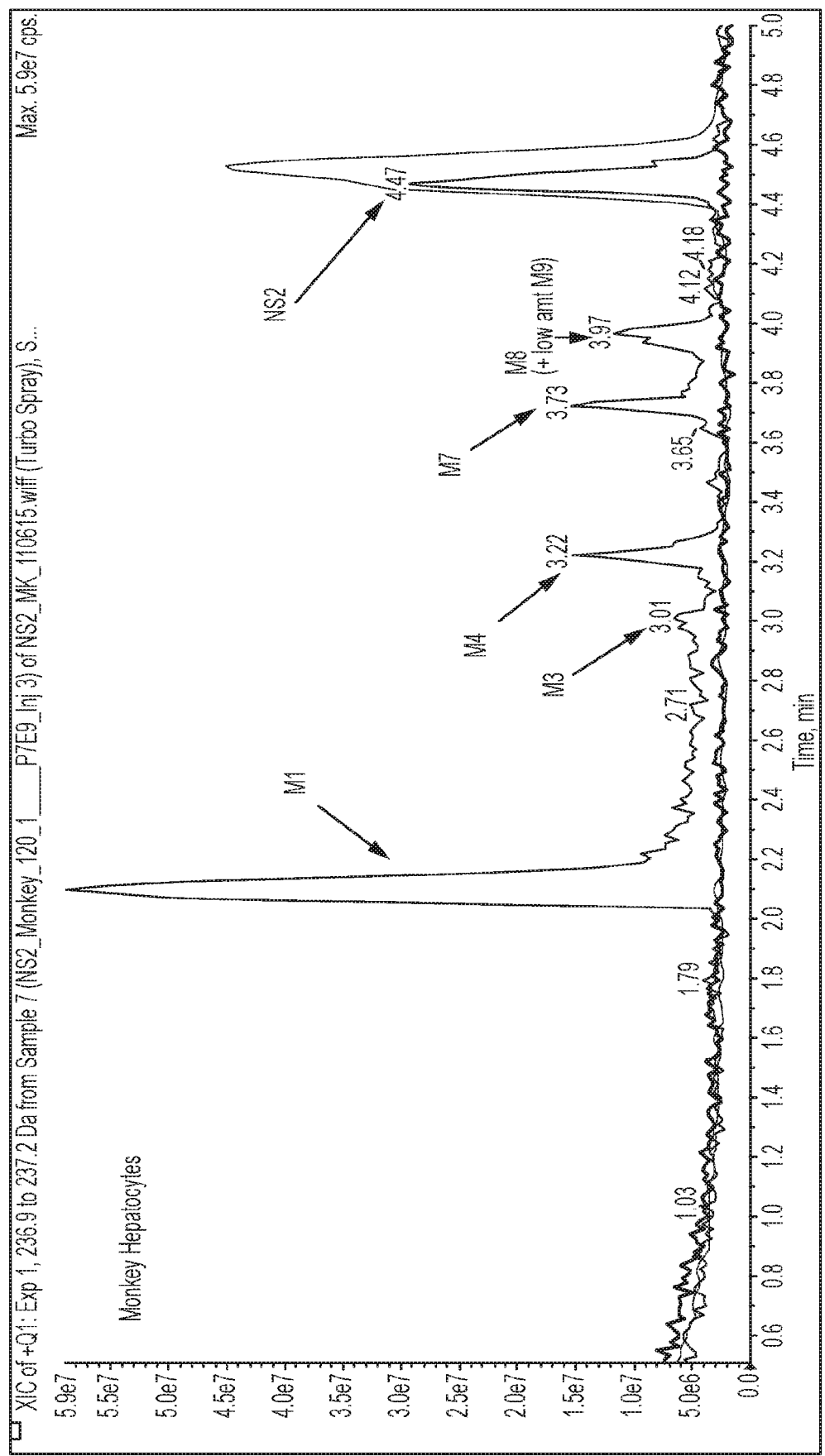
FIG. 2 shows overlays of EICs of the metabolite profiles of NS2 at 0 min and 120 min in monkey hepatocytes compared with a reference (blank hepatocytes). As the overlays show, after 120 min NS2 is metabolized to M1, M3, M4, M7, M8, and a low amount of M9, with some unchanged NS2 remaining.
Figure 3:
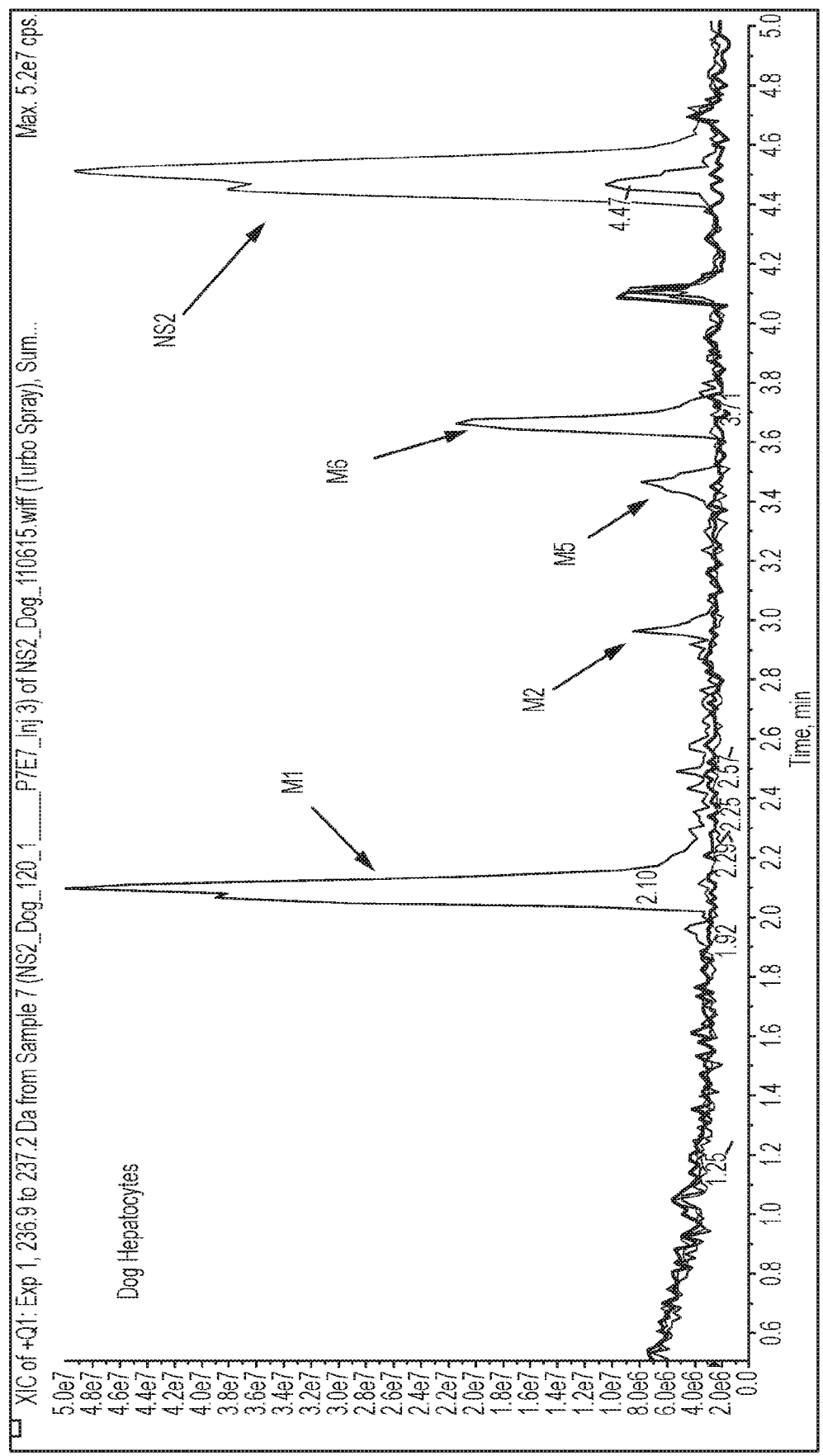
FIG. 3 shows overlays of EICs of the metabolite profiles of NS2 at 0 min and 120 min in dog hepatocytes compared with a reference (blank hepatocytes). As the overlays show, after 120 min NS2 is metabolized to M1, M2, M5, and M6, with some unchanged NS2 remaining.
Figure 4:
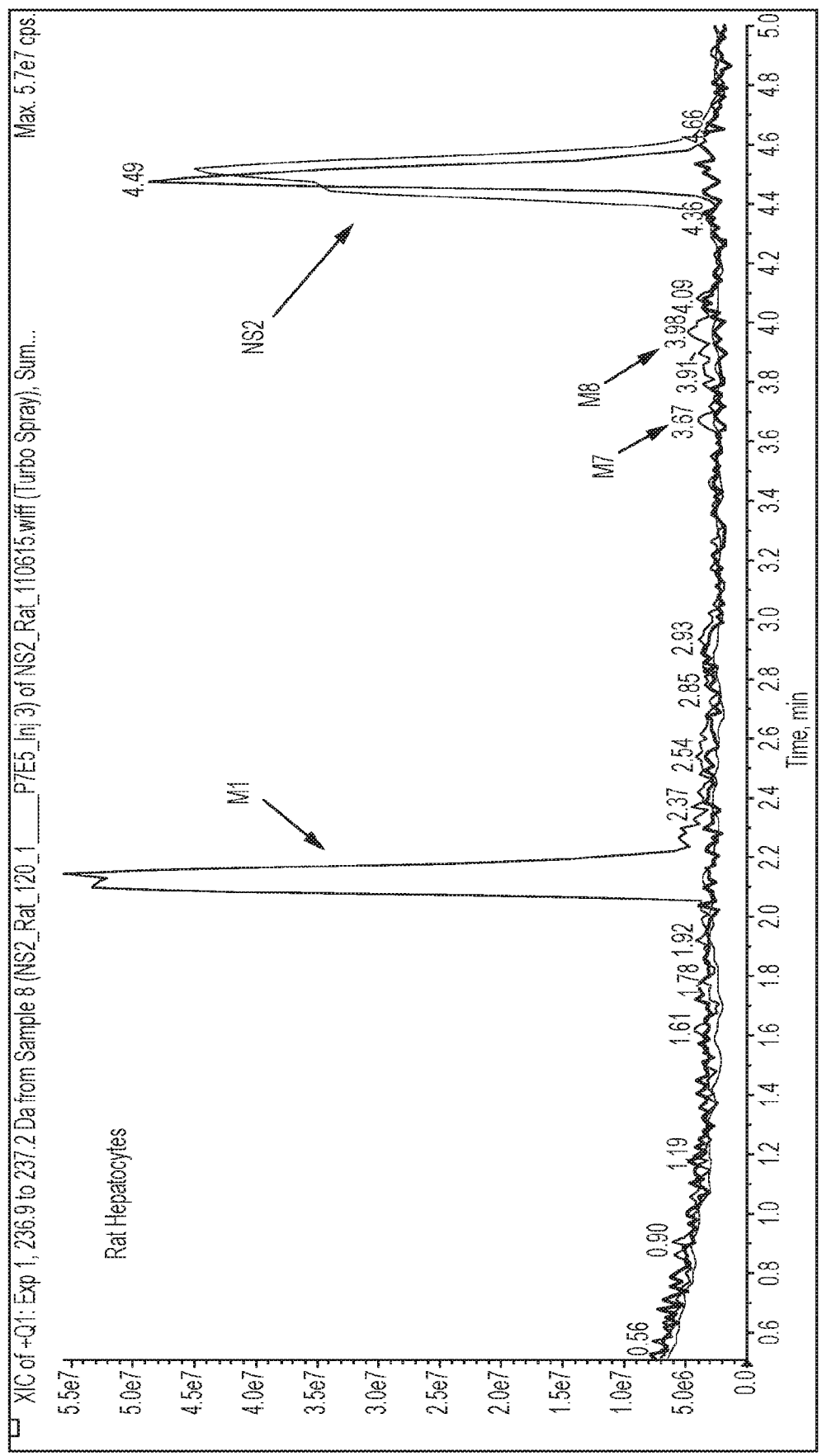
FIG. 4 shows overlays of EICs of the metabolite profiles of NS2 at 0 min and 120 min in rat hepatocytes compared with a reference (blank hepatocytes). As the overlays show, after 120 min NS2 is metabolized to M1, M7, and M8, with some unchanged NS2 remaining.

It was surprisingly found that deuteration of NS2 greatly reduced the number and amounts of metabolites in human hepatocytes. As summarized in Tables 6A and 6B below, the proteo-(non-deuterium enriched) form of NS2 was significantly metabolized over the course of only 120 mo by rat, dog, monkey, or human hepatocytes. For example, dog hepatocytes metabolized NS2 into two different mono-oxidation products (M1 and M2) and two different glutathione (GSH) conjugates (M5 and M6), as evaluated by LC retention times and mass spectrometry data (see FIG. 3). Cyno monkey hepatocytes metabolized NS2 into a mono-oxidation metabolite (M), four oxidation+glucuronidation metabolites (M3, M4, M7, and M9), and a glucuronidation metabolite (M) (see FIG. 2). Human hepatocytes metabolized NS2 into a mono-oxidation metabolite (M), two oxidation+glucuronidation metabolites (M7 and M9), and a glucuronidation metabolite (M) (see FIG. 1).

Relative degree of observed metabolite formation is denoted by "+", with ++++ being the most abundant metabolite (assuming that the ionization potential of the parent is similar to that of the metabolites)

TABLE 6B

Peak Areas of Observed Metabolites

| | Peak Areas Observed Metabolites (T-120 mm) | | | |
|---|---|---|---|---|
| Analyte | Rat | Dog | Cyno Monkey | Human |
| NS2 | 3.14E+08 | 4.79E+07 | 1.74E+08 | 4.41E+08 |
| M1 | 4.25E+08 | 2.83E+08 | 4.47E+08 | 2.57E+08 |
| M2 | | 1.58E+07 | | |
| M3 | | | 7.50E+06 | |
| M4 | | | 1.92E+07 | |
| M5 | | 1.69E+07 | | |
| M6 | | 7.67E+07 | | |
| M7 | trace | | 1.35E+07 | 1.62E+07 |
| M8 | trace | | 3.15E+07 | 4.67E+07 |
| M9 | | | 1.22E+07 | 1.51E+07 |

Mass spectral analysis of NS2, each metabolite M1-M9, deuterated NS2, and the metabolite produced in human hepatocytes from deuterated NS2 are shown in FIGS. 6-17.

Figure 5:
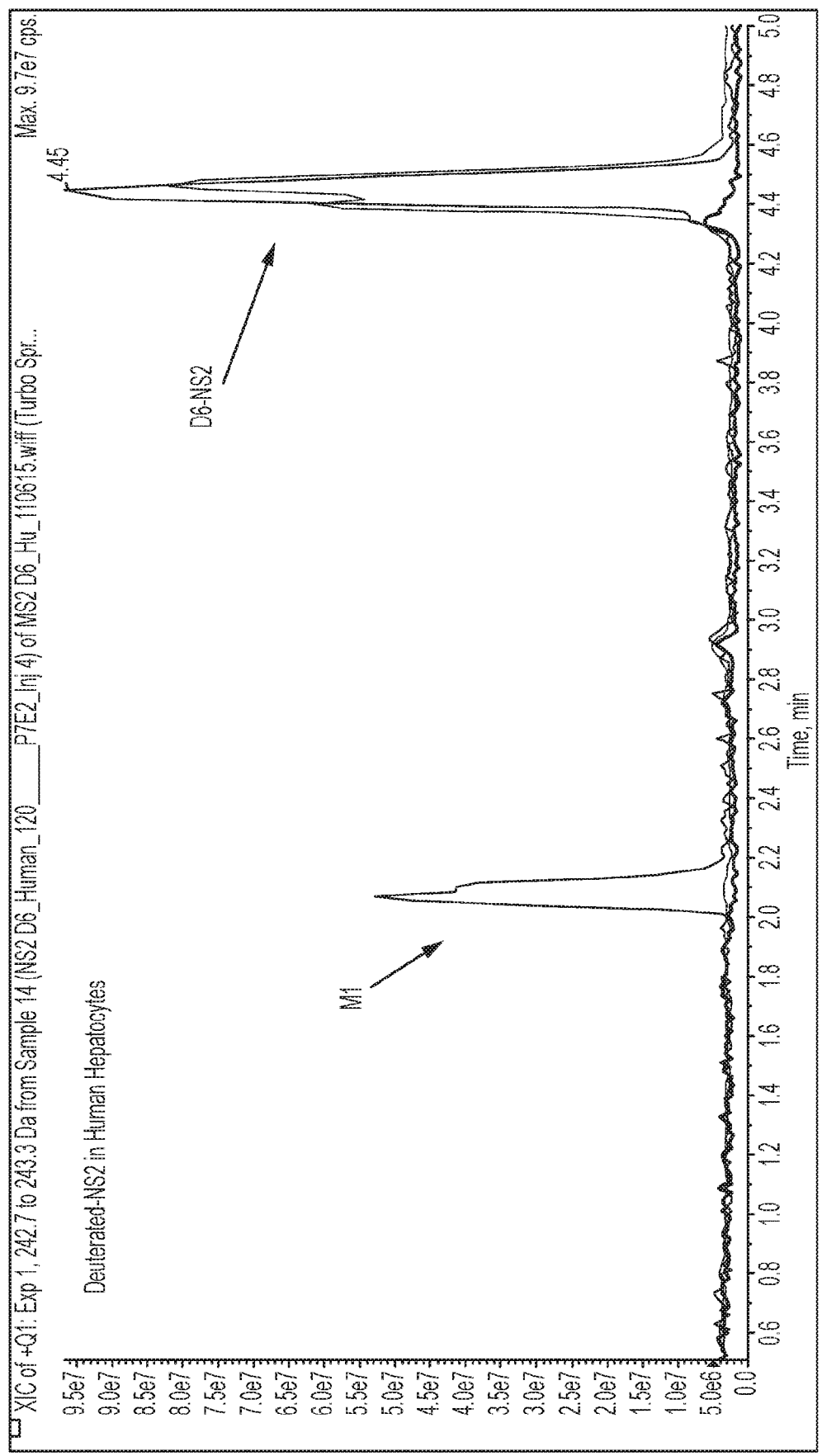
FIG. 5 shows overlays of EICs of the metabolite profiles of Deuterated NS2 (NS2-D6; compound I-1) at 0 min and 120 min in human hepatocytes compared with a reference (blank hepatocytes). As the overlays show, after 120 min NS2-D6 is metabolized to a small amount of M1, with mostly unchanged NS2-D6 remaining.
Figure 6:
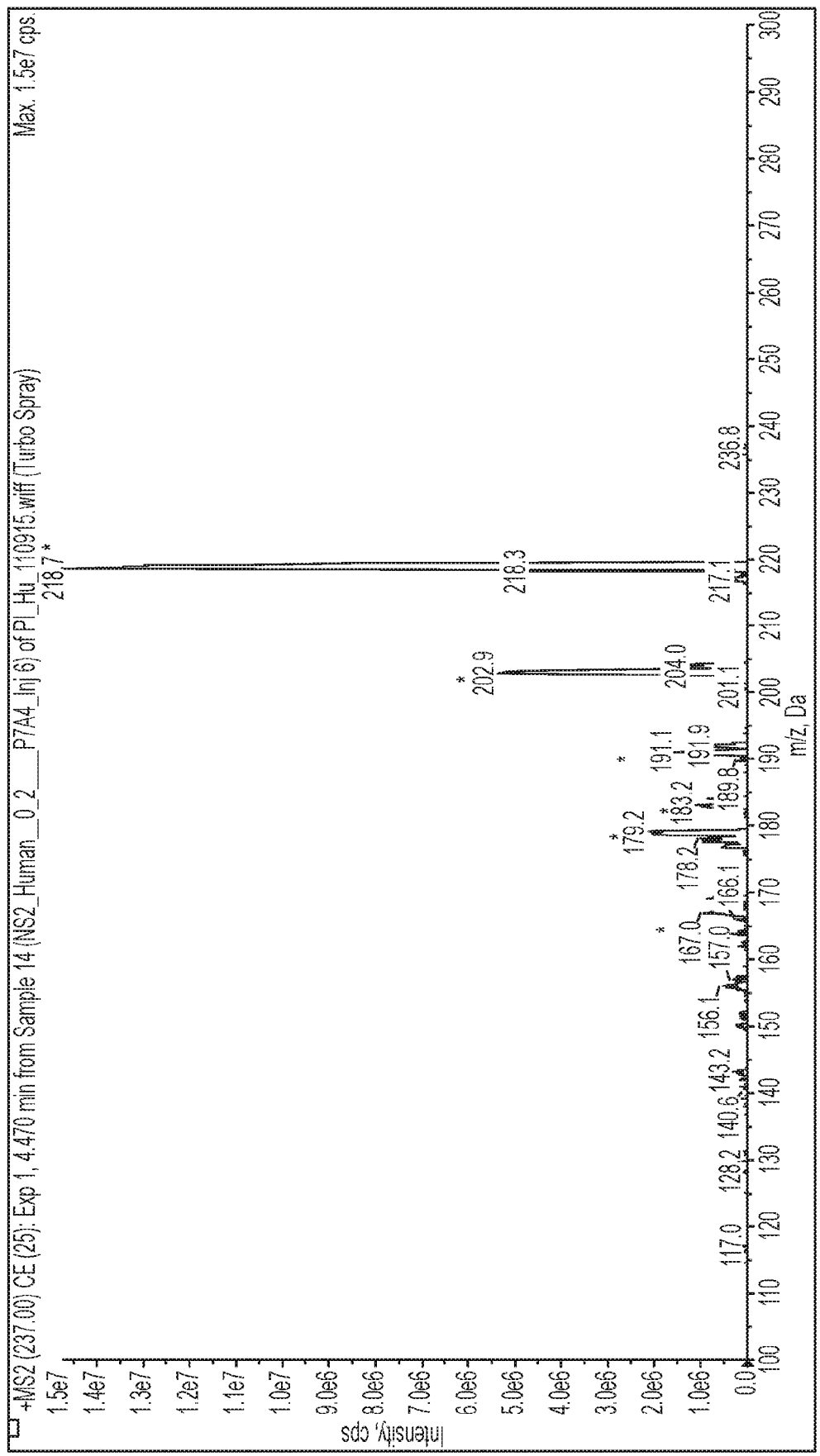
FIG. 6 shows mass spectral analysis of NS2 (m/z=237).
Figure 7:
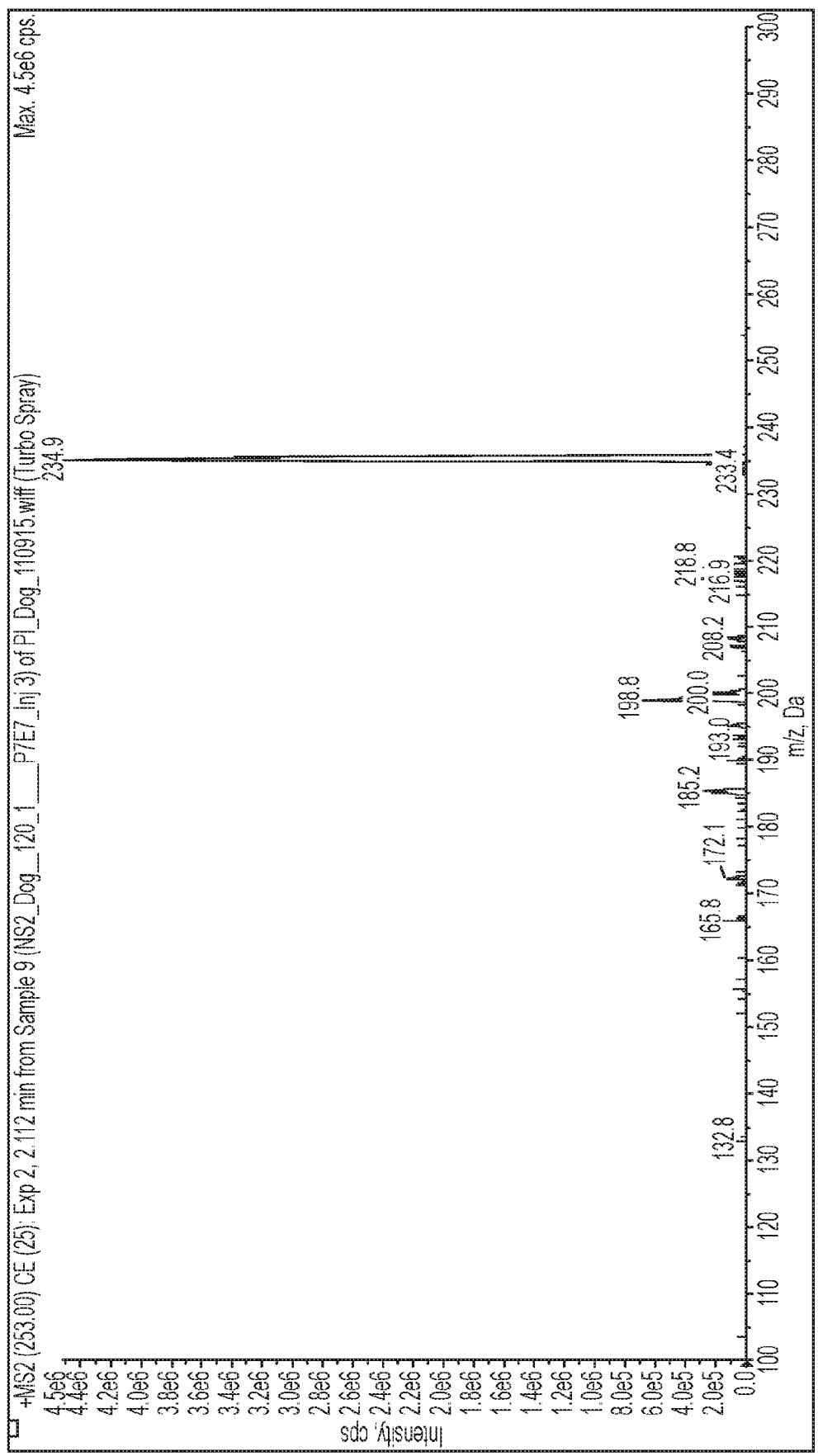
FIG. 7 shows mass spectral analysis of metabolite M1 (m/z=253, RT=2.1 min).
Figure 8:
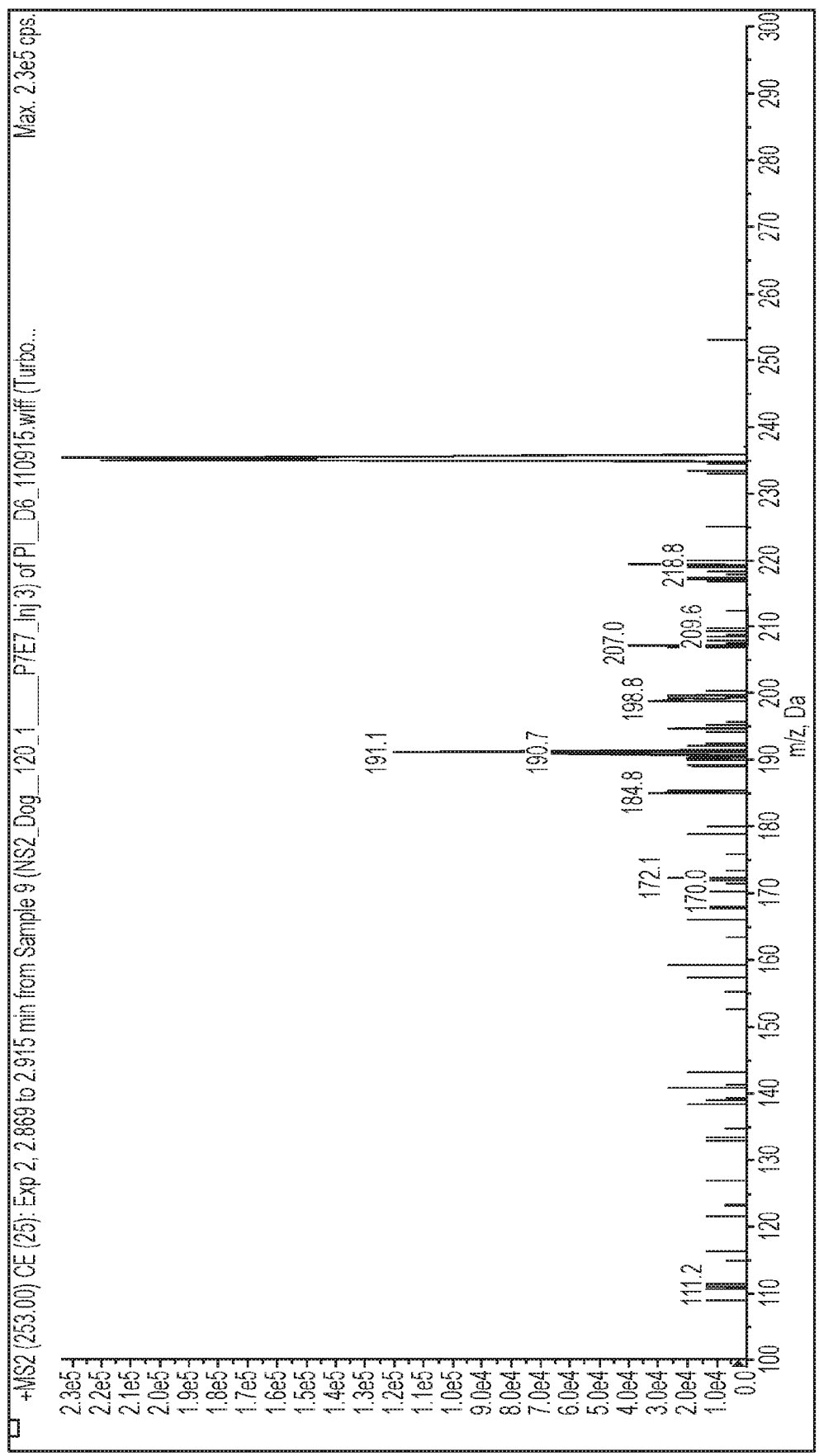
FIG. 8 shows mass spectral analysis of metabolite M2 (m/z=253, RT=2.9 min).
Figure 9:
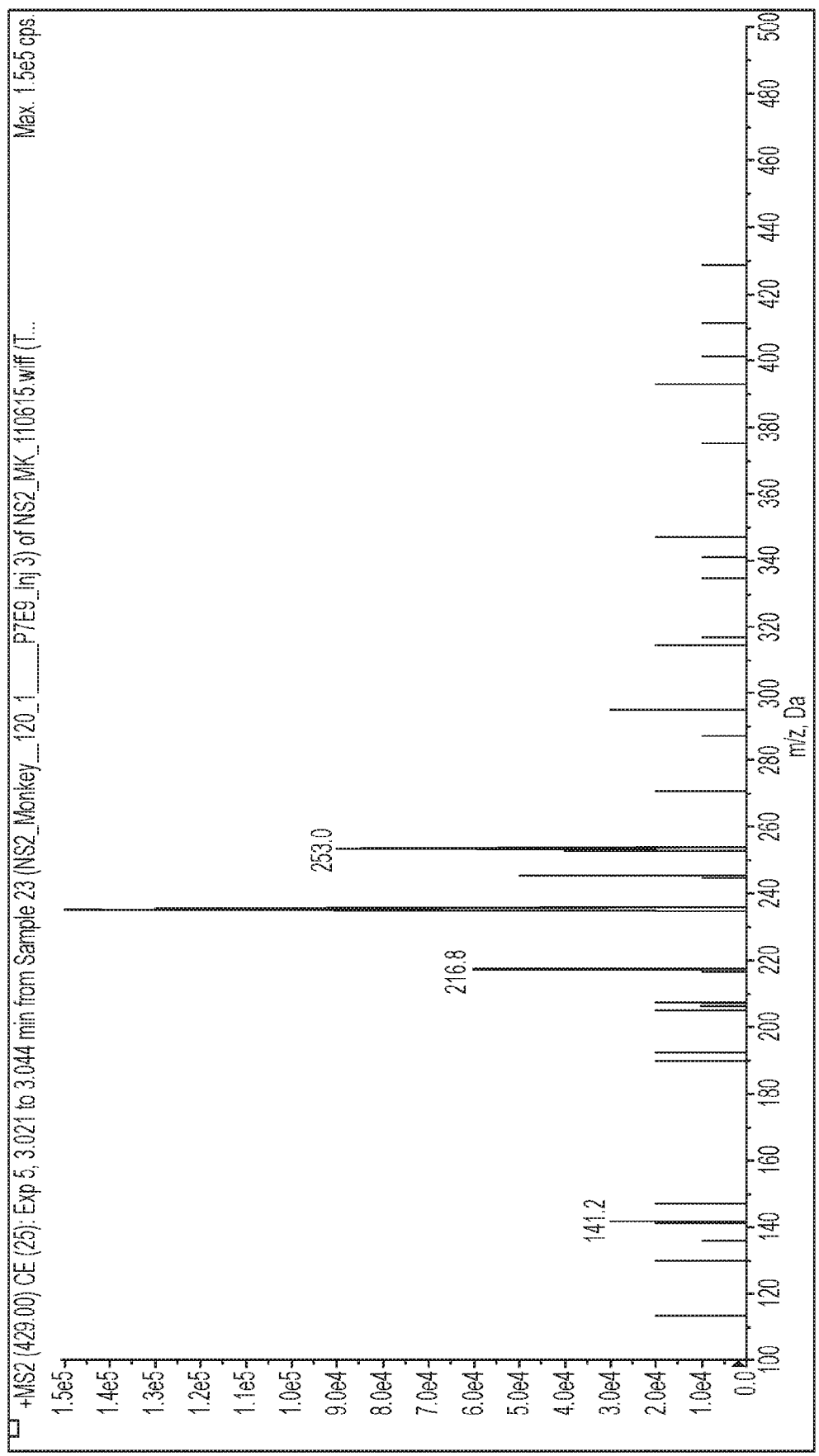
FIG. 9 shows mass spectral analysis of metabolite M3 (m/z=429, RT=3.0 min).
Figure 10:
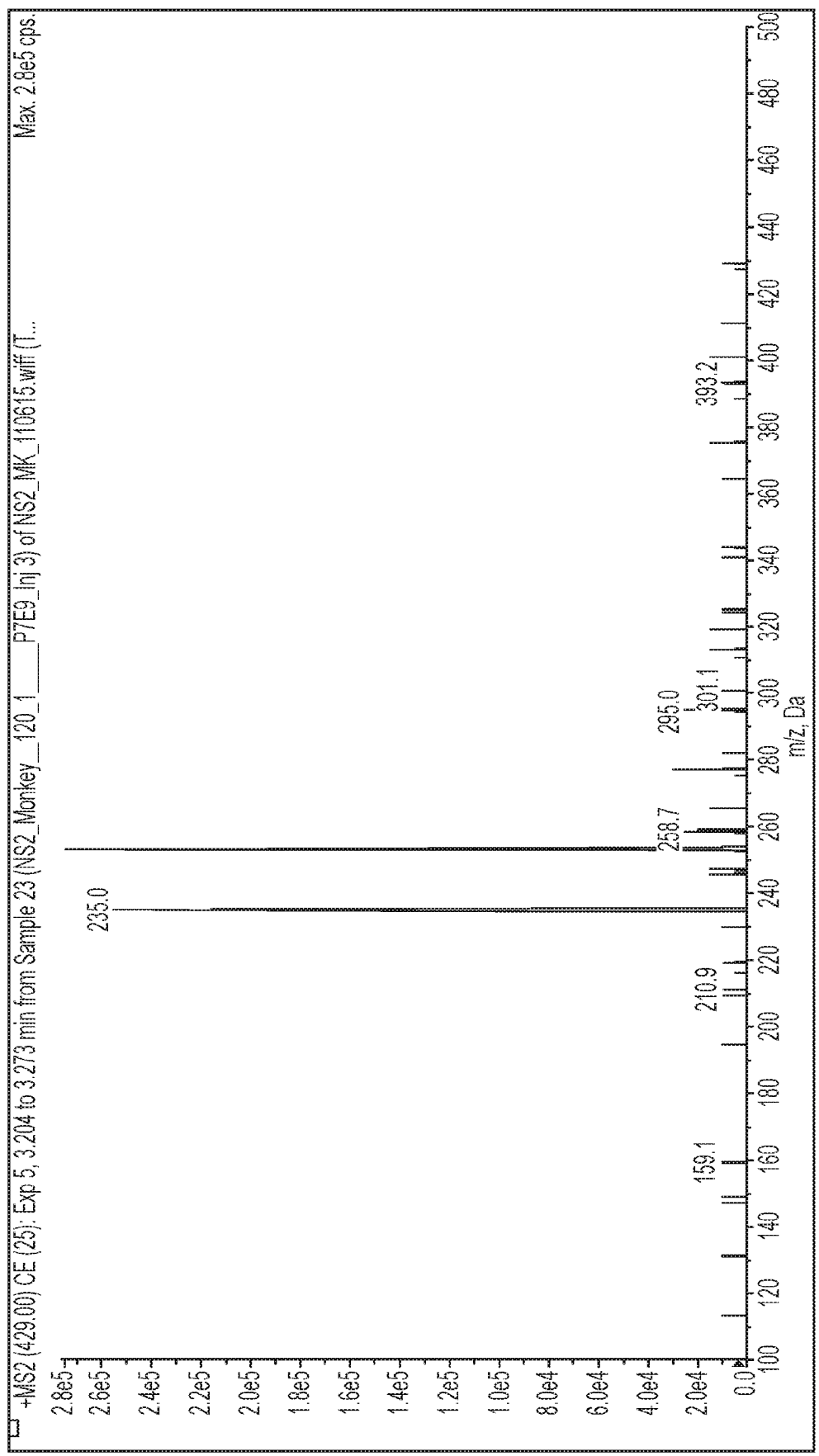
FIG. 10 shows mass spectral analysis of metabolite M4 (m/z=429, RT=3.2 min).
Figure 11:
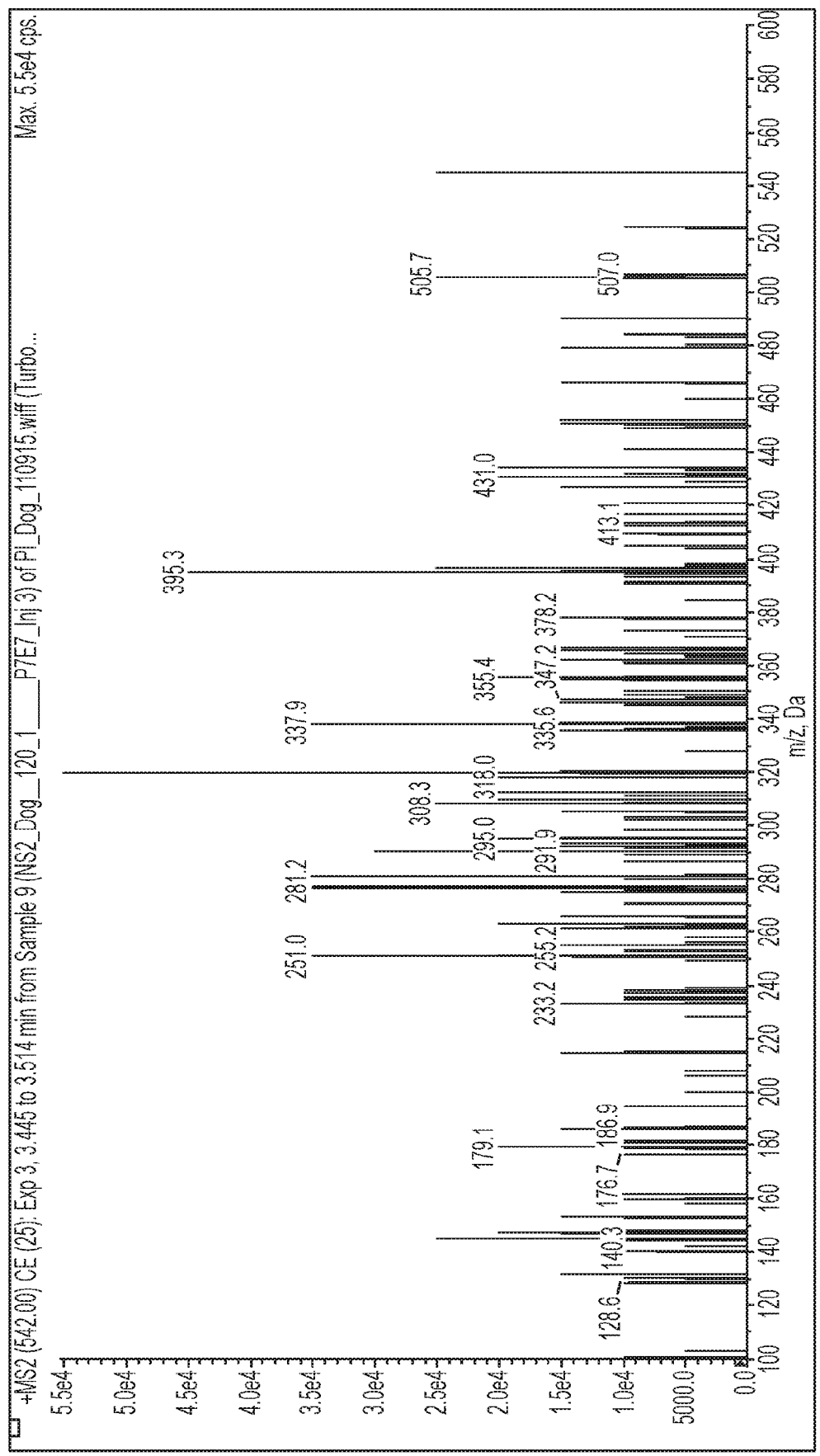
FIG. 11 shows mass spectral analysis of metabolite M5 (m/z=542, RT=3.5 min).
Figure 12:
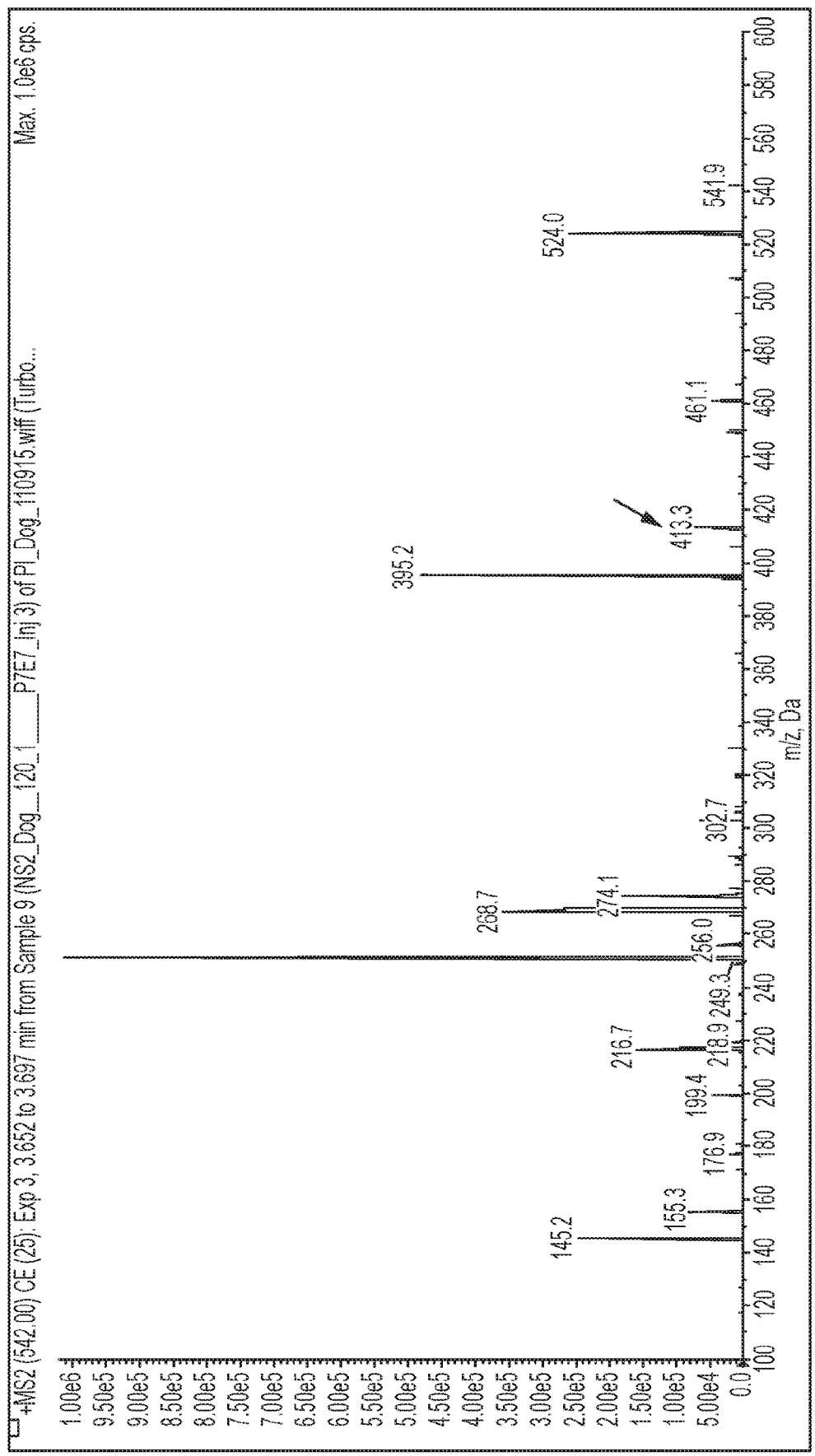
FIG. 12 shows mass spectral analysis of metabolite M6 (m/z=542, RT=3.7 min). Note: m/z of 413 represents a neutral loss (NL) of 129, indicative of GSH fragmentation pattern.
Figure 13:
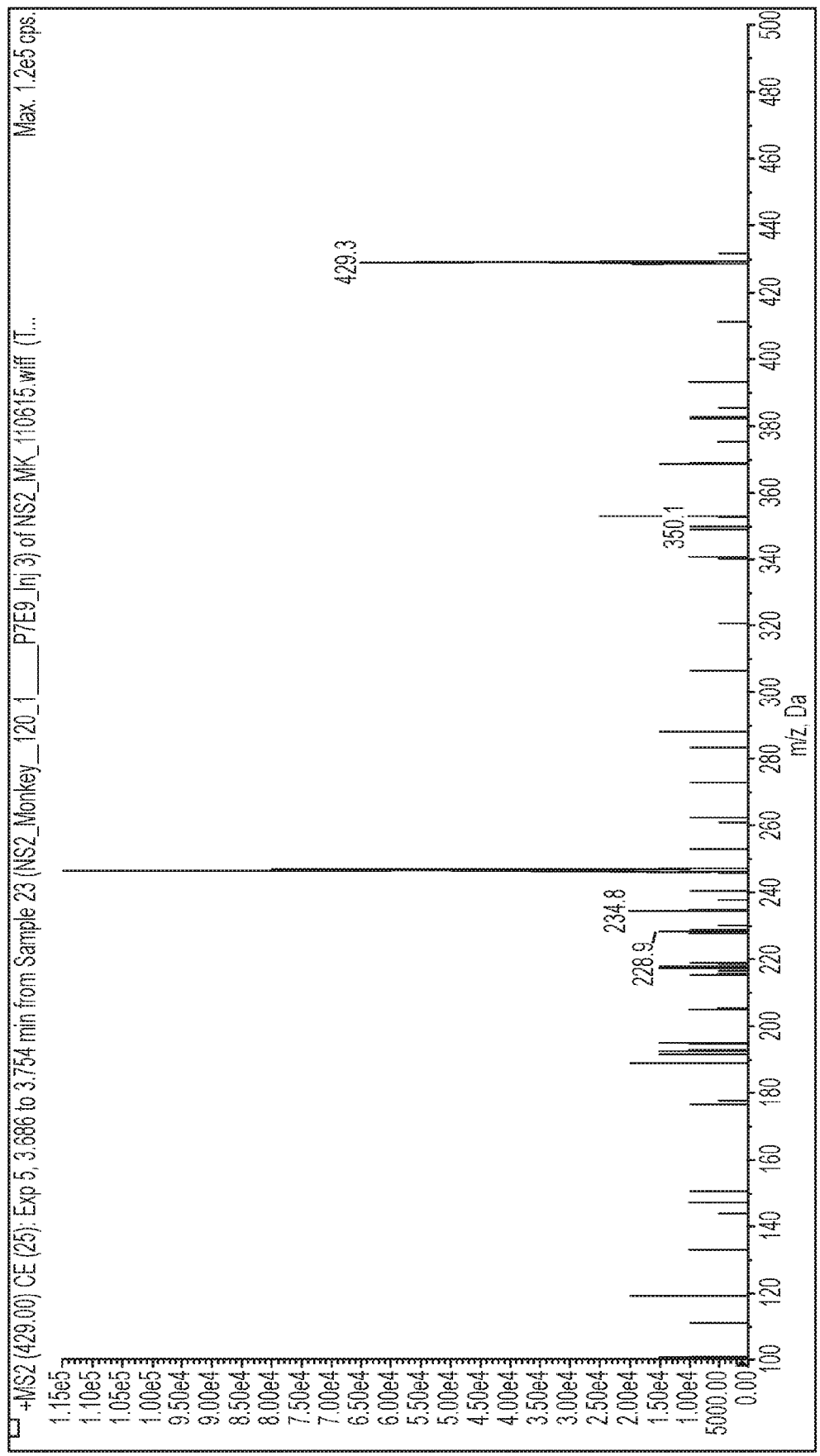
FIG. 13 shows mass spectral analysis of metabolite M7 (m/z=429, RT=3.7 min).
Figure 14:
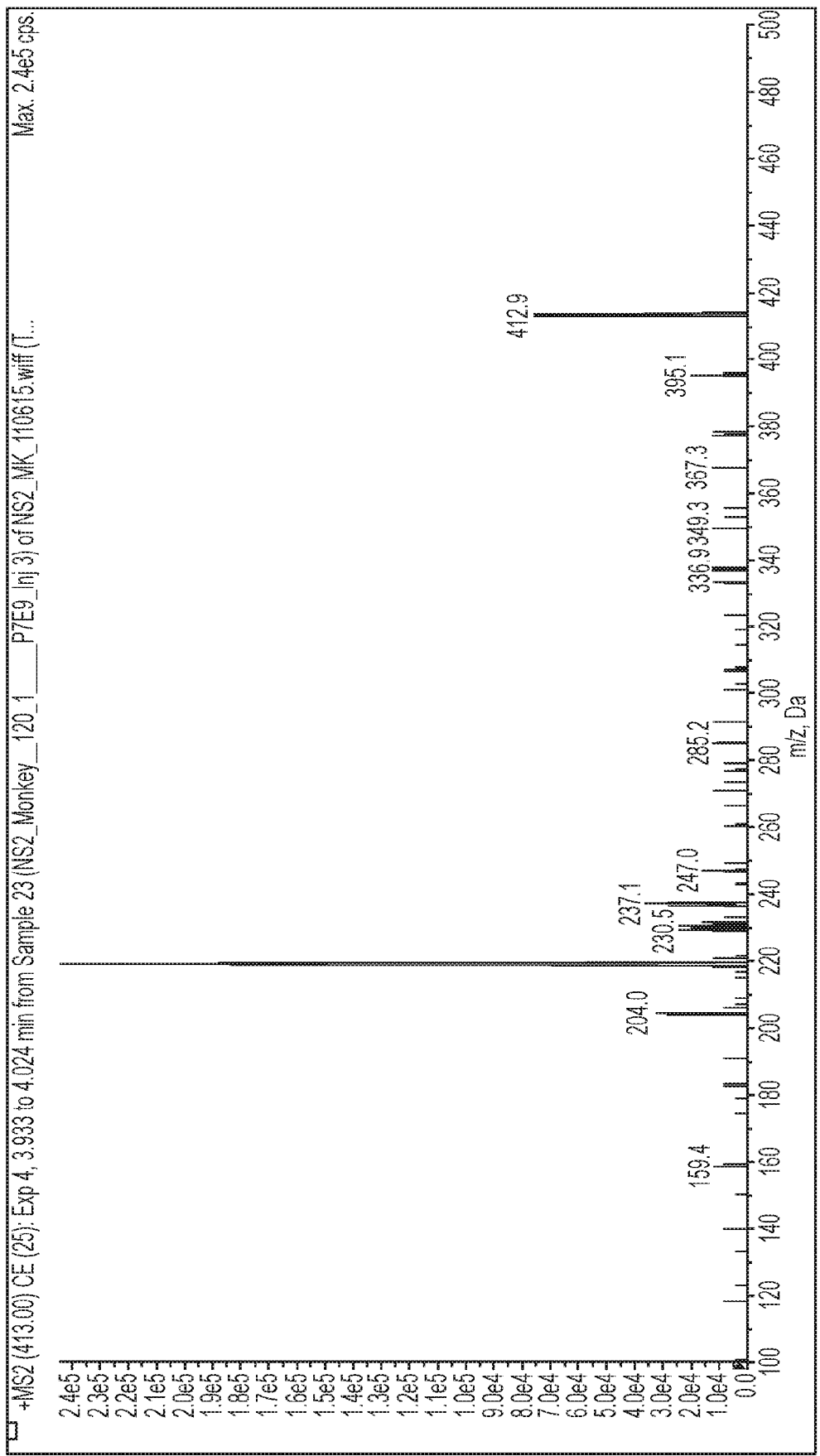
FIG. 14 shows mass spectral analysis of metabolite M8 (m/z=413, RT=3.9 min).
Figure 15:
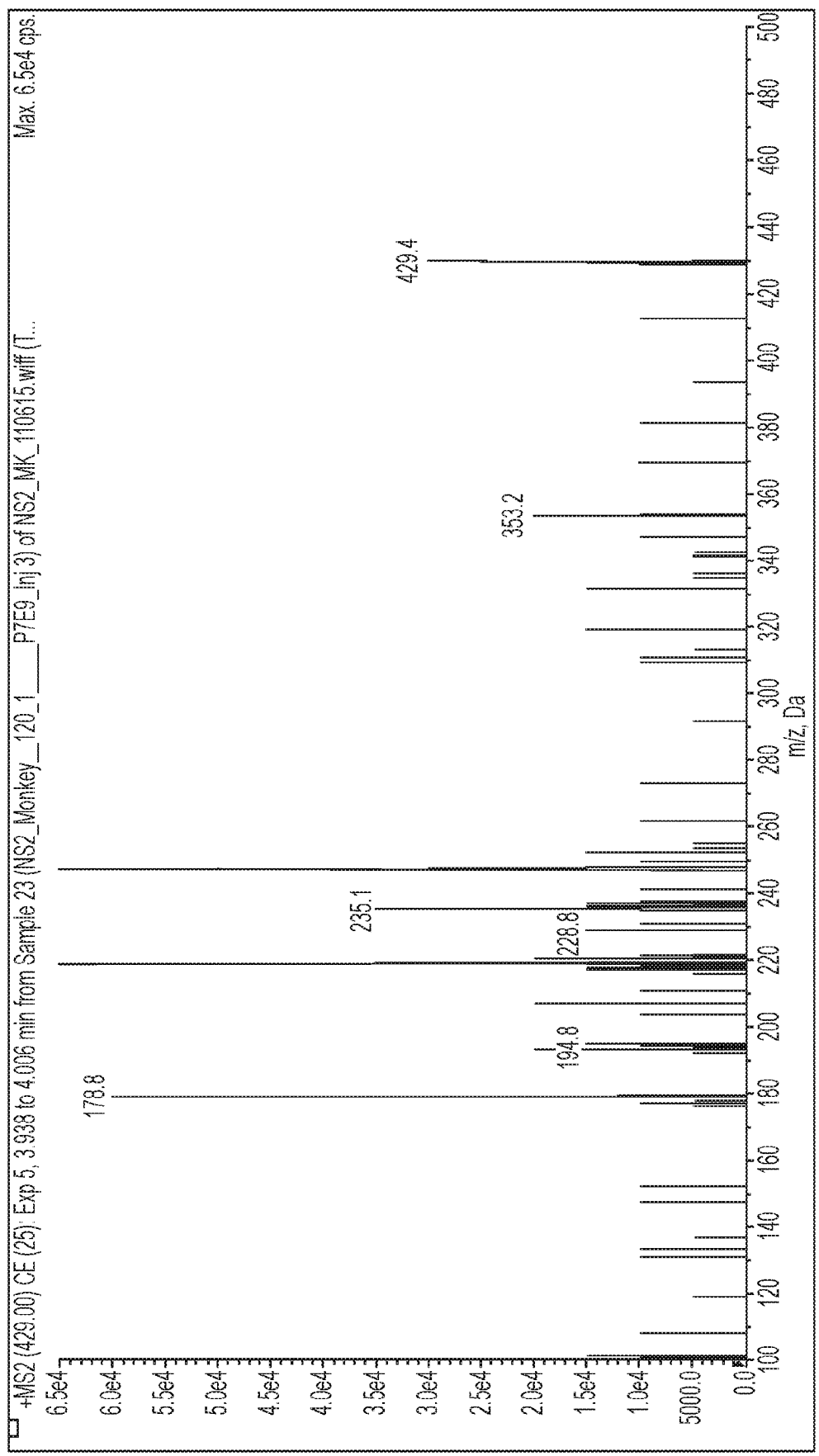
FIG. 15 shows mass spectral analysis of metabolite M9 (m/z=429, RT=3.9 min).
Figure 16:
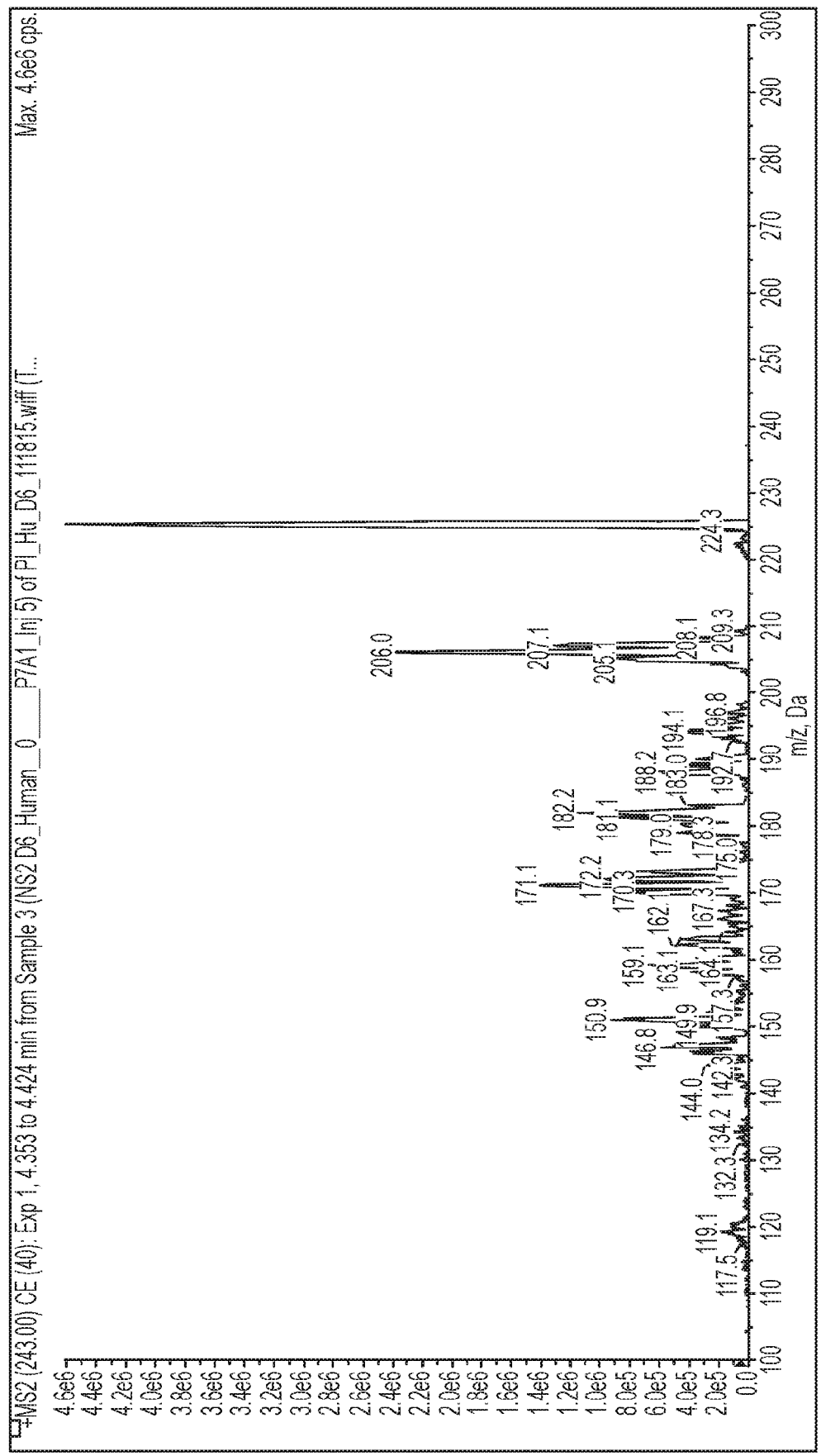
FIG. 16 shows mass spectral analysis of NS2-D6 (compound I-1; m/z=243).
Figure 17:
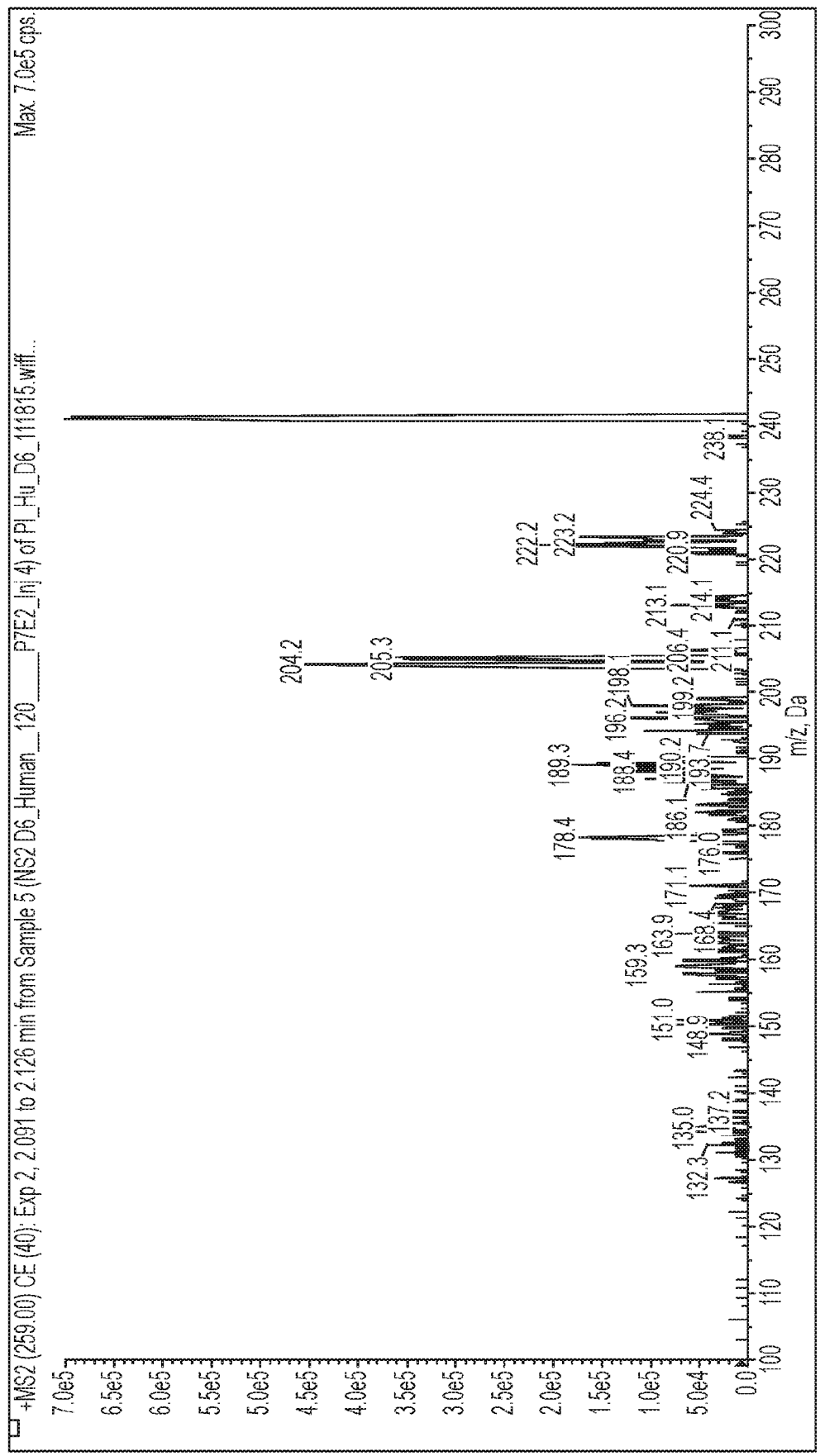
FIG. 17 shows mass spectral analysis of metabolite 1 of NS2-D6 (m/z=259).

In contrast to non-deuterium-enriched NS2, exposure of deuterium-enriched NS2 (i.e., compound I-1, or NS2-D36 in Table 7) to human hepatocytes for 120 min resulted in mono-oxidation metabolite M1 as the sole detectable metabolite (see Table 7 and FIGS. 5 and 17). The amount of M1 produced was also greatly reduced relative to that produced when non-deuterated NS2 was exposed to human hepatocytes (compare FIGS. 1 and 5). Such a dramatic reduction in metabolite production could not have been predicted in advance.

TABLE 6A

Metabolite Profiling of NS2 in Hepatocytes: Data Summary

| | Retention | | | | Observed Metabolites (T-120 min) | | | |
|---|---|---|---|---|---|---|---|---|
| Analyte | Time (min) | m/z | m/z shift | Possible Biotransformation | Rat | Dog | Cyno Monkey | Human |
| NS2 | 4.4 | 237 | — | Parent | NA | NA | NA | NA |
| M1 | 2.1 | 253 | +16 | mono-oxidation | ++++ | ++++ | ++++ | ++++ |
| M2 | 2.9 | 253 | +16 | mono-oxidation | | + | | |
| M3 | 3.0 | 429 | +192 | oxidation + glucuronidation | | | + | |
| M4 | 3.2 | 429 | +192 | oxidation + glucuronidation | | | ++ | |
| M5 | 3.5 | 542 | +305 | GSH-conjugation | | + | | |
| M6 | 3.7 | 542 | +305 | GSH-conjugation | | ++ | | |
| M7 | 1.7 | 429 | +192 | oxidation + glucuronidation | trace | | ++ | + |
| M8 | 3.98 | 413 | +176 | glucuronidation | trace | | ++ | ++ |
| M9 | 3.9 | 429 | +192 | oxidation + glucuronidation | | | + | + | m/z: Mass-to-Charge ratio of analyte
NA = Not applicable

TABLE 7

Metabolite Profiling of Deuterated NS2 in Human Hepatocytes: Data Summary

| Analyte | Retention Time (min) | m/z | m/z shift | Possible Biotransformation | Observed Metabolites (T-120 min) Human |
|---|---|---|---|---|---|
| NS2-D6 | 4.4 | 243 | — | Parent | NA |
| M1 | 2.1 | 259 | +16 | mono-oxidation | ++ | m/z: Mass-to-Charge ratio of analyte
NA = Not applicable

Relative degree of observed metabolite formation is denoted by "+", with ++++ being the most abundant metabolite (assuming that the ionization potential of the parent is similar with the metabolites) Note: Based on the number of observed metabolites, deuterated-NS2 exhibited less metabolism over the course of 2 hours relative to the non-deuterated NS2 molecule.

The results shown in Table 7 are also surprising in that the reduction in the number and amount of metabolites may not simply be due to deuterium incorporation making an enzymatically-catalyzed rate-determining step more difficult. Rather, the observed m/z of 259 is consistent with all six deuterium atoms being retained in the mono-oxidation product. Without wishing to be bound by theory, this may indicate that the deuterium enrichment is influencing metabolism at a remote location on the molecule, and perhaps not simply through, e.g., a primary kinetic isotype effect.

References: 1) McGinnity, D. F. et al. (2004). "Evaluation of fresh and cryopreserved hepatocytes as in vitro drug metabolism tools for the prediction of metabolic clearance." Drug Metab. Dispos. 32(11):1247-1253. 2) Sahi, J. et al. (2010). "Hepatocytes as a tool in drug metabolism, transport and safety evaluations in drug discovery."*Current Drug Discov. Technol.* 7(3):188-198.

Example 12: Evaluation of Dose Responses for Protective Activity from Hydrogen Peroxide Toxicity in Dissociated Hippocampal Cultures for NS2 (i.e. Non-Deuterated NS2)

Experimental Plan for NS2 Dose Response Evaluation for Protection from Hydrogen Peroxide Toxicity:
A. Test Agent: NS2 FW: 236
  1. Source 1: CoreRx lot 093-FOR CNS2; amount used: 6.4 mg; micro-milled sample (average particle size is about 16 micron); was derived from J-Star Lot BR-NS2-11-01
  2. Source 2: J-Star lot BR-NS2-1; amount used: 6 mg; non-milled sample
B. Formulations and Stock Solution Preparation
  Two types of formulation were compared: dimethyl sulfoxide (DMSO) and Captisol®
  1. Captisol® formulation: Captisol® was dissolved at 5 mg/ml (i.e., at 0.5%) in Dulbecco's Phosphate Buffered Saline (DPBS). A 10 mM NS2 stock solution (stock A) was prepared by dissolving 1 mg (4.24 μmol) into 0.42 ml of the Captisol® solution to give an initial stock of 10 μmol/ml or 10 mM (i.e., 2.38 mg/mL). The stock solution was clear after vortex mixing.
  2. DMSO formulation: DMSO was used as a comparator to Captisol®. Five mg (21.12 μmol) of NS2 was dissolved in 0.21 mL of DMSO for a 100 mM stock solution (i.e., 23.8 mg/mL). The 100 mM NS2 DMSO formulation was clear. Log dilutions were done with DPBS. Upon dilution 1:10 to 10 mM with DPBS, the solution became cloudy, but, cleared after extensive vortex mixing. In general, our benchmark concentration goal for DMSO in primary neuronal cultures is less than 0.1%, to avoid pharmacological actions of DMSO. Note that 1% DMSO was used for the 1 mM test concentration of NS2. No apparent toxicity was observed in the assays in the 5 hr test (see results from Experiment 9 below).
C. Details on the Preparation of Stock Solutions
  NS2 in Captisol®:
    1. Stock A was 10 mM NS2 in 0.5% Captisol®. Added 10 μl into 100 μl for a final concentration of 1 mM NS2, in 0.05% Captisol®, in each well.
    2. Stock B was prepared by adding 50 μl of stock A to 450 μl of DPBS to yield a 1 mM solution of NS2. Added 10 μl into 100 μl DPBS for a final concentration of 100 μM NS2 in 0.005% Captisol®.
    3. Stock C was prepared by adding 50 μl of stock B into 450 μl of DPBS to yield a 100 μM solution of NS2. Added 10 μl into 100 μl DPBS for a final concentration of 10 μM NS2 in 0.0005% Captisol®.
    4. Stock D was prepared by adding 50 μl of stock C into 450 μl of DPBS to yield a 10 μM solution of NS2. Added 10 μl into 100 μl DPBS for a final concentration of 1 μM NS2 in 0.00005% Captisol®.
    5. Stock E was prepared by adding 50 μl of stock D into 450 μl of DPBS to yield a 1 μM solution of NS2. Added 10 μl into 100 μl DPBS for a final concentration of 0.1 μM NS2 in 0.000005% Captisol®.
  NS2 in DMSO:
    1. Stock A was 100 mM NS2 in 100% DMSO.
    2. Stock B was prepared by adding 50 μl of stock A into 450 μl of DPBS for a final concentration of 10 mM NS2. Added 10 μl into 100 μl DPBS to yield a final concentration of 1 mM NS2 in 1% DMSO.
    3. Stock C was prepared by adding 50 μl of stock B into 450 μl of DPBS for a final concentration of 1 mM NS2. Added 10 μl into 100 μl DPBS to yield a final concentration of 100 μM NS2 in 0.1% DMSO.
    4. Stock D was prepared by adding 50 μl of stock C into 450 μl of DPBS for a final concentration of 100 μM NS2. Added 10 μl into 100 μl DPBS to yield a final concentration of 10 μM NS2 in 0.01% DMSO.
    5. Stock E was prepared by adding 50 μl of stock D into 450 μl of DPBS for a final concentration of 10 μM NS2. Added 10 μl into 100 μl DPBS to yield a final concentration of 1 μM NS2 in 0.001% DMSO.
    6. Stock F was prepared by adding 50 μl of stock E into 450 μl of DPBS for a final concentration of 1 μM NS2. Added 10 μl into 100 μl DPBS for a final concentration of 0.1 μM NS2 in 0.0001% DMSO.
  In all cases, 10 μl of the appropriate dilution was added to 100 μl for a total volume of 110 μl in the well.
D. Culture Conditions Designed to Detect NS2-Mediated Neuroprotection from Oxidative Stress Associated with Hydrogen Peroxide
  1. Rat hippocampal cultures were prepared as previously described (Brenneman D E, Smith G R, Zhang Y, Du Y, Kondaveeti S K, Zdilla M J, Reitz A B. (2012) J. Molecular Neuroscience, 47:368-379). Under these conditions, the cultures are at least 90% neuronal. The most abundant non-neuronal cells are astrocytes.
  2. All cultures were prepared into a 96-well format at a plating density of 10K cells per well. Cultures were treated between day 10 and day 21 after dissociation of E18 hippocampal tissue. For these experiments, all plates were treated on day 13. In all experiments, the hydrogen peroxide was added to the cultures 10 minutes after treatment with NS2 or cannabidiol (CBD). For each treatment condition, the number of replicates was five.

3. All cultures were plated in B27/Neural Basal Medium. On the day of treatment, all cultures were given a complete change of medium into B27/Neural Basal Medium without antioxidants.

4. As previously determined (Brenneman et al., 2012), 10 µM hydrogen peroxide was used to produce toxicity and oxidative stress. As described previously [Jarrett, SG, Liang, L-P, Hellier, J L, Staley, K J and Patel, M. (2008) Neurobiol. Dis 30(1): 130-138], 10 µM hydrogen peroxide has been observed in the hippocampus of rats with a kainate model of status epilepticus.

5. The positive control used in all studies was 10 µM cannabidiol (CBD), a known antioxidant agent [Hampson et al. (1998), Proc. Nat. Acad. Sci 95:8268-8273] that is protective against oxidative stress in primary neurons [Brenneman, DE, Petkanas, D and Kinney, W. A. (2014) Annual Symposium on the Cannabinoids, page 129].

6. Neither the negative control wells, the hydrogen peroxide wells, nor the positive control wells contained any drug vehicle.

E. Assays

Both assays used in this study have been described in detail [Brenneman D E, Smith G R, Zhang Y, Du Y, Kondaveeti S K, Zdilla M J, Reitz A B. (2012) J. Molecular Neuroscience, 47:368-379].

1. The CFDA neuronal viability assay. In this assay, the CFDA dye is taken up by all live cells and cleaved by esterases to release fluorescein. The neuronal specificity is achieved because neurons cannot remove this dye, whereas efflux of the dye from non-neuronal cells can occur over time. After washing away the extracellular dye, the cultures were read in a fluorimeter; intracellular dye intensity is proportional to the live neuronal population. Original reference: Petroski, RE and Geller H M. (1994) Selective labeling of embryonic neurons cultures on astrocyte monolayers with 5(6)-carboxyfluorescein diacetate (CFDA) J. Neurosci. Methods 52:23.32. The mean control level for each experiment is shown as a longdashed reference line.

2. A cell death assay, using propidium iodide, was conducted simultaneously with the CFDA assay in the same well. This dye is excluded from live cells and binds to the DNA of dead cells. The assay detects both necrotic and apoptotic cell death; it does not distinguish between neuronal cell death and non-neuronal cell death. See Sarafian T A, Kouyoumjian S, Tashkin D, Roth M D. (2002) Tox. Letters. 133: 171-179. The mean control level is shown as a medium-dashed reference line.

3. Reagents used:
   a. Hydrogen Peroxide solution, 30 wt %; Sigma-Aldrich (216736-100 ml, Lot MKBV382V)
   b. Captisol® (Lot 17CX01-HQ-00088) provided by Aldeyra Therapeutics
   c. Dimethyl Sulfoxide; Sigma-Aldrich (472301-100 ml) Batch 21096 JK
   d. Propidium Iodide Sigma-Aldrich (P4864-10 ml; 1 mg/ml solution in water)
   e. CFDA [5(6)-Carboxyfluorescein Diacetate] Sigma-Aldrich Product Number: 21879-100 mg-F
   f. Cannabidiol solution, 10 mg/ml in ethanol; Sigma-Aldrich Product Number: 90899-1 ml
   g. Dulbecco's Phosphate Buffered Saline. Gibco (14190-144) Lot 1165767

4. Data Analyses
   a. Data Acquisition: Data were stored on Advanced Neural Dynamics computers for analyses. Data acquisition was performed on Cytofluor Fluorimeter and transferred to Excel spreadsheet for analysis with Sigma Plot 11.
   b. Statistical Analysis: All data were statistically analyzed by an Analysis of Variance with the Multiple Comparisons versus Control Group (Holm-Sidak) method. Statistical significance was taken at the $P<0.05$ level. In all cases, comparisons were made to the negative control (10 µM hydrogen peroxide treatment).
   c. Methodology for $EC_{50}$ determination:
      i. A broad concentration range was chosen to screen NS2 in an $EC_{50}$ potency analysis. A log-based concentration series from 0.1 µM to 1 mM was used, recognizing that further analysis involving half-log concentration may be necessary to assess $EC_{50}$ s.
      ii. A nonlinear regression analysis was used to determine the equation of the line that best fits the data. (Four parameter Logistic curve)
      iii. Based on the Logistic equation below, the $EC_{50}$ s for neuroprotection were calculated and plotted by SigmaPlot 11 to determine the concentration required to produce half-maximal responses for both assays. Drop lines were used to show the axes intersections determining the $EC_{50}$.

Four Parameter Logistic Equation $$y = \min + \frac{\max - \min}{1 + \left(\frac{x}{EC50}\right)^{-Hillslope}}$$

This results in a typical dose-response curve with a variable slope parameter. It is sometimes abbreviated as 4PL. The four parameters are: min (bottom of the curve), max (top of the curve). $EC_{50}$=Concentration of ligand that produced 50% of maximal effective response.

5. Summary of Results

Table 8 shows a summary of protection studies for NS2 (i.e., non-deuterated NS2) in rat hippocampal cultures.

TABLE 8

Summary of Protection Studies for N52 in Rat Hippocampal Cultures

| Assay | Compound | Formulation | Full Efficacy Concentration** | No effect Concentration | EC50 ± SE |
|---|---|---|---|---|---|
| CFDA | NS2 CoreRx | Captisol® | 100 µM | 1 µM | 6.8 ± 3.6 µM |
| CFDA | NS2 CoreRx | DMSO | 100 µM | 1 µM | 9.8 µM * |
| CFDA | NS2 J-Star | Captisol® | 100 µM | 1 µM | 9.1 ± 2.8 µM |
| CFDA | NS2 J-Star | DMSO | 100 µM | 1 µM | 2.6 µM * |
| PI | NS2 CoreRx | Captisol® | 10 µM | 1 µM | 1.3 µM * |
| PI | NS2 CoreRx | DMSO | 10 µM | 1 µM | 1.3 µM * |

TABLE 8-continued

Summary of Protection Studies for N52 in Rat Hippocampal Cultures

| Assay | Compound | Formu-lation | Full Efficacy Concen-tration** | No effect Concen-tration | EC50 ± SE |
|---|---|---|---|---|---|
| PI | NS2 J-Star | Captisol ® | 10 µM | 1 µM | 2.8 µM * |
| PI | NS2 J-Star | DMSO | 10 µM | 1 µM | 1.1 µM * |
| CFDA | None | Captisol ® | | | Not active |
| PI | None | DMSO | | | Not active |

* Because of the steep nature of the logistic curve observed for these data sets, further analysis using half-log concentrations may be necessary to determine the $EC_{50}$ under these conditions. The posted values should be considered estimates.
**Concentration of test agent showing assay response levels not significantly different from that of no treatment controls.

6. Graphical Analyses of Experimental Findings and Raw Data
   a. Experiment 1: Dose response to micro-milled NS2 (CoreRx) in Captisol®. Effect on neuronal viability after co-treatment with 10 µM hydrogen peroxide.
      i. NS2 Source: CoreRx, micro-milled
      ii. Formulation: Initial stock was formulated in 0.5% Captisol®
      iii. Assay: CFDA
      iv. Toxin: 10 µM hydrogen peroxide
      v. Duration of treatment: 5 hours
      vi. Growth medium: B27/neurobasal medium without antioxidants
      vii. Culture matrix: poly-L-lysine
      viii. Conclusions: The $EC_{50}$ was observed at 6.8 µM; full efficacy relative to controls (CBD+HP and no-treatment control) was observed at 100 µM NS2.

Figure 18:
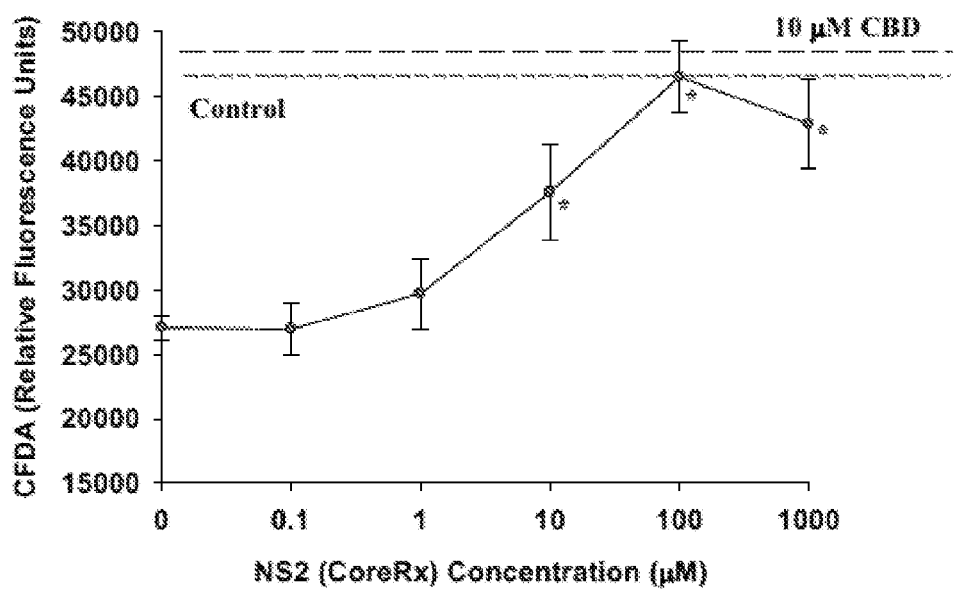
FIG. 18 shows the effect of NS2 (CoreRx) on neuronal viability after co-treatment with 10 µM hydrogen peroxide for 5 hours.
Figure 19:
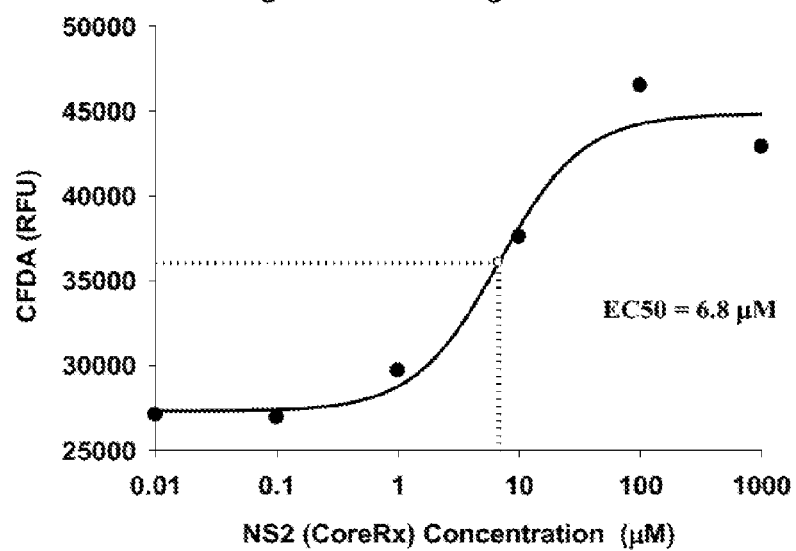
FIG. 19 shows a graph fitting the CFDA (in relative fluorescence units) data at varying NS2 (CoreRx; in Captisol®) concentrations to a curve from which is derived the $EC_{50}$ value.

NS2 is fully neuroprotective against hydrogen peroxide toxicity at 100 µM in this assay. Results are shown in Table 9 and FIGS. 18 and 19.

TABLE 9

Effect on Neuronal Viability After Co-Treatment with 10 µM Hydrogen Peroxide

| Statistical Analysis | Control | CBD + HP 10 µM | NS2 + HP 1 mM | NS2 + HP 100 µM | NS2 + HP 10 µM | NS2 + HP 1 µM | NS2 + HP 0.1 µM | HP 10 µM |
|---|---|---|---|---|---|---|---|---|
| | 45216 | 45216 | 45216 | 55866 | 41262 | 31538 | 31107 | 24829 |
| | 42919 | 53439 | 45216 | 47620 | 27827 | 24829 | 29842 | 27827 |
| | 47620 | 50134 | 35167 | 45216 | 48549 | 30050 | 27827 | 29430 |
| | 47620 | 52763 | 53439 | 45216 | 39139 | 23428 | 19585 | 25008 |
| | 48706 | 42919 | 35405 | 38622 | 31107 | 38622 | 26294 | 28320 |
| Mean | 46416* | 48894* | 42889* | 46508* | 37577* | 29693 | 26931 | 27083 |
| Std Error | 1044 | 2078 | 3448 | 2778 | 3697 | 2703 | 2014 | 921 |
| P value* | <0.001 | <0.001 | <0.001 | <0.001 | <0.002 | N.S. | N.S. | N.S. |
| % of Control | 100 ± 2 | 105 ± 4 | 92 ± 07 | 100 ± 6 | 80 ± 8 | 64 ± 6 | 58 ± 4 | 58 ± 2 |

* Significantly different from treatment with 10 µM hydrogen peroxide alone.
N.S.: Not significantly different from treatment with 10 µM hydrogen peroxide alone.

b. Experiment 2: Dose response to micro-milled NS2 (CoreRx) in Captisol®. Effect on cell death after co-treatment with 10 µM hydrogen peroxide.
   i. NS2 Source: CoreRx (micro-milled)
   ii. Formulation: Initial stock was formulated in 0.5% Captisol®
   iii. Assay: Propidium Iodide
   iv. Toxin: 10 µM hydrogen peroxide
   v. Duration of treatment: 5 hours
   vi. Growth medium: B27/neurobasal medium without antioxidants
   vii. Culture matrix: poly-L-lysine
   viii. Conclusions: The $EC_{50}$ was observed at 1.3 µM; full efficacy relative to controls (CBD+HP and no-treatment control) was observed at 10 µM NS2.

Figure 20:
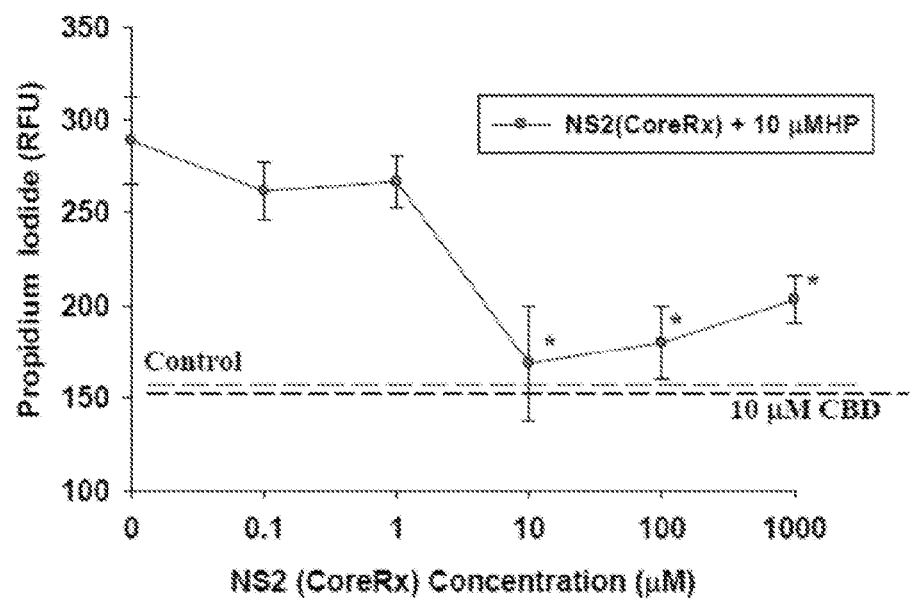
FIG. 20 shows the effect of NS2 (CoreRx) on cell death in hippocampal cultures after co-treatment with 10 µM hydrogen peroxide for 5 hours. *indicates data points that are significantly different from HP treatment alone.
Figure 21:
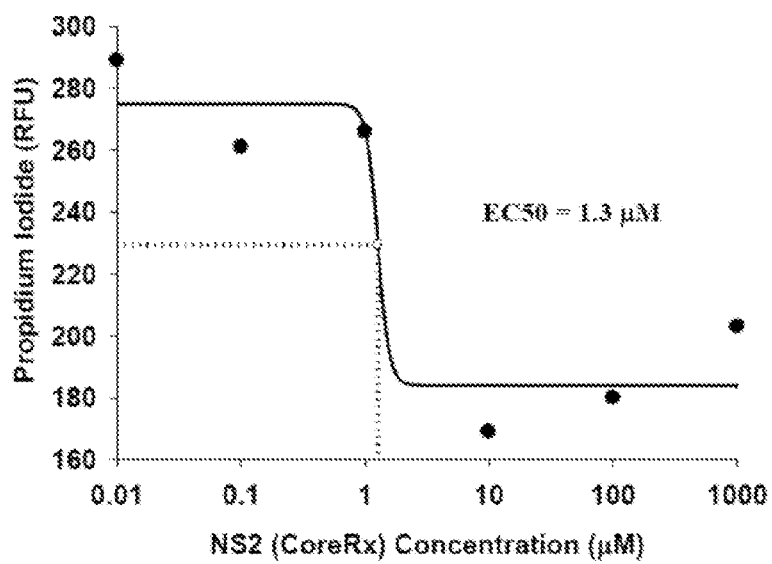
FIG. 21 shows a graph fitting the propidium iodide data (in relative fluorescence units) at varying NS2 (CoreRx; in Captisol®) concentrations to a curve from which the $EC_{50}$ value is derived.

NS2 is fully neuroprotective against hydrogen peroxide toxicity with this assay. These data suggest that the protective effect against cell death may be slightly more potent than that observed for neuronal viability. Results are shown in Table 10 and FIGS. 20 and 21.

TABLE 10

Effect of NS2 (CoreRx) on Cell Death in Hippocampal Cultures After Co-treatment with 10 µM Hydrogen Peroxide for 5 hours

| Statistical Analysis | Control | CBD + HP 10 µM | NS2 + HP 1 mM | NS2 + HP 100 µM | NS2 + HP 10 µM | NS2 + HP 1 µM | NS2 + HP 0.1 µM | HP 10 µM |
|---|---|---|---|---|---|---|---|---|
| | 140 | 144 | 246 | 144 | 180 | 319 | 246 | 315 |
| | 180 | 121 | 184 | 180 | 57 | 246 | 246 | 306 |

TABLE 10-continued

Effect of NS2 (CoreRx) on Cell Death in Hippocampal Cultures After Co-treatment with 10 μM Hydrogen Peroxide for 5 hours

| Statistical Analysis | Control | CBD + HP 10 μM | NS2 + HP 1 mM | NS2 + HP 100 μM | NS2 + HP 10 μM | NS2 + HP 1 μM | NS2 + HP 0.1 μM | HP 10 μM |
|---|---|---|---|---|---|---|---|---|
|  | 137 | 192 | 180 | 192 | 246 | 254 | 246 | 209 |
|  | 144 | 117 | 188 | 246 | 180 | 246 | 246 | 346 |
|  | 180 | 180 | 217 | 137 | 180 | 267 | 323 | 267 |
| Mean | 156* | 151* | 203* | 180* | 169* | 266 | 261 | 289 |
| Std Error | 10 | 15 | 13 | 20 | 31 | 14 | 15 | 24 |
| P value* | <0.001 | <0.001 | <0.003 | <0.001 | <0.001 | N.S. | N.S. | N.S. |
| % of Control | 100 ± 6 | 97 ± 9 | 130 ± 8 | 115 ± 13 | 108 ± 20 | 171 ± 9 | 167 ± 10 | 185 ± 15 |

* Significantly different from treatment with 10 μM hydrogen peroxide alone.
N.S.: Not significantly different from treatment with 10 μM hydrogen peroxide alone.

c. Experiment 3: Dose response to micro-milled NS2 (CoreRx) in DMSO. Effect on neuronal viability after co-treatment with 10 μM hydrogen peroxide.
  i. NS2 Source: CoreRx (micro-milled)
  ii. Formulation: Initial stock was formulated in 100% DMSO
  iii. Assay: CFDA
  iv. Toxin: 10 μM hydrogen peroxide
  v. Duration of treatment: 5 hours
  vi. Growth medium: B27/neurobasal medium without antioxidants
  vii. Culture matrix: poly-L-lysine
  viii. Conclusions: The $EC_{50}$ was observed at 9.8 μM; full efficacy relative to controls (CBD+HP and no-treatment control) was observed at 100 μM NS2.

Figure 22:
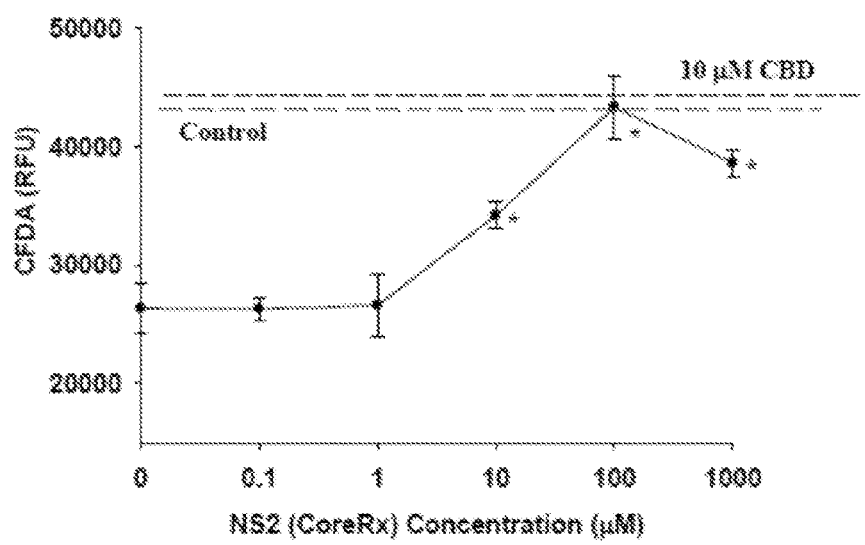
FIG. 22 shows the effect of NS2 (CoreRx; in DMSO) on neuronal viability after co-treatment with 10 mM hydrogen peroxide for 5 hours. *indicates data points that are significantly different from HP treatment alone.
Figure 23:
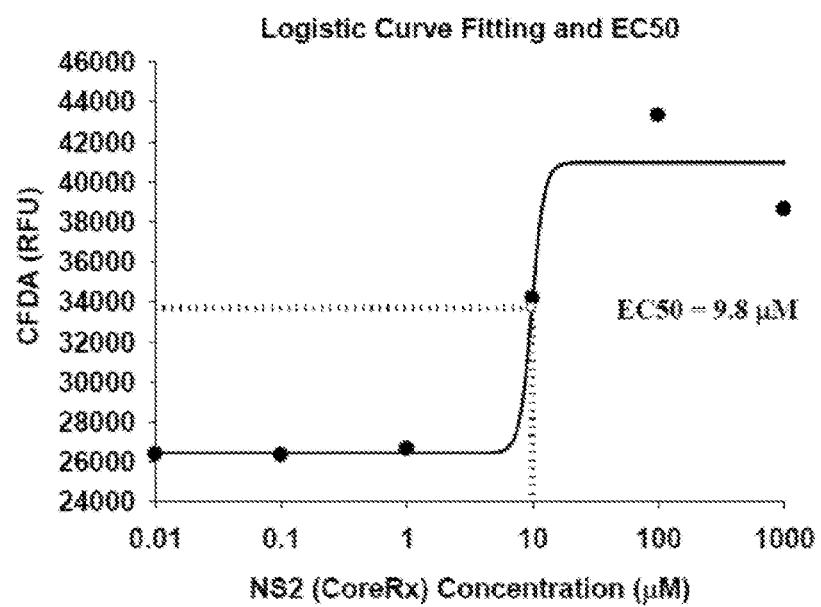
FIG. 23 shows a graph fitting the CFDA (in relative fluorescence units) data at varying NS2 (CoreRx; in DMSO) concentrations to a curve from which is derived the $EC_{50}$ value.

The use of DMSO as a formulation produced an $EC_{50}$ that was very similar to that observed with Captisol®. NS2 is fully neuroprotective against hydrogen peroxide toxicity in this assay. Results are shown in Table 11 and FIGS. 22 and 23.

d. Experiment 4: Dose response to micro-milled NS2 (CoreRx) in DMSO. Effect on cell death after co-treatment with 10 μM hydrogen peroxide.
  i. NS2 Source: CoreRx (micro-milled)
  ii. Formulation: Initial stock was formulated in 100% DMSO
  iii. Assay: Propidium Iodide
  iv. Toxin: 10 μM hydrogen peroxide
  v. Duration of treatment: 5 hours
  vi. Growth medium: B27/neurobasal medium without antioxidants
  vii. Culture matrix: poly-L-lysine
  viii. Conclusions: The $EC_{50}$ was observed at 1.3 μM; full efficacy relative to controls (CBD+HP and no-treatment control) was observed at 10 μM NS2.

Figure 24:
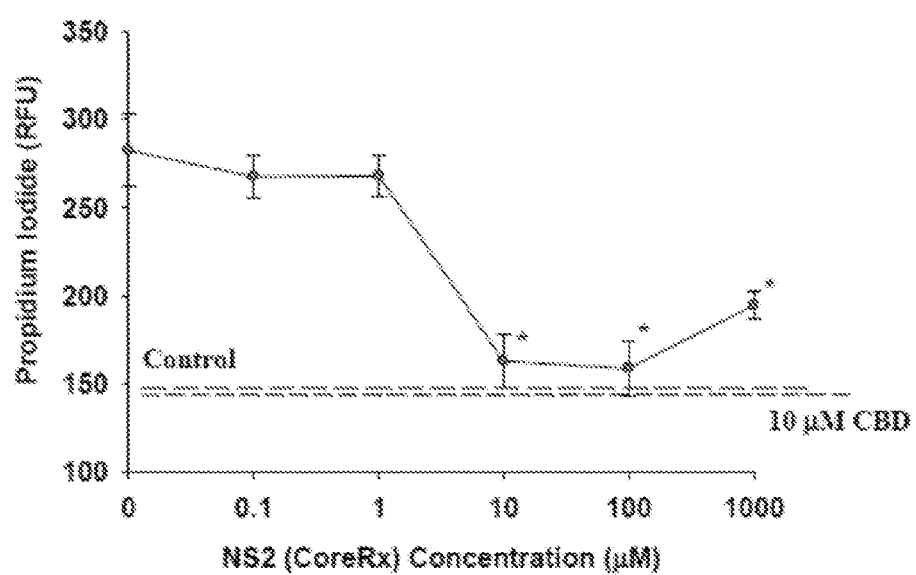
FIG. 24 shows the effect of NS2 (CoreRx; in DMSO) on cell death in hippocampal cultures after co-treatment with 10 µM hydrogen peroxide. *indicates data points that are significantly different from HP treatment alone.
Figure 25:
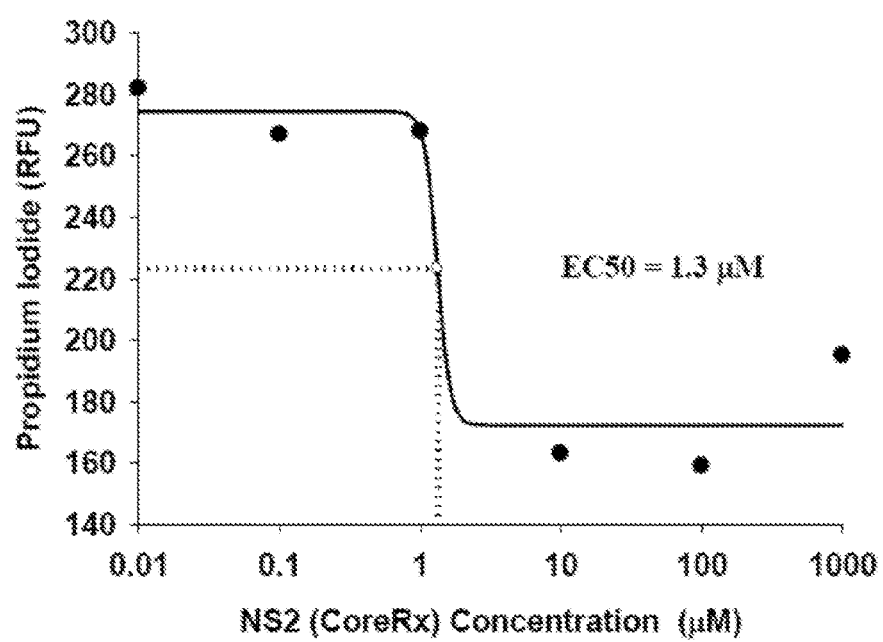
FIG. 25 shows a graph fitting the propidium iodide date (in relative fluorescence units) at varying NS2 (CoreRx; in DMSO) concentrations to a curve from which the $EC_{50}$ value is derived.

NS2 is fully neuroprotective against hydrogen peroxide toxicity with this assay. These data suggest that the protective effect against cell death may be slightly more potent than that observed for neuronal viability. Results are shown in Table 12 and FIGS. 24 and 25.

TABLE 11

Effect of NS2 (CoreRx; in DMSO) on Neuronal Viability After Co-Treatment with 10 mM Hydrogen Peroxide for 5 hours

| Statistical Analysis | Control | CBD + HP 10 μM | NS2 + HP 1 mM | NS2 + HP 100 μM | NS2 + HP 10 μM | NS2 + HP 1 μM | NS2 + HP 0.1 μM | HP 10 μM |
|---|---|---|---|---|---|---|---|---|
|  | 47420 | 49934 | 38422 | 42719 | 38422 | 20765 | 23428 | 20844 |
|  | 38939 | 48038 | 36415 | 40792 | 32661 | 32886 | 26094 | 31447 |
|  | 40792 | 42719 | 42719 | 42439 | 32661 | 32886 | 27627 | 31338 |
|  | 39199 | 42719 | 39139 | 53580 | 32661 | 23228 | 25189 | 24899 |
|  | 48706 | 38422 | 36415 | 37108 | 34496 | 23400 | 29230 | 23228 |
| Mean | 43011* | 44366* | 38622* | 43328* | 34180* | 26633 | 26314 | 26351 |
| Std Error | 2097 | 2064 | 1158 | 2751 | 1118 | 2595 | 997 | 2157 |
| P value* | <0.001 | <0.001 | <0.001 | <0.001 | <0.009 | N.S. | N.S. | N.S. |
| % of Control | 100 ± 5 | 103 ± 5 | 90 ± 3 | 101 ± 6 | 79 ± 3 | 62 ± 6 | 61 ± 2 | 61 + 5 |

* Significantly different from treatment with 10 μM hydrogen peroxide alone.
N.S.: Not significantly different from treatment with 10 μM hydrogen peroxide alone.

TABLE 12

Effect of NS2 (CoreRx in DMSO) on Cell Death in Hippocampal Cultures After Co-Treatment with 10 μM Hydrogen Peroxide

| Statistical Analysis | Control | CBD + HP 10 μM | NS2 + HP 1 mM | NS2 + HP 100 μM | NS2 + HP 10 μM | NS2 + HP 1 μM | NS2 + HP 0.1 μM | HP 10 μM |
|---|---|---|---|---|---|---|---|---|
| | 117 | 180 | 204 | 125 | 180 | 254 | 246 | 315 |
| | 133 | 180 | 180 | 180 | 188 | 263 | 263 | 246 |
| | 144 | 117 | 221 | 180 | 192 | 254 | 254 | 346 |
| | 180 | 125 | 188 | 192 | 117 | 254 | 315 | 246 |
| | 129 | 117 | 180 | 117 | 137 | 315 | 259 | 259 |
| Mean | 141* | 144* | 195* | 159* | 163* | 268 | 267 | 282 |
| Std Error | 11 | 15 | 8 | 16 | 15 | 12 | 12 | 20 |
| P value* | <0.001 | <0.001 | <0.001 | <0.001 | <0.001 | N.S. | N.S. | N.S. |
| % of Control | 100 ± 8 | 102 ± 11 | 138 ± 6 | 113 ± 11 | 115 ± 11 | 190 ± 9 | 189 ± 9 | 200 ± 14 |

* Significantly different from treatment with 10 μM hydrogen peroxide alone.
N.S.: Not significantly different from treatment with 10 μM hydrogen peroxide alone.

e. Experiment 5: Dose response to non-milled NS2 (J-Star) in Captisol®. Effect on neuronal viability after co-treatment with 10 μM hydrogen peroxide.
  i. NS2 Source: J-Star (non-milled)
  ii. Formulation: Initial stock was formulated in 0.5% Captisol®
  iii. Assay: CFDA
  iv. Toxin: 10 μM hydrogen peroxide
  v. Duration of treatment: 5 hours
  vi. Growth medium: B27/neurobasal medium without antioxidants
  vii. Culture matrix: poly-L-lysine
  viii. Conclusions: The $EC_{50}$ was observed at 9.1 μM; full efficacy relative to controls (CBD+HP and no-treatment control) was observed at 100 μM NS2.

Figure 26:
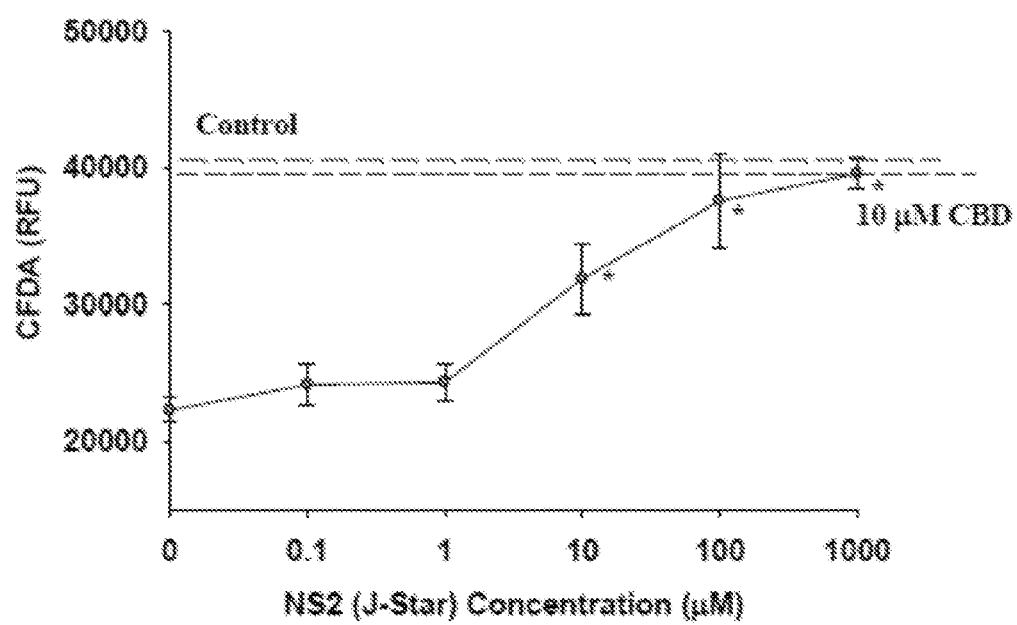
FIG. 26 shows dose response data for non-milled NS2 (J-Star) in Captisol® demonstrating the effect on neuronal viability after co-treatment with 10 µM hydrogen peroxide. *indicates data points that are significantly different from HP treatment alone.
Figure 27:
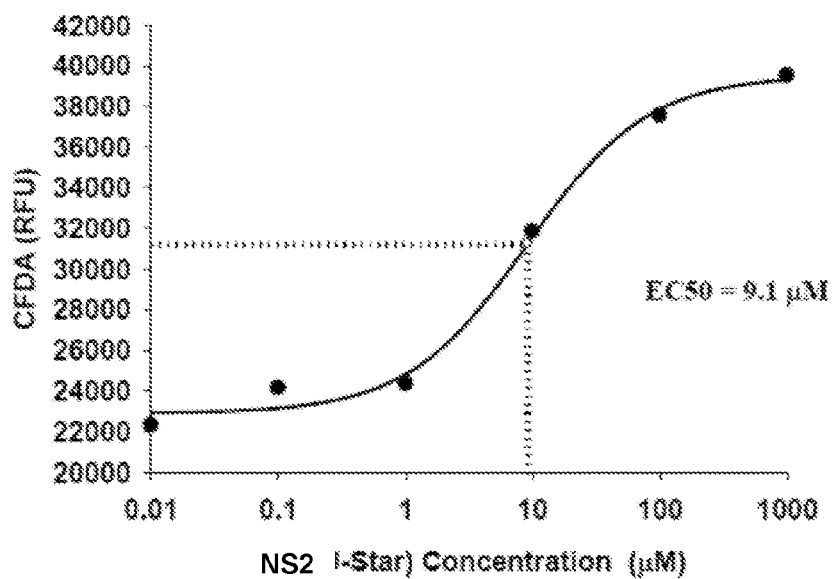
FIG. 27 shows a graph fitting the CFDA (in relative fluorescence units) data at varying NS2 (J-Star; in DMSO) concentrations to a curve from which is derived the $EC_{50}$ value.

NS2 is fully neuroprotective against hydrogen peroxide toxicity with this assay. Results are shown in Table 13 and FIGS. 26 and 27.

f. Experiment 6: Dose response to non-milled NS2 (J-Star) in Captisol®. Effect on cell death after co-treatment with 10 μM hydrogen peroxide.
  i. NS2 Source: J-Star (non-milled)
  ii. Formulation: Initial stock was formulated in 0.5% Captisol®
  iii. Assay: Propidium Iodide
  iv. Toxin: 10 μM hydrogen peroxide
  v. Duration of treatment: 5 hours
  vi. Growth medium: B27/neurobasal medium without antioxidants
  vii. Culture matrix: poly-L-lysine
  viii. Conclusions: The $EC_{50}$ was observed at 2.8 μM; full efficacy relative to controls (CBD+HP and no-treatment control) was observed at 10 μM NS2.

Figure 28:
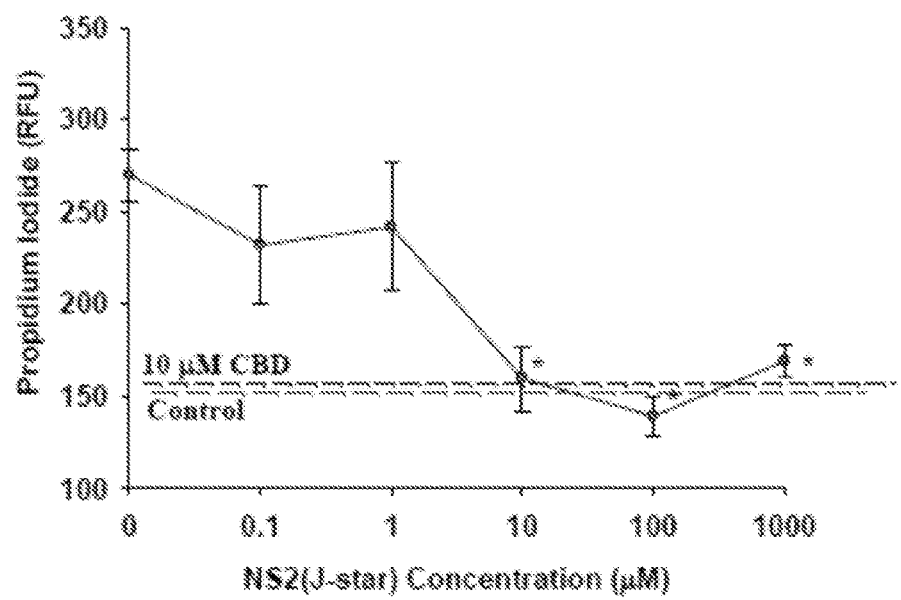
FIG. 28 shows dose response data for non-milled NS2 (J-Star) in Captisol® demonstrating the effect on cell death in hippocampal cultures after co-treatment with 10 µM hydrogen peroxide. *indicates data points that are significantly different from HP treatment alone.
Figure 29:
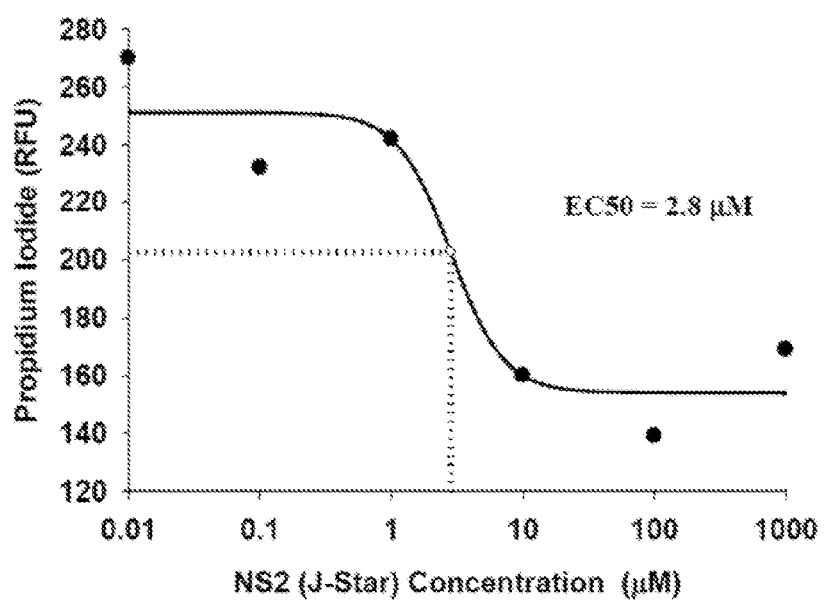
FIG. 29 shows a graph fitting the propidium iodide data (in relative fluorescence units) at varying NS2 (non-milled (J-Star) in Captisol®) concentrations to a curve from which the $EC_{50}$ value is derived.

NS2 is fully neuroprotective against hydrogen peroxide toxicity with this assay. These data suggest that the protective effect against cell death may be slightly more potent than that observed for neuronal viability. Results are shown in Table 14 and FIGS. 28 and 29.

TABLE 13

Dose Response Data for Non-Milled NS2 (J-Star) in Captisol® Showing Effect on Neuronal Viability after Co-Treatment with 10 μM Hydrogen Peroxide

| Statistical Analysis | Control | CBD + HP 10 μM | NS2 + HP 1 mM | NS2 + HP 100 μM | NS2 + HP 10 μM | NS2 + HP 1 μM | NS2 + HP 0.1 μM | HP 10 μM |
|---|---|---|---|---|---|---|---|---|
| | 40722 | 36415 | 38422 | 36415 | 37407 | 22135 | 21242 | 25171 |
| | 41535 | 38422 | 40722 | 31538 | 36861 | 24829 | 26094 | 21889 |
| | 41198 | 41884 | 38622 | 29230 | 32861 | 26094 | 22053 | 23428 |
| | 40992 | 43711 | 43200 | 42919 | 26756 | 28021 | 22089 | 19885 |
| | 36415 | 38809 | 36615 | 47620 | 25171 | 20609 | 29230 | 21162 |
| Mean | 40172* | 40858* | 39516* | 37544* | 31811* | 24338 | 24142 | 22307 |
| Std Error | 949 | 5136 | 1128 | 3442 | 2525 | 1335 | 1528 | 917 |
| P value* | <0.001 | <0.001 | <0.001 | <0.001 | <0.001 | N.S. | N.S. | N.S. |
| % of Control | 100 ± 2 | 102 ± 12 | 98 ± 3 | 93 ± 9 | 79 ± 6 | 61 ± 3 | 60 ± 4 | 56 ± 2 |

* Significantly different from treatment with 10 μM hydrogen peroxide alone.
N.S.: Not significantly different from treatment with 10 μM hydrogen peroxide alone.

TABLE 14

Dose Response Data for Non-Milled NS2 (J-Star) in Captisol ® Showing Effect on
Cell Death after Co-Treatment with 10 µM Hydrogen Peroxide

| Statistical Analysis | Control | CBD + HP 10 µM | NS2 + HP 1 mM | NS2 + HP 100 µM | NS2 + HP 10 µM | NS2 + HP 1 µM | NS2 + HP 0.1 µM | HP 10 µM |
|---|---|---|---|---|---|---|---|---|
| | 140 | 180 | 180 | 129 | 117 | 184 | 204 | 271 |
| | 144 | 144 | 133 | 129 | 196 | 315 | 180 | 323 |
| | 140 | 117 | 172 | 125 | 117 | 337 | 246 | 246 |
| | 117 | 121 | 180 | 180 | 180 | 180 | 350 | 246 |
| | 164 | 200 | 180 | 133 | 188 | 192 | 180 | 263 |
| Mean | 141* | 152* | 169* | 139* | 160* | 242 | 232 | 270 |
| Std Error | 7 | 16 | 9 | 10 | 18 | 35 | 32 | 14 |
| P value* | <0.001 | <0.001 | <0.001 | <0.001 | <0.001 | N.S. | N.S. | N.S. |
| % of Control | 100 ± 5 | 108 ± 11 | 120 ± 6 | 99 ± 7 | 113 ± 12 | 172 ± 24 | 165 ± 22 | 191 ± 10 |

*Significantly different from treatment with 10 µM hydrogen peroxide alone.

N.S.: Not significantly different from treatment with 10 µM hydrogen peroxide alone.

g. Experiment 7: Dose response to non-milled NS2 (J-Star) in DMSO. Effect on neuronal viability after co-treatment with 10 µM hydrogen peroxide.
  i. NS2 Source: J-Star (non-milled)
  ii. Formulation: Initial stock was formulated in 100% DMSO
  iii. Assay: CFDA
  iv. Toxin: 10 µM hydrogen peroxide
  v. Duration of treatment: 5 hours
  vi. Growth medium: B27/neurobasal medium without antioxidants
  vii. Culture matrix: poly-L-lysine
  viii. Conclusions: The $EC_{50}$ was observed at 2.6 µM; full efficacy relative to controls (CBD+HP and no-treatment control) was observed at 100 µM NS2.

Figure 30:
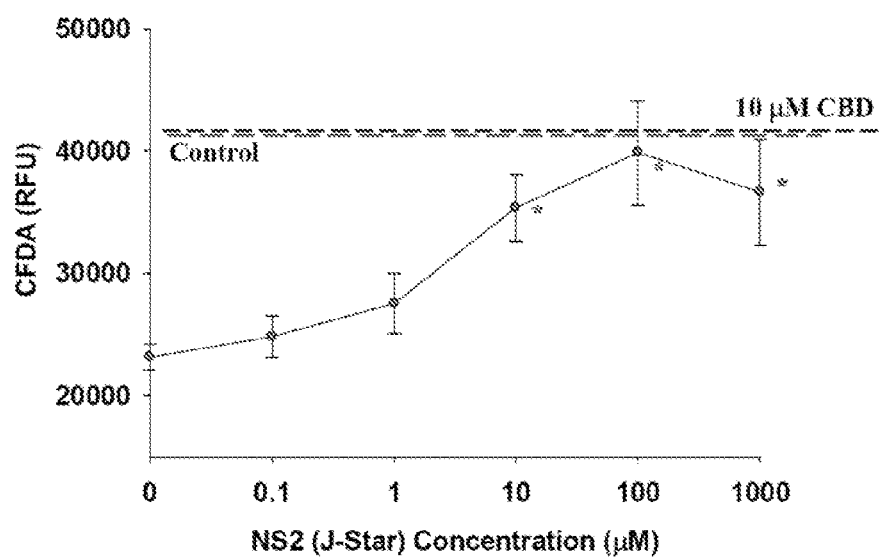
FIG. 30 shows dose response data for non-milled NS2 (J-Star) in DMSO demonstrating the effect on neuronal viability in hippocampal cultures after co-treatment with 10 µM hydrogen peroxide. *indicates data points that are significantly different from HP treatment alone.
Figure 31:
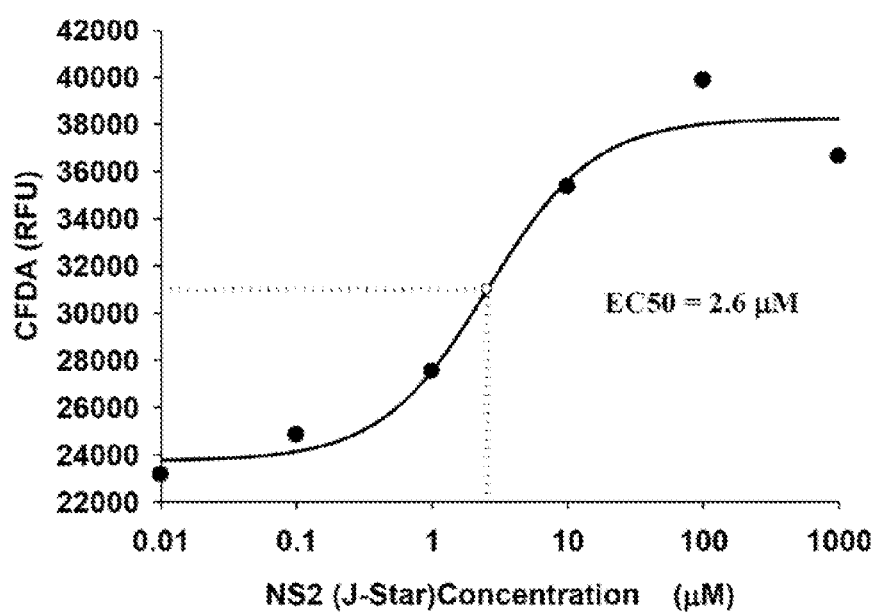
FIG. 31 shows a graph fitting the CFDA (in relative fluorescence units) data at varying non-milled NS2 ((J-Star) in DMSO) concentrations to a curve from which is derived the $EC_{50}$ value.

NS2 is fully neuroprotective against hydrogen peroxide toxicity with this assay. Results are shown in Table 15 and FIGS. 30 and 31.

h. Experiment 8: Dose response to non-milled NS2 (J-Star) in DMSO. Effect on cell death after co-treatment with 10 µM hydrogen peroxide.
  i. NS2 Source: J-Star (non-milled)
  ii. Formulation: Initial stock was formulated in 100% DMSO
  iii. Assay: Propidium Iodide
  iv. Toxin: 10 µM hydrogen peroxide
  v. Duration of treatment: 5 hours
  vi. Growth medium: B27/neurobasal medium without antioxidants
  vii. Culture matrix: poly-L-lysine
  vii. Conclusions: The $EC_{50}$ was observed at 1.1 µM; full efficacy relative to controls (CBD+HP and no-treatment control) was observed at 10 µM NS2.

Figure 32:
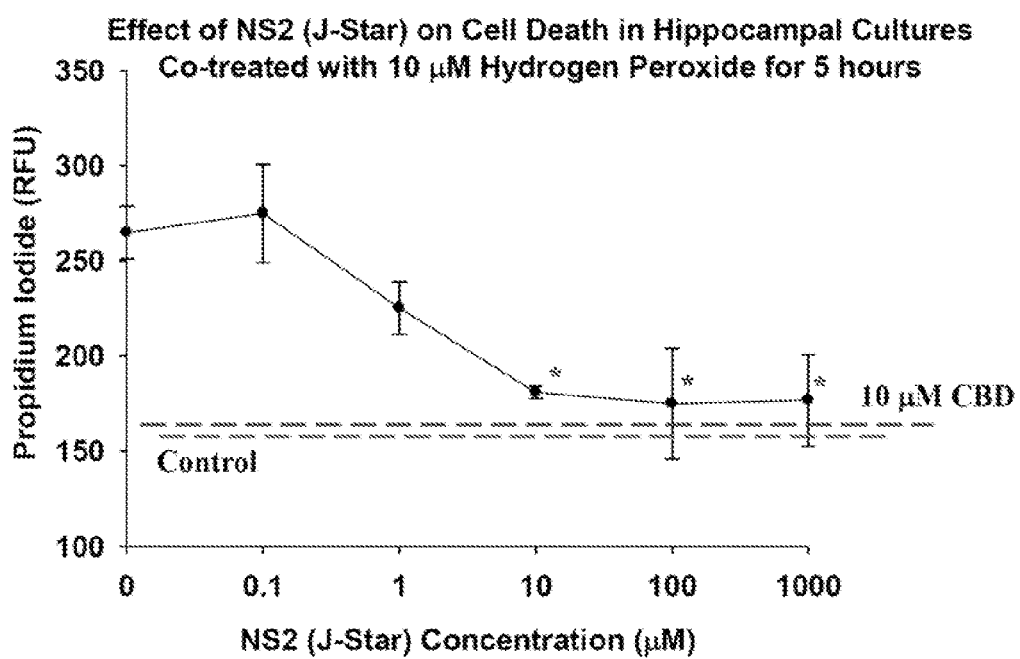
FIG. 32 shows dose response data for non-milled NS2 (J-Star) in DMSO showing effect on cell death in hippocampal cells after co-treatment with 10 µM hydrogen peroxide. *indicates data points that are significantly different from HP treatment alone.
Figure 33:
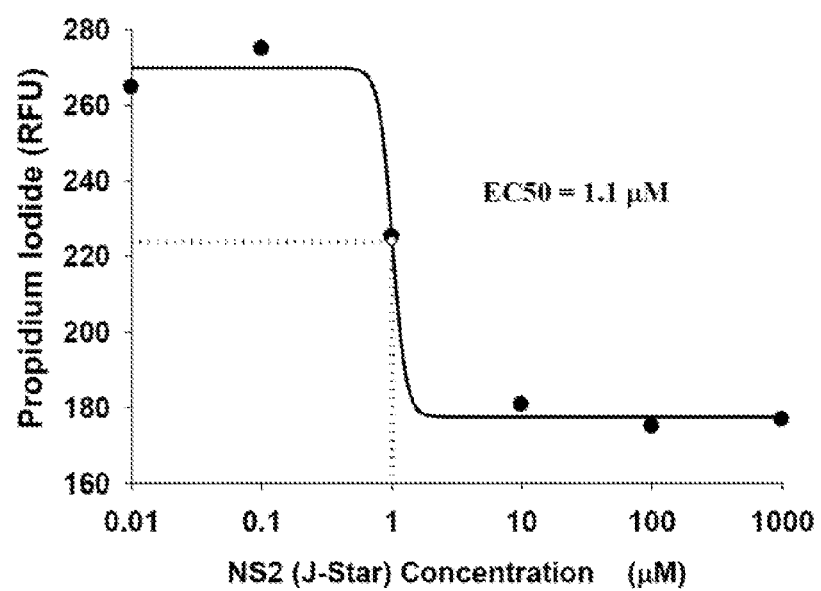
FIG. 33 shows a graph fitting the propidium iodide data (in relative fluorescence units) at varying non-milled NS2 ((J-Star) in DMSO) concentrations to a curve from which the $EC_{50}$ value is derived.

NS2 is fully neuroprotective against hydrogen peroxide toxicity with this assay. These data suggest that the protective effect against cell death may be slightly more potent than that observed for neuronal viability. Results are shown in Table 16 and FIGS. 32 and 33.

TABLE 15

Dose Response Data for Non-Milled NS2 (J-Star) in DMSO Showing Effect on
Neuronal Viability after Co-Treatment with 10 µM Hydrogen Peroxide

| Statistical Analysis | Control | CBD + HP 10 µM | NS2 + HP 1 mM | NS2 + HP 100 µM | NS2 + HP 10 µM | NS2 + HP 1 µM | NS2 + HP 0.1 µM | HP 10 µM |
|---|---|---|---|---|---|---|---|---|
| | 40722 | 47620 | 45216 | 42919 | 31214 | 20809 | 23600 | 19585 |
| | 42919 | 34696 | 39269 | 38622 | 33768 | 29430 | 25371 | 24829 |
| | 42919 | 48238 | 26576 | 38622 | 33425 | 23257 | 31107 | 25462 |
| | 43342 | 41535 | 26294 | 26294 | 32194 | 34696 | 22089 | 22089 |
| | 38622 | 36615 | 45807 | 52763 | 46105 | 29430 | 21926 | 23772 |
| Mean | 41705* | 41741* | 36632* | 39844* | 35341* | 27524 | 24819 | 23147 |
| Std Error | 897 | 2763 | 4318 | 4260 | 2729 | 2470 | 1690 | 1058 |
| P value * | <0.001 | <0.001 | <0.002 | <0.001 | <0.004 | N.S. | N.S. | N.S. |
| % of Control | 100 ± 2 | 100 ± 7 | 88 ± 10 | 96 ± 10 | 85 ± 7 | 66 ± 6 | 60 ± 4 | 56 ± 3 |

*Significantly different from treatment with 10 µM hydrogen peroxide alone.

N.S.: Not significantly different from treatment with 10 µM hydrogen peroxide alone.

TABLE 16

Dose Response Data for Non-Milled NS2 (J-Star) in DMSO Showing Effect on
Cell Death after Co-Treatment with 10 μM Hydrogen Peroxide

| Statistical Analysis | Control | CBD + HP 10 μM | NS2 + HP 1 mM | NS2 + HP 100 μM | NS2 + HP 10 μM | NS2 + HP 1 μM | NS2 + HP 0.1 μM | HP 10 μM |
|---|---|---|---|---|---|---|---|---|
| | 180 | 180 | 180 | 125 | 180 | 246 | 246 | 254 |
| | 117 | 133 | 204 | 125 | 180 | 196 | 315 | 246 |
| | 180 | 117 | 133 | 246 | 172 | 246 | 204 | 319 |
| | 164 | 129 | 117 | 246 | 180 | 188 | 350 | 246 |
| | 144 | 184 | 250 | 133 | 192 | 250 | 259 | 259 |
| Mean | 157* | 161* | 177* | 175* | 181* | 225 | 275 | 265 |
| Std Error | 12 | 12 | 24 | 29 | 3 | 14 | 26 | 14 |
| P value * | <0.001 | <0.001 | <0.002 | <0.002 | <0.003 | N.S. | N.S. | N.S. |
| % of Control | 100 ± 8 | 103 ± 8 | 113 ± 15 | 111 ± 18 | 115 ± 2 | 143 ± 9 | 175 ± 17 | 169 ± 9 |

Figure 34:
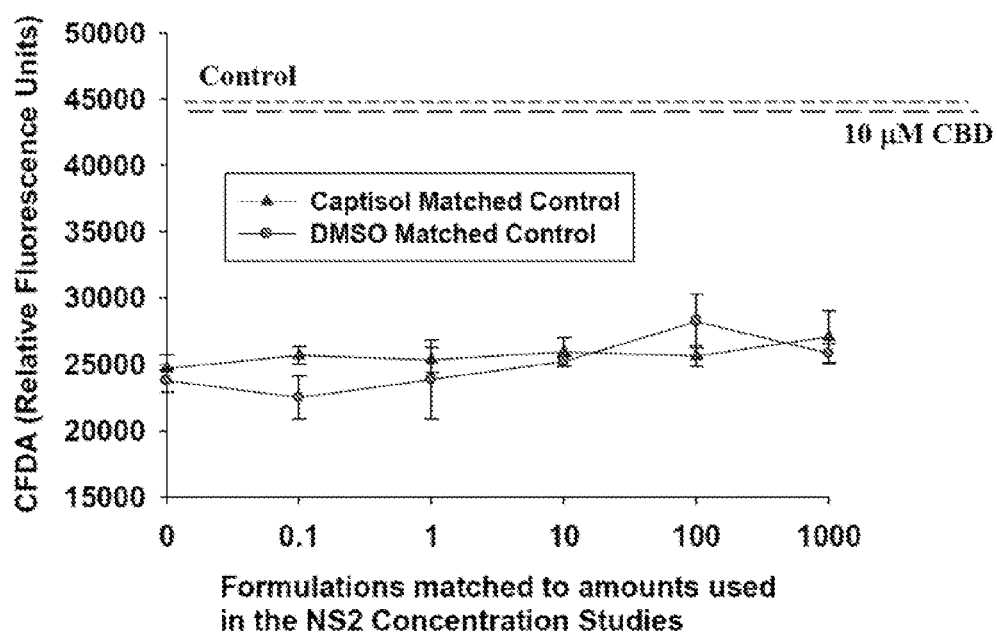
FIG. 34 shows dose response data for the formulation vehicles on neuronal cell viability after co-treatment with 10 µM hydrogen peroxide.

*Significantly different from treatment with 10 μM hydrogen peroxide alone.
N.S.: Not significantly different from treatment with 10 μM hydrogen peroxide alone.

i. Experiment 9: Dose response to Formulation vehicles. Effect on neuronal viability after co-treatment with 10 μM hydrogen peroxide.
   i. Test agents: Captisol® [Cap; (5 mg/ml i.e., 0.5%)] and 1% DMSO (abbreviated to DM; 1% was the highest concentration used). The amounts used for the formulations were matched to those used in the NS2 studies.
   ii. Assay: CFDA
   iii. Toxin: 10 μM hydrogen peroxide
   iv. Duration of treatment: 5 hours
   v. Growth medium: B27/neurobasal medium without antioxidants
   vi. Culture matrix: poly-L-lysine
   vii. Conclusions: There was no detectible effect on neuronal viability from either Captisol® or DMSO when tested under the same conditions as for NS2. Results are shown in Tables 17 and 18 and FIG. 34.

TABLE 17

Dose Response Data for Formulation Vehicles Showing Effect on Neuronal
Viability after Co-Treatment with 10 μM Hydrogen Peroxide

| Statistical Analysis | Control | CBD + HP 10 μM | Cap + HP 500 μγ/ml | Cap + HP 50 μg/ml | Cap + HP 5 μg/ml | Cap + HP 500 pg/ml | Cap + HP 50 pg/ml | HP 10 μM |
|---|---|---|---|---|---|---|---|---|
| | 52563 | 52563 | 24629 | 26471 | 23833 | 23228 | 27627 | 24629 |
| | 34496 | 34496 | 29230 | 24629 | 25171 | 28219 | 23833 | 26094 |
| | 49934 | 42719 | 20687 | 27627 | 23833 | 25171 | 24718 | 23228 |
| | 38422 | 42719 | 31107 | 26188 | 27627 | 26471 | 26094 | 21889 |
| | 45016 | 45216 | 29746 | 23228 | 29230 | 23572 | 26094 | 27627 |
| Mean | 44086* | 43543* | 27080 | 25629 | 25939 | 25332 | 25673 | 24693 |
| Std Error | 3398 | 2893 | 1934 | 767 | 1076 | 927 | 651 | 1014 |
| P value * | <0.001 | <0.001 | N.S. | N.S. | N.S. | N.S. | N.S. | N.S. |
| % of Control | 100 ± 8 | 99 ± 7 | 61 ± 4 | 58 ± 2 | 59 ± 2 | 57 ± 2 | 58 ± 2 | 56 ± 2 |

*Significantly different from treatment with 10 μM hydrogen peroxide alone.
N.S.: Not significantly different from treatment with 10 μM hydrogen peroxide alone.

TABLE 18

Dose Response Data for Formulation Vehicles Showing Effect on Neuronal
Viability after Co-Treatment with 10 μM Hydrogen Peroxide

| Statistical Analysis | Control | CBD + HP 10 μM | DM + HP 1% | DM + HP 0.1% | DM + HP .01% | DM + HP .001% | DM + HP .0001% | HP 10 μM |
|---|---|---|---|---|---|---|---|---|
| | 52563 | 52563 | 24629 | 31665 | 24629 | 21003 | 23228 | 22218 |
| | 34496 | 34496 | 24629 | 25171 | 26094 | 32661 | 28219 | 23428 |
| | 49934 | 42719 | 24629 | 32886 | 24629 | 29230 | 19685 | 24899 |
| | 38422 | 42719 | 27627 | 22089 | 26094 | 18215 | 19385 | 21889 |
| | 45016 | 45216 | 27627 | 29333 | 24629 | 18215 | 21971 | 26482 |
| Mean | 44086* | 43543* | 25828 | 28229 | 25215 | 23865 | 22498 | 23783 |
| Std Error | 3398 | 2893 | 734 | 2022 | 359 | 2985 | 1599 | 857 |
| P value * | <0.001 | <0.001 | N.S. | N.S. | N.S. | N.S. | N.S. | N.S. |
| % of Control | 100 ± 8 | 99 ± 7 | 59 ± 2 | 64 ± 5 | 57 ± 1 | 54 ± 7 | 51 ± 4 | 54 ± 2 |

Figure 35:
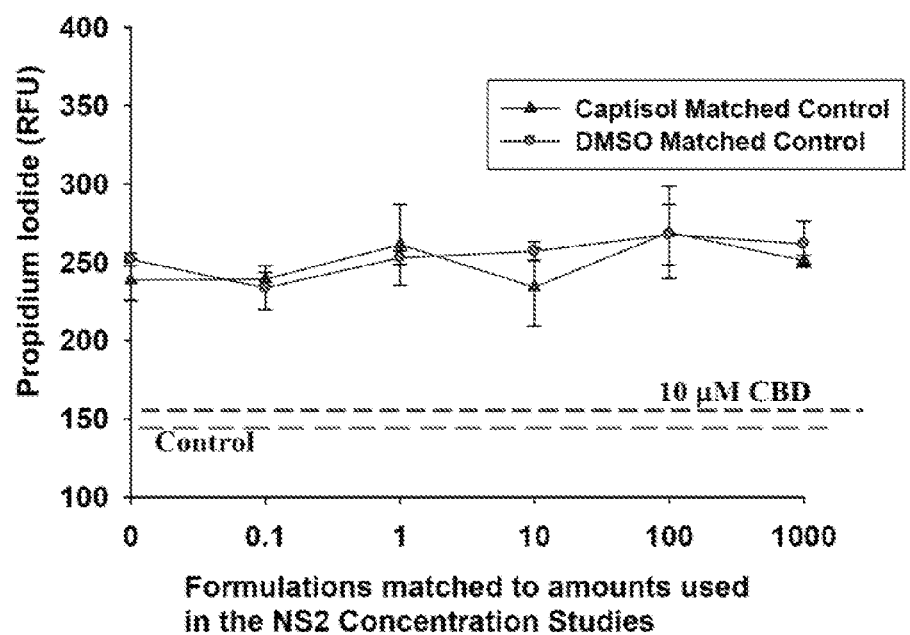
FIG. 35 shows dose response data for the formulation vehicles on cell death after co-treatment with 10 µM hydrogen peroxide.

*Significantly different from treatment with 10 μM hydrogen peroxide alone.
N.S.: Not significantly different from treatment with 10 μM hydrogen peroxide alone.

j. Experiment 10: Dose response to Formulation vehicles. Effect on cell death after co-treatment with 10 µM hydrogen peroxide.
   i. Test agents: Captisol® [CP (5 mg/ml i.e., 0.5%)] and DMSO (abbreviated to DM; 1% was the highest used)
   ii. Assay: Propidium Iodide
   iii. Toxin: 10 µM hydrogen peroxide
   iv. Duration of treatment: 5 hours
   v. Growth medium: B27/neurobasal medium without antioxidants
   vi. Culture matrix: poly-L-lysine
   vii. Conclusions: There was no detectible effect on cell death from either Captisol® or DMSO when tested under the same conditions as for NS2. Results are shown in Tables 19 and 20 and FIG. 35.

NS2 in the CFDA neuronal viability assay, whereas the no effect concentration for both formulations and batches was 1 µM.

D. Non-linear curve fitting Logistic analyses indicated that NS2 $EC_{50}$ s in the CFDA neuronal viability assay ranged from 3 to 10 µM. The best available $EC_{50}$ estimate is from the CoreRx NS2 (milled) formulated in Captisol®, which showed an $EC_{50}$ of 7±4 µM. All the $EC_{50}$s from the different NS2 formulations for the CFDA assays fall within this range. It is our conclusion that the two compound batches and the two formulations are characterized by their substantial similarity.

E. NS2 exhibited protective activity against hydrogen peroxide toxicity in the Propidium Iodide (PI) assay. This was observed with both formulations and with both compound batches.

TABLE 19

Dose Response Data for Formulation Vehicles Showing Effect on Cell Death after Co-Treatment with 10 µM Hydrogen Peroxide

| Statistical Analysis | Control | CBD + HP 10 µM | Cap + HP 500 µg/ml | Cap + HP 50 µg/ml | Cap + HP 5 mg/ml | Cap + HP 500 pg/ml | Cap + HP 50 pg/ml | HP 10 µM |
|---|---|---|---|---|---|---|---|---|
|  | 125 | 140 | 246 | 246 | 246 | 246 | 229 | 263 |
|  | 144 | 133 | 246 | 254 | 250 | 246 | 229 | 188 |
|  | 117 | 180 | 263 | 180 | 140 | 180 | 246 | 246 |
|  | 180 | 184 | 250 | 350 | 246 | 315 | 246 | 246 |
|  | 144 | 156 | 250 | 315 | 288 | 319 | 246 | 250 |
| Mean | 142* | 159* | 251 | 269 | 234 | 261 | 239 | 239 |
| Std Error | 11 | 10 | 3 | 29 | 25 | 26 | 4 | 13 |
| P value * | <0.001 | <0.003 | N.S. | N.S. | N.S. | N.S. | N.S. | N.S. |
| % of Control | 100 ± 8 | 112 ± 7 | 177 ± 2 | 189 ± 20 | 165 ± 18 | 184 ± 18 | 168 ± 3 | 168 ± 9 |

Cap = Captisol ® vehicle.
*Significantly different from treatment with 10 µM hydrogen peroxide alone.
N.S.: Not significantly different from treatment with 10 µM hydrogen peroxide alone.

TABLE 20

Dose Response Data for Formulation Vehicles Showing Effect on Cell Death after Co-Treatment with 10 µM Hydrogen Peroxide

| Statistical Analysis | Control | CBD + HP 10 µM | DM + HP 1% | DM + HP 0.1% | DM + HP .01% | DM + HP .001% | DM + HP .0001% | HP 10 µM |
|---|---|---|---|---|---|---|---|---|
|  | 125 | 140 | 250 | 297 | 276 | 267 | 246 | 267 |
|  | 144 | 133 | 246 | 297 | 267 | 259 | 246 | 254 |
|  | 117 | 180 | 315 | 276 | 246 | 246 | 184 | 246 |
|  | 180 | 184 | 230 | 192 | 250 | 246 | 267 | 246 |
|  | 144 | 156 | 267 | 276 | 246 | 246 | 225 | 246 |
| Mean | 142* | 159* | 262 | 268 | 257 | 253 | 234 | 252 |
| Std Error | 11 | 10 | 15 | 19 | 6 | 4 | 14 | 4 |
| P value * | <0.001 | <0.003 | N.S. | N.S. | N.S. | N.S. | N.S. | N.S. |
| % of Control | 100 ± 8 | 112 ± 7 | 185 ± 11 | 189 ± 13 | 181 ± 4 | 178 ± 3 | 165 ± 10 | 177 ± 3 |

DM = DMSO vehicle.
*Significantly different from treatment with 10 µM hydrogen peroxide alone.
N.S.: Not significantly different from treatment with 10 µM hydrogen peroxide alone.

7. Summary of Observations and Conclusions

A. NS2 exhibited neuroprotective activity against hydrogen peroxide toxicity in the CFDA assay, with both formulations (DMSO and Captisol®) and with both compound batches (CoreRx and J-Star, milled and non-milled, respectively).

B. The neuroprotective effect of NS2 in the CFDA assay was equal to the control (no HP treatment) and positive control (CBD), indicating full protection.

C. Full protection relative to controls was observed with both NS2 formulations and NS2 batches at 100 µM F. The protective effect of NS2 in the PI assay was equal to that of the control (no HP treatment) and positive control (CBD), indicating full protection.

G. Full protection relative to no-treatment controls was observed with both NS2 formulations and NS2 batches at 10 µM NS2 in the PI assay, whereas the no effect concentration for both formulations and batches was 1 µM. It was a consistent finding that the NS2 response in the cell death assay exhibited greater potency for full protection than in the CFDA assay. It should be recognized that the cell death assay is not specific to neurons and may involve non-neuronal cells that are present in this model CNS system.

H. Non-linear Logistic curve fitting indicated that $EC_{50}$s for the PI assay ranged from 1.1 to 2.8 µM. However, the steep nature of the Logistic curve with this assay made estimates difficult without the measurement of half-log concentration responses to help define the inflection point of the curves. The best available estimate is the mean value for all PI data, which is 2±1 µM. It is our conclusion that the two compound batches and the two formulations were characterized by their substantial similarity. Because of the narrow response ranges in the PI assay, further analysis may be required to refine the $EC_{50}$ estimate. These data suggest that NS2 may be more potent in preventing cell death than in increasing neuronal viability against hydrogen peroxide toxicity.

I. The toxic signal produced by 10 µM hydrogen peroxide was typical of a wide variety of oxidative stressors (ethanol, heavy metals, ammonium acetate, and glutamate) that have been tested in the past, with decreases from control ranging from 30 to 50%.

J. The positive control (10 µM cannabidiol) was active on every test plate, indicating that the model system was responding in a typical manner.

Example 13: Dose Responses for Three Deuterated Compounds Assessing Protective Activity From Hydrogen Peroxide Toxicity in Dissociated Hippocampal Cultures A. Experimental Plan for Dose Response Evaluation for Protection from Hydrogen Peroxide Toxicity.
  1. Test Agents:
    a. ALD-6—batch 1 (Legacy ID: NS2-D6 or compound I-1); amount used: 5.0 mg; MW=242.734
    b. ALD-5—batch 1 (Legacy ID: D3); amount used: 6.1 mg; MW=203.24; structure:

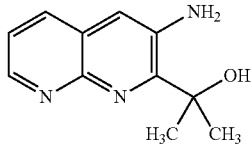

c. ALD-2—batch 1 Legacy ID: D2); amount used: 5.6 mg; MW=203.24; structure:

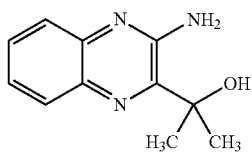

2. Formulation and Stock Solution Preparation
    a. Dimethyl sulfoxide (DMSO) at 100% was used for all samples.
    b. Observations:
      i. ALD-6: (5 mg, 20.6 µmol) of ALD-6 was dissolved in 0.206 ml of DMSO for a 100 mM stock solution. The 100 mM ALD-6/DMSO solution was clear. Log dilutions were done with DPBS. Upon dilution from 1:10 to 10 mM with DPBS, the solution became cloudy, but cleared after vortex mixing. In general, the benchmark concentration goal for DMSO in primary neuronal cultures is less than 0.1%, to avoid pharmacological effects from the DMSO. Note that 0.3% DMSO was used for the 300 µM test concentration of all samples. No apparent toxicity was observed in the assays after the 5 hr test.
      ii. ALD-5: The 100 mM stock solution of ALD-5 was prepared by dissolving 6.1 mg (30 µmol) into 0.3 ml of DMSO. The ALD-5/DMSO mixture was a clear yellow solution. Log dilutions were done with DPBS. Upon dilution from 1:10 to 10 mM with DPBS, the solution remained a clear yellow solution.
      iii. ALD-2: The 100 mM stock solution of ALD-2 was prepared by dissolving 5.6 mg (27.55 µmol) into 0.275 ml of DMSO. The ALD-2/DMSO mixture was a clear amber solution. Log dilutions were done with DPBS. Upon dilution from 1:10 to 10 mM with DPBS, the solution remained a clear amber solution.
    c. Details on the preparation of stock solutions: Compound dilution in DMSO/DPBS
      i. Stock A was 100 mM of compound in 100% DMSO.
      ii. Stock B was prepared by adding 50 µl of stock A into 450 µl of DPBS for a final concentration of 10 mM. Added 3.3 µl into 100 µl DPBS to yield a final concentration of 300 µM in 0.3% DMSO.
      iii. Stock C was prepared by adding 50 µl of stock B into 450 µl of DPBS for a final concentration of 1 mM. Added 10 µl into 100 µl DPBS to yield a final concentration of 100 µM in 0.1% DMSO.
      iv. Stock D was prepared by adding 50 µl of stock C into 450 µl of DPBS for a final concentration of 100 µM. Added 10 µl into 100 µl DPBS to yield a final concentration of 10 µM in 0.01% DMSO.
      v. Stock E was prepared by adding 50 µl of stock D into 450 µl of DPBS for a final concentration of 10 µM. Added 10 µl into 100 µl DPBS to yield a final concentration of 1 µM in 0.001% DMSO.
      vi. Stock F was prepared by adding 50 µl of stock E into 450 µl of DPBS for a final concentration of 1 µM. Added 10 µl into 100 µl DPBS for a final concentration of 0.1 µM in 0.0001% DMSO.
      vii. 10 µl of the appropriate dilution was added to 90 µl for a total volume of 100 µl in the well.
  3. Culture conditions designed to detect neuroprotection from oxidative stress associated with hydrogen peroxide:
    a. Rat hippocampal cultures were prepared as previously described (Brenneman D E, Smith G R, Zhang Y, Du Y, Kondaveeti S K, Zdilla M J, Reitz A B. (2012) J. Molecular Neuroscience, 47:368-379). Under these conditions, the cultures are at least 90% neuronal. The most abundant non-neuronal cells are astrocytes. Rat E18 hippocampal tissue was purchased from Brain Bits, LLC (Springfield IL). Tissue was stored in Hibernate E medium for transport.
    b. All cultures were prepared into a 96-well format at a plating density of 10K cells per well. Cultures were treated between day 10 and day 21 after dissociation of E18 hippocampal tissue. For these experiments, all plates were treated on day 13. In all experiments, the hydrogen peroxide was added to the cultures 10 minutes after treatment with the test agent or positive control (cannabidiol). For each treatment condition, the number of replicates was five.
c. All cultures were plated in B27/Neural Basal Medium. On the day of treatment, all cultures were given a complete change of medium into serum-free B27/Neural Basal Medium without antioxidants.
d. As previously determined (Brenneman et al., 2012), 10 µM hydrogen peroxide was used to produce toxicity and oxidative stress. As described previously (Jarrett, SG, Liang, L-P, Hellier, J L, Staley, K J and Patel, M. (2008) Neurobiol. Dis 30(1): 130-138) 10 µM hydrogen peroxide has been observed in the hippocampus of rats with a kainate model of status epilepticus.
e. The positive control used in all studies was 10 µM cannabidiol, a known antioxidant agent (Hampson et al. (1998), Proc. Nat. Acad. Sci. 95:8268-8273) that is protective against oxidative stress in primary neurons (Brenneman, DE, Petkanas, D and Kinney, W. A. (2014) Annual Symposium on the Cannabinoids, page 129).
f. Neither the negative control wells, the hydrogen peroxide wells, nor the positive control wells contained any drug vehicle.

4. Assays:

Both assays used in this study have been described in detail (Brenneman D E, Smith G R, Zhang Y, Du Y, Kondaveeti S K, Zdilla M J, Reitz A B. (2012) J. Molecular Neuroscience, 47:368-379).
a. The CFDA neuronal viability assay: In this assay, the CFDA dye is taken up by all live cells and cleaved by esterases to release fluorescein. The neuronal specificity is achieved because neurons cannot remove this dye, whereas efflux of the dye from non-neuronal cells can occur over time. After washing away the extracellular dye, the cultures were read in a fluorimeter; intracellular dye intensity is proportional to the live neuronal population. Original reference: Petroski, RE and Geller H M, (1994) "Selective labeling of embryonic neurons cultures on astrocyte monolayers with 5(6)-carboxyfluorescein diacetate (CFDA)," J Neurosci. Methods 52:23.32. The mean control level for each experiment is shown as a long-dashed reference line.
b. A cell death assay, using propidium iodide, was conducted simultaneously with the CFDA assay in the same well. This dye is excluded from live cells and binds to the DNA of dead cells. The assay detects both necrotic and apoptotic cell death; it does not distinguish between neuronal cell death and non-neuronal cell death. See Sarafian T A, Kouyoumjian S, Tashkin D, Roth M D. (2002) Tox. Letters. 133: 171-179. The mean control level is shown as a red medium-dashed reference line.
c. Reagents used
   i. Hydrogen Peroxide solution, 30 wt %; Sigma-Aldrich (216736-100 ml, Lot MKBV382V)
   ii. Dimethyl Sulfoxide; Sigma-Aldrich (472301-100 ml) Batch 21096 JK
   iii. Propidium Iodide; Sigma-Aldrich (P4864-10 ml; 1 mg/ml solution in water)
   iv. CFDA [5(6)-Carboxyfluorescein Diacetate] Sigma-Aldrich Product Number: 21879-100 mg-F
   v. Cannabidiol solution, 10 mg/ml in ethanol; Sigma-Aldrich Product Number: 90899-1 ml
   vi. Dulbecco's Phosphate Buffered Saline (DPBS). Gibco (14190-144) Lot 1165767

5. Data Analyses:
a. Data Acquisition: Data were stored on Advanced Neural Dynamics computers for analyses. Data acquisition was performed on Cytofluor Fluorimeter and transferred to Excel spreadsheet for analysis with Sigma Plot 11.
b. Statistical Analysis: All data were statistically analyzed by an Analysis of Variance with the Multiple Comparisons versus Control Group (Holm-Sidak) method. Statistical significance was taken at the $P<0.05$ level. In all cases, comparisons were made to the negative control (10 µM hydrogen peroxide treatment).
c. Methodology for $EC_{50}$ determination:
   i. A broad concentration range was chosen to screen the compounds in an $EC_{50}$ potency analysis. A log-based concentration series from 0.1 µM to 300 µM was used.
   ii. A nonlinear regression analysis was used to determine the equation of the line that best fits the data. (Four parameter Logistic curve)
   iii. Based on the Logistic equation used in the preceding Example, the $EC_{50}$ s for neuroprotection were calculated and plotted by SigmaPlot 11 to determine the concentration required to produce half-maximal responses for both assays. Drop lines were used to show the axes intersections determining the $EC_{50}$.

B. Summary of Protection Studies for Aldeyra Compounds in Rat Hippocampal Cultures

TABLE 21

Summary of Protection Studies Data

| Assay | Compound | Formulation | Full Efficacy Concentration* | No effect Concentration | EC50 ± SE |
|---|---|---|---|---|---|
| CFDA | ALD-6 | DMSO | 100 µM | 1 µM | 6.8 ± 1.2 µM |
| CFDA | ALD-5 | DMSO | Inactive | Inactive | Inactive |
| CFDA | ALD-2 | DMSO | Inactive | Inactive | Inactive |
| PI | ALD-6 | DMSO | 10 µM | 0.1 µM | 0.32 ± 0.03 µM |
| PI | ALD-5 | DMSO | Inactive | Inactive | Inactive |
| PI | ALD-2 | DMSO | Inactive | Inactive | Inactive |

*Concentration of test agent showing assay response levels not significantly different from that of no treatment controls.

C. Graphical Analyses of Experimental Findings and Raw Data

Figure 36:
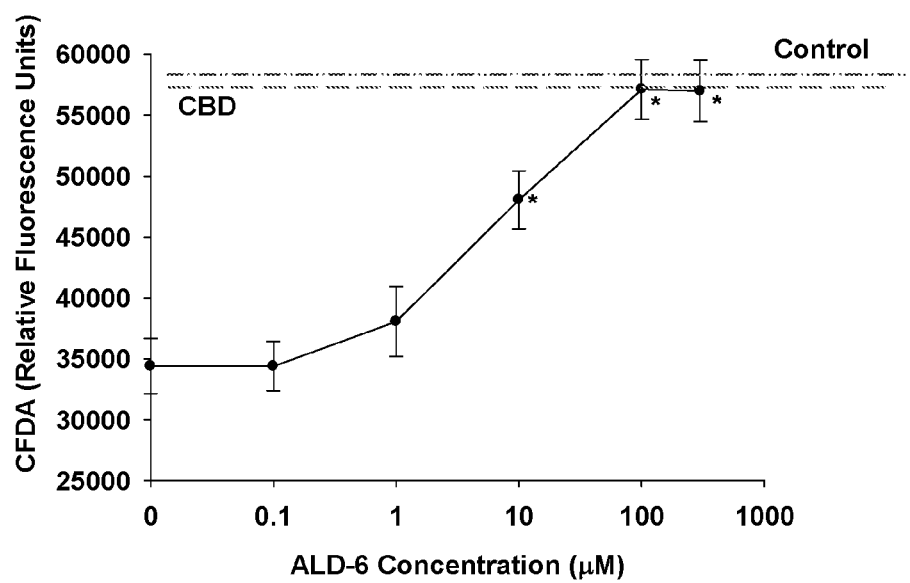
FIG. 36 shows the effect of ALD-6 (compound I-1) on neuronal viability in hippocampal cultures treated with 10 µM hydrogen peroxide. *indicates data points that are significantly different from HP treatment alone.
Figure 37:
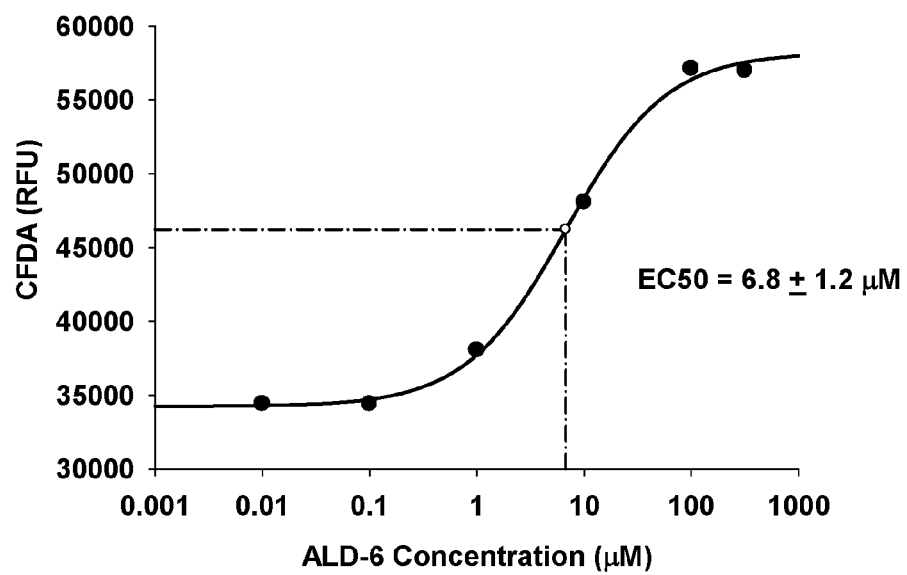
FIG. 37 shows the calculated logistic curve and $EC_{50}$ value for neuronal viability assay using hippocampal cultures treated with ALD-6.

1. Experiment 1: Dose response of ALD-6. Effect on neuronal viability after co-treatment with 10 µM hydrogen peroxide.
   a. Formulation: DMSO
   b. Assay: CFDA
   c. Toxin: 10 µM hydrogen peroxide
   d. Duration of treatment: 5 hours
   e. Growth medium: B27/neurobasal medium without antioxidants
   f. Culture matrix: poly-L-lysine
   g. Conclusions: The $EC_{50}$ was observed at 6.8±1.2 µM; full efficacy relative to controls (CBD+HP and no-treatment control) was observed at 100 µM ALD-6. ALD-6 is fully neuroprotective against hydrogen peroxide toxicity at 100 µM in this assay. Results are shown in Table 22 and FIGS. 36 and 37.

TABLE 22

Dose Response Data for ALD-6 Showing Effect on Neuronal Viability after Co-Treatment with 10 μM Hydrogen Peroxide

| Statistical Analysis | Control | CBD + HP 10 μM | ALD6 + HP 300 μM | ALD6 + HP 100 μM | ALD6 + HP 10 μM | ALD6 + HP 1 μM | ALD6 + HP 0.1 μM | HP 10 μM |
|---|---|---|---|---|---|---|---|---|
| | 59551 | 67121 | 65778 | 61821 | 47737 | 43459 | 41244 | 31224 |
| | 55935 | 52880 | 53184 | 50555 | 53184 | 40839 | 36732 | 32978 |
| | 61821 | 55631 | 53184 | 57177 | 45333 | 33090 | 31224 | 43036 |
| | 59247 | 64665 | 53184 | 52880 | 53184 | 43340 | 31224 | 34419 |
| | 54201 | 67958 | 59551 | 63181 | 40839 | 29547 | 31547 | 30376 |
| Mean | 58151* | 57221* | 56976* | 57123* | 48055* | 38055 | 34394 | 34407 |
| Std Error | 1363 | 1977 | 2522 | 2449 | 2368 | 2845 | 2007 | 2268 |
| P value * | <0.001 | <0.001 | <0.001 | <0.001 | <0.001 | N.S. | N.S. | N.S. |
| % of Control | 100 ± 2 | 98 ± 3 | 98 ± 4 | 98 ± 4 | 83 ± 4 | 65 ± 5 | 59 ± 3 | 59 ± 4 |

*Significantly different from treatment with 10 μM hydrogen peroxide alone.
N.S.: Not significantly different from treatment with 10 μM hydrogen peroxide alone.

Figure 38:
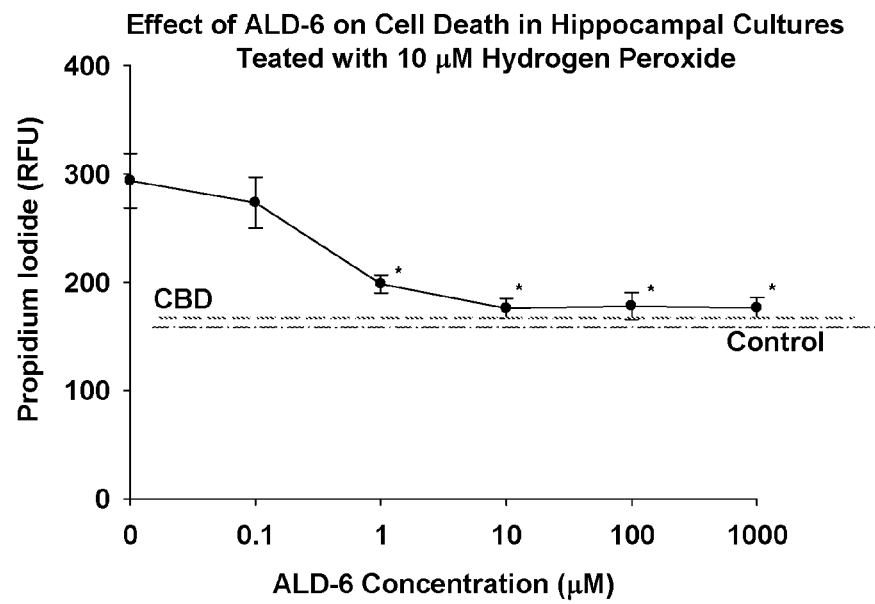
FIG. 38 shows dose response effect of ALD-6 on cell death after co-treatment with 10 µM hydrogen peroxide. *indicates data points that are significantly different from HP treatment alone.
Figure 39:
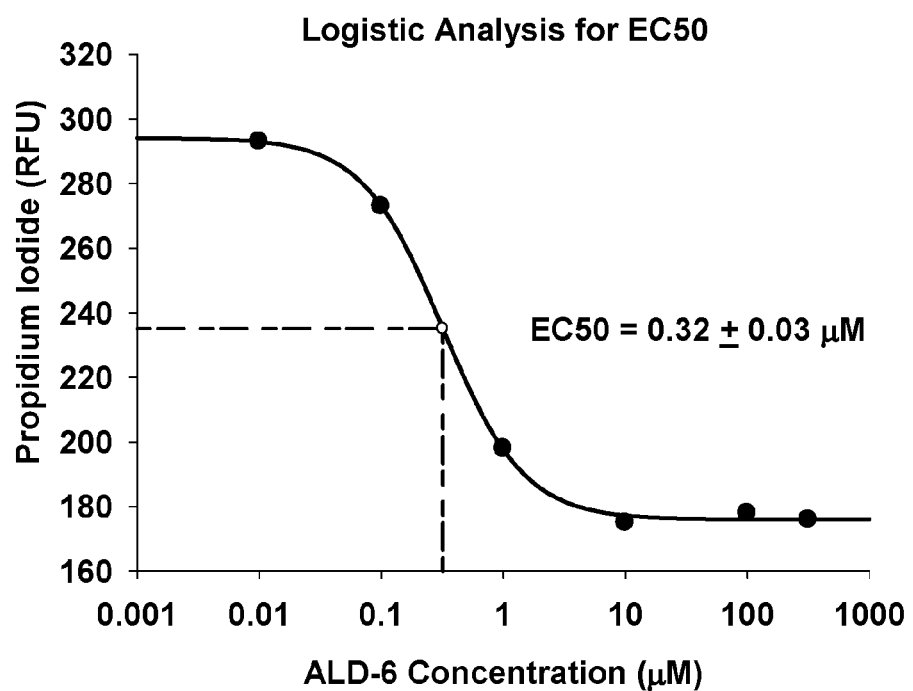
FIG. 39 shows the calculated logistic curve and $EC_{50}$ value for cell death assay using hippocampal cultures treated with ALD-6.

2. Experiment 2: Dose response effect of ALD-6 on cell death after co-treatment with 10 μM hydrogen peroxide.
   a. Formulation: DMSO
   b. Assay: Propidium Iodide
   c. Toxin: 10 μM hydrogen peroxide
   d. Duration of treatment: 5 hours
   e. Growth medium: B27/neurobasal medium without antioxidants
   f. Culture matrix: poly-L-lysine
   g. Conclusions: The $EC_{50}$ was observed at 0.32±0.03 μM; full efficacy relative to controls (CBD+HP and no-treatment control) was observed at 10 μM ALD-6. ALD-6 is fully neuroprotective against hydrogen peroxide toxicity in this assay. These data suggest that the protective effect against cell death is more potent than that observed for neuronal viability. Results are shown in Table 23 and FIGS. 38 and 39.

Figure 40:
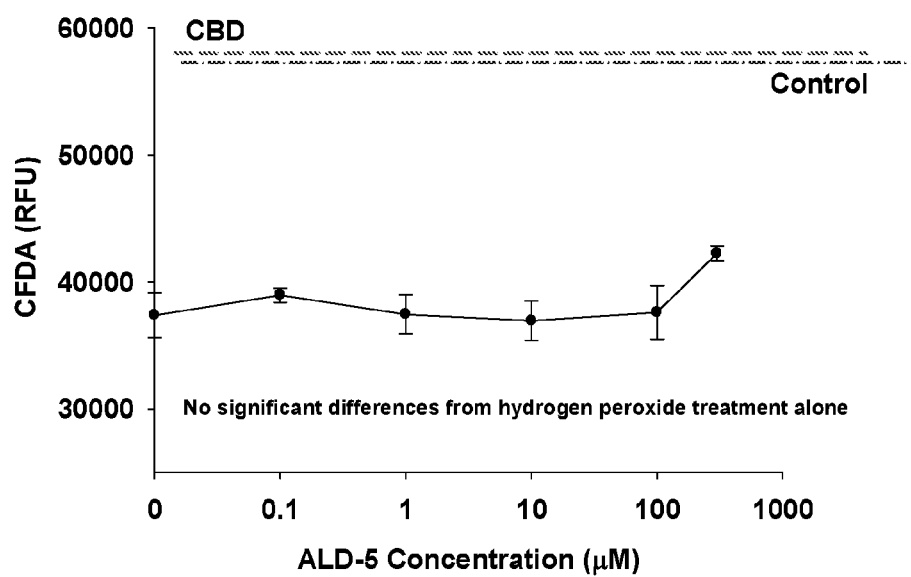
FIG. 40 shows dose response effect of ALD-5 on neuronal viability after co-treatment with 10 µM hydrogen peroxide.

3. Experiment 3: Dose response to ALD-5 in DMSO. Effect on neuronal viability after co-treatment with 10 μM hydrogen peroxide.
   a. Formulation: DMSO
   b. Assay: CFDA
   c. Toxin: 10 μM hydrogen peroxide
   d. Duration of treatment: 5 hours
   e. Growth medium: B27/neurobasal medium without antioxidants
   f. Culture matrix: poly-L-lysine
   g. Conclusions: There was no statistically significant neuroprotective activity from ALD-5 against hydrogen peroxide toxicity from 0.1 to 300 μM. Results are shown in Table 24 and FIG. 40.

TABLE 23

Dose Response Data for ALD-6 Showing Effect on Neuronal Viability after Co-Treatment with 10 μM Hydrogen Peroxide

| Statistical Analysis | Control | CBD + HP 10 μM | ALD6 + HP 300 μM | ALD6 + HP 100 μM | ALD6 + HP 10 μM | ALD6 + HP 1 μM | ALD6 + HP 0.1 μM | HP 10 μM |
|---|---|---|---|---|---|---|---|---|
| | 159 | 119 | 159 | 167 | 179 | 214 | 225 | 225 |
| | 159 | 159 | 189 | 193 | 183 | 183 | 250 | 366 |
| | 171 | 171 | 189 | 206 | 189 | 223 | 294 | 294 |
| | 163 | 123 | 147 | 189 | 189 | 183 | 242 | 255 |
| | 171 | 197 | 197 | 135 | 139 | 189 | 356 | 329 |
| Mean | 165* | 154* | 176* | 178* | 176* | 198* | 273 | 294 |
| Std Error | 3 | 15 | 10 | 12 | 9 | 8 | 24 | 25 |
| P value * | <0.001 | <0.001 | <0.001 | <0.001 | <0.001 | <0.001 | N.S. | N.S. |
| % of Control | 100 ± 2 | 93 ± 9 | 107 ± 6 | 108 ± 7 | 107 ± 5 | 120 ± 5 | 165 ± 15 | 178 ± 15 |

*Significantly different from treatment with 10 μM hydrogen peroxide alone.
N.S.: Not significantly different from treatment with 10 μM hydrogen peroxide alone.

TABLE 24

Dose Response Data for ALD-5 Showing Effect on Neuronal Viability after Co-Treatment with 10 μM Hydrogen Peroxide

| Statistical Analysis | Control | CBD + HP 10 μM | ALD5 + HP 300 μM | ALD5 + HP 100 μM | ALD5 + HP 10 μM | ALD5 + HP 1 μM | ALD5 + HP 0.1 μM | HP 10 μM |
|---|---|---|---|---|---|---|---|---|
| | 55631 | 58812 | 40839 | 41143 | 39126 | 42756 | 39043 | 34930 |
| | 58508 | 51551 | 43036 | 43743 | 37102 | 35588 | 38739 | 41244 |
| | 58508 | 58812 | 41143 | 32978 | 41379 | 34189 | 40839 | 41925 |
| | 57357 | 55983 | 44028 | 36732 | 34115 | 38997 | 38739 | 33203 |
| | 54068 | 62790 | 42201 | 33429 | 32978 | 35707 | 37350 | 35588 |
| Mean | 56814* | 57590* | 42249 | 37605 | 36940 | 37447 | 38942 | 37378 |
| Std Error | 865 | 1858 | 592 | 2119 | 1552 | 1544 | 558 | 1764 |
| P value * | <0.001 | <0.001 | N.S. | N.S. | N.S. | N.S. | N.S. | N.S. |
| % of Control | 100 ± 2 | 101 ± 3 | 74 ± 1 | 66 ± 4 | 65 ± 3 | 66 ± 3 | 69 ± 1 | 66 ± 3 |

*Significantly different from treatment with 10 μM hydrogen peroxide alone.
N.S.: Not significantly different from treatment with 10 μM hydrogen peroxide alone.

Figure 41:
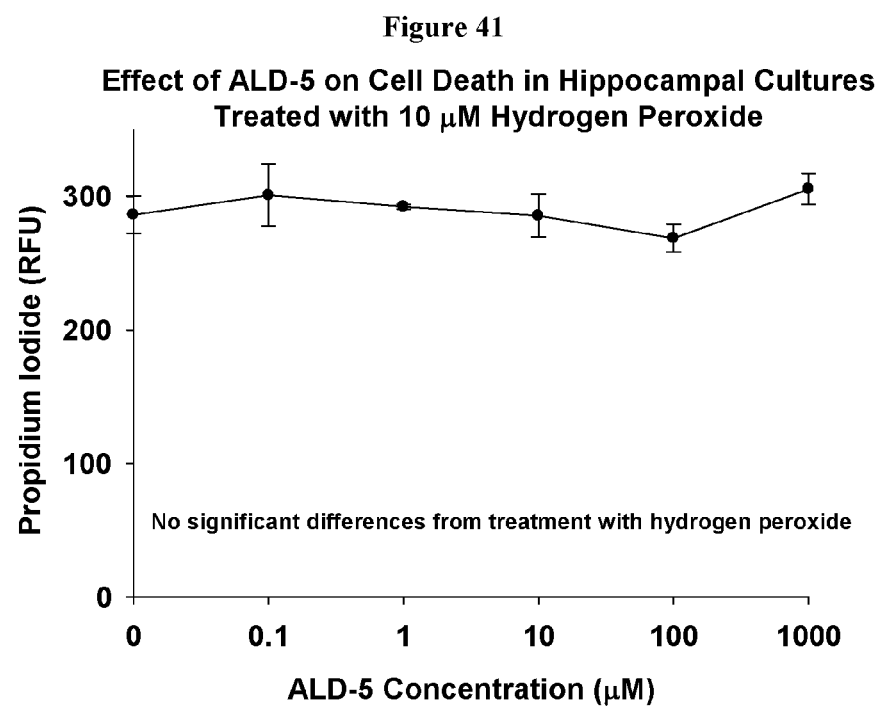
FIG. 41 shows dose response effect of ALD-5 on cell death after co-treatment with 10 μM hydrogen peroxide.

4. Experiment 4: Dose response to ALD-5. Effect on cell death after co-treatment with 10 μM hydrogen peroxide.
   a. Formulation: DMSO
   b. Assay: Propidium Iodide
   c. Toxin: 10 μM hydrogen peroxide
   d. Duration of treatment: 5 hours
   e. Growth medium: B27/neurobasal medium without antioxidants
   f. Culture matrix: poly-L-lysine
   g. Conclusions: There was no statistically significant protection from cell death from 0.1 to 300 μM ALD-5. Results are shown in Table 25 and FIG. 41.

Figure 42:
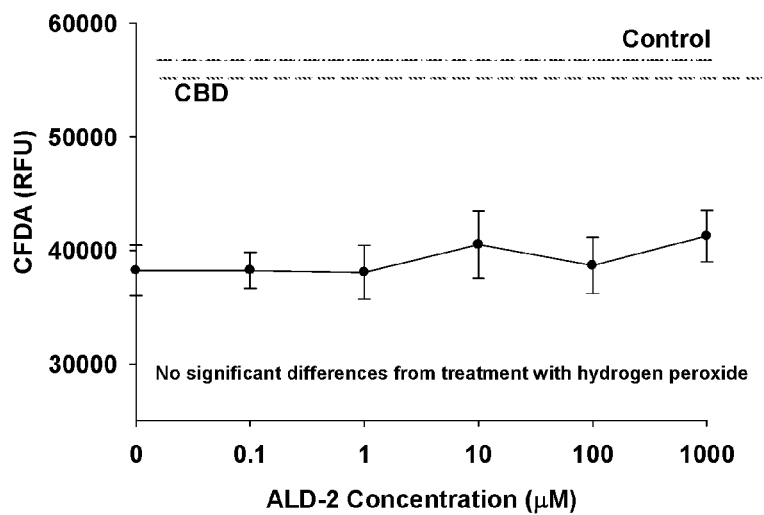
FIG. 42 shows dose response effect of ALD-2 on neuronal viability after co-treatment with 10 μM hydrogen peroxide.

5. Experiment 5: Dose response to ALD-2. Effect on neuronal viability after co-treatment with 10 μM hydrogen peroxide.
   a. Formulation: DMSO
   b. Assay: CFDA
   c. Toxin: 10 μM hydrogen peroxide
   d. Duration of treatment: 5 hours
   e. Growth medium: B27/neurobasal medium without antioxidants
   f. Culture matrix: poly-L-lysine
   g. Conclusions: ALD-2 had no statistically significant neuroprotection from decreases in neuronal viability in hydrogen peroxide-treated cultures. Results are shown in Table 26 and FIG. 42.

TABLE 25

Dose Response Data for ALD-5 Showing Effect on Cell Death after Co-Treatment with 10 μM Hydrogen Peroxide

| Statistical Analysis | Control | CBD + HP 10 μM | ALD5 + HP 300 μM | ALD5 + HP 100 μM | ALD5 + HP 10 μM | ALD5 + HP 1 μM | ALD5 + HP 0.1 μM | HP 10 μM |
|---|---|---|---|---|---|---|---|---|
| | 159 | 147 | 294 | 294 | 225 | 294 | 294 | 258 |
| | 123 | 164 | 293 | 255 | 294 | 294 | 294 | 294 |
| | 159 | 164 | 352 | 250 | 294 | 294 | 366 | 255 |
| | 179 | 83 | 294 | 250 | 294 | 285 | 225 | 330 |
| | 127 | 123 | 294 | 294 | 320 | 294 | 325 | 294 |
| Mean | 149* | 136* | 305 | 269 | 285 | 292 | 301 | 286 |
| Std Error | 11 | 15 | 12 | 10 | 16 | 2 | 23 | 14 |
| P value * | <0.001 | <0.001 | N.S. | N.S. | N.S. | N.S. | N.S. | N.S. |
| % of Control | 100 ± 7 | 91 ± 10 | 205 ± 8 | 181 ± 7 | 191 ± 11 | 196 ± 1 | 202 ± 15 | 192 ± 9 |

*Significantly different from treatment with 10 μM hydrogen peroxide alone.
N.S.: Not significantly different from treatment with 10 μM hydrogen peroxide alone.

TABLE 26

Dose Response Data for ALD-2 Showing Effect on Neuronal Viability after Co-Treatment with 10 µM Hydrogen Peroxide

| Statistical Analysis | Control | CBD + HP 10 µM | ALD2 + HP 300 µM | ALD2 + HP 100 µM | ALD2 + HP 10 µM | ALD2 + HP 1 µM | ALD2 + HP 0.1 µM | HP 10 µM |
|---|---|---|---|---|---|---|---|---|
|  | 58877 | 55631 | 43036 | 45628 | 43601 | 43743 | 40839 | 34813 |
|  | 58508 | 54240 | 45924 | 35522 | 38997 | 36732 | 33885 | 40839 |
|  | 56160 | 50251 | 45628 | 36732 | 50251 | 43036 | 40839 | 43036 |
|  | 55631 | 62291 | 36732 | 43176 | 36732 | 35522 | 40839 | 31224 |
|  | 55807 | 52880 | 35048 | 32311 | 32978 | 31331 | 34813 | 41244 |
| Mean | 56997* | 55059* | 41274 | 38674 | 40512 | 38073 | 38243 | 38231 |
| Std Error | 700 | 2015 | 2270 | 2478 | 2981 | 2351 | 1596 | 2233 |
| P value * | <0.001 | <0.001 | N.S. | N.S. | N.S. | N.S. | N.S. | N.S. |
| % of Control | 100 ± 1 | 97 ± 4 | 72 ± 4 | 68 ± 4 | 71 ± 5 | 67 ± 4 | 67 ± 3 | 67 ± 4 |

*Significantly different from treatment with 10 µM hydrogen peroxide alone.
N.S.: Not significantly different from treatment with 10 µM hydrogen peroxide alone.

Figure 43:
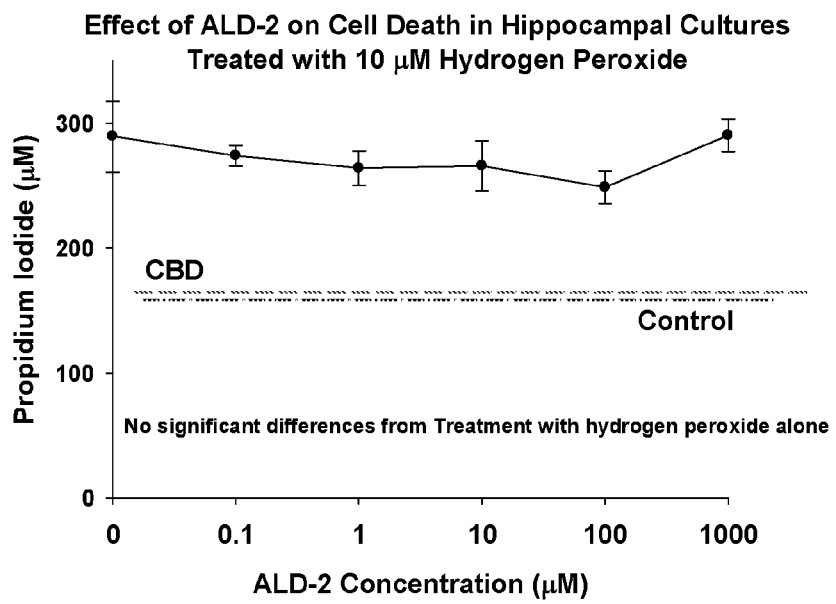
FIG. 43 shows dose response effect of ALD-2 on cell death after co-treatment with 10 μM hydrogen peroxide.

6. Experiment 6: Dose response to ALD-2. Effect on cell death after co-treatment with 10 µM hydrogen peroxide.
   a. Formulation: DMSO
   b. Assay: Propidium Iodide
   c. Toxin: 10 µM hydrogen peroxide
   d. Duration of treatment: 5 hours
   e. Growth medium: B27/neurobasal medium without antioxidants
   f. Culture matrix: poly-L-lysine
   g. Conclusions: There was no statistically significant protection from cell death produced by hydrogen peroxide after treatment with ALD-2. Results are shown in Table 27 and FIG. 43.

e. ALD-6 exhibited protective activity from cell death from hydrogen peroxide treatment in the Propidium Iodide (PI) assay.
   f. The protective effect of ALD-6 from cell death in the PI assay was not statistically different from that of the control (no HP treatment) and positive control (CBD) values, indicating full protection.
   g. Full protection relative to no-treatment control values was observed with ALD-6 at 10 µM in the PI assay, whereas the no-effect concentration was 0.1 µM. ALD-6 response in the cell death assay exhibited greater potency than in the CFDA assay. It should be recognized that the cell death assay is not

TABLE 27

Dose Response Data for ALD-2 Showing Effect on Cell Death after Co-Treatment with 10 µM Hydrogen Peroxide

| Statistical Analysis | Control | CBD + HP 10 µM | ALD2 + HP 300 µM | ALD2 + HP 100 µM | ALD2 + HP 10 µM | ALD2 + HP 1 µM | ALD2 + HP 0.1 µM | HP 10 µM |
|---|---|---|---|---|---|---|---|---|
|  | 143 | 104 | 294 | 294 | 225 | 242 | 266 | 398 |
|  | 159 | 175 | 242 | 225 | 225 | 298 | 294 | 255 |
|  | 159 | 139 | 302 | 225 | 293 | 229 | 258 | 242 |
|  | 159 | 159 | 294 | 258 | 329 | 294 | 294 | 294 |
|  | 175 | 147 | 320 | 242 | 258 | 258 | 259 | 259 |
| Mean | 159* | 145* | 290 | 249 | 266 | 264 | 274 | 290 |
| Std Error | 5 | 12 | 13 | 13 | 20 | 14 | 8 | 28 |
| P value * | <0.001 | <0.001 | N.S. | N.S. | N.S. | N.S. | N.S. | N.S. |
| % of Control | 100 ± 3 | 91 ± 8 | 182 ± 8 | 157 ± 8 | 167 ± 13 | 166 ± 9 | 172 ± 5 | 182 ± 18 |

*Significantly different from treatment with 10 µM hydrogen peroxide alone.
N.S.: Not significantly different from treatment with 10 µM hydrogen peroxide alone.

7. Summary of Observations and Conclusions
   a. ALD-6 exhibited neuroprotective activity against hydrogen peroxide toxicity in the CFDA assay.
   b. The neuroprotective effect of ALD-6 in the CFDA assay was not statistically different from the control (no HP treatment) and positive control (CBD) values, indicating full protection.
   c. Full protection relative to controls was observed at 100 µM ALD-6 in the CFDA neuronal viability assay. The no-effect concentration for ALD-6 in the CFDA assay was 1 µM.
   d. Non-linear curve fitting Logistic analyses indicated that the $EC_{50}$ of ALD-6 in the CFDA neuronal viability assay was 6.8±1.2 µM.

specific to neurons and may involve non-neuronal cells that are present in this model CNS system.
   h. Non-linear Logistic curve fitting indicated that the $EC_{50}$ for ALD-6 in the PI assay was 0.32±0.03 µM.
   i. Treatment with ALD-5 or ALD-2 from 0.1 to 300 µM did not produce statistically significant neuroprotection from hydrogen peroxide treatment alone as assessed with CFDA assay.
   j. Treatment with ALD-5 or ALD-2 from 0.1 to 300 µM did not produce statistically significant protection from cell death produced by hydrogen peroxide treatment as assessed with the PI assay.
   k. The toxic signal produced by 10 µM hydrogen peroxide was typical of a wide variety of oxidative stressors (ethanol, heavy metals, ammonium acetate, and glutamate) that have been tested in the past, with decreases from control ranging from 30 to 50%.
l. The positive control (10 μM cannabidiol) was active on every test plate, indicating that the model system was responding in a typical protective manner.

Example 14: In Vivo Pharmacology of NS2-D6 (Compound I-1)

NS2-D6 (Compound ID 100029054-1; Batch Number 1603356191) was tested in binding and enzyme uptake assays. Compound binding was calculated as a % inhibition of the binding of a radioactively labeled ligand specific for each target. Compound enzyme inhibition effect was calculated as a % inhibition of control enzyme activity. Results showing an inhibition or stimulation higher than 50% are considered to represent significant effects of the test compounds. Such effects were observed here and are listed in the following tables.

Reference Compounds

In each experiment and if applicable, the respective reference compound was tested concurrently with NS2-D6, and the data were compared with historical values determined at the same research facility. The experiment was conducted in accordance with industry standard operating procedures.

Results

Table 28 summarizes the enzyme inhibition results.

TABLE 28

Summary of Enzyme Inhibition Results

| Assay | 1.0E−05M |
|---|---|
| 5-HT$_{2B}^{(h)}$ (agonist radioligand) | 62.5% |
| acetylcholinesterase (h) | 52.9% |
| MAO-A (antagonist radioligand) | 68.5% |
| MT$_3$ (ML$_2$) (agonist radioligand) | 71.1% |
| PR (h) (agonist radioligand) | 60.9% |

Figure 44:
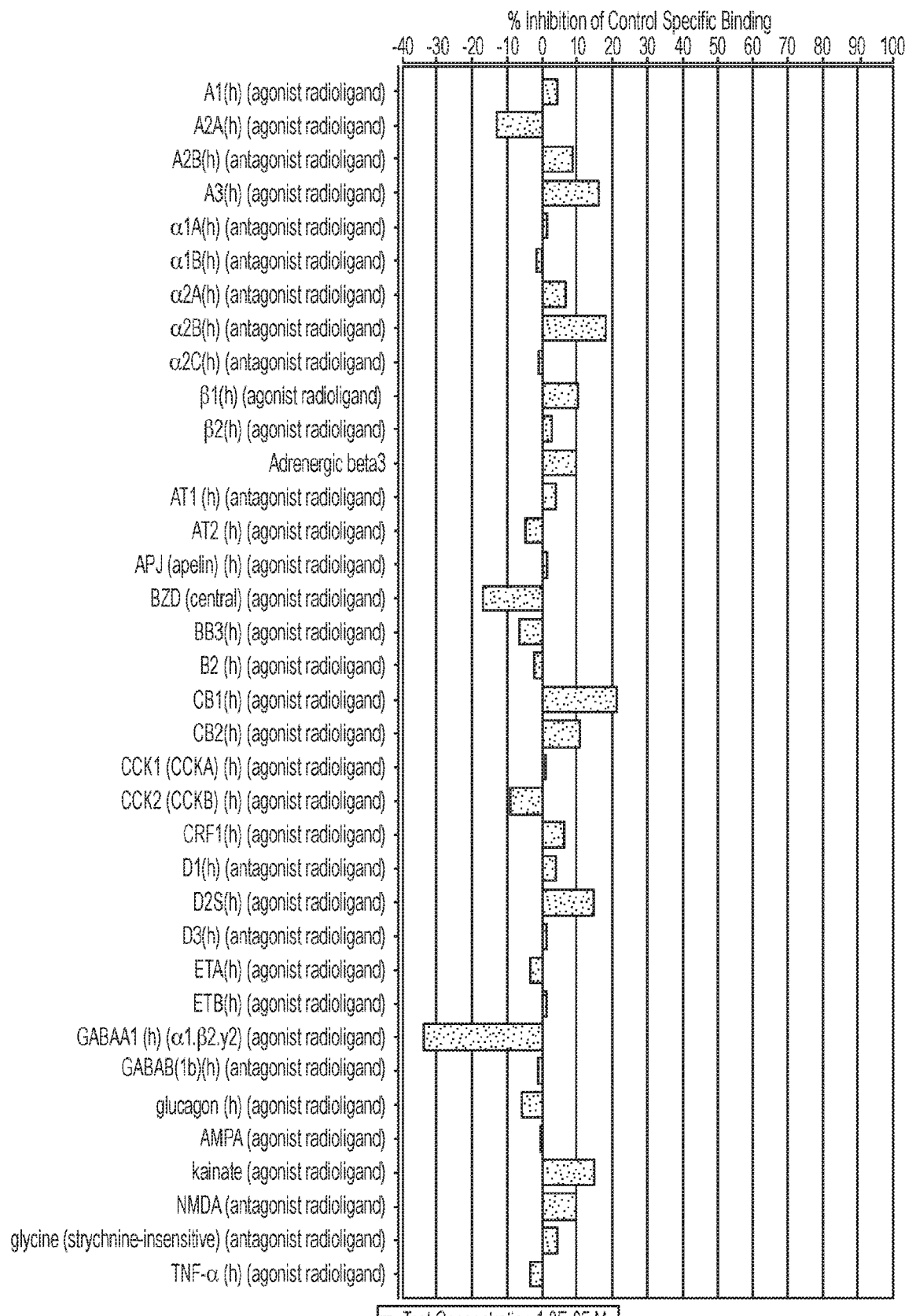
FIGS. 44-46 show a histogram of specific binding results for NS2-D6 expressed as a percentage of the specific binding of each control compound.
Figure 45:
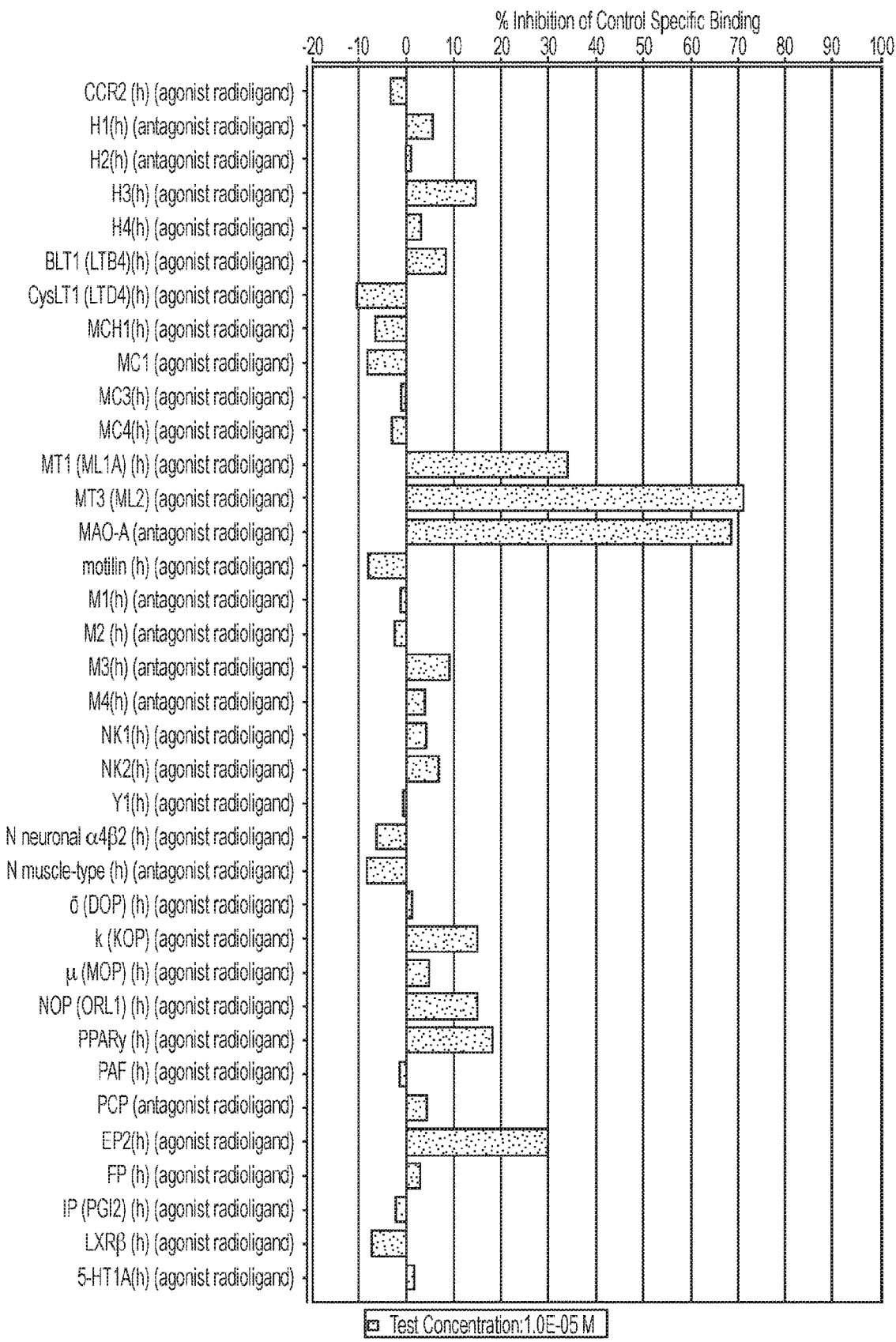
Figure 46:
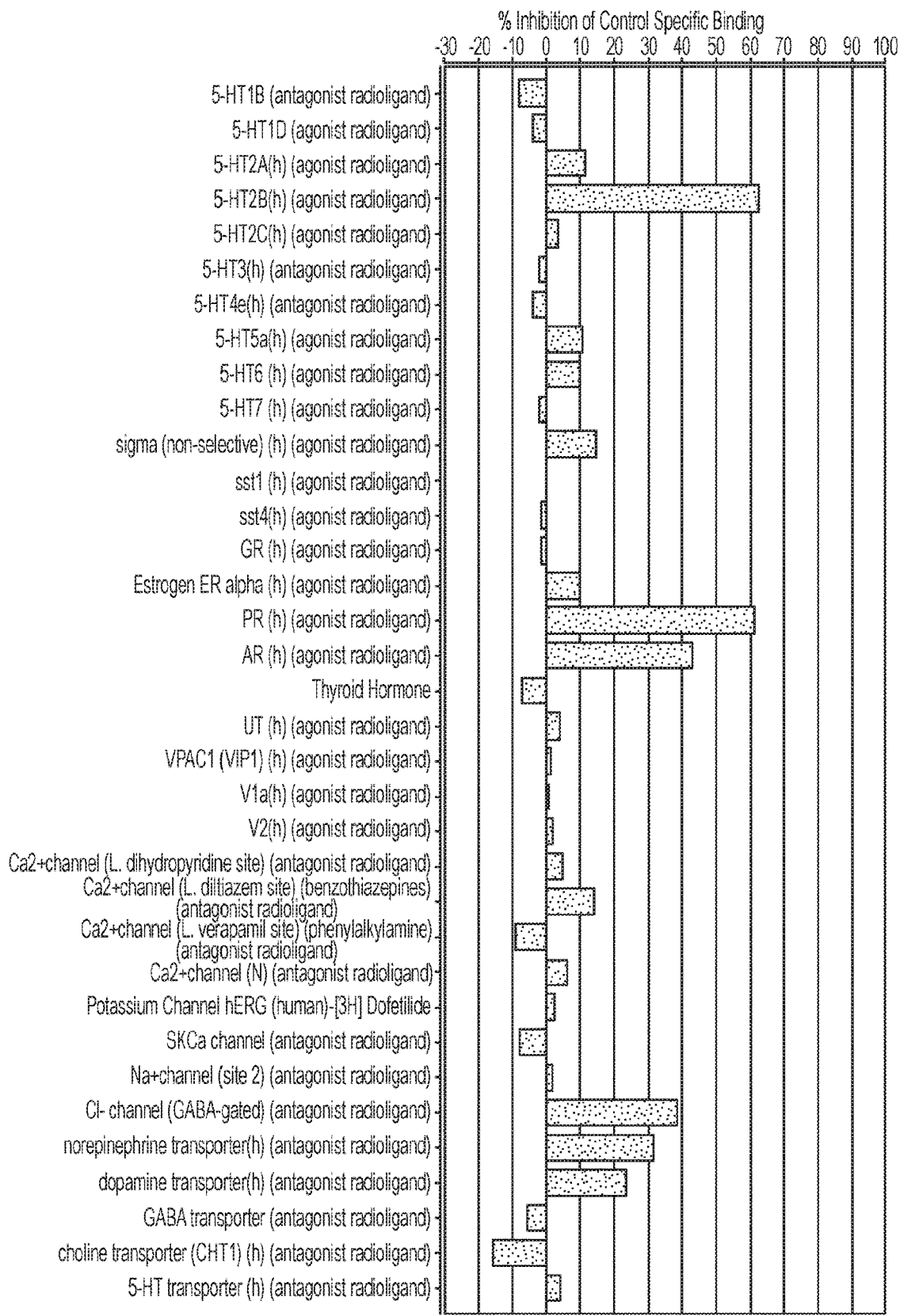

Test compound results are shown in FIGS. 44-46. Table 29 shows specific binding results for NS2-D6.

TABLE 29

Test Compound Results

| Compound I.D. | Client Compound Test I.D. | Concentration | % Inhibition of Control Specific Binding | | |
|---|---|---|---|---|---|
| | | | 1$^{st}$ | 2$^{nd}$ | Mean |
| A$_1$(h) (agonist radioligand) | | | | | |
| 100029054-1 | NS2-d6 | 1.0E−05M | 3.5 | 5.3 | 4.4 |
| A$_{2A\,(h)}$ (agonist radioligand) | | | | | |
| 100029054-1 | NS2-d6 | 1.0E−05M | −11.2 | −15.0 | −13.1 |
| A$_{2B}$(h) (antagonist radioligand) | | | | | |
| 100029054-1 | NS2-d6 | 1.0E−05M | 13.2 | 4.3 | 8.7 |
| A$_3$(h) (antagonist radioligand) | | | | | |
| 100029054-1 | NS2-d6 | 1.0E−05M | 17.3 | 15.1 | 16.2 |
| α$_{1A}$(h) (antagonist radioligand) | | | | | |
| 100029054-1 | NS2-d6 | 1.0E−05M | 6.1 | −3.3 | 1.4 |
| α$_{1B}$(h) (antagonist radioligand) | | | | | |
| 100029054-1 | NS2-d6 | 1.0E−05M | −1.8 | 1.0 | −0.4 |
| α$_{2A}$(h) (antagonist radioligand) | | | | | |
| 100029054-1 | NS2-d6 | 1.0E−05M | 3.2 | 10.0 | 6.6 |
| α$_{2B}$(h) (antagonist radioligand) | | | | | |
| 100029054-1 | NS2-d6 | 1.0E−05M | 15.9 | 20.8 | 18.4 |
| α$_{2C}$(h) (antagonist radioligand) | | | | | |
| 100029054-1 | NS2-d6 | 1.0E−05M | −8.0 | 6.2 | −0.9 |
| β$_1$(h) (agonist radioligand) | | | | | |
| 100029054-1 | NS2-d6 | 1.0E−05M | 9.7 | 11.0 | 10.3 |
| β$_2$(h) (agonist radioligand) | | | | | |
| 100029054-1 | NS2-d6 | 1.0E−05M | −0.6 | 5.8 | 2.6 |
| Adrenergic beta3 | | | | | |
| 100029054-1 | NS2-d6 | 1.0E−05M | 16.2 | 3.0 | 9.6 |
| AT$_1$(h) (antagonist radioligand) | | | | | |
| 100029054-1 | NS2-d6 | 1.0E−05M | 10.7 | −3.3 | 3.7 |
| AT$_2$(h) (agonist radioligand) | | | | | |
| 100029054-1 | NS2-d6 | 1.0E−05M | −3.5 | −5.6 | −4.6 |
| APJ (apelin)(h) (agonist radioligand) | | | | | |
| 100029054-1 | NS2-d6 | 1.0E−05M | 0.8 | 2.2 | 1.5 |

TABLE 29-continued

| | Test Compound Results | | | | |
|---|---|---|---|---|---|
| | Client Compound | Test | % Inhibition of Control Specific Binding | | |
| Compound I.D. | I.D. | Concentration | $1^{st}$ | $2^{nd}$ | Mean |
| | BZD (central) (agonist radioligand) | | | | |
| 100029054-1 | NS2-d6 | 1.0E−05M | −17.2 | −16.6 | −16.9 |
| | $BB_3$(h) (agonist radioligand) | | | | |
| 100029054-1 | NS2-d6 | 1.0E−05M | −17.1 | 4.6 | −6.3 |
| | $B_2$(h) (agonist radioligand) | | | | |
| 100029054-1 | NS2-d6 | 1.0E−05M | −4.5 | 0.1 | −2.2 |
| | $CB_1$(h) (agonist radioligand) | | | | |
| 100029054-1 | NS2-d6 | 1.0E−05M | 21.9 | 20.7 | 21.3 |
| | $CB_2$(h) (agonist radioligand) | | | | |
| 100029054-1 | NS2-d6 | 1.0E−05M | 16.6 | 5.0 | 10.8 |
| | $CCK_1$ ($CCK_A$) (h) (agonist radioligand) | | | | |
| 100029054-1 | NS2-d6 | 1.0E−05M | −10.0 | 11.9 | 0.9 |
| | $CCK_2$ ($CCK_B$) (h) (agonist radioligand) | | | | |
| 100029054-1 | NS2-d6 | 1.0E−05M | −3.6 | −14.6 | −9.1 |
| | $CRF_1$(h) (agonist radioligand) | | | | |
| 100029054-1 | NS2-d6 | 1.0E−05M | 6.7 | 5.7 | 6.2 |
| | $D_1$(h) (antagonist radioligand) | | | | |
| 100029054-1 | NS2-d6 | 1.0E−05M | 0.8 | 6.6 | 3.7 |
| | $D_{2S}$(h) (agonist radioligand) | | | | |
| 100029054-1 | NS2-d6 | 1.0E−05M | 15.2 | 14.4 | 14.8 |
| | $D_3$(h) (antagonist radioligand) | | | | |
| 100029054-1 | NS2-d6 | 1.0E−05M | 6.2 | −4.1 | 1.1 |
| | $ET_A$(h) (agonist radioligand) | | | | |
| 100029054-1 | NS2-d6 | 1.0E−05M | −0.8 | −5.8 | −3.3 |
| | $ET_B$(h) (agonist radioligand) | | | | |
| 100029054-1 | NS2-d6 | 1.0E−05M | 7.6 | −5.4 | 1.1 |
| | $GAB_{A1}$(h) (α1 β2, y2)(agonist radioligand) | | | | |
| 100029054-1 | NS2-d6 | 1.0E−05M | −45.9 | −21.1 | −33.5 |
| | $GABA_{B(1b)}$(h) (antagonist radioligand) | | | | |
| 100029054-1 | NS2-d6 | 1.0E−05M | −7.2 | 5.2 | −1.0 |
| | glucagon(h) (agonist radioligand) | | | | |
| 100029054-1 | NS2-d6 | 1.0E−05M | −4.2 | −6.9 | −5.6 |
| | AMPA (agonist radioligand) | | | | |
| 100029054-1 | NS2-d6 | 1.0E−05M | −5.9 | 5.1 | −0.4 |
| | kainate (agonist radioligand) | | | | |
| 100029054-1 | NS2-d6 | 1.0E−05M | 17.5 | 12.1 | 14.8 |
| | NMDA (antagonist radioligand) | | | | |
| 100029054-1 | NS2-d6 | 1.0E−05M | 5.5 | 14.6 | 10.1 |
| | glycine (strychnine-insenstive) (antagonist radioligand) | | | | |
| 100029054-1 | NS2-d6 | 1.0E−05M | −7.7 | 16.2 | 4.2 |
| | TNF-α (h) (agonist radioligand) | | | | |
| 100029054-1 | NS2-d6 | 1.0E−05M | −6.5 | −0.9 | −3.7 |
| | CCR2 (h) (agonist radioligand) | | | | |
| 100029054-1 | NS2-d6 | 1.0E−05M | −12.4 | 6.2 | −3.1 |
| | $H_1$(h) (antagonist radioligand) | | | | |
| 100029054-1 | NS2-d6 | 1.0E−05M | −8.6 | 19.9 | 5.6 |
| | $H_2$(h) (antagonist radioligand) | | | | |
| 100029054-1 | NS2-d6 | 1.0E−05M | 1.1 | −0.5 | 0.3 |

TABLE 29-continued

Test Compound Results

| Compound I.D. | Client Compound I.D. | Test Concentration | % Inhibition of Control Specific Binding | | |
|---|---|---|---|---|---|
| | | | $1^{st}$ | $2^{nd}$ | Mean |
| | $H_3$(h) (agonist radioligand) | | | | |
| 100029054-1 | NS2-d6 | 1.0E−05M | 15.3 | 13.9 | 14.6 |
| | $H_4$(h) (agonist radioligand) | | | | |
| 100029054-1 | NS2-d6 | 1.0E−05M | 9.8 | −3.3 | 3.2 |
| | $BLT_1$ ($LTB_4$)(h) (agonist radioligand) | | | | |
| 100029054-1 | NS2-d6 | 1.0E−05M | 9.6 | 7.0 | 8.3 |
| | $CysLT_1$($LTD_4$)(h) (agonist radioligand) | | | | |
| 100029054-1 | NS2-d6 | 1.0E−05M | −3.6 | −17.1 | −10.4 |
| | $MCH_1$ (h) (agonist radioligand) | | | | |
| 100029054-1 | NS2-d6 | 1.0E−05M | −3.7 | −9.3 | −6.5 |
| | $MC_1$ (agonist radioligand) | | | | |
| 100029054-1 | NS2-d6 | 1.0E−05M | −10.5 | −5.7 | −8.1 |
| | $MC_3$ (h) (agonist radioligand) | | | | |
| 100029054-1 | NS2-d6 | 1.0E−05M | −1.4 | 0.6 | −0.4 |
| | $MC_4$ (h) (agonist radioligand) | | | | |
| 100029054-1 | NS2-d6 | 1.0E−05M | −2.8 | −3.0 | −2.9 |
| | $MT_1$($ML_{1A}$)(h) (agonist radioligand) | | | | |
| 100029054-1 | NS2-d6 | 1.0E−05M | 30.0 | 37.7 | 33.9 |
| | $MT_3$ ($ML_2$)(h) (agonist radioligand) | | | | |
| 100029054-1 | NS2-d6 | 1.0E−05M | 69.0 | 73.3 | 71.1 |
| | MAO-A (antagonist radioligand) | | | | |
| 100029054-1 | NS2-d6 | 1.0E−05M | 66.4 | 70.7 | 68.5 |
| | motilin (h) (antagonist radioligand) | | | | |
| 100029054-1 | NS2-d6 | 1.0E−05M | −12.2 | −3.9 | −8.0 |
| | $M_1$ (h) (antagonist radioligand) | | | | |
| 100029054-1 | NS2-d6 | 1.0E−05M | −2.6 | 0.5 | −1.1 |
| | $M_2$ (h) (antagonist radioligand) | | | | |
| 100029054-1 | NS2-d6 | 1.0E−05M | −4.2 | −0.4 | −2.3 |
| | $M_3$ (h) (antagonist radioligand) | | | | |
| 100029054-1 | NS2-d6 | 1.0E−05M | 4.6 | 13.6 | 9.1 |
| | $M_4$ (h) (antagonist radioligand) | | | | |
| 100029054-1 | NS2-d6 | 1.0E−05M | −1.0 | 9.2 | 4.1 |
| | $NK_1$ (h) (agonist radioligand) | | | | |
| 100029054-1 | NS2-d6 | 1.0E−05M | 4.2 | 4.1 | 4.2 |
| | $NK_2$ (h) (agonist radioligand) | | | | |
| 100029054-1 | NS2-d6 | 1.0E−05M | 18.6 | −4.5 | 7.0 |
| | $Y_1$ (h) (agonist radioligand) | | | | |
| 100029054-1 | NS2-d6 | 1.0E−05M | −8.7 | 7.5 | −0.6 |
| | N neuronal α4β2 (h) (agonist radioligand) | | | | |
| 100029054-1 | NS2-d6 | 1.0E−05M | −5.7 | −6.7 | −6.2 |
| | N muscle-type (h) (antagonist radioligand) | | | | |
| 100029054-1 | NS2-d6 | 1.0E−05M | −16.8 | 0.7 | −8.1 |
| | δ (DOP)(h) (agonist radioligand) | | | | |
| 100029054-1 | NS2-d6 | 1.0E−05M | 3.8 | −1.4 | 1.2 |
| | κ (KOP) (h) (agonist radioligand) | | | | |
| 100029054-1 | NS2-d6 | 1.0E−05M | 13.3 | 16.2 | 14.8 |
| | μ (MOP) (h) (agonist radioligand) | | | | |
| 100029054-1 | NS2-d6 | 1.0E−05M | 3.0 | 6.8 | 4.9 |

TABLE 29-continued

Test Compound Results

| | | | % Inhibition of Control Specific Binding | | |
|---|---|---|---|---|---|
| Compound I.D. | Client Compound I.D. | Test Concentration | $1^{st}$ | $2^{nd}$ | Mean |
| | NOP (ORLI) (h) (agonist radioligand) | | | | |
| 100029054-1 | NS2-d6 | 1.0E−05M | 10.8 | 18.7 | 14.8 |
| | PPARγ (h) (agonist radioligand) | | | | |
| 100029054-1 | NS2-d6 | 1.0E−05M | 13.1 | 23.6 | 18.3 |
| | PAF (h) (agonist radioligand) | | | | |
| 100029054-1 | NS2-d6 | 1.0E−05M | −10.1 | 7.4 | −1.3 |
| | PCP (antagonist radioligand) | | | | |
| 100029054-1 | NS2-d6 | 1.0E−05M | 2.1 | 6.5 | 4.3 |
| | $EP_2$(h) (agonist radioligand) | | | | |
| 100029054-1 | NS2-d6 | 1.0E−05M | 18.1 | 41.5 | 29.8 |
| | FP (h) (agonist radioligand) | | | | |
| 100029054-1 | NS2-d6 | 1.0E−05M | 10.7 | −4.5 | 3.1 |
| | IP ($PGI_2$) (h) (agonist radioligand) | | | | |
| 100029054-1 | NS2-d6 | 1.0E−05M | 5.0 | −9.1 | −2.0 |
| | LXRβ (h) (agonist radioligand) | | | | |
| 100029054-1 | NS2-d6 | 1.0E−05M | −10.5 | −3.9 | −7.2 |
| | $5\text{-HT}_{1A}$ (h) (agonist radioligand) | | | | |
| 100029054-1 | NS2-d6 | 1.0E−05M | 5.4 | −1.8 | 1.8 |
| | $5\text{-HT}_{1B}$ (h) (antagonist radioligand) | | | | |
| 100029054-1 | NS2-d6 | 1.0E−05M | −16.3 | 0.5 | −7.9 |
| | $5\text{-HT}_{1D}$ (h) (agonist radioligand) | | | | |
| 100029054-1 | NS2-d6 | 1.0E−05M | −3.4 | −5.1 | −4.2 |
| | $5\text{-HT}_{2A}$ (h) (agonist radioligand) | | | | |
| 100029054-1 | NS2-d6 | 1.0E−05M | 5.4 | 17.8 | 11.6 |
| | $5\text{-HT}_{2B}$ (h) (agonist radioligand) | | | | |
| 100029054-1 | NS2-d6 | 1.0E−05M | 60.8 | 64.2 | 62.5 |
| | $5\text{-HT}_{2C}$ (h) (agonist radioligand) | | | | |
| 100029054-1 | NS2-d6 | 1.0E−05M | −3.1 | 10.0 | 3.4 |
| | $5\text{-HT}_3$ (h) (antagonist radioligand) | | | | |
| 100029054-1 | NS2-d6 | 1.0E−05M | −3.0 | 2.2 | −0.4 |
| | $5\text{-HT}_{4e}$ (h) (antagonist radioligand) | | | | |
| 100029054-1 | NS2-d6 | 1.0E−05M | −5.5 | −2.6 | −4.1 |
| | $5\text{-HT}_{5a}$ (h) (antagonist radioligand) | | | | |
| 100029054-1 | NS2-d6 | 1.0E−05M | 3.8 | 17.3 | 10.6 |
| | $5\text{-HT}_6$ (h) (agonist radioligand) | | | | |
| 100029054-1 | NS2-d6 | 1.0E−05M | 1.1 | 17.7 | 9.4 |
| | $5\text{-HT}_7$ (h) (agonist radioligand) | | | | |
| 100029054-1 | NS2-d6 | 1.0E−05M | 2.3 | −5.6 | −1.7 |
| | sigma (non-selective) (h) (agonist radioligand) | | | | |
| 100029054-1 | NS2-d6 | 1.0E−05M | 16.3 | 13.5 | 14.9 |
| | $sst_1$ (h) (agonist radioligand) | | | | |
| 100029054-1 | NS2-d6 | 1.0E−05M | −5.1 | 5.0 | −0.1 |
| | $sst_4$ (h) (agonist radioligand) | | | | |
| 100029054-1 | NS2-d6 | 1.0E−05M | 3.1 | −5.9 | −1.4 |
| | GR (h) (agonist radioligand) | | | | |
| 100029054-1 | NS2-d6 | 1.0E−05M | −6.7 | 4.1 | −1.3 |
| | Estrogen ER alpha (h) (agonist radioligand) | | | | |
| 100029054-1 | NS2-d6 | 1.0E−05M | 15.8 | 4.3 | 10.1 |

TABLE 29-continued

Test Compound Results

| Compound I.D. | Client Compound Test I.D. | Concentration | % Inhibition of Control Specific Binding | | |
|---|---|---|---|---|---|
| | | | 1st | 2nd | Mean |
| PR (h) (agonist radioligand) | | | | | |
| 100029054-1 | NS2-d6 | 1.0E−05M | 58.7 | 63.1 | 60.9 |
| AR (h) (agonist radioligand) | | | | | |
| 100029054-1 | NS2-d6 | 1.0E−05M | 41.4 | 44.3 | 42.8 |
| Thyroid Hormone | | | | | |
| 100029054-1 | NS2-d6 | 1.0E−05M | −7.9 | −5.9 | −6.9 |
| UT(h) (agonist radioligand) | | | | | |
| 100029054-1 | NS2-d6 | 1.0E−05M | 3.1 | 4.9 | 4.0 |
| $VPAC_1$ ($VIP_1$) (h) (agonist radioligand) | | | | | |
| 100029054-1 | NS2-d6 | 1.0E−05M | 0.2 | 1.9 | 1.1 |
| $V_{1a}$ (h) (agonist radioligand) | | | | | |
| 100029054-1 | NS2-d6 | 1.0E−05M | 2.1 | −1.2 | 0.5 |
| $V_2$ (h) (agonist radioligand) | | | | | |
| 100029054-1 | NS2-d6 | 1.0E−05M | 0.4 | 2.9 | 1.7 |
| $Ca^{2+}$ channel (L. dihydropyridine site) (antagonist radioligand) | | | | | |
| 100029054-1 | NS2-d6 | 1.0E−05M | 5.9 | 3.8 | 4.9 |
| $Ca^{2+}$ channel (L. diltiazem site) (benzothiazepines) (antagonist radioligand) | | | | | |
| 100029054-1 | NS2-d6 | 1.0E−05M | 14.8 | 13.3 | 14.0 |
| $Ca^{2+}$ channel (L. verapamil site) (phenylalkylamine) (antagonist radioligand) | | | | | |
| 100029054-1 | NS2-d6 | 1.0E−05M | −6.5 | −11.8 | −9.1 |
| $Ca^{2+}$ channel (N) (antagonist radioligand) | | | | | |
| 100029054-1 | NS2-d6 | 1.0E−05M | 4.6 | 8.1 | 6.3 |
| Potassium Channel hERG (human)- [3H] Dofetilide | | | | | |
| 100029054-1 | NS2-d6 | 1.0E−05M | 8.0 | −2.8 | 2.6 |
| $SK_{Ca}$ channel (antagonist radioligand) | | | | | |
| 100029054-1 | NS2-d6 | 1.0E−05M | −10.8 | −4.5 | −7.7 |
| $Na^+$ channel (site 2) (antagonist radioligand) | | | | | |
| 100029054-1 | NS2-d6 | 1.0E−05M | −2.7 | 6.2 | 1.8 |
| $Cl^-$ channel (GABA-gated) (antagonist radioligand) | | | | | |
| 100029054-1 | NS2-d6 | 1.0E−05M | 33.9 | 42.6 | 38.2 |
| norepinephrine transporter (h) (antagonist radioligand) | | | | | |
| 100029054-1 | NS2-d6 | 1.0E−05M | 33.9 | 29.1 | 31.5 |
| dopamine transporter (h) (antagonist radioligand) | | | | | |
| 100029054-1 | NS2-d6 | 1.0E−05M | 19.9 | 27.3 | 23.6 |
| GABA transporter (h) (antagonist radioligand) | | | | | |
| 100029054-1 | NS2-d6 | 1.0E−05M | −6.1 | −4.5 | −5.3 |
| choline transporter (CHT1)(h) (antagonist radioligand) | | | | | |
| 100029054-1 | NS2-d6 | 1.0E−05M | −17.9 | −13.1 | −15.5 |
| 5-HT transporter (h) (antagonist radioligand) | | | | | |
| 100029054-1 | NS2-d6 | 1.0E−05M | 2.9 | 5.2 | 4.0 |

Table 30 shows $IC_{50}$, $K_i$, and nil values for various reference compounds that were compared with NS2-D6.

TABLE 30

| Reference Compound Results | | | |
|---|---|---|---|
| Compound I.D. | $IC_{50}$ (M) | $K_i$ (M) | nH |
| $A_1$ (h)(agonist radioligand) | | | |
| CPA | 3.3E−09M | 1.3E−09M | 1.2 |
| $A_{2A}$ (h) (agonist radioligand) | | | |
| NECA | 3.7E−08M | 3.1E−08M | 0.8 |
| $A_{2B}$ (h) (antagonist radioligand) | | | |
| NECA | 5.5E−07M | 5.1E−07M | 0.9 |
| $A_3$ (h) (agonist radioligand) | | | |
| IB-MECA | 2.8E−10M | 1.6E−10M | 0.8 |
| $\alpha_{1A}$ (h) (antagonist radioligand) | | | |
| WS 4101 | 2.5E−10M | 1.2E−10M | 1.1 |
| $\alpha_{1B}$ (h) (antagonist radioligand) | | | |
| prazosin | 2.5E−10M | 6.7E−11M | 1.2 |
| $\alpha_{2A}$ (h) (antagonist radioligand) | | | |
| yohimbine | 7.5E−09M | 3.3E−09M | 1.3 |
| $\alpha_{2B}$ (h) (antagonist radioligand) | | | |
| yohimbine | 7.6E−09M | 5.0E−09M | 1.0 |
| $\alpha_{2C}$ (h) (antagonist radioligand) | | | |
| yohimbine | 4.3E−09M | 1.4E−09M | 1.3 |
| β1 (h) (agonist radioligand) | | | |
| atenolol | 3.1E−07M | 1.7E−07M | 0.9 |
| β2 (h) (agonist radioligand) | | | |
| ICI 118551 | 1.3E−09M | 4.5E−10M | 1.8 |
| Adrenergic beta3 | | | |
| Alprenolo 1 | 1.4E−07M | 1.0E−07M | 0.6 |
| $AT_1$ (h) (antagonist radioligand) | | | |
| saralasin | 1.4E−09M | 6.9E−10M | 1.1 |
| $AT_2$ (h) (agonist radioligand) | | | |
| angiotensin-II | 1.2E−10M | 5.9E−11M | 0.8 |
| APJ (apelin) (h) (agonist radioligand) | | | |
| apelin-13.TFA | 2.7E−10M | 2.5E−10M | 1.0 |
| BZD (central) (agonist radioligand) | | | |
| diazepam | 7.4E−09M | 6.2E−09M | 0.9 |
| $BB_3$ (h) (agonist radioligand) | | | |
| Bn(6-14) | 9.8E−09M | 6.0E−09M | 1.0 |
| $B_2$ (h) (agonist radioligand) | | | |
| NPC 567 | 2.4E−08M | 1.2E−08M | 1.0 |
| $CB_1$ (h) (agonist radioligand) | | | |
| CP 55940 | 1.1E−09M | 9.5E−10M | 1.2 |
| CB2 (h) (agonist radioligand) | | | |
| WIN 55212-2 | 2.1E−09M | 1.4E−09M | 1.0 |
| $CCK_1$ ($CCK_A$) (h)(agonist radioligand) | | | |
| CCK-8s | 1.1E−10M | 8.3E−11M | 0.9 |
| $CCK_2$($CCK_B$) (h)(agonist radioligand) | | | |
| CCK-8s | 1.1E−10M | 4.6E−11M | 1.0 |
| $CRF_1$ (h) (agonist radioligand) | | | |
| sauvagine | 5.5E−10M | 3.4E−10M | 1.0 |
| $D_1$ (h) (antagonist radioligand) | | | |
| SCH 23390 | 2.1E−10M | 8.4E−11M | 0.7 |

TABLE 30-continued

Reference Compound Results

| Compound I.D. | IC$_{50}$ (M) | K$_i$ (M) | nH |
|---|---|---|---|
| D$_{2S}$ (h) (agonist radioligand) | | | |
| 7-OH-DPAT | 1.2E−09M | 4.8E−10M | 0.7 |
| D$_3$(h) (antagonist radioligand) | | | |
| (*) butaclamol | 1.5E−09M | 3.2E−10M | 1.0 |
| ET$_A$ (h) (agonist radioligand) | | | |
| endothelin-1 | 5.4E−11M | 2.7E−11M | 1.0 |
| ET$_B$ (h) (agonist radioligand) | | | |
| endothelin-3 | 2.5E−11M | 1.4E−11M | 0.9 |
| GABA$_{A1}$ (h) (α1,(β2, γ2) (agonist radioligand) | | | |
| muscimol | 7.0E−08M | 4.7E−08M | 0.8 |
| GABA$_{B(1b)}$ (h) (antagonist radioligand) | | | |
| CGP 54626 | 2.9E−09M | 1.5E−09M | 0.7 |
| glucagon (h) (agonist radioligand) | | | |
| glucagon | 1.5E−09M | 1.1E−09M | 0.6 |
| AMPA (agonist radioligand) | | | |
| L-glutamate | 2.8E−07M | 2.6E−07M | 0.9 |
| kainate (agonist radioligand) | | | |
| kainic acid | 2.3E−08M | 1.8E−08M | 0.9 |
| NMDA (antagonist radioligand) | | | |
| CGS 19755 | 2.1E−07M | 1.7E−07M | 0.9 |
| glycine (strychnine-insensitive) (antagonist radioligand) | | | |
| glycine | 1.4E−07M | 1.3E−07M | 1.0 |
| TNF-α (h) (agonist radioligand) | | | |
| TNF-alpha | 6.9E−11M | 2.3E−11M | 1.3 |
| CCR2 (h) (agonist radioligand) | | | |
| MCP-1 | 2.9E−11M | 1.2E−11M | 1.6 |
| H$_1$ (h) (antagonist radioligand) | | | |
| pyrilamine | 2.5E−09M | 1.6E−09M | 1.3 |
| H$_2$ (h) (antagonist radioligand) | | | |
| cimetidine | 6.5E−07M | 6.3E−07M | 0.8 |
| H$_3$ (h) (agonist radioligand) | | | |
| (R)a-Me-histamine | 1.9E−09M | 4.7E−10M | 1.4 |
| H$_4$ (h) (agonist radioligand) | | | |
| imetit | 4.4E−09M | 1.9E−09M | 0.9 |
| BLT$_1$ (LTD$_4$) (h) (agonist radioligand) | | | |
| LTB$_4$ | 4.2E−10M | 2.1E−10M | 0.8 |
| CysLT$_1$ (LTD$_4$) (h) (agonist radioligand) | | | |
| LTD$_4$ | 7.0E−10M | 3.1E−10M | 1.0 |
| MCH$_1$ (h) (agonist radioligand) | | | |
| human MCH | 4.9E−11M | 4.5E−11M | 1.0 |
| MC$_1$ (agonist radioligand) | | | |
| NDP-α-MSH | 1.8E−10M | 8.9E−11M | 1.0 |
| MC$_3$ (h) (agonist radioligand) | | | |
| NDP-α-MSH | 2.0E−10M | 1.7E−10M | 1.2 |
| MC$_4$ (h) (agonist radioligand) | | | |
| NDP-α-MSH | 4.8E−10M | 4.4E−10M | 0.7 |
| MT$_1$ (ML$_{1A}$) (h) (agonist radioligand) | | | |
| melatonin | 2.0E−10M | 1.6E−10M | 1.6 |
| MT$_3$ (ML$_2$) (agonist radioligand) | | | |
| melatonin | 7.2E−08M | 7.1E−08M | 0.8 |

TABLE 30-continued

| Reference Compound Results | | | |
|---|---|---|---|
| Compound I.D. | IC$_{50}$ (M) | K$_i$ (M) | nH |
| *MAO-A (antagonist radioligand)* | | | |
| clorgyline | 1.7E−09M | 1.0E−09M | 1.7 |
| *motilin (h) (agonist radioligand)* | | | |
| [Nleu$^{13}$]-motilin | 2.0E−09M | 1.7E−09M | 1.1 |
| *M$_1$ (h) (antagonist radioligand)* | | | |
| pirenzepine | 2.2E−08M | 1.9E−08M | 1.0 |
| *M$_2$ (h) (antagonist radioligand)* | | | |
| methoctramine | 4.9E−08M | 3.4E−08M | 0.8 |
| *M$_3$ (h) (antagonist radioligand)* | | | |
| 4-DAMP | 1.8E−09M | 1.3E−09M | 1.3 |
| *M$_4$ (h) (antagonist radioligand)* | | | |
| 4-DAMP | 1.5E−09M | 9.5E−10M | 1.2 |
| *NK$_1$ (h) (agonist radioligand)* | | | |
| (Sar$^9$,Met(O$_2$)$^{11}$]-SP | 4.9E−10M | 2.2E−10M | 1.6 |
| *NK$_2$ (h) (agonist radioligand)* | | | |
| [Nleu$^{10}$]-NKA (4-10) | 3.1E−09M | 1.7E−09M | 0.8 |
| *Y$_1$ (h) (agonist radioligand)* | | | |
| NPY | 9.4E−11M | 6.7E−11M | 1.3 |
| *N neuronal α4β2 (h) (agonist radioligand)* | | | |
| nicotine | 4.5E−09M | 1.5E−09M | 0.9 |
| *N muscle-type (h) (antagonist radioligand)* | | | |
| α-bungarotoxin | 2.3E−09M | 2.1E−09M | 1.2 |
| *δ (DOP) (h) (agonist radioligand)* | | | |
| DPDPE | 2.7E−09M | 1.6E−09M | 0.9 |
| *κ (KOP) (agonist radioligand)* | | | |
| U50488 | 9.3E−10M | 6.2E−10M | 1.0 |
| *μ (MOP) (h) (agonist radioligand)* | | | |
| DAMGO | 2.8E−10M | 1.2E−10M | 0.7 |
| *NOP (ORL1) (h) (agonist radioligand)* | | | |
| nociceptin | 8.4E−10M | 1.1E−10M | 1.1 |
| *PPAR$_\gamma$ (h) (agonist radioligand)* | | | |
| rosiglitazone | 1.2E−08M | 6.1E−09M | 0.9 |
| *PAF (h) (agonist radioligand)* | | | |
| C$_{16}$-PAF | 5.8E−09M | 2.9E−09M | 1.8 |
| *PCP (antagonist radioligand)* | | | |
| MK 801 | 9.2E−09M | 5.2E−09M | 1.3 |
| *EP$_2$ (h) (agonist radioligand)* | | | |
| PGE2 | 3.4E−09M | 1.7E−09M | 1.1 |
| *FP (h) (agonist radioligand)* | | | |
| PGF2alpha | 1.9E−09M | 1.2E−09M | 0.9 |
| *IP (PGI$_2$) (h) (agonist radioligand)* | | | |
| iloprost | 1.8E−08M | 1.0E−08M | 0.9 |
| *LXRβ (h) (agonist radioligand)* | | | |
| 22(R)-hydroxycholesterol | 4.0E−06M | 2.7E−06M | 1.1 |
| *5-HT$_{1A}$ (h) (agonist radioligand)* | | | |
| 8-OH-DPAT | 5.8E−10M | 3.6E−10M | 0.8 |
| *5-HT$_{1B}$ (antagonist radioligand)* | | | |
| serotonin | 4.9E−09M | 3.0E−09M | 0.9 |
| *5-HT$_{1D}$ (agonist radioligand)* | | | |
| serotonin | 2.4E−09M | 8.1E−10M | 1.2 |

TABLE 30-continued

Reference Compound Results

| Compound I.D. | | $IC_{50}$ (M) | $K_i$ (M) | nH |
|---|---|---|---|---|
| | 5-HT$_{2A}$ (h) (agonist radioligand) | | | |
| (±)DOI | | 3.4E−10M | 2.5E−10M | 0.7 |
| | 5-HT$_{2B}$ (h) (agonist radioligand) | | | |
| (±)DOI | | 6.9E−09M | 3.4E−09M | 0.9 |
| | 5-HT$_{2C}$ (h) (agonist radioligand) | | | |
| (±)DOI | | 5.3E−10M | 4.7E−10M | 1.1 |
| | 5-HT$_3$ (h) (antagonist radioligand) | | | |
| MDL 72222 | | 6.9E−09M | 4.8E−09M | 0.9 |
| | 5-HT$_{4e}$ (h) (antagonist radioligand) | | | |
| serotonin | | 2.7E−07M | 8.9E−08M | 0.7 |
| | 5-HT$_{5a}$ (h) (agonist radioligand) | | | |
| serotonin | | 1.5E−07M | 7.5E−08M | 1.0 |
| | 5-HT$_6$ (h) (agonist radioligand) | | | |
| serotonin | | 2.0E−07M | 9.3E−08M | 1.1 |
| | 5-HT$_7$ (h) (agonist radioligand) | | | |
| serotonin | | 3.4E−10M | 1.3E−10M | 1.0 |
| | sigma (non-selective) (h) (agonist radioligand) | | | |
| haloperidol | | 6.3E−08M | 5.1E−08M | 0.7 |
| | sst$_1$ (h) (agonist radioligand) | | | |
| somatostatin-28 | | 2.0E−10M | 1.9E−10M | 0.8 |
| | sst$_4$ (h) (agonist radioligand) | | | |
| somatostatin-14 | | 9.1E−10M | 8.9E−10M | 0.9 |
| | GR (h) (agonist radioligand) | | | |
| dexamethasone | | 4.9E−09M | 2.4E−09M | 1.2 |
| | Estrogen ER alpha (h) (agonist radioligand) | | | |
| Diethylstilbestrol | | 3.7E−10M | 1.0E−10M | 1.9 |
| | PR (h) (agonist radioligand) | | | |
| promegestone | | 4.7E−10M | 3.8E−10M | 1.6 |
| | AR (h) (agonist radioligand) | | | |
| mibolerone | | 1.6E−09M | 6.9E−10M | 1.2 |
| | Thyroid Hormone | | | |
| Triiodothyronine | | 4.2E−11M | 2.3E−11M | 1.1 |
| | UT (h) (agonist radioligand) | | | |
| urotensin-II | | 7.7E−10M | 5.8E−10M | 1.1 |
| | VPAC$_1$ (VIP$_1$) (h) (agonist radioligand) | | | |
| VIP | | 3.5E−10M | 1.9E−10M | 1.9 |
| | V$_{1a}$ (h) (agonist radioligand) | | | |
| [d(CH$_2$)$_5$$^1$, Tyr(ME)$_2$]-AVP | | 1.4E−09M | 8.8E−10M | 1.0 |
| | V$_2$ (h) (agonist radioligand) | | | |
| AVP | | 4.3E−10M | 3.1E−10M | 0.7 |
| | Ca$^{2+}$ channel (L. dihydropyridine site) (antagonist radioligand) | | | |
| nitrendipine | | 3.0E−10M | 1.9E−10M | 1.1 |
| | Ca$^{2+}$ channel (L. diltiazem site) (benzothiazepines) (antagonist radioligand) | | | |
| diltiazem | | 6.8E−08M | 5.3E−08M | 1.1 |
| | Ca$^{2+}$ channel (L. verapamil site) (phenylalkylamine) (antagonist radioligand) | | | |
| D 600 | | 2.7E−08M | 1.3E−08M | 0.5 |
| | Ca$^{2+}$ channel (N) (antagonist radioligand) | | | |
| ω-conotoxin GVIA | | 1.7E−12M | 6.8E−13M | 0.8 |
| | Potassium Channel hERG (human)-[3H] Dofetilide | | | |
| Terfenadine | | 3.4E−08M | 2.3E−08M | 0.8 |

TABLE 30-continued

| Compound I.D. | IC$_{50}$ (M) | K$_i$ (M) | nH |
|---|---|---|---|
| Reference Compound Results | | | |
| SK$_{Ca}$ channel (antagonist radioligand) | | | |
| apamin | 8.8E−12M | 4.4E−12M | 1.0 |
| Na$^+$ channel (site 2) (antagonist radioligand) | | | |
| veratridine | 3.9E−06M | 3.5E−06M | 0.8 |
| Cl$^−$ channel (GABA-gated) (antagonist radioligand) | | | |
| picrotoxinin | 2.8E−07M | 2.4E−07M | 1.0 |
| norepinephrine transporter (h) (antagonist radioligand) | | | |
| protriptyline | 2.8E−09M | 2.1E−09M | 1.0 |
| dopamine transporter (h) (antagonist radioligand) | | | |
| BTCP | 9.5E−09M | 5.0E−09M | 1.1 |
| GABA transporter (h) (antagonist radioligand) | | | |
| nipecotic acid | 2.5E−06M | 2.5E−06M | 0.8 |
| choline transporter (CHT1)(h) (antagonist radioligand) | | | |
| hemicholinium-3 | 7.5E−09M | 4.2E−09M | 1.0 |
| 5-HT transporter (h) (antagonist radioligand) | | | |
| imipramine | 2.7E−09M | 1.3E−09M | 1.3 |

Figure 47:
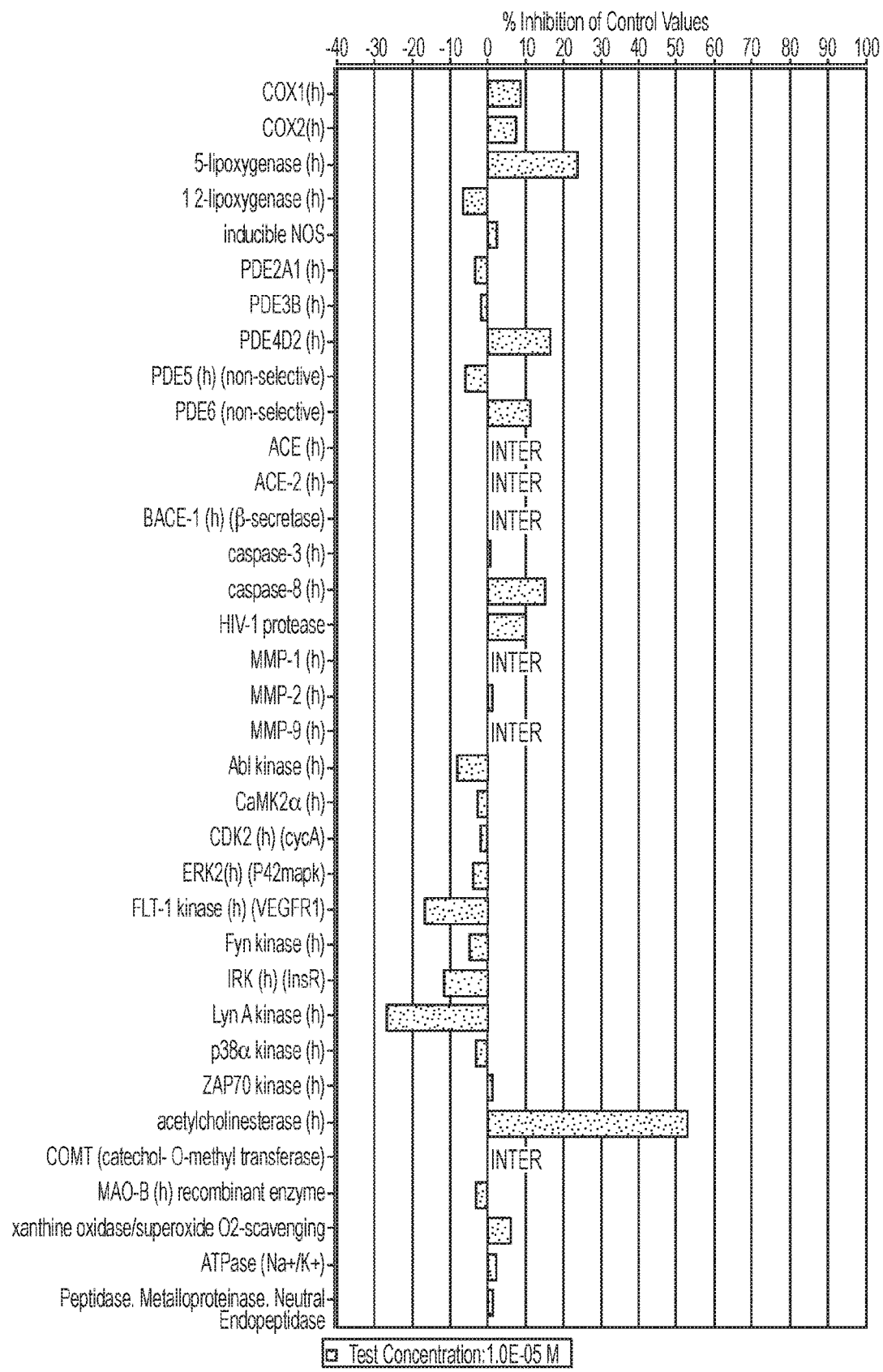
FIG. 47 shows a histogram of in vitro pharmacology results in enzyme and uptake assays for NS2-D6.

FIG. 47 shows a histogram of in vitro pharmacology results in enzyme and uptake assays for NS2-D6.

Table 31 shows 00 inhibition of control values for NS2-D6.

TABLE 31

| | | | % inhibition of Control Values | | | Flags | |
|---|---|---|---|---|---|---|---|
| Compound I.D. | Client Compound I.D. | Test Concentration | 1$^{st}$ | 2$^{nd}$ | Mean | 1$^{st}$ | 2$^{nd}$ |
| COX1(h) | | | | | | | |
| 100029054-1 | NS2-d6 | 1.0E−05M | 20.1 | −2.6 | 8.8 | | |
| COX2(h) | | | | | | | |
| 100029054-1 | NS2-d6 | 1.0E−05M | 12.8 | 3.0 | 7.9 | | |
| 5-lipoxygenase (h) | | | | | | | |
| 100029054-1 | NS2-d6 | 1.0E−05M | 23.5 | 24.8 | 24.2 | | |
| 12-lipoxygenase (h) | | | | | | | |
| 100029054-1 | NS2-d6 | 1.0E−05M | −9.4 | −4.1 | −6.7 | | |
| inducible NOS | | | | | | | |
| 100029054-1 | NS2-d6 | 1.0E−05M | 2.8 | −2.0 | 0.4 | | |
| PDE2A1 (h) | | | | | | | |
| 100029054-1 | NS2-d6 | 1.0E−05M | 17.1 | −24.5 | −3.7 | | |
| PDE3B (h) | | | | | | | |
| 100029054-1 | NS2-d6 | 1.0E−05M | 0.9 | −4.5 | −1.8 | | |
| PDE4D2 (h) | | | | | | | |
| 100029054-1 | NS2-d6 | 1.0E−05M | 15.9 | 16.9 | 16.4 | | |
| PDE5 (h) (non-selective) | | | | | | | |
| 100029054.1 | NS2-d6 | 1.0E−05M | −8.6 | −2.9 | −5.7 | | |
| PDE6 (non-selective) | | | | | | | |
| 100029054.1 | NS2-d6 | 1.0E−05M | 4.1 | 18.9 | 11.5 | | |
| ACE (h) | | | | | | | |
| 100029054.1 | NS2-d6 | 1.0E−05M | 127.6 | 131.0 | 129.3 | INTER | INTER |
| ACE-2 (h) | | | | | | | |
| 100029054-1 | NS2-d6 | 1.0E−05M | 23.8 | 26.2 | 25.0 | INTER | INTER |

TABLE 31-continued

Test Compound Results

| Compound I.D. | Client Compound I.D. | Test Concentration | % inhibition of Control Values | | | Flags | |
|---|---|---|---|---|---|---|---|
| | | | 1st | 2nd | Mean | 1st | 2nd |
| BACE-1 (h) (β-secretase) | | | | | | | |
| 100029054-1 | NS2-d6 | 1.0E−05M | −4.1 | −5.7 | −4.9 | INTER | INTER |
| caspase-3 (h) | | | | | | | |
| 100029054-1 | NS2-d6 | 1.0E−05M | −2.0 | 2.5 | 0.2 | | |
| caspase-8 (h) | | | | | | | |
| 100029054-1 | NS2-d6 | 1.0E−05M | 14.7 | 16.4 | 15.6 | | |
| HIV-1 protease | | | | | | | |
| 100029054-1 | NS2-d6 | 1.0E−05M | 16.6 | 4.8 | 10.7 | | |
| MMP-1 (h) | | | | | | | |
| 100029054-1 | NS2-d6 | 1.0E−05M | 45.3 | 10.7 | 28.0 | INTER | INTER |
| MMP-2 (h) | | | | | | | |
| 100029054-1 | NS2-d6 | 1.0E−05M | 4.9 | −2.4 | 1.3 | | |
| MMP-9 (h) | | | | | | | |
| 100029054-1 | NS2-d6 | 1.0E−05M | 4.5 | 4.4 | 4.4 | INTER | INTER |
| Abl kinase (h) | | | | | | | |
| 100029054-1 | NS2-d6 | 1.0E−05M | −4.8 | −11.6 | −8.2 | | |
| CaMK2α (h) | | | | | | | |
| 100029054-1 | NS2-d6 | 1.0E−05M | 0.2 | −6.5 | −3.1 | | |
| CDK2 (h) (cycA) | | | | | | | |
| 100029054-1 | NS2-d6 | 1.0E−05M | 1.2 | −5.1 | −1.9 | | |
| ERK$_2$ (h) (P42$^{mapk}$) | | | | | | | |
| 100029054-1 | NS2-d6 | 1.0E−05M | −6.3 | −1.3 | −3.8 | | |
| FLT-1 kinase (h) (VEGFR1) | | | | | | | |
| 100029054-1 | NS2-d6 | 1.0E−05M | −15.5 | −18.8 | −17.2 | | |
| Fyn kinase (h) | | | | | | | |
| 100029054-1 | NS2-d6 | 1.0E−05M | −8.6 | −0.3 | −4.5 | | |
| IRK (h)(InsR) | | | | | | | |
| 100029054-1 | NS2-d6 | 1.0E−05M | −15.1 | −7.9 | −11.5 | | |
| Lyn A kinase (h) | | | | | | | |
| 100029054-1 | NS2-d6 | 1.0E−05M | −17.7 | −35.7 | −26.7 | | |
| p38α kinase (h) | | | | | | | |
| 100029054-1 | NS2-d6 | 1.0E−05M | −3.2 | −3.1 | −3.2 | | |
| ZAP70 kinase (h) | | | | | | | |
| 100029054-1 | NS2-d6 | 1.0E−05M | 0.4 | 1.5 | 1.0 | | |
| acetylcholinesterase (h) | | | | | | | |
| 100029054-1 | NS2-d6 | 1.0E−05M | 45.8 | 60.1 | 52.9 | | |
| COMT (catechol-O-methyl transferase) | | | | | | | |
| 100029054-1 | NS2-d6 | 1.0E−05M | 5.8 | 14.7 | 10.3 | INTER | INTER |
| MAO-B (h) recombinant enzyme | | | | | | | |
| 100029054-1 | NS2-d6 | 1.0E−05M | −3.1 | −3.7 | −3.4 | | |
| xanthine oxidase/superoxide O$_2^-$ scavenging | | | | | | | |
| 100029054-1 | NS2-d6 | 1.0E−05M | −3.1 | 15.6 | 6.3 | | |
| ATPase (Na+/K+) | | | | | | | |
| 100029054-1 | NS2-d6 | 1.0E−05M | 5.2 | −0.4 | 2.4 | | |
| Peptidase, Metalloproteinase, Neutral Endopeptidase | | | | | | | |
| 100029054-1 | NS2-d6 | 1.0E−05M | 0.3 | 3.0 | 1.7 | | |

INTER: Test compound interferes with the assay detection method.

Table 32 shows IC$_{50}$ and nH values for reference compounds.

TABLE 32

Reference Compound IC$_{50}$ and nH Values

| Compound I.D. | IC$_{50}$ (M) | nH |
|---|---|---|
| COX1(h) | | |
| Diclofenac | 5.7E−09M | 1.6 |
| COX2(h) | | |
| NS398 | 6.8E−08M | 1.3 |
| 5-lipoxygenase (h) | | |
| NDGA | 2.3E−07M | 1.6 |
| 12-lipoxygenase (h) | | |
| NDGA | 5.1E−07M | 1.2 |
| inducible NOS | | |
| 1400W | 4.0E−08M | 1.4 |
| PDE2A1 (h) | | |
| EHNA | 1.1E−06M | 0.8 |
| PDE3B (h) | | |
| milrinone | 1.0E−06M | 0.9 |
| PDE4D2 (h) | | |
| Ro 20-1724 | 8.2E−07M | 1.0 |
| PDE5 (h) (non-selective) | | |
| dipyridamole | 1.8E−06M | 1.1 |
| PDE6 (non-selective) | | |
| zaprinast | 1.8E−07M | 1.0 |
| ACE (h) | | |
| captopril | 5.7E−10M | 1.2 |
| ACE-2 (h) | | |
| Ac-GG-26-NH$_2$ | 2.9E−07M | 2.4 |
| BACE-1 (h) ((β-secretase) | | |
| OM 99-2 | 1.2E−07M | 1.4 |
| caspase-3 (h) | | |
| Ac-DEVD-CHO | 2.0E−09M | 1.1 |
| caspase-8 (h) | | |
| Ac-IETD-CHO | 2.8E−08M | 0.8 |
| HIV-1 protease | | |
| pepstatin A | 2.2E−06M | 1.9 |
| MMP-1 (h) | | |
| GM6001 | 1.6E−09M | 1.3 |
| MMP-2 (h) | | |
| GM6001 | 1.5E−09M | 1.3 |
| MMP-9 (h) | | |
| GM6001 | 5.4E−10M | 0.9 |
| Abl kinase (h) | | |
| staurosporine | 2.6E−07M | 1.4 |
| CaMK2α (h) | | |
| AIP | 2.6E−07M | 1.1 |
| CDK2 (h) (cycA) | | |
| staurosporine | 6.9E−09M | 1.0 |
| ERK$_2$ (h) (P42$^{mapk}$) | | |
| staurosporine | 6.9E−07M | 1.0 |
| FLT-1 kinase (h) (VEGFR1) | | |
| staurosporine | 7.0E−09M | 0.7 |
| Fyn kinase (h) | | |
| PP1 | 1.0E−07M | >3 |
| IRK (h) (InsR) | | |
| staurosporine | 1.6E−08M | 0.9 |
| Lyn A kinase (h) | | |
| staurosporine | 1.2E−08M | 1.9 |
| p38α kinase (h) | | |
| SB202190 | 3.0E−08M | 1.0 |
| ZAP70 kinase (h) | | |
| staurosporine | 1.1E−07M | 1.4 |
| acetylcholinesterase (h) | | |
| galanthamine | 7.6E−07M | 1.0 |
| COMT (catechol-O-methyl transferase) | | |
| Ro 41-0960 | 3.0E−08M | 1.7 |
| MAO-B (h) recombinant enzyme | | |
| deprenyl | 3.5E−08M | 1.4 |
| xanthine oxidase/superoxide 0$_2^-$ scavenging | | |
| allopurinol | 2.0E−06M | 1.3 |
| ATPase (Na+/K+) | | |
| ouabain | 1.0E−06M | 1.3 |
| Peptidase, Metalloproteinase, Neutral Endopeptidase | | |
| Phosphoramidon | 1.6E−08M | 0.9 |

Table 33 shows test compound results of NS2-D6 on guanylyl cyclase.

TABLE 33

Test Compound Results with Guanylyl Cyclase

| Client Compound I.D. | Test Compound I.D. | Concentration | % of Control Values | | |
|---|---|---|---|---|---|
| | | | 1$^{st}$ | 2$^{nd}$ | Mean |
| guanylyl cyclase (h) (activator effect) | | | | | |
| 100029054-1 | NS2-d6 | 1.0E−05M | 0.2 | 0.3 | 0.2 |

Table 34 shows reference compound EC$_{50}$ results on guanylyl cyclase.

TABLE 34

Reference Compound Results with Guanylyl Cyclase

| Compound I.D. | EC$_{50}$(M) | nH |
|---|---|---|
| guanylyl cyclase (h) (activator effect) | | |
| sodium nitroprusside | 3.5E−06M | 2.2 |

Results showing an inhibition (or stimulation for assays run in basal conditions) higher than 50% are considered to represent significant effects of the test compounds. 50% is the most common cut-off value for further investigation (determination of IC$_{50}$ or EC$_{50}$ values from concentration-response curves). Results showing an inhibition (or stimulation) between 25% and 50% are indicative of weak to moderate effects (in most assays, they should be confirmed by further testing as they are within a range where more inter-experimental variability can occur). Results showing an inhibition (or stimulation) lower than 25% are not considered significant and mostly attributable to variability of the signal around the control level.

Low to moderate negative values have no real meaning and are attributable to variability of the signal around the control level. High negative values (≥50%) that are sometimes obtained with high concentrations of test compounds are generally attributable to nonspecific effects of the test compounds in the assays. On rare occasions they could suggest an allosteric effect of the test compound.

Experimental Conditions

Table 35 summarizes binding assay conditions

TABLE 35

Binding Assay Conditions

| Assay | Source | Ligand | Conc. | Kd | Non Specific | Incubation | Detection Method | Bibl. |
|---|---|---|---|---|---|---|---|---|
| $A_1$(h) (agonist radioligand) | human recombinant (CHO cells) | [$^3$H]CCPA | 1 nM | 0.7 nM | CPA (10 μM) | 60 min RT | Scintillation counting | 198 |
| $A_{2A}$(h)(agonist radioligand) | human recombinant (HEK-293 cells) | [$^3$H]CGS 21680 | 6 nM | 27 nM | NECA (10 μM) | 120 min RT | Scintillation counting | 141 |
| $A_{2B}$(h) (antagonist radioligand) | human recombinant (HEK-293 cells) | [$^3$H]CPX | 5 nM | 65 nM | NECA (100 μM) | 60 min RT | Scintillation counting | 229 |
| $A_3$(h) (antagonist radioligand) | human recombinant (HEK-293 cells) | [$^{125}$I]AB-MECA | 0.15 nM | 0.22 nM | IB-MECA (1 μM) | 120 min RT | Scintillation counting | 206 |
| $\alpha_{1A}$(h) (antagonist radioligand) | human recombinant (CHO cells) | [$^3$H]prazosin | 0.1 nM | 0.1 nM | epinephrine (0.1 μM) | 60 min RT | Scintillation counting | 897 |
| $\alpha_{1B}$(h) (antagonist radioligand) | human recombinant (CHO cells) | [$^3$H]prazosin | 0.15 nM | 0.055 nM | phentolamine (10 μM) | 60 min RT | Scintillation counting | 701 |
| $\alpha_{2A}$(h) (antagonist radioligand) | human recombinant (CHO cells) | [$^3$H]RX 821002 | 1 nM | 0.8 nM | (−)epinephrine (100 μM) | 60 min RT | Scintillation counting | 542 |
| $\alpha_{2B}$(h) (antagonist radioligand) | human recombinant (CHO cells) | [$^3$H]RX 821002 | 2.5 nM | 5 nM | (−)epinephrine (100 μM) | 60 min RT | Scintillation counting | 56 |
| $\alpha_{2C}$(h) (antagonist radioligand) | human recombinant (CHO cells) | [$^3$H]RX 821002 | 2 nM | 0.95 nM | (−)epinephrine (100 μM) | 60 min RT | Scintillation counting | 56 |
| $\beta_1$(h) (agonist radioligand) | human recombinant (HEK-293 cells) | [$^3$H](−)CGP 12177 | 0.3 nM | 0.39 nM | alprenolol (50 μM) | 60 min RT | Scintillation counting | 548 |
| $\beta_2$(h) (agonist radioligand) | human recombinant (CHO cells) | [$^3$H](−)CGP 12177 | 0.3 nM | 0.15 nM | alprenolol (50 μM) | 120 min RT | Scintillation counting | 794 |
| Adrenergic beta3 | human recombinant (HEK-293 cells) | [125I] Cyanopindolol | 0.5 nM | 1.5 nM | Alprenolol(100 (0.0 μM) | 90 min 25° C. | Scintillation counting | 1277 |
| $AT_1$(h) (antagonist radioligand) | human recombinant (HEK-293 cells) | [$^{125}$I][Sar$^1$, Ile$^8$]-AT-II | 0.05 nM | 0.05 nM | angiotensin-II (10 μM) | 120 min 37° C. | Scintillation counting | 776 |
| $AT_2$(h) (agonist radioligand) | human recombinant (HEK-293 cells) | [$^{125}$I]GCP 42112A | 0.01 nM | 0.01 nM | angiotensin-II (1 μM) | 4 hr 37° C. | Scintillation counting | 248 |
| APJ (apelin)(h) (agonist radioligand) | human recombinant (CHO cells) | [$^{125}$I] [Glpr$^{65}$, Nle$^{75}$], Tyr$^{77}$-apelin-13 | 0.03 nM | 0.06 nM | apelin-13 (1 μM) | 120 min RT | Scintillation counting | 846 |
| $BB_3$(h) (agonist radioligand) | human recombinant (CHO cells) | [$^{125}$I]Bn(6-14) | 0.01 nM | 0.16 nM | Bn (6-14) (1 μM) | 60 min RT | Scintillation counting | 287 |
| $B_2$(h) (agonist radioligand) | human recombinant (CHO cells) | [$^3$H]bradykinin | 0.3 nM | 0.32 nM | bradykinin (1 μM) | 60 min RT | Scintillation counting | 346 |
| $CB_1$(h) (agonist radioligand) | human recombinant (CHO cells) | [$^3$H](−)CP 55940 | 0.5 nM | 3.5 nM | WIN 55212-2 (10 μM) | 120 min 37° C. | Scintillation counting | 857 |
| $CB_2$(h) (agonist radioligand) | human recombinant (CHO cells) | [$^3$H]WIN 55212-2 | 0.8 nM | 1.5 nM | WIN 55212-2 (5 μM) | 120 min 37° C. | Scintillation counting | 165 |

TABLE 35-continued

Binding Assay Conditions

| Assay | Source | Ligand | Conc. | Kd | Non Specific | Incubation | Detection Method | Bibl. |
|---|---|---|---|---|---|---|---|---|
| $CCK_1$ ($CCK_A$) (h) (agonist radioligand) | human recombinant (CHO cells) | [$^{125}$I]CCK-8s | 0.08 nM | 0.24 nM | CCK-8s (1 μM) | 60 min RT | Scintillation counting | 562 |
| $CCK_2$ ($CCK_B$) (h) (agonist radioligand) | human recombinant (CHO cells) | [$^{125}$I]CCK-8s | 0.08 nM | 0.054 nM | CCK-8s (1 μM) | 60 min RT | Scintillation counting | 134 |
| $CRF_1$(h) (agonist radioligand) | human recombinant (CHO cells) | [$^{125}$I]sauvagine | 0.075 nM | 0.12 nM | sauvagine (0.5 μM) | 120 min RT | Scintillation counting | 557 |
| $D_1$(h) (antagonist radioligand) | human recombinant (CHO cells) | [$^3$H]SCH 23390 | 0.3 nM | 0.2 nM | SCH 23390 (1 μM) | 60 min RT | Scintillation counting | 281 |
| $D_{2S}$(h) (agonist radioligand) | human recombinant (HEK-293 cells) | [$^3$H]7-OH-DPAT | 1 nM | 0.68 nM | butaclamol (10 μM) | 60 min RT | Scintillation counting | 87 |
| $D_3$(h) (antagonist radioligand) | human recombinant (CHO cells) | [$^3$H]methyl-spiperone | 0.3 nM | 0.085 nM | (+)butaclamol (10 μM) | 60 min RT | Scintillation counting | 145 |
| $ET_A$(h) (agonist radioligand) | human recombinant (CHO cells) | [$^{125}$I]endothelin-1 | 0.03 nM | 0.03 nM | endothelin-1 (100 μM) | 120 min 37° C. | Scintillation counting | 30 |
| $ET_B$(h) (agonist radioligand) | human recombinant (CHO cells) | [$^{125}$I]endothelin-1 | 0.03 nM | 0.04 nM | endothelin-1 (0.1 μM) | 120 min 37° C. | Scintillation counting | 541 |
| $GABA_{A1}$(h) (α1 β2, γ2)(agonist radioligand) | human recombinant (CHO cells) | [$^3$H]muscimol | 15 nM | 30 nM | muscimol (10 μM) | 120 min RT | Scintillation counting | 109 |
| $GABA_{B(1b)}$(h) (antagonist radioligand) | human recombinant (CHO cells) | [$^3$H]CGP 54626 | 1 nM | 1 nM | CGP 52432 (100 μM) | 120 min RT | Scintillation counting | 508 |
| glucagon(h) (agonist radioligand) | human recombinant (CHO cells) | [$^{125}$I]glucagon | 0.025 nM | 0.069 nM | glucagon (1 μM) | 120 min RT | Scintillation counting | 624 |
| TNF-α (h) (agonist radioligand) | U-937 cells | [$^{125}$I]TNF-α | 0.1 nM | 0.05 nM | TNF-α (10 μM) | 120 min 4° C. | Scintillation counting | 26 |
| CCR2 (h) (agonist radioligand) | human recombinant (HEK-293 cells) | [$^{125}$I]MCP-1 | 0.01 nM | 0.007 nM | MCP-1 (10 nM) | 60 min RT | Scintillation counting | 13 |
| $H_1$(h) (antagonist radioligand) | human recombinant (HEK-293 cells) | [$^3$H]pyrilamine | 1 nM | 1.7 nM | pyrilamine (1 μM) | 60 min RT | Scintillation counting | 492 |
| $H_2$(h) (antagonist radioligand) | human recombinant (CHO cells) | [$^{125}$I]APT | 0.075 nM | 2.9 nM | tiotidine (100 μM) | 120 min RT | Scintillation counting | 540 |
| $H_3$(h) (agonist radioligand) | human recombinant (CHO cells) | [$^3$H]N$^\alpha$-Me-histamine | 1 nM | 0.32 nM | (R)α-Me-histamine (1 μM) | 60 min RT | Scintillation counting | 563 |
| $H_4$(h) (agonist radioligand) | human recombinant (HEK-293 cells) | [$^3$H]histamine | 10 nM | 7.6 nM | imetit (1 μM) | 60 min RT | Scintillation counting | 631 |
| $BLT_1$ ($LTB_4$)(h) (agonist radioligand) | human recombinant (CHO cells) | [$^3$H]LTB$_4$ | 0.2 nM | 0.2 nM | LTB$_4$ (0.2 μM) | 60 min RT | Scintillation counting | 616 |
| $CysLT_1$ ($LTD_4$)(h) (agonist radioligand) | human recombinant (CHO cells) | [$^3$H]LTD$_4$ | 0.3 nM | 0.24 nM | LTD$_4$ (1 μM) | 60 min RT | Scintillation counting | 618 |
| $MCH_1$ (h) (agonist radioligand) | human recombinant (CHO cells) | [$^{125}$I]Phe$^{13}$, Tyr$^{19}$]-MCH | 0.1 nM | 1 nM | human MCH (0.1 μM) | 60 min RT | Scintillation counting | 526 |
| $MC_1$ (agonist radioligand) | B-16-F1 cells (endogenous) | [$^{125}$I]NDP-α-MSH | 0.05 nM | 0.05 nM | NDP-α-MSH (1 μM) | 90 min RT | Scintillation counting | 390 |
| $MC_3$ (h) (agonist radioligand) | human recombinant (CHO cells) | [$^{125}$I]NDP-α-MSH | 0.075 nM | 0.4 nM | NDP-α-MSH (1 μM) | 60 min 37° C. | Scintillation counting | 211 |
| $MC_4$ (h) (agonist radioligand) | human recombinant (CHO cells) | [$^{125}$I]NDP-α-MSH | 0.05 nM | 0.54 nM | NDP-α-MSH (1 μM) | 120 min 37° C. | Scintillation counting | 211 |
| $MT_1$ ($ML_{1A}$)(h) (agonist radioligand) | human recombinant (CHO cells) | [$^{125}$I]2-iodomelatonin | 0.01 nM | 0.04 nM | melatonin (1 μM) | 60 min RT | Scintillation counting | 639 |

TABLE 35-continued

Binding Assay Conditions

| Assay | Source | Ligand | Conc. | Kd | Non Specific | Incubation | Detection Method | Bibl. |
|---|---|---|---|---|---|---|---|---|
| MT$_3$ (ML$_2$)(h) (agonist radioligand) | Hamster brain | [$^{125}$I]2-iodomelatonin | 0.1 nM | 4.8 nM | melatonin (30 µM) | 60 min 4° C. | Scintillation counting | 186 |
| motillin (h) (antagonist radioligand) | human recombinant (CHO cells) | [$^{125}$I]motilin | 0.05 nM | 0.26 nM | [Nleu$^{13}$]-motilin (1 µM) | 120 min RT | Scintillation counting | 285 |
| M$_1$ (h) (antagonist radioligand) | human recombinant (CHO cells) | [$^3$H]pirenzepine | 2 nM | 13 nM | atropine (1 µM) | 60 min RT | Scintillation counting | 59 |
| M$_2$ (h) (antagonist radioligand) | human recombinant (CHO cells) | [$^3$H]AF-DX 384 | 2 nM | 4.6 nM | atropine (1 µM) | 60 min RT | Scintillation counting | 59 |
| M$_3$ (h) (antagonist radioligand) | human recombinant (CHO cells) | [$^3$H]4-DAMP | 0.2 nM | 0.5 nM | atropine (1 µM) | 60 min RT | Scintillation counting | 546 |
| M$_4$ (h) (antagonist radioligand) | human recombinant (CHO cells) | [$^3$H]4-DAMP | 0.2 nM | 0.32 nM | atropine (1 µM) | 60 min RT | Scintillation counting | 59 |
| NK$_1$ (h) (agonist radioligand) | U373MG uppsala | [$^{125}$I]-Substance P LYS3 | 0.05 nM | 0.04 nM | [Sar$^9$, Met(O$_2$)$^{11}$]-SP (1 µM) | 30 min RT | Scintillation counting | 104 |
| NK$_2$ (h) (agonist radioligand) | human recombinant (CHO cells) | [$^{125}$I]NKA | 0.1 nM | 0.12 nM | [Nieu $^{10}$]-NKA (4-10) (300 µM) | 60 min RT | Scintillation counting | 3 |
| Y$_1$ (h) (agonist radioligand) | SK-N-MC cells (endogenous) | [$^{125}$I]peptide YY | 0.025 nM | 0.06 nM | NPY (1 µM) | 120 min 37° C. | Scintillation counting | 391 |
| N neuronal α4β2 (h) (agonist radioligand) | SH-SY5Y cells (human recombinant) | [$^3$H]cytisine | 0.6 nM | 0.3 nM | nicotine (10 µM) | 120 min 4° C. | Scintillation counting | 1084 |
| N muscle-type (h) (antagonist radioligand) | TE671 cells (endogenous) | [$^{125}$I]α-bungarotoxin | 0.5 nM | 5 nM | a-bungarotoxin (5 µM) | 120 min RT | Scintillation counting | 524 |
| δ (DOP) (h) (agonist radioligand) | human recombinant (CHO cells) | [$^3$H]DADLE | 0.5 nM | 0.73 nM | naltrexone (10 µM) | 120 min RT | Scintillation counting | 501 |
| κ (KOP) (h) (agonist radioligand) | rat recombinant (CHO cells) | [$^3$H]U 69593 | 1 nM | 2 nM | naloxone (10 µM) | 60 min RT | Scintillation counting | 771 |
| µ (MOP) (h) (agonist radioligand) | human recombinant (HEK-293 cells) | [$^3$H]DAMGO | 0.5 nM | 0.35 nM | naloxone (10 µM) | 120 min RT | Scintillation counting | 260 |
| NOP (ORL1) (h) (agonist radioligand) | human recombinant (HEK-293 cells) | [$^3$H]nociceptin | 0.2 nM | 0.4 nM | nociceptin (1 µM) | 60 min RT | Scintillation counting | 7 |
| PPARγ (h) (agonist radioligand) | human recombinant (E. coli) | [$^3$H]rosiglitazone | 5 nM | 5.7 nM | rosiglitazone (10 µM) | 120 min 4° C. | Scintillation counting | 567 |
| PAF (h) (agonist radioligand) | human recombinant (CHO cells) | [$^3$H]C$_{16}$-PAF | 1.5 nM | 1.5 nM | WEB 2086 (10 µM) | 60 min RT | Scintillation counting | 531 |
| EP$_2$ (h) (agonist radioligand) | human recombinant (HEK-293 cells) | [$^3$H]PGE$_2$ | 3 nM | 3 nM | PGE2 (10 µM) | 120 min RT | Scintillation counting | 781 |
| FP(h) (agonist radioligand) | human recombinant (HEK-293 cells) | [$^3$H]PGF$_{2α}$ | 2 nM | 3.83 nM | cloprostenol (10 µM) | 60 min RT | Scintillation counting | 781 |
| IP(PGI$_2$)(h) (agonist radioligand) | human recombinant (HEK-293 cells) | [$^3$H]iloprost | 6 nM | 8 nM | iloprost (10 µM) | 60 min RT | Scintillation counting | 781 |
| LXRβ(h) (agonist radioligand) | human recombinant (BL21/DE3 cells) | [$^3$H]hydroxycholesterol | 25 nM | 55 nM | 22(R)-hydroxycholesterol (30 µM) | 60 min RT | Scintillation counting | 856 |
| 5-HT$_{1A}$ (h) (agonist radioligand) | human recombinant (HEK-293 cells) | [$^2$H]8-OH-DPAT | 0.3 nM | 0.5 nM | 8-OH-DPAT (10 µM) | 60 min RT | Scintillation counting | 164 |

TABLE 35-continued

Binding Assay Conditions

| Assay | Source | Ligand | Conc. | Kd | Non Specific | Incubation | Detection Method | Bibl. |
|---|---|---|---|---|---|---|---|---|
| 5-HT$_{1B}$ (h) (antagonist radioligand) | rat cerebral codex | [$^{125}$I]CYP (+30 µM isoproterenol) | 0.1 nM | 0.16 nM | serotonin (10 µM) | 120 min 37° C. | Scintillation counting | 111 |
| 5-HT$_{1D}$ (h) (agonist radioligand) | rat recombinant (CHO cells) | ($^3$H]serotonin | 1 nM | 0.5 nM | serotonin (10 µM) | 60 min RT | Scintillation counting | 777 |
| 5-HT$_{2A}$ (h) (agonist radioligand) | human recombinant (HEK-293 cells) | [$^{125}$I]($^+$)DOI | 0.1 nM | 0.2 nM | ($^+$)DOI (1 µM) | 60 min RT | Scintillation counting | 288 |
| 5-HT$_{2B}$ (h) (agonist radioligand) | human recombinant (CHO cells) | [$^{125}$I]($^+$)DOI | 0.2 nM | 0.2 nM | ($^+$)DOI (1 µM) | 60 min RT | Scintillation counting | 571 |
| 5-HT$_{2C}$ (h) (agonist radioligand) | human recombinant (HEK-293 cells) | [$^{125}$I]($^+$)DOI | 0.1 nM | 0.9 nM | ($^+$)DOI (10 µM) | 60 min 37° C. | Scintillation counting | 288 |
| 5-HT$_{4\,e}$ (h) (antagonist radioligand) | human recombinant (CHO cells) | [$^3$H]GR 113808 | 0.3 nM | 0.15 nM | serotonin (100 µM) | 60 min 37° C. | Scintillation counting | 309 |
| 5-HT$_{5a}$ (h) (antagonist radioligand) | human recombinant (HEK-293 cells) | [$^3$H]LSD | 1.5 nM | 1.5 nM | serotonin (100 µM) | 120 min 37° C. | Scintillation counting | 193 |
| 5-HT$_6$ (h) (agonist radioligand) | human recombinant (CHO cells) | [$^3$H]LSD | 2 nM | 1.8 nM | serotonin (100 µM) | 120 min 37° C. | Scintillation counting | 161 |
| 5-HT$_7$ (h) (agonist radioligand) | human recombinant (CHO cells) | [$^3$H]LSD | 4 nM | 2.3 nM | serotonin (10 µM) | 120 min RT | Scintillation counting | 217 |
| sigma (non-selective) (h) (agonist radioligand) | Jurkat cells (endogenous) | [3H]DTG | 10 nM | 41 nM | Haloperidol (10 µM) | 120 min RT | Scintillation counting | 1136 |
| sst$_1$ (h) (agonist radioligand) | human recombinant (CHO cells) | [$^{125}$I]Tyr$^{11}$-somatostatin-1 4 | 0.1 nM | 1 nM | somatostatin-2 8 (1 µM) | 180 min 37° C. | Scintillation counting | 761 |
| sst$_4$ (h) (agonist radioligand) | human recombinant (CHO cells) | [$^{125}$I]Tyr$^{11}$-somatostatin-1 4 | 0.1 nM | 5.9 nM | somatostatin-1 4 (1 µM) | 120 min RT | Scintillation counting | 296 |
| GR (h) (agonist radioligand) | IM-9 cells (cytosol) | [$^3$H]dexamethasone | 1.5 nM | 1.5 nM | triamcinolone (10 µM) | 6 hr 4° C. | Scintillation counting | 283 |
| Estrogen ER alpha (h) (agonist radioligand) | human recombinant (sf9 cells) | [3H]Estradiol | 0.5 nM | 0.20 nM | Diethylstilbestrol (1 µM) | 120 min RT | Scintillation counting | 1280 |
| PR (h) (agonist radioligand) | T47D cells (cytosol) | [$^3$H]progesterone | 0.5 nM | 2 nM | promegestone (1 µM) | 20 hr 4° C. | Scintillation counting | 930 |
| AR (h) (agonist radioligand) | LNCaP cells (cytosol) | [$^3$H]methyltrienolone | 1 nM | 0.8 nM | mibolerone (1 µM) | 24 hr 4° C. | Scintillation counting | 498 |
| Thyroid Hormone | rat liver | [125I] Triodothymnine | 0.03 nM | 0.034 nM | Triodothymnine (1.0 µM) | 1080 min 4° C. | Scintillation counting | 1289 |
| UT(h) (agonist radioligand) | human recombinant (CHO cells) | [$^{125}$I]urotensin-II | 0.1 nM | 0.29 nM | urotensin-II (3 µM) | 120 min RT | Scintillation counting | 622 |
| VPAC$_1$ (VIP$_1$)(h) (agonist radioligand) | human recombinant (CHO cells) | [$^{125}$I]VIP | 0.04 nM | 0.05 nM | VIP (1 µM) | 60 min RT | Scintillation counting | 50 |
| V$_{1a}$ (h) (agonist radioligand) | human recombinant (CHO cells) | [$^3$H]AVP | 0.3 nM | 0.5 nM | AVP (1 µM) | 60 min RT | Scintillation counting | 343 |
| V$_2$ (h) (agonist radioligand) | human recombinant (CHO cells) | [$^3$H]AVP | 0.3 nM | 0.76 nM | AVP (1 µM) | 120 min RT | Scintillation counting | 343 |
| Ion channels | | | | | | | | |
| BZD (central) (agonist radioligand) | rat cerebral cortex | [$^3$H]flunitrazepam | 0.4 nM | 2.1 nM | diazepam (3 µM) | 60 min 4° C. | Scintillation counting | 227 |
| AMPA (agonist radioligand) | rat cerebral cortex | [$^3$H]AMPA | 8 nM | 82 nM | L-glutamate (1 mM) | 60 min 4° C. | Scintillation counting | 166 |
| kainate (agonist radioligand) | rat cerebral cortex | [$^3$H]kainic acid | 5 nM | 19 nM | L-glutamate (1 mM) | 60 min 4° C. | Scintillation counting | 160 |
| NMDA (antagonist radioligand) | rat cerebral cortex | [$^3$H]CGP 39653 | 5 nM | 23 nM | L-glutamate (100 µM) | 60 min 4° C. | Scintillation counting | 221 |

TABLE 35-continued

| Assay | Source | Ligand | Conc. | Kd | Non Specific | Incubation | Detection Method | Bibl. |
|---|---|---|---|---|---|---|---|---|
| glycine (strychnine-insenstive) (antagonist radioligand) | rat cerebral cortex | [³H]MDL 105,519 | 0.5 nM | 5 nM | glycine (1 mM) | 45 min 0° C. | Scintillation counting | 219 |
| PCP (antagonist radioligand) | rat cerebral cortex | [³H]TCP | 10 nM | 13 nM | MK 801 (10 μM) | 120 min 37° C. | Scintillation counting | 257 |
| 5-HT$_3$ (h) (antagonist radioligand) | human recombinant (CHO cells) | [³H]BRL 43694 | 0.5 nM | 1.15 nM | MDL 72222 (10 μM) | 120 min RT | Scintillation counting | 109 |
| Ca$^{2+}$ channel (L, dihydropyridine site) (antagonist radioligand) | rat cerebral cortex | [³H]nitrendipine | 0.1 nM | 0.18 nM | nitrendipine (1 μM) | 90 min RT | Scintillation counting | 996 |
| Ca$^{2+}$ channel (L, diltiazem site) (benzothiazepines) (antagonist radioligand) | rat cerebral cortex | [³H]diltiazem | 15 nM | 52 nM | diltiazem (10 μM) | 120 min RT | Scintillation counting | 212 |
| Ca$^{2+}$ channel (L, verapamil site) (phenylalkylamine) (antagonist radioligand) | rat cerebral cortex | [³H]D888 | 3 nM | 3 nM | D 600 (10 μM) | 120 min RT | Scintillation counting | 194 |
| Ca$^{2+}$ channel (N) (antagonist radioligand) | rat cerebral cortex | [¹²⁵I]ω-conotoxin GVIA | 0.001 nM | 0.0007 nM | w-conotoxin GVIA (10 μM) | 30 min RT | Scintillation counting | 259 |
| Potassium Channel hERG (human)-[3H] Dofetilide | human recombinant (HEK-293 cells) | [³H]Dofetilide | 3 nM | 6.6 nM | Terfenadine (25 μM) | 60 min RT | Scintillation counting | 1398 |
| SK$_{Ca}$ channel (antagonist radioligand) | rat cerebral cortex | [¹²⁵I]apamin | 0.007 nM | 0.007 nM | apamin (100 μM) | 60 min 4° C. | Scintillation counting | 112 |
| Na$^+$ channel (site 2) (antagonist radioligand) | rat cerebral cortex | [³H]batrachotoxinin | 10 nM | 91 nM | veratridine (300 μM) | 60 min 37° C. | Scintillation counting | 28 |
| Cl$^-$ channel (GABA-gated) (antagonist radioligand) | rat cerebral cortex | [³⁵S]TBPS | 3 nM | 14.6 nM | picrotoxinin (20 μM) | 120 min RT | Scintillation counting | 136 |
| Transporters | | | | | | | | |
| norepinephrine transporter (h) (antagonist radioligand) | human recombinant (CHO cells) | [³H]nisoxetine | 1 nM | 2.9 nM | desipramine (1 μM) | 120 min 4° C. | Scintillation counting | 190 |
| dopamine transporter (h) (antagonist radioligand) | human recombinant (CHO cells) | [³H]BTCP | 4 nM | 4.5 nM | BTCP (10 μM) | 120 min 4° C. | Scintillation counting | 190 |
| GABA transporter (antagonist radioligand) | rat cerebral cortex | [³H]GABA (+10 μM isoguvacine) (+10 μM baclofen) | 10 nM | 4600 nM | GABA (1 mM) | 30 min RT | Scintillation counting | 214 |
| choline transporter (CHT1) (h) (antagonist radioligand) | human recombinant (CHO cells) | [³H]hemicholinium-3 | 3 nM | 3.9 nM | hemicholinium-3 (10 μM) | 60 min RT | Scintillation counting | 648 |
| 5-HT transporter (h) (antagonist radioligand) | human recombinant (CHO cells) | [³H]imipramine | 2 nM | 1.7 nM | imipramine (10 μM) | 60 min RT | Scintillation counting | 566 |
| Other enzymes | | | | | | | | |
| MAO-A (antagonist radioligand) | rat cerebral cortex | [³H]Ro 41-1049 | 10 nM | 14 nM | clorgyline (1 μM) | 60 min 37° C. | Scintillation counting | 36 |

Table 36 shows enzyme and uptake assay conditions.

TABLE 36

Enzyme and Uptake Assay Conditions

| Assay | Source | Substrate/Stimulus/Tracer | Incubation | Measured Component | Detection Method | Bibl. |
|---|---|---|---|---|---|---|
| Kinases | | | | | | |
| Abl kinase (h) | human recombinant (insect cells) | ATP + Ulight-TK peptide (100 nM) | 60 min RT | phospho-Ulight-TK peptide | LANCE | 556 |
| CaMK2α (h) | human recombinant | ATP + Ulight-CGSGSGRPRTSSF AEG (50 nM) | 30 min RT | phospho-Ulight-CGSGSGRPRTSSF AEG | LANCE | 647 |
| CDK2 (h) (cycA) | human recombinant | ATP + Ulight-CFFKNIVTPRTPPP SQGK-amide (50 nM) | 30 min RT | phospho-Ulight-CFFKNIVTPRTPPP SQGK-amide | LANCE | 469 |
| ERK$_2$ (h) (P42$^{mapk}$) | human recombinant (*E. coli*) | ATP + Ulight-CFFKNIVTPRTPPP SQGK-amide (100 nM) | 15 min RT | phospho-Ulight-CFFKNIVTPRTPPP SQGK-amide | LANCE | 671 |
| FLT-1 kinase (h) (VEGFRI) | human recombinant (Sf9 cells) | ATP + Ulight-TK peptide (100 nM) | 15 min RT | phospho-Ulight-TK peptide | LANCE | 650 |
| Fyn kinase (h) | human recombinant (insect cells) | ATP + biotinyl-βAβAβ AYQAEENTYDEYEN (2 μM) | 60 min RT | phospho-biotinyl-βAβAβ AYQAEENTYDEYEN | HTRF | 626 |
| IRK (h) (InsR) | human recombinant | ATP + Ulight-Poly GAT[EAY(1:1:1)]n (50 nM) | 10 min RT | phospho-Ulight-Poly GAT[EAY(1:1:1)]n | LANCE | 467 |
| Lyn A kinase (h) | human recombinant (insect cells) | ATP + biotinyl-βAβAβ AKVEKIGEGTYGVVYK (400 nM) | 120 min RT | phospho-biotinyl-βAβAβ AKVEKIGEGTYGVV YK | HTRF | 41 |
| p38a kinase (h) | human recombinant (*E. coli*) | ATP + Ulight-CFFKNIVTPRTPPP SQGK-amide (100 nM) | 60 min RT | phospho-Ulight-CFFKNIVTPRTPPP SQGK-amide | LANCE | 620 |
| ZAP70 kinase (h) | human recombinant (insect cells) | ATP + biotinyl-βAβAβ ADEEEYFIPP (2 μM) | 15 min RT | phospho-biotinyl-βAβAβ ADEEEYFIPP | HTRF | 556 |
| Other enzymes | | | | | | |
| COX1(h) | human recombinant | Arachidonic acid (3 μM) + ADHP (25 μM) | 3 min RT | Resorufin (oxydized ADHP) | Fluorimetry | 1480 |
| COX2(h) | human recombinant (Sf9 cells) | Arachidonic acid (2 μM) + ADHP (25 μM) | 5 min RT | Resorufin (oxydized ADHP) | Fluorimetry | 1480 |
| 5-lipoxygenase (h) | human recombinant (Sf9 cells) (cytosol) | arachidonic acid (25 μM) | 20 min RT | rhodamine 123 | Fluorimetry | 1068 |
| 12-lipoxygenase (h) | human platelets | arachidonic acid (4 μM) | 5 min RT | ferric oxidation of xylenol orange | Photometry | 472 |
| inducible NOS | mouse recombinant (*E. coli*) | L-arginine (100 μM) | 120 min 37"C | NO$_2$ | Photometry | 236 |
| PDE2A1 (h) | human recombinant (Sf9 cells) | [3H]cAMP + cAMP (2 μM) | 20 min RT | [3H]5'AMP | Scintillation counting | 1399 |
| PDE3B (h) | human recombinant (Sf9 cells) | [3H]cAMP + cAMP (0.5 μM) | 20 min RT | [3H]5'AMP | Scintillation counting | 1399 |
| PDE4D2 (h) | human recombinant (Sf9 cells) | [3H]cAMP + cAMP (0.5 μM) | 20 min RT | [$^3$H]5'AMP | Scintillation counting | 1399 |
| PDE5 (h) (non-selective) | human platelets | [$^3$H]cGMP + cGMP (1 μM) | 60 min RT | [3H]5'GMP | Scintillation counting | 263 |
| PDE6 (non-selective) | bovine retina | [$^3$H]cGMP + cGMP (2 μM) | 60 min RT | [3H]5'GMP | Scintillation counting | 306 |
| ACE (h) | human recombinant | Abz-FRK(Dnp)-P-OH (15 μM) | 30 min 37° C. | Abz-Phe-Arg | Fluorimetry | 1128 |
| ACE-2 (h) | human recombinant (murine cells) | Mca-Tyr-Val-Ala-Asp-Pro-Ala-Lys-(DNP)-OH (10 μM) | 20 min RT | Mca peptides | Fluorimetry | 802 |
| BACE-1 (h) (β-secretase) | human recombinant (murine cells) | Mca-S-E-V-N-L-D-A-E-F R-K(Dnp)-R-R—NH$_2$ (6 μM) | 60 min RT | Mca-S-E-V-N-L—NH$_2$ | Fluorimetry | 462 |
| caspase-3 (h) | human recombinant (*E. coli*) | benzyloxycarbonyl-Asp-Glu-Val-Asp-AFC (3.6 μM) | 60 min RT | AFC | Fluorimetry | 476 |
| caspase-8 (h) | human recombinant (*E. coli*) | benzyloxycarbonyl-Ile-Glu-Thr-Asp-AFC (10 μM) | 45 min 37° C. | AFC | Fluorimetry | 408 |

TABLE 36-continued

Enzyme and Uptake Assay Conditions

| Assay | Source | Substrate/Stimulus/Tracer | Incubation | Measured Component | Detection Method | Bibl. |
|---|---|---|---|---|---|---|
| HIV-1 protease | protein viral recombinant (E. coli) | antranilyl-HIV (75 μM) | 40 min 37° C. | N-terminal tripeptide | Fluorimetry | 244 |
| MMP-1 (h) | human recombinant (E. coli) | DNP-Pro-Cha-Gly-Cys(Me)-His-Ala-Lys(n-Me-Abz)-NH$_2$ (10 μM) | 40 min 37° C. | Cys(Me)-His-Ala-Lys(n-Me-Abz)-NH$_2$ | Fluorimetry | 342 |
| MMP-2 (h) | human recombinant | NFF-2 (10 μM) | 90 min 37° C. | Mca-Arg-Pro-Lys-Pro-Tyr-Ala | Fluorimetry | 297 |
| MMP-9 (h) | human recombinant | NFF-2 (10 μM) | 90 min 37° C. | Mca-Arg-Pro-Lys-Pro-Tyr-Ala | Fluorimetry | 297 |
| guanylyl cyclase (h) (activator effect) | human recombinant | GTP (10 μM) (100 μM SNP for control) | 10 min RT | cGMP | HTRF | 1076 |
| acetylcholinesterase (h) | human recombinant (HEK-293 cells) | Acetylthiocholine (400 μM) | 30 min RT | 5 thio 2 nitrobenzoic acid | Photometry | 63 |
| COMT (catechol-0-methyl transferase) | porcine liver | esculetin (1 μM) | 30 min 37° C. | scopoletin | Fluorimetry | 519 |
| MAO-B (h) recombinant enzyme | human recombinant | D-Luciferin derivative (4 μM) | 60 min 37° C. | methyl ester luciferin | Luminescence | 1134 |
| xanthine oxidase/superoxide 02-scavenging | purified xanthine oxidase from bovine milk | hypoxanthine (10 μM) | 10 min RT | O$_2^-$ + uric acid | Photometry | 153 |
| ATPase(Na$^+$/K$^+$) | porcine cerebral cortex | ATP (2 mM) | 60 min 37° C. | Pi | Photometry | 71 |
| Peptidase, Metalloproteinase, Neutral Endopeptidase | Human Raji cells | Glutaryl-Ala-Ala-Phe-4-methoxy-2-naphthylamide | 30 min 37° C. | Glutaryl-Ala-Ala-Phe-4-Methoxy-2-naphthylamide -->4-Methoxy-2-naphthylamine | Photometry | 1352, 1353 |

Analysis and Expression of Results

In Vitro Pharmacology: Binding Assays

The results are expressed as a percent of control specific binding: (Measured specific binding/Control specific binding)×100; and as a percent inhibition of control specific binding: 100−((Measured specific binding/Control specific binding)×100) obtained in the presence of NS2-D6.

The IC$_{50}$ values (concentration causing a half-maximal inhibition of control specific binding) and Hill coefficients (nH) were determined by non-linear regression analysis of the competition curves generated with mean replicate values using Hill equation curve fitting:

$$Y = D + \left[\frac{A-D}{1+(C/C_{50})^{nH}}\right]$$

where Y=specific binding, A=left asymptote of the curve, D=right asymptote of the curve, C=compound concentration, C$_{50}$=IC$_{50}$, and nH=slope factor. This analysis was performed using software developed at Cerep (Hill software) and validated by comparison with data generated by the commercial software SigmaPlot® 4.0 for Windows® (© 1997 by SPSS Inc.). The inhibition constants (K$_i$) were calculated using the Cheng Prusoff equation:

$$K_i = \frac{IC_{50}}{(1+L/K_D)}$$

where L=concentration of radioligand in the assay, and KD=affinity of the radioligand for the receptor. A scatchard plot is used to determine the KD.

In Vitro Pharmacology: Enzyme and Uptake Assays

The results are expressed as a percent of control specific activity: (Measured specific activity/Control specific activity)×100; and as a percent inhibition of control specific activity: 100−((Measured specific activity/Control specific activity)×100) obtained in the presence of NS2-D6.

The IC$_{50}$ values (concentration causing a half-maximal inhibition of control specific activity), EC$_{50}$ values (concentration producing a half-maximal increase in control basal activity), and Hill coefficients (nH) were determined by non-linear regression analysis of the inhibition/concentration-response curves generated with mean replicate values using Hill equation curve fitting:

$$Y = D + \left[\frac{A-D}{1+(C/C_{50})^{nH}}\right]$$

where Y=specific activity, A=left asymptote of the curve, D=right asymptote of the curve, C=compound concentration, C$_{50}$=IC$_{50}$ or EC$_{50}$, and nH=slope factor. This analysis was performed using software developed at Cerep (Hill software) and validated by comparison with data generated by the commercial software SigmaPlot® 4.0 for Windows® (© 1997 by SPSS Inc.).

BIBLIOGRAPHY

3. Aharony, D. et al. (1993), Mol. Pharmacol., 44: 356-363.
7. Ardati, A. et al. (1997), Mol. Pharmacol., 51: 816-824.

13. Berkhout, T. A. et al. (1997), J. Biol. Chem., 272: 16404-16413.
26. Brockhaus, M. et al. (1990), Proc. Natl. Acad. Sci. U.S.A., 87: 3127-3131.
28. Brown, G. B. (1986), J. Neurosci., 6: 2064-2070.
30. Buchan, K. W. et al. (1994), Brit. J. Pharmacol., 112: 1251-1257.
36. Cesura, A. M. et al. (1990), Mol. Pharmacol., 37: 358-366.
41. Cheng, H. C. et al. (1992), J. Biol. Chem., 267: 9248-9256.
50. Couvineau, A. et al. (1985), Biochem. J., 231: 139-143.
56. Devedjian, J. C. et al. (1994), Eur. J. Pharmacol., 252: 43-49.
59. Dorje, F. et al. (1991), J. Pharmacol. Exp. Ther., 256: 727-733.
63. Ellman, G. L. et al. (1961), Biochem. Pharmacol., 7: 88-95.
71. Fiske, C. M. and Subbarow, Y. (1925), J. Biol. Chem., 66: 375-400.
87. Grandy, D. K. et al. (1989), Proc. Natl. Acad. Sci. U.S.A., 86: 9762-9766.
104. Heuillet, E. et al. (1993), J. Neurochem., 60: 868-876.
109. Hope, A. G. et al. (1996), Brit. J. Pharmacol., 118: 1237-1245.
111. Hoyer, D. et al. (1985), Eur. J. Pharmacol., 118: 1-12.
112. Hugues, M. et al. (1982), J. Biol. Chem., 257: 2762-2769.
134. Lee, Y. M. et al. (1993), J. Biol. Chem., 268: 8164-8169.
136. Lewin, A. H. et al. (1989), Mol. Pharmacol., 35: 189-194.
141. Luthin, D. R. et al. (1995), Mol. Pharmacol., 47: 307-313.
145. Mackenzie, R. G. et al. (1994), Eur. J. Pharmacol., 266: 79-85.
153. McCord, J. K. and Fridovich, I. (1969), J. Biol. Chem., 244: 6049-6055.
160. Monaghan, D. T. and Cotman, C. W. (1982), Brain Res., 252: 91-100.
161. Monsma, F. J. et al. (1993), Mol. Pharmacol., 43: 320-327.
164. Mulheron, J. G. et al. (1994), J. Biol. Chem., 269: 12954-12962.
165. Munro, S. et al. (1993), Nature, 365: 61-65.
166. Murphy, D. E. et al. (1987), Neurochem. Res., 12: 775-781.
180. Pacholczyk, T. et al. (1991), Nature, 350: 350-354.
186. Pickering, D. S. and Niles, L. P. (1990), Eur. J. Pharmacol., 175: 71-77.
190. Pristupa, Z. B. et al. (1994), Mol. Pharmacol., 45: 125-135.
193. Rees, S. et al. (1994), FEBS Lett., 355: 242-246.
194. Reynolds, I. J. et al. (1986), J. Pharmacol. Exp. Ther., 237: 731-738.
198. Rivkees, S. A. et al. (1995), J. Biol. Chem., 270: 20485-20490.
206. Salvatore, C. A. et al. (1993), Proc. Natl. Acad. Sci. U.S.A., 90: 10365-10369.
211. Schioth, H. B. et al. (1997), Neuropeptides, 31: 565-571.
212. Schoemaker, H. and Langer, S. Z. (1985), Eur. J. Pharmacol., 111: 273-277.
214. Shank, R. P. et al. (1990), J. Neurochem., 54: 2007-2015.
217. Shen, Y. et al. (1993), J. Biol. Chem., 268: 18200-18204.
219. Baron, B. M. et al. (1996), J. Pharmacol. Exp. Ther., 279: 62-68.
221. Sills, M. A. et al. (1991), Eur. J. Pharmacol., 192: 19-24.
227. Speth, R. C. et al. (1979), Life Sci., 24: 351-358.
229. Stehle, J. H. et al. (1992), Mol. Endocrinol., 6: 384-393.
236. Tayeh, M. A. and Marletta, M. A. (1989), J. Biol. Chem., 264: 19654-19658.
244. Toth, M. V. and Marshall, G. R. (1990), Int. J. Protein Res., 36: 544-550.
248. Tsuzuki, S. et al. (1994), Biochem. Biophys. Res. Commun., 200: 1449-1454.
257. Vignon, J. et al. (1986), Brain Res., 378: 133-141.
259. Wagner, J. A. et al. (1988), J. Neurosci., 8: 3354-3359.
260. Wang, J. B. et al. (1994), FEBS Lett., 338: 217-222.
263. Weishaar, R. E. et al. (1986), Biochem. Pharmacol., 35: 787-800.
281. Zhou, Q. Y. et al. (1990), Nature, 347:76-80.
283. Clark, A. F. et al. (1996), Invest. Ophtalmol. Vis. Sci., 37: 805-813.
285. Feighner, S. D. et al. (1999), Science, 284: 2184-2188.
287. Mantey, S. A. et al. (1997), J. Biol. Chem., 272: 26062-26071.
288. Bryant, H. U. et al. (1996), Life Sci., 15: 1259-1268.
296. Rohrer, L. et al. (1993), Proc. Natl. Acad. Sci. U.S.A., 90: 4196-4200.
297. Nagase, N. et al. (1994), J. Biol. Chem., 269: 20952-20957.
306. Ballard, A. S. et al. (1998), J. Urol., 159: 2164-2171.
309. Mialet, J. et al. (2000), Brit. J. Pharmacol., 129: 771-781.
342. Bickett, D. A. et al. (1993), Anal. Biochem., 212: 58-64.
343. Tahara, A. et al. (1998), Brit. J. Pharmacol., 125: 1463-1470.
346. Pruneau, D. et al. (1998), Brit. J. Pharmacol., 125: 365-372.
390. Siegrist, W. et al. (1988), J. Recep. Res., 8: 323-343.
391. Wieland, H. A. et al. (1995), J. Pharmacol. Exp. Ther., 275: 143-149.
408. Karahashi, H. and Amano, F. (2000), Biol. Pharm. Bull., 23: 140-144.
462. Ermolieff, J. et al. (2000), Biochemistry, 39: 12450-12456.
467. Al-Hasani, H. et al. (1994), FEBS Lett., 349: 17-22.
469. Meijer, L. et al. (1997), Eur. J. Biochem., 243: 527-536.
472. Waslidge, N. B. and Hayes, D. J. (1995), Anal. biochem., 231: 354-358.
476. Mittl, P. R. E. et al. (1997), J. Biol. Chem., 272: 6539-6547.
492. Smit, M. J. et al. (1996), Brit. J. Pharmacol., 117: 1071-1080.
498. Zava, D. T. et al. (1979), Endocrinology, 104: 1007-1012.
501. Simonin, F. et al. (1994), Mol. Pharmacol., 46: 1015-1021.
508. Green, A. et al. (2000), Brit. J. Pharmacol., 131: 1766-1774.
519. Muller-Enoch, D. et al. (1976), Z. Naturforsch., 31: 280-284.
524. Lukas, R. J. (1986), J. Neurochem., 46: 1936-1941.
526. Mac Donald, D. et al. (2000), Mol. Pharmacol., 58: 217-225.
531. Fukunaga, K. et al. (2001), J. Biol. Chem., 276: 43025-43030.
540. Leurs, R. et al. (1994), Brit. J. Pharmacol., 112: 847-854.
541. Fuchs, S. et al. (2001), Mol. Med., 7: 115-124.

542. Langin, D. et al. (1989), Eur. J. Pharmacol., 167: 95-104.
546. Peralta, E. G. et al. (1987), Embo. J., 6: 3923-3929.
548. Levin, M. C. et al. (2002), J. Biol. Chem., 277: 30429-30435.
556. Park, Y. M. et al. (1999), Anal. Biochem., 269: 94-104.
557. Palchaudhuri, M. R. et al. (1998), Eur. J. Biochem., 258: 78-84.
562. Bignon, E. et al. (1999), J. Pharmacol. Exp. Ther. 289: 742-751.
563. Lovenberg, T. W. et al. (1999), Mol. Pharmacol., 55: 1101-1107.
566. Tatsumi, M. et al. (1999), Eur. J. Pharmacol., 368: 277-283.
567. Ferry, G. et al. (2001), Eur. J. Pharmacol., 417: 77-89.
571. Choi, D. S. et al. (1994), FEBS Lett., 352: 393-399.
616. Yokomizo, T. et al. (2001), J. Biol. Chem., 276: 12454-12459.
618. Martin, V. et al. (2001), Biochem. Pharmacol., 62: 1193-1200.
620. Frantz, B. et al. (1998), Biochemistry, 37: 13846-13853.
622. Maguire, J. J. et al. (2000), Brit. J. Pharmacol., 131: 441-446.
624. Chicchi, G. G. et al. (1997), J. Biol. Chem., 272: 7765-7769.
626. Dente, L. et al. (1997), J. Mol. Biol., 269: 694-703.
631. Liu, C. et al. (2001), J. Pharmacol. Exp. Ther., 299: 121-130.
639. Witt-Enderby, P. A. and Dubocovich, M. L. (1996), Mol. Pharmacol., 50: 166-174.
647. Ichida, A. and Fujisawa, H. (1995), J. Biol. Chem., 270: 2163-2170.
648. Apparsundaram, S. et al. (2000), Biochem. Biophys. Res. Commun., 276: 862-867.
650. Itokawa, T. et al. (2002), Mol. Cancer Ther., 1: 295-302.
657. Rinaldi-Carmona, M. et al. (1996), J. Pharmacol. Exp. Ther., 278: 871-878.
671. Bardwell, A. J. et al. (2003), Biochem. J., 370: 1077-1085.
701. Ford, A. P. D. W. et al. (1997), Brit. J. Pharmacol., 121: 1127-1135.
761. Patel, C. Y. and Srikant, C. B. (1994), Endocrinology, 135: 2814-2817.
771. Meng, F. et al. (1993), Proc. Natl. Acad. Sci. U.S.A., 90: 9954-9958.
776. Le, M. T. et al. (2005), Eur. J. Pharmacol., 513: 35-45.
777. Wurch, T. et al. (1997), J. Neurochem., 68: 410-418.
781. Abramovitz, M. et al. (2000), Biochem. Biophys. Acta., 1483: 285-293.
794. Joseph, S. S. et al. (2004), Naun.-Sch. Arch. Pharm., 369: 525-532.
802. Huang, L. et al. (2003), J. Biol. Chem., 278: 15532-15540.
846. Katugampola, S. D. et al. (2001), Brit. J. Pharmacol., 132: 1255-1260.
856. Janowski, B. A. et al. (1999), Proc. Natl. Acad. Sci. USA, 96: 266-271.
897. Schwinn, D. A. et al. (1990), J. Biol. Chem., 265: 8183-8189.
930. Sarup, J. C. et al. (1988), J. Biol. Chem., 263: 5624-5633.
996. Gould, R. J. et al. (1982), Proc. Natl. Acad. Sci. USA., 79: 3656-3660.
1068. Pufahl, R. A. et al. (2007), Anal. Biochem., 364: 204-212.
1076. Lee, Y. C. et al. (2000), Proc. Natl. Acad. Sci. USA, 20: 10763-10768.
1084. Gopalakrishnan, M. et al. (1996), J. Pharmacol. Exp. Ther., 276: 289-297.
1096. Wang, X. K. (2001), Acta. Pharmacol. Sin., 22: 521-523.
1128. Fernandes, T. et al. (2010), Braz J Med Biol Res., 43: 837-842.
1134. Tsugeno, Y. et al. (1995), J. Biochem., 1995; 118 (5) 974-80.
1136. GANAPATHY ME. et al. (1999), JPET, 289: 251-260.
1277. Feve B, Elhadri K, Quignard-Boulange A and Pairault J (1994), Feve B et al. Proc Natl Acad Sci USA. 91:5677, 1994.
1280. Obourn J D, Koszewski N J and Notides A C (1993), Obourn J D et al. Biochemistry 32(24):6229, 1993.
1289. Inoue A, Yamakawa J, Yukioka M and Morisawa S (1983), Inoue A et al. Anal Biochem. 134(1):176, 1983.
1352. Shipp M A, Vijayaraghavan J, Schmidt E V, Masteller E L, D'Adamio L, Hersh L B and Reinherz E L (1989), Shipp M A et al. Proc Natl Acad Sci USA. 86:297, 1989.
1353. Erdos E G and Skidgel R A (1989), Erdos E G and Skidgel R A. FASEB J. 3:145, 1989. 1398. Huang X P1, Mangano T, Hufeisen S, Setola V, Roth B L., Assay Drug Dev Technol. 2010 December; 8(6):727-42.
1399. Maurice D. H. et al. (2014), Nat Rev Drug Discov., 13: 290-314.
1480. Pattaraporn Vanachayangkul and William H. Tolleson (2012), Hindawi Publishing Corporation, Enzyme Research, Volume 2012, Article ID 416062, 7.

We claim:
1. A compound of Formula II-B:

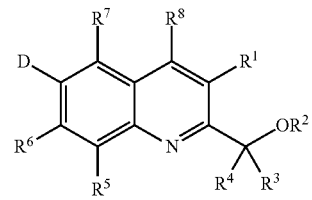

or a pharmaceutically acceptable salt thereof, wherein:
$R^1$ is selected from —$NH_2$, —NHD, or —$ND_2$;
$R^2$ is selected from hydrogen or deuterium;
$R^3$ and $R^4$ are independently selected from —$CH_3$, —$CH_2D$, —$CHD_2$, or —$CD_3$; and
$R^5$, $R^6$, $R^7$, and $R^8$ are each independently selected from hydrogen or deuterium.

2. The compound of claim 1, wherein $R^1$ is —$NH_2$.
3. The compound of claim 2, wherein $R^2$ is hydrogen.
4. The compound of claim 3, wherein $R^3$ is —$CH_3$.
5. The compound of claim 4, wherein $R^4$ is —$CH_3$.
6. The compound of claim 1, wherein $R^8$ is hydrogen and at least one of $R^1$, $R^2$, $R^3$, $R^4$, $R^5$, $R^6$, or $R^7$ is or contains deuterium.
7. The compound of claim 1, wherein each of $R^5$, $R^6$, $R^7$, and $R^8$ is as defined in an entry set forth in the table below:

| Entry | $R^5$ | $R^6$ | $R^7$ | $R^8$ |
|---|---|---|---|---|
| i | H | H | H | H |
| ii | H | H | H | D |
| iii | H | H | D | H |

-continued

| Entry | R⁵ | R⁶ | R⁷ | R⁸ |
|---|---|---|---|---|
| iv | H | D | H | H |
| v | D | H | H | H |
| vi | H | H | D | D |
| vii | H | D | H | D |
| viii | D | H | H | D |
| ix | H | D | D | H |
| x | D | H | D | H |
| xi | D | D | H | H |
| xii | H | D | D | D |
| xiii | D | H | D | D |
| xiv | D | D | H | D |
| xv | D | D | D | H |
| xvi | D | D | D | D | or a pharmaceutically acceptable salt thereof.

8. The compound of claim 1, wherein the compound is of the following structure:

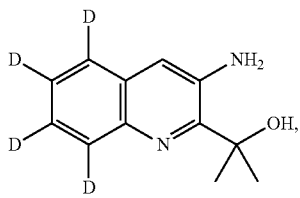 [SMILES: [2H]c1c([2H])c([2H])c2nc(C(C)(C)O)c(N)cc2c1[2H]]

or a pharmaceutically acceptable salt thereof.

9. The compound of claim 1, wherein each position of deuterium enrichment in the compound comprises deuterium in an amount of about 50% or greater.

10. The compound of claim 8, wherein each position of deuterium enrichment in the compound comprises deuterium in an amount of 90% or greater.

11. A pharmaceutical composition comprising a compound according to claim 1 and a pharmaceutically acceptable adjuvant, carrier, or vehicle.

12. The pharmaceutical composition according to claim 11, in combination with an additional therapeutic agent.

13. A method of treating, preventing, or reducing a risk of a disease, disorder, condition, or cosmetic indication in which aldehyde toxicity is implicated in a subject in need thereof, comprising administering topically or systemically to the subject a composition comprising a compound according to claim 1 or a pharmaceutically acceptable salt or a pharmaceutical composition thereof.

14. The method according to claim 13, wherein the disease, disorder, or condition is an ocular disorder.

15. The method of claim 14, wherein the ocular disorder is macular degeneration or Stargardt disease.

16. The method of claim 14, wherein the ocular disorder is selected from the group consisting of dry eye syndrome, cataracts, keratoconus, bullous and other keratopathy, Fuch's endothelial dystrophy, allergic conjunctivitis, ocular cicatricial pemphigoid, conditions associated with PRK healing and other corneal healing, conditions associated with tear lipid degradation or lacrimal gland dysfunction, uveitis, scleritis, ocular Stevens Johnson Syndrome, and ocular rosacea.

17. The method of claim 13, wherein the disease, disorder, or condition is a skin disease, disorder, or condition selected from the group consisting of psoriasis, topical (discoid) lupus, contact dermatitis, atopic dermatitis, allergic dermatitis, radiation dermatitis, acne vulgaris, Sjogren-Larsson Syndrome and other ichthyosis, and the cosmetic indication is selected from the group consisting of solar elastosis/wrinkles, skin tone firmness, puffiness, eczema, smoke or irritant induced skin changes, dermal incision, and a skin condition associated with a burn or wound.

18. The method of claim 13, wherein the disease, disorder, or condition is an autoimmune, immune-mediated, inflammatory, cardiovascular, or neurological disease, or diabetes, metabolic syndrome, or a fibrotic disease.

19. The method of claim 13, wherein the disease, disorder, or condition is selected from the group consisting of lupus, scleroderma, asthma, chronic obstructive pulmonary disease (COPD), rheumatoid arthritis, inflammatory bowel disease, sepsis, atherosclerosis, ischemic-reperfusion injury, Parkinson's disease, Alzheimer's disease, succinic semialdehyde dehydrogenase deficiency, multiple sclerosis, and amyotrophic lateral sclerosis.

20. The method of claim 13, wherein the disease, disorder, or condition is an age-related disease, disorder, or condition.

* * * * *